United States Patent [19]
MacKenzie et al.

[11] Patent Number: 5,968,923
[45] Date of Patent: Oct. 19, 1999

[54] (AZETIDIN-1-YLALKYL) LACTAMS AS TACHYKININ ANTAGONISTS

[75] Inventors: Alexander Roderick MacKenzie; Allan Patrick Marchington; Sandra Dora Meadows; Donald Stuart Middleton, all of Sandwich, United Kingdom

[73] Assignee: Pfizer Inc., New York, N.Y.

[21] Appl. No.: 08/798,534

[22] PCT Filed: Jul. 29, 1995

[86] PCT No.: PCT/EP95/03054

§ 371 Date: Feb. 10, 1997

§ 102(e) Date: Feb. 10, 1997

[87] PCT Pub. No.: WO96/05193

PCT Pub. Date: Feb. 22, 1996

[30] Foreign Application Priority Data

Aug. 9, 1994 [GB] United Kingdom ............... 9416084
Sep. 6, 1994 [GB] United Kingdom ............... 9417898

[51] Int. Cl.$^6$ ............... A61K 31/445; A61K 401/06; A61K 413/14; A61K 451/02
[52] U.S. Cl. ............ 514/210; 540/524; 540/544; 544/60; 544/62; 544/130; 544/141; 544/364; 544/372; 544/373; 546/187; 546/196; 546/201; 546/205; 546/208; 546/212; 546/216; 548/314.7; 548/455; 548/466; 548/467; 548/518; 548/950
[58] Field of Search ............... 540/524, 544; 544/60, 62, 130, 141, 364, 372, 373; 546/201, 205, 208, 196, 212, 216, 187; 548/950, 518, 467, 314.7, 455, 466; 514/210

[56] References Cited

U.S. PATENT DOCUMENTS 5,340,822  8/1994  Edmonds -Alt et al. ............ 514/316

(List continued on next page.)

FOREIGN PATENT DOCUMENTS

A0474561  3/1992  European Pat. Off. .

(List continued on next page.)

*Primary Examiner*—Richard L. Raymond
*Assistant Examiner*—Brenda Coleman
*Attorney, Agent, or Firm*—Peter C. Richardson; Paul H. Ginsburg; Jolene W. Appleman

[57] ABSTRACT

The present invention provides compounds of formula (I) and the pharmaceutically acceptable salts thereof, wherein R is $C_3$–$C_7$ cycloalkyl, aryl or $C_1$–$C_6$ alkyl, said $C_1$–$C_6$ alkyl, said $C_1$–$C_6$ alkyl being optionally substituted by fluoro, COOH, —COO($C_1$–$C_4$ alkyl), $C_3$–$C_7$ cycloalkyl, adamantyl, aryl or het$^1$, and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro ($C_1$–$C_4$) alkyl and fluoro ($C_1$–$C_4$)Alkoxy; $R_1$ is phenyl, naphthyl, thienyl, benzothie- nyl or indolyl, each optionally substituted by 1 or 2 substituents each independently selected from $C_1$–$C_4$ alkyl, $C_1$–$C_4$ alkoxy, halo and trifluormethyl; $R^2$ is —$CO_2H$, —$CONR^3R^4$, —$CONR^5(C_3$–$C_7$ cycloalkyl), —$NR^5(C_2$–$C_5$ alkanoyl), —$NR^3R^4$, —$NR^5CONR^5R^6$, ($C_3$–$C_7$ cycloalkyl-$C_1$–$C_4$ alkyl)$R^5$N—, —$NR^5COCF_3$, —$NR^5SO_2CF_3$, —$NR^5$($SO_2$ $C_1$–$C_4$ alkyl), —$NR^5SO_2NR^5R^6$, —$NR^5(SO_2$ aryl), —$N$(aryl) ($SO_2C_1$–$C_4$ alkyl), —$OR^5$, —$O(C_3$–$C_7$ cycloalkyl), —$SO_2NR^5R^6$, het$^3$ or a group of formulas: (a), (b), (c), (d), (e), (f), (g) or (h); X is $C_1$–$C_4$ alkylene; $X^1$ is a direct link or $C_1$–$C_6$ alkylene; $X^2$ is a direct link, CO, $SO_2$, or $NR^5CO$; and m is 0, 1 or 2; together with intermediates used in the preparation of compositions containing and the use as tachykinin angatonists of such derivatives.

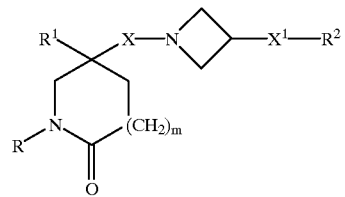

(I)

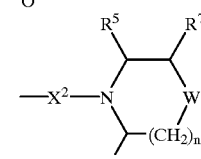

(a)

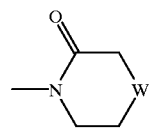

(b)

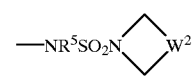

(c)

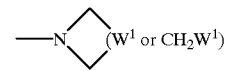

(d)

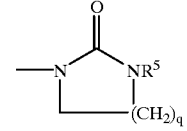

(e)

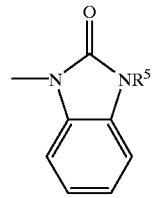

(f)

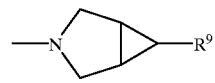

(g)

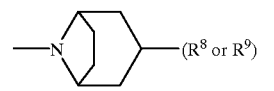

(h)

12 Claims, No Drawings

U.S. PATENT DOCUMENTS

| | | | |
|---|---|---|---|
| 5,472,958 | 12/1995 | Gunn et al. | 514/210 |
| 5,534,510 | 7/1996 | Abe et al. | 514/210 |
| 5,565,474 | 10/1996 | Baroni et al. | 514/210 |

FOREIGN PATENT DOCUMENTS

| | | |
|---|---|---|
| A0512901 | 11/1992 | European Pat. Off. . |
| A0515240 | 11/1992 | European Pat. Off. . |
| A0615751 | 9/1994 | European Pat. Off. . |
| A0625509 | 11/1994 | European Pat. Off. . |
| A0630887 | 12/1994 | European Pat. Off. . |
| A9007534 | 12/1991 | France . |
| 9410146 | 5/1994 | WIPO . |
| 9417045 | 8/1994 | WIPO . |
| 9422822 | 10/1994 | WIPO . |
| 9429309 | 12/1994 | WIPO . |
| 9505377 | 2/1995 | WIPO . |
| 9512577 | 5/1995 | WIPO . |

(AZETIDIN-1-YLALKYL) LACTAMS AS TACHYKININ ANTAGONISTS

Priority is claimed under 35 U.S.C. #371 from PCT/EP95/30504 filed Jul. 29, 1995.

This invention relates to lactams. More particularly, this invention relates to azetidinylalkyllactam derivatives and to processes for the preparation of, intermediates used in the preparation of, compositions containing and uses of, such derivatives.

The present azetidinylalkyllactam derivatives are antagonists of tachykinins, including NKA, NKB and Substance P, acting at the human neurokinin-1 ($NK_1$), neurokinin-2 ($NK_2$) or neurokinin-3 ($NK_3$) receptor, or a combination thereof. The derivatives are therefore useful for preventing or treating an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as poison ivy, a vasospastic disease such as angina or Reynaud's disease, a fibrosing or collagen disease such as scleroderma or eosinophillic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpetic neuralgia, a neuropathological disorder such as Alzheimer's disease or multiple sclerosis, a disorder related to immune enhancement or suppression such as systemic lupus erythematosis, a rheumatic disease such as fibrositis or emesis, cough, acute or chronic pain or migraine. The present derivatives are particularly potent and selective antagonists of achykinins, including NKA, NKB and Substance P, acting at the human $NK_2$ eceptor. They are particularly useful for treating or preventing an inflammatory isease such as arthritis, psoriasis, asthma or inflammatory bowel disease, a entral nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a burn, herpetic neuralgia or post-herpetic neuralgia, cough or acute or chronic pain.

The present invention provides compounds of the formula:

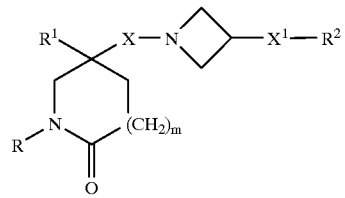

(I)

and the pharmaceutically acceptable salts thereof, wherein

R is $C_3$–$C_7$ cycloalkyl, aryl or $C_1$–$C_6$ alkyl, said $C_1$–$C_6$ alkyl being optionally substituted by fluoro, —COOH, —COO($C_1$–$C_4$ alkyl), $C_3$–$C_7$ cycloalkyl, adamantyl, aryl or het[1], and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro($C_1$–$C_4$)alkyl and fluoro ($C_1$–$C_4$)alkoxy;

$R^1$ is phenyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;

$R^2$ is —$CO_2H$, —$CONR^3R^4$, —$CONR^5(C_3$–$C_7$ cycloalkyl), —NR ($C_2$–$C_5$ alkanoyl), —$NR^3R^4$, —$NR^5CONR^5R^6$, ($C_3$–$C_7$ cycloalkyl-$C_1$–$C_4$ alkyl)$R^5N$—, ($C_3$–$C_7$ cycloalkyl-$C_1$–$C_4$ alkyl)$_2N$—, —$NR^5COCF_3$, —$NR^5SO_2CF_3$, —$NR^5(SO_2C_1$–$C_4$ alkyl), —$NR^5SO_2NR^5R^6$, —$NR^5(SO_2$ aryl), —N(aryl)($SO_2$ $C_1$–$C_4$ alkyl), —$OR^5$, —O($C_3$–$C_7$ cycloalkyl), —$SO_2NR^5R^6$, het[3] or a group of the formula:

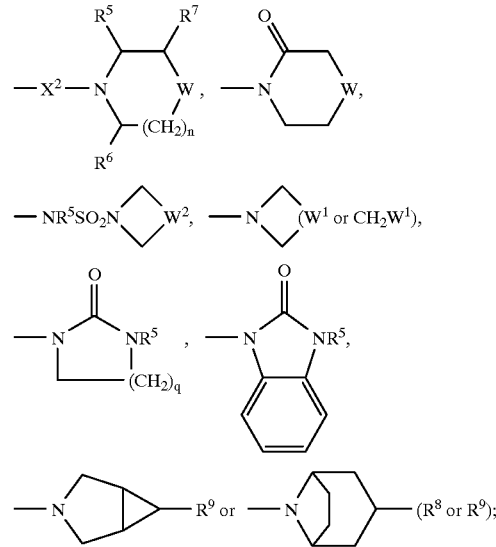

$R^3$ and $R^4$ are each independently selected from H and $C_1$–$C_4$ alkyl optionally substituted by hydroxy, $C_1$–$C_4$ alkoxy, —S(O)$_p$($C_1$–$C_4$ alkyl), amino, —NH($C_1$–$C_4$ alkyl), —N($C_1$–$C_4$ alkyl)2 or het[2];

$R^5$ and $R^6$ are each independently selected from H, $C_1$–$C_4$ alkyl and $C_3$–$C_7$ cycloalkyl-$C_1$–$C_4$ alkyl, said $C_1$–$C_4$ alkyl and $C_3$–$C_7$ cycloalkyl-$C_1$–$C_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5$($SO_2C_1$–$C_4$ alkyl), —$NR^5SO_2NR^5R^6$, —$NR^5COO$($C_1$–$C_4$ alkyl), —$NR^5CONR^5R^6$, —$NR^5(SO_2$ morpholino), —$NR^5(SO_2$ aryl), —N(aryl)($SO_2$ $C_1$–$C_4$ alkyl) or a group of the formula:

X is $C_1$–$C_4$ alkylene;

$X^1$ is a direct link or $C_1$–$C_6$ alkylene;

$X^2$ is a direct link, CO, $SO_2$ or $NR^5CO$;

W is methylene, CO, CH(OH), C(OH)$_2$, CH($C_1$–$C_4$ alkoxy), $CHCO_2H$, $CHCO_2$($C_1$–$C_4$ alkyl), $CHCONR^5R^6$, CHF, $CF_2$, CH(azetidin-1-yl), CH(pyrrolidin-1-yl), CH(piperidin-1-yl), CH(morpholino), CH(benzoxazol-2-yl), $CHR^9$, O, $S(O)_p$, $NR^5$, $N(C_3$–$C_7$ cycloalkyl), $NSO_2(C_1$–$C_4$ alkyl), $NSO_2NR^5R^6$, $NSO_2CF_3$, $NSO_2$(morpholino), $NSO_2$(aryl),

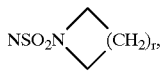

$NCONR^5R^6$, $NCOR^5$, NCO(aryl) or $NCO_2(C_1$–$C_4$ alkyl);

$W^1$ is methylene, CO, CH(OH), C(OH)$_2$, CH($C_1$–$C_4$ alkoxy), $CHCO_2H$, $CHCO_2$($C_1$–$C_4$ alkyl), $CHCONR^5R^6$, CHF, $CF_2$, CH(azetidin-1-yl), CH(pyrrolidin-1-yl), CH(piperidin-1-yl), CH(morpholino) or $CHR^9$;

$W^2$ is $W^1$, —$CH_2W^1$—, —$CH_2WCH_2$— or —$CH_2CH_2WCH_2$—;

m is 0, 1 or 2;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R^9$ and W, means naphthyl or phenyl, each optionally substituted by $C_1$–$C_4$ alkyl, halo, —$OR^5$, fluoro($C_1$–$C_4$)alkyl, $C_2$–$C_5$ alkanoyl, —$CONR^5R^6$, —$SO_2NR^5R^6$ or phenyl;

"het$^1$", used in the definition of R, means thienyl or a 5- or 6-membered ring heteroaryl group containing either 1 or 2 nitrogen heteroatoms, or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro($C_1$–$C_4$)alkyl and fluoro($C_1$–$C_4$)alkoxy;

"het$^2$", used in the definitions of $R^3$ and $R^4$, means a 4- to 7-membered ring, non-aromatic, heterocyclic group containing 1 or 2 heteroatoms each independently selected from nitrogen, oxygen and $S(O)_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —$CONR^5R^6$ or —$SO_2NR^5R^6$ substituent;

and "het$^3$", used in the definition of $R^2$, means an optionally benzo-fused, N-linked, 5-membered ring heteroaryl group containing from 1 to 4 nitrogen heteroatoms, optionally substituted, including in the benzo-fused portion, by 1 or 2 substituents each independently selected from $C_1$–$C_4$ alkyl, fluoro and fluoro($C_1$–$C_4$)alkyl.

In the above definitions, the term "halo" means fluoro, chloro, bromo or iodo and alkyl, alkylene and alkoxy groups containing three or more carbon atoms and alkanoyl groups containing four or more carbon atoms can be straight- or branched-chain.

Preferably, R is $C_1$–$C_6$ alkyl optionally substituted by —COOH, —COO($C_1$–$C_4$ alkyl), $C_3$–$C_7$ cycloalkyl, aryl or het$^1$, said cycloalkyl being optionally substituted by 1 or 2 substituents each independently selected from $C_1$–$C_4$ alkyl and fluoro.

More preferably, R is $C_1$–$C_6$ alkyl optionally substituted by —COOH, —COO($C_1$–$C_4$ alkyl), $C_3$–$C_7$ cycloalkyl optionally substituted by 1 or 2 substituents each independently selected from $C_1$–$C_4$ alkyl and fluoro, phenyl optionally substituted by 1 or 2 substituents each independently selected from $C_1$–$C_4$ alkyl, halo, $C_1$–$C_4$ alkoxy, fluoro($C_1$–$C_4$)alkyl, $C_2$–$C_5$ alkanoyl, —$SO_2N(C_1$–$C_4$ alkyl)$_2$ and phenyl, or a 5- or 6-membered ring heteroaryl group containing 1 or 2 nitrogen heteroatoms.

Yet more preferably, R is $C_1$–$C_6$ alkyl optionally substituted by —COOH, —COO($C_1$–$C_4$ alkyl), $C_3$–$C_7$ cycloalkyl optionally substituted by 1 or 2 substituents each independently selected from methyl and fluoro, phenyl optionally substituted by 1 or 2 substituents each independently selected from methyl, fluoro, chloro, methoxy, trifluoromethyl, acetyl, —$SO_2N(CH_3)_2$ and phenyl, or pyridinyl.

Yet further preferably, R is 5-carboxypentyl, 5-tert-butyloxycarbonylpentyl, cyclopropylmethyl, dicyclopropylmethyl, cyclobutylmethyl, cyclopentylmethyl, cyclohexylmethyl, 2-methylcyclohexylmethyl, 4,4-difluorocyclohexylmethyl, 2-cyclopropylethyl, 2,2-dicyclopropylethyl, 1-cyclohexylethyl, 2-cyclohexylethyl, cycloheptylmethyl, benzyl, 2-methylbenzyl, 3-methylbenzyl, 4-methylbenzyl, 4-fluorobenzyl, 2,4-dichlorobenzyl, 3-methoxybenzyl, 2-trifluoromethylbenzyl, 3,5-di(trifluoromethyl)benzyl, 3-acetylbenzyl, 3-(N,N-dimethylsulphamoyl)benzyl, 4-phenylbenzyl, 1-phenylethyl, 2-pyridinylmethyl, 3-pyridinylmethyl or 4-pyridinylmethyl.

Most preferably, R is cyclopropylmethyl, dicyclopropylmethyl, 2-cyclopropylethyl, 2,2-dicyclopropylethyl, cyclohexylmethyl, 4,4-difluorocyclohexylmethyl, cycloheptylmethyl or benzyl.

Preferably, $R^1$ is phenyl optionally substituted by 1 or 2 halo substituents.

More preferably, $R^1$ is phenyl optionally substituted by 1 or 2 substituents each independently selected from fluoro and chloro.

Yet more preferably, $R^1$ is phenyl, 3,4-difluorophenyl, 3-chlorophenyl, 4-chlorophenyl or 3,4-dichlorophenyl.

Most preferably, $R^1$ is 3,4-difluorophenyl, 4-chlorophenyl or 3,4-dichlorophenyl.

Preferably, $R^2$ is —$CONR^3R^4$, —$CONR^5(C_3$–$C_7$ cycloalkyl), —$NR^3R^4$, het$^3$ or a group of the formula:

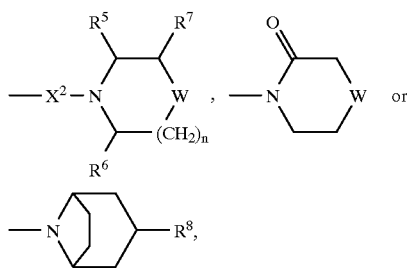

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CH($C_1$–$C_4$ alkoxy), CHCO$_2$H, CHCO$_2$($C_1$–$C_4$ alkyl), CH(benzoxazol-2-yl), CHNR$^5$R$^6$, CHNR$^5$COR$^5$, CHNR$^5$(SO$_2$ $C_1$–$C_4$ alkyl), CHNR$^5$COO($C_1$–$C_4$ alkyl), O, S(O)$_p$, NR$^5$, NSO$_2$($C_1$–$C_4$ alkyl), NSO$_2$NR$^5$R$^6$, NSO$_2$ (morpholino), NCONR$^5$R$^6$, NCOR$^5$, NCO(aryl) or NC$_2$ ($C_1$–$C_4$ alkyl), n is 1 or 2 when W is other than methylene and is 0 or 1 when W is methylene, and p is 0,1 or 2.

More preferably, $R^2$ is —CONR$^3$R$^4$, —CONR$^5$(C$_3$–C$_7$ cycloalkyl), —NR$^3$R$^4$, a N-linked, 5-membered ring heteroaryl group containing 1 or 2 nitrogen heteroatoms, or a group of the formula:

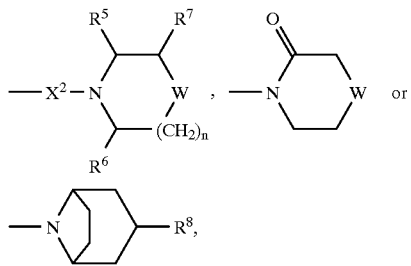

where $R^3$ and $R^4$ are each independently selected from methyl and $C_1$–$C_4$ alkyl substituted by hydroxy or methoxy, $R^5$ and $R^6$ are each independently selected from H, methyl, trifluoromethyl and cyclopropylmethyl, $R^7$ is H, hydroxy or phenyl, $R^8$ is hydroxy or acetyloxy, W is methylene, CH(OH), CHOCH$_3$, CHOCH$_2$CH$_3$, CHO(CH$_2$)$_2$CH$_3$, CHOC(CH$_3$)$_3$, CHCO$_2$H, CHCO$_2$CH$_3$, CHCO$_2$CH$_2$CH$_3$, CH (benzoxazol-2-yl), CHNH$_2$, CHNHCH$_2$(cyclopropyl), CHNHCOCH$_3$, CHNHSO$_2$CH$_3$, CHNHCO$_2$C(CH$_3$)$_3$, O, S(O)$_p$, NH, NCH$_3$, NCH$_2$(cyclopropyl), NSO$_2$CH$_3$, NSO$_2$NH$_2$, NSO$_2$NHCH$_3$, NSO$_2$N(CH$_3$)$_2$, NSO$_2$ (morpholino), NCONH$_2$, NCONHCH$_3$, NCOCH$_3$, NCOCF$_3$, NCO(phenyl) or NCO$_2$C(CH$_3$)$_3$, n is 1 or 2 when W is other than methylene and is 0 or 1 when W is methylene, and p is 0, 1 or 2.

Yet more preferably, $R^2$ is N-(2-methoxyethyl)-N-methylcarbamoyl, N-cyclohexylcarbamoyl, N-(2-hydroxyethyl)-N-methylamino, N-(2-hydroxy-2-methylpropyl)-N-methylamino, N-(2-methoxyethyl)-N-methylamino, imidazol-1-yl, 3-hydroxypyrrolidin-1-yl, piperidin-1-yl, 2,6-dimethylpiperidin-1-yl, 3-hydroxypiperidin-1-yl, 4-hydroxypiperidin-1-yl, 4-methoxypiperidin-1-yl, 4-ethoxypiperidin-1-yl, 4-(n-propoxy)piperidin-1-yl, 4-(t-butoxy)piperidin-1-yl, 4-carboxypiperidin-1-yl, 4-methoxycarbonylpiperidin-1-yl, 4-ethoxycarbonylpiperidin-1-yl, 4-(benzoxazol-2-yl) piperidin-1-yl, 4-aminopiperidin-1-yl, 4-cyclopropyl-methylaminopiperidin-1-yl, 4-acetamidopiperidin-1-yl, 4-methanesulphonamido-piperidin- 1-yl, 4-(t-butoxycarbonylamino)piperidin-1-yl, morpholino, 2-phenylmorpholino, homomorpholino, thiomorpholino, 1-oxothiomorpholino, 1,1-dioxothiomorpholino, piperazin-1-yl, 4-methylpiperazin-1-yl, 4-cyclopropylmethyl-piperazin-1-yl, 4-methanesulphonylpiperazin-1-yl, 4-aminosulphonylpiperazin-1-yl, 4-methylaminosulphonylpiperazin-1-yl, 4-dimethylaminosulphonylpiperazin-1-yl, 4-morpholinosulphonylpiperazin-1-yl, 4-carbamoylpiperazin-1-yl, 4-N-methylcarbamoylpiperazin-1-yl, 4-acetylpiperazin-1-yl, 4-trifluoroacetylpiperazin-1-yl, 4-benzoylpiperazin-1-yl, 4-(t-butoxycarbonyl)piperazin-1-yl, pyrrolidin-1-ylcarbonyl, piperidin-1-ylcarbonyl, 3-oxomorpholino, 3-hydroxy-8-azabicyclo[3,2, 1 ]oct-8-yl or 3-acetyloxy-8-azabicyclo[3,2, 1 ]oct-8-yl.

Most preferably, $R^2$ is 4-aminopiperidin-1-yl, 4-carboxypiperidin-1-yl, 4-hydroxypiperidin-1-yl, morpholino, 1-oxothiomorpholino, 4-aminosulphonylpiperazin-1-yl, 4-methanesulphonylpiperazin-1-yl, 4-methylaminosulphonylpiperazin-1-yl or 4-morpholinosulphonylpiperazin-1-yl.

Further preferred examples of $R^2$ include 4-fluoropiperidin-1-yl, 4,4-difluoropiperidin-1-yl, 4-oxopiperidin-1-yl, 4-(pentafluorophenylsulphonyl) -piperazin-1-yl and 4-(4-fluorophenylsulphonyl)piperazin-1-yl.

Preferably, X is ethylene or propylene.
Most preferably, X is ethylene.
Preferably, $X^1$ is a direct link.
Preferably, $X^2$ is a direct link or CO.
Most preferably, $X^2$ is a direct link.
Preferably, m is 1.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1–19 (1977).

A compound of the formula (I) may contain one or more asymmetric carbon atoms and may therefore exist in two or more stereoisomeric forms. The present invention includes the individual stereoisomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

The preferred compounds of the formula (I) and salts thereof where X is —CH$_2$CH$_2$— have the (S)-stereochemistry at the position of attachment of the X and R$^1$ groups to the lactam ring.

Preferred examples of a compound of the formula (I) are those wherein:

(i) R is cyclopropylmethyl, R$^1$ is 3,4-dichlorophenyl, R$^2$ is morpholino, X is —CH$_2$CH$_2$—, X$^1$ is a direct link and m is 1;

(ii) R is 4,4-difluorocyclohexylmethyl, R$^1$ is 3,4-dichlorophenyl, R$^2$ is morpholino, X is —CH$_2$CH$_2$—, X$^1$ is a direct link and m is 1;

(iii) R is 4,4-difluorocyclohexylmethyl, R$^1$ is 3,4-dichlorophenyl, R$^2$ is 4-aminopiperidin-1-yl, X is —CH$_2$CH$_2$—, X$^1$ is a direct link and m is 1;

(iv) R is cyclopropylmethyl, R$^1$ is 3,4-dichlorophenyl, R$^2$ is 4-aminosulphonylpiperazin-1-yl, X is —CH$_2$CH$_2$—, X$^1$ is a direct link and m is 1;

(v) R is 4,4-difluorocyclohexylmethyl, R$^1$ is 3,4-dichlorophenyl, R$^2$ is 4-hydroxypiperidin-1-yl, X is —CH$_2$CH$_2$—, X$^1$ is a direct link and m is 1;

(vi) R is 2-cyclopropylethyl, R$^1$ is 3,4-dichlorophenyl, R$^2$ is morpholino, X is —CH$_2$CH$_2$—, X$^1$ is a direct link and m is 1;

(vii) R is 2-cyclopropylethyl, R$^1$ is 3,4-dichlorophenyl, R$^2$ is 4-methanesulphonylpiperazin-1-yl, X is —CH$_2$CH$_2$—, X$^1$ is a direct link and m is 1;

(viii) R is cyclopropylmethyl, R$^1$ is 3,4-dichlorophenyl, R$^2$ is 4-fluoropiperidin-1-yl, X is —CH$_2$CH$_2$—, X$^1$ is a direct link and m is 1;

(ix) R is 4,4-difluorocyclohexylmethyl, R$^1$ is 3,4-dichlorophenyl, R$^2$ is 4-oxopiperidin-1-yl, X is —CH$_2$CH$_2$—, X$^1$ is a direct link and m is 1;

(x) R is cyclopropylmethyl, R$^1$ is 3,4-dichlorophenyl, R$^2$ is 4-carboxypiperidin-1-yl, X is —CH$_2$CH$_2$—, X$^1$ is a direct link and m is 1; or (xi) R is cyclohexylmethyl, R$^1$ is 3,4-dichlorophenyl, R$^2$ is 4-carboxypiperidin-1-yl, X is —CH$_2$CH$_2$—, X$^1$ is a direct link and m is 1:

or any such compound with the (S)-stereochemistry at the position of attachment of the X and R$^1$ groups to the lactam ring, or a pharmaceutically acceptable salt of any thereof.

The compounds of the formula (I) provided by the invention can be prepared by the following methods:

1) The compounds of the formula (I) where X is (C$_0$–C$_3$ alkylene)CH$_2$—, the methylene group of which is attached to the azetidine nitrogen atom, and R, R$^1$, R$^2$, X$^1$ and m are as previously defined for a compound of the formula (I) can be prepared by reductive amination using as starting materials a compound of the formula:

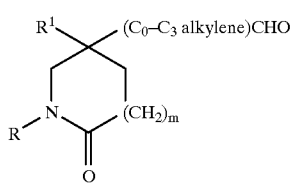

(II)

where R, R$^1$ and m are as previously defined for a compound of the formula (I), and a compound of the formula:

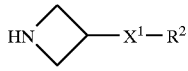

(III)

, or an acid addition salt thereof, where R$^2$ and X$^1$ are as previously defined for a compound of the formula (I). The reaction is preferably carried out in the presence of a suitable acid, e.g. acetic acid.

The reaction proceeds via the initial formation of an intermediate iminium salt of the formula:

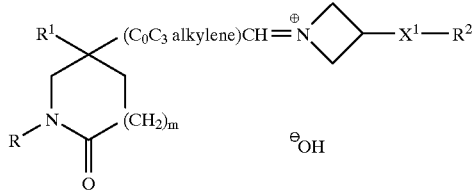

(IIIA)

which may stable and isolatable. The reaction is preferably carried out without isolation of the intermediate of the formula (IIIA) in which case it is reduced in situ to provide a compound of formula (I).

In a typical procedure, an aldehyde of the formula (II) is first reacted with an azetidine of the formula (III) in a suitable solvent, e.g. tetrahydrofuran, and the mixture then treated with a suitable reducing agent, e.g. sodium triacetoxyborohydride or sodium cyanoborohydride, in the presence of a suitable acid, e.g. acetic acid, to give the required product. If an acid addition salt of an azetidine of the formula (III) is used as a starting material, a suitable acid acceptor, e.g. triethylamine, can be added prior to the addition of the reducing agent.

The reaction is typically carried out at room temperature.

The starting aldehydes of the formula (II) can be prepared by the method shown in the Scheme I:

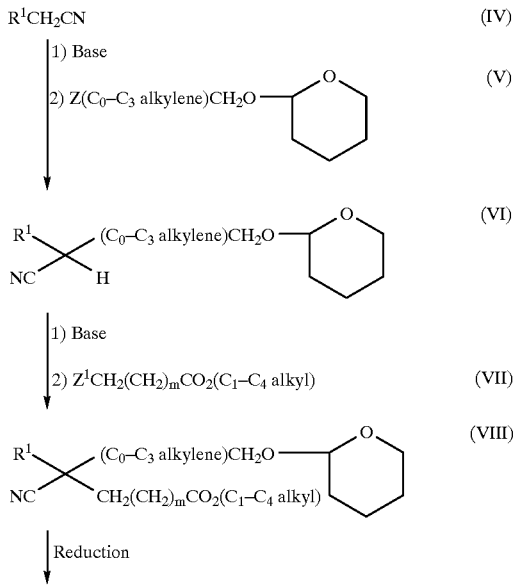

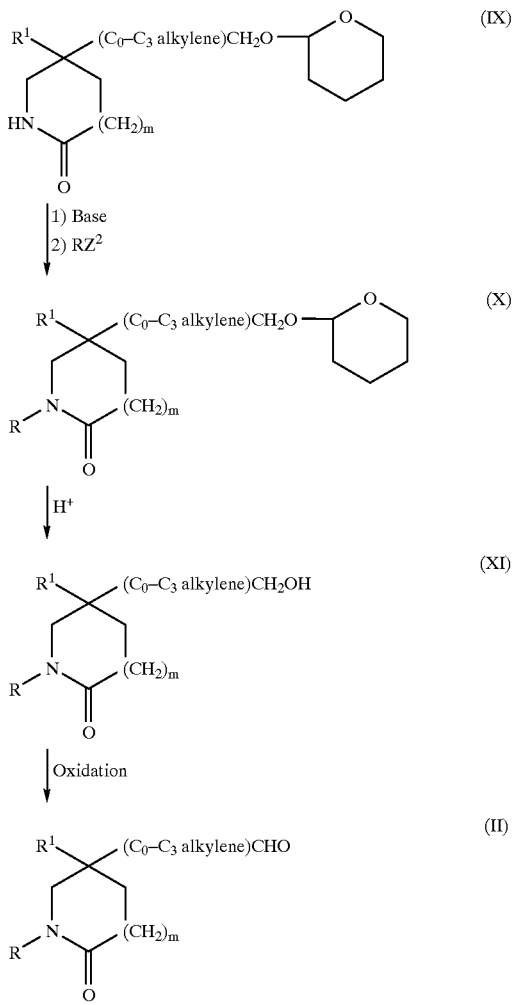

where R, $R^1$ and m are as previously defined for a compound of the formula (I) and Z, $Z^1$ and $Z^2$ are each a suitable leaving group, e.g. chloro, bromo, iodo, methanesulphonyloxy, p-toluenesulphonyloxy or trifluoromethylsulphonyloxy.

In a typical procedure, an arylmethynitrile of the formula (IV) is first deprotonated using a suitable base, e.g. sodium hydride, and then alkylated in situ with an alkylating agent of the formula (V) where Z is preferably bromo. The reaction is typically carried out in a suitable solvent, e.g. tetrahydrofuran, at about 0° C. for the deprotonation and at about room temperature for the alkylation. The reaction can also be carried out under phase transfer conditions using a suitable base, e.g. sodium hydroxide, a suitable phase transfer catalyst, e.g. tetra-n-butylammonium chloride, and a suitable solvent, e.g. cyclohexane, n-pentane or toluene.

The acetonitrile derivative of the formula (VI) that is produced is then first deprotonated using a suitable base, e.g. lithium diisopropylamide, and then alkylated in situ with a compound of the formula (VII) where $Z^1$ is preferably bromo. The reaction is typically carried out in a suitable solvent, e.g. tetrahydrofuran, at about −70° C., warming to about room temperature to complete the reaction. Tetra-n-butylammonium iodide can optionally be added following addition of the compound of the formula (VII) to increase the rate of reaction.

The compound of the formula (VIII) prepared is then reduced and cyclised to a lactam of the formula (IX) under suitable conditions, e.g. using Raney nickel under an atmosphere of hydrogen at atmospheric pressure and room temperature using ammoniacal ethanol as the solvent.

The lactam of the formula (IX) is then first deprotonated using a suitable base, e.g. sodium hydride, and then alkylated in situ with a compound of the formula $RZ^2$ where $Z^2$ is preferably bromo, methanesulphonyloxy or p-toluenesulphonyloxy. The reaction is typically carried out in a suitable solvent, e.g. dimethylformamide, and at about room temperature.

The lactam of the formula (X) produced is then treated with a saturated solution of hydrogen chloride in a suitable $C_1$–$C_4$ alcohol, e.g. methanol, at about room temperature to remove the tetrahydropyran protecting group. The deprotection can also be carried out using a suitable ion exchange resin, e.g. Amberlyst 15 (trade mark), and in a suitable solvent, e.g. methanol.

The alcohol of the formula (XI) prepared is oxidised to an aldehyde of the formula (II) under suitable conditions, e.g. under Swern oxidation conditions (oxalyl chloride, dimethylsulphoxide, triethylamine, and using dichloromethane as the solvent).

The starting azetidines of the formula (III) may be prepared by conventional methods.

2) The compounds of the formula (I) where X, $X^1$, R, $R^1$, $R^2$ and m are as previously defined for a compound of the formula (I) except those compounds where R is trifluoromethyl, —$CF_2$($C_1$–$C_5$ alkyl optionally substituted by fluoro) or aryl, can be prepared by alkylation of a N-deprotonated form of a compound of the formula:

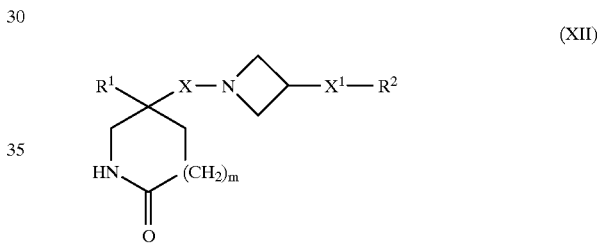

where X, $X^1$, $R^1$, $R^2$ and m are as previously defined for a compound of the formula (I), with a compound of the formula:

$RZ^2$ where R is as previously defined for this method and $Z^2$ is a suitable leaving group, e.g. chloro, bromo, iodo, methanesulphonyloxy p-toluenesulphonyloxy or trifluoromethylsulphonyloxy.

In a typical procedure, a compound of the formula (XII) is first deprotonated with a suitable base, e.g. sodium hydride, and then alkylated in situ with a compound of the formula $RZ^2$ where $Z^2$ is preferably chloro, bromo or methanesulphonyloxy. The reaction is typically carried out in a suitable solvent, e.g. dimethylformamide, at from room temperature to 50° C.

Alternatively, the reaction can be carried out by reacting the starting materials of the formulae (XII) and $RZ^2$ together in the presence of a suitable base, e.g. potassium hydroxide, and in a suitable solvent, e.g. dimethylsulphoxide, at about room temperature. If a compound of the formula $RZ^2$ where $Z^2$ is chloro is used, potassium iodide may also be added to increase the rate of reaction.

The starting materials of the formula (XII) can be prepared by conventional methods such as by adaptation of the preparation described in Method (1) and Scheme I (i.e. by omission of the N-alkylation step to form compounds of the formula (X)).

The starting compounds of the formula $RZ^2$ can be prepared by conventional methods.

3) All the compounds of the formula (I) where X, $X^1$, R, $R^1$, $R^2$ and m are as previously defined for a compound of the formula (I) can be prepared by reaction of a compound of the formula:

(XIII)

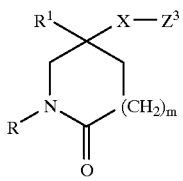

where X, R, $R^1$ and m are as previously defined for a compound of the formula (I) and $Z^3$ is a suitable leaving group, e.g. chloro, bromo, iodo, methanesulphonyloxy, trifluoromethanesulphonyloxy or p-toluenesulphonyloxy, with a compound of the formula:

(III)

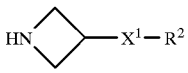

where $R^2$ is as previously defined for a compound of the formula (I).

In a typical procedure, a compound of the formula (XIII), where $Z^3$ is preferably methanesulphonyloxy, is reacted with a compound of the formula (III) in the presence of a suitable acid acceptor, e.g. triethylamine or potassium carbonate or a combination thereof, in a suitable solvent, e.g. acetonitrile, and at about the reflux temperature thereof. The compound of the formula (III) can be prepared in situ from an acid addition salt thereof by using a molar excess of the acid acceptor. The starting materials of the formula (XIII) may be prepared by conventional methods such as by hydroxy functional group transformation of alcohols of the formula (XI), e.g. where $Z^3$ is methanesulphonyloxy, by reaction of an alcohol of the formula (XI) with methanesulphonyl chloride in the presence of a suitable acid acceptor such as triethylamine.

4) The compounds of the formula (I) where $R^1$ is phenyl and X, $X^1$, R, $R^2$ and m are as previously defined for a compound of the formula (I) can be prepared by hydrogenolysis of a compound of the formula (I) where $R^1$ is phenyl substituted by chloro, bromo or iodo and X, $X^1$, R, $R^2$ and m are as previously defined for a compound of the formula (I).

In a typical procedure the hydrogenolysis is carried out in ammoniacal ethanol using a suitable catalyst, e.g. Raney nickel or, preferably, palladium-on-carbon, at about 50° C. and under an atmosphere of hydrogen at about 345 kPa (50 psi).

5) The compounds of the formula (I) where $R^2$ is a group of the formula:

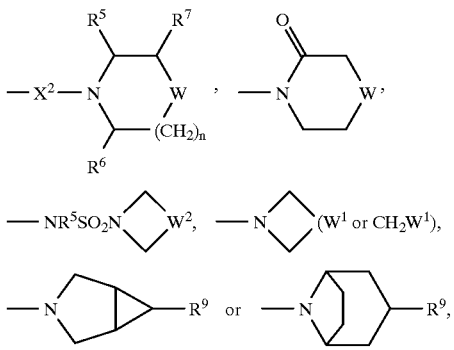

$R^9$ is —$NHR^5$, W is NH or $CHNHR^5$, $W^1$ is $CHNHR^5$, $W^2$ is $W^1$, —$H_2W^1$—, —$CH_2WCH_2$— or —$CH_2CH_2WCH_2$—, and X, $X^1$, $X^2$, R, $R^1$, $R^5$, $R^6$, $R^7$, m and n are as previously defined for a compound of the formula (I), can be prepared by deprotection of a compound of the formula:

(XIV)

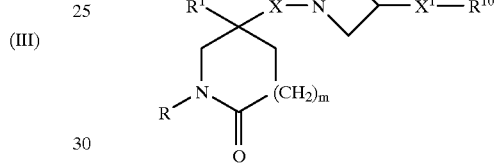

where $R^{10}$ is a group of the formula:

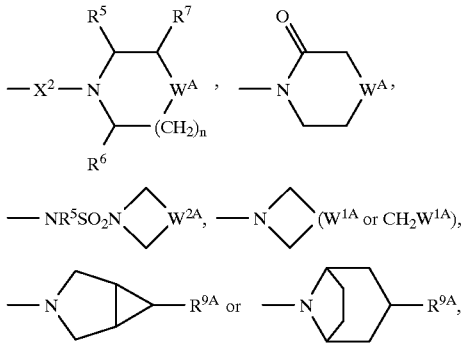

, respectively, $R^{9A}$ is —$NZ^4R^5$, $W^A$ is $NZ^4$ or $CHNZ^4R^5$, $W^{1A}$ is $CHNZ^4R^5$, $W^{2A}$ is $W^{1A}$, —$CH_2W^{1A}$—, —$CH_2W^ACH_2$— or —$CH_2CH_2W^ACH_2$—, X, $X^1$, $X^2$, R, $R^1$, $R^4$, $R^5$, $R^6$, $R^7$, m and n are as previously defined for a compound of the formula (I) and $Z^4$ is a suitable protecting group, e.g. t-butoxycarbonyl (e.g. a compound of the formula (I) where W is $NCO_2C(CH_3)_3$ or $R^9$ is —$NR^5CO_2C(CH_3)_3$) or benzyloxycarbonyl.

Suitable protecting groups that may be used in this Method, together with methods for deprotection, are well known to the skilled person, e.g. see Greene et al, "Protective Groups in Organic Synthesis", Second Edition, 1991, Wiley-Interscience.

In a typical procedure where $Z^4$ is t-butoxycarbonyl, the deprotection can be carried out using trifluoroacetic acid in a suitable solvent, e.g. dichloromethane, at room temperature.

The starting materials of the formula (XIV) can be prepared by conventional methods such as by appropriate adaptation of the Methods described herein for preparing the compounds of the formula (I).

6) The compounds of the formula (I) where $R^2$ is a group of the formula:

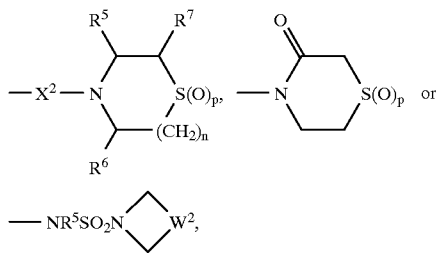

where p is 1 or 2, $W^2$ is —$CH_2S(O)_pCH_2$— or —$CH_2CH_2S(O)_pCH_2$— and X, $X^1$, $X^2$, R, $R^1$, $R^5$, $R^6$, $R^7$, m and n are as previously defined for a compound of the formula (I) can be prepared by oxidation of a compound of the formula (I) where $R^2$ is a group of the formula:

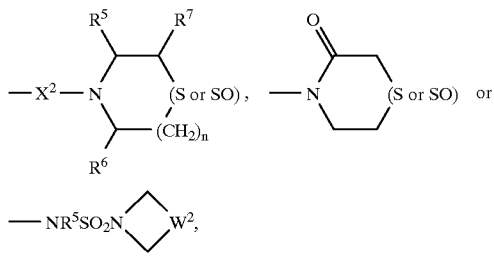

, as appropriate, wherein $W^2$ is —$CH_2$(S or SO)$CH_2$— or —$CH_2CH_2$(S or SO)$CH_2$—, and X, $X^1$, $X^2$, R, $R^1$, $R^5$, $R^6$, $R^7$, m and n are as previously defined for a compound of the formula (I). The oxidation is carried out with at least one molar equivalent of a suitable oxidising agent when converting a sulphoxide to a sulphone, at least two molar equivalents of a suitable oxidising agent when converting a sulphide to a sulphone and substantially one molar equivalent of a suitable oxidising agent for the conversion of a sulphide to a sulphoxide.

Suitable oxidising agents and conditions for this purpose are aqueous hydrogen peroxide solution under basic conditions (e.g. in the presence of potassium carbonate, acetonitrile and using methanol as the solvent) or m-chloroperbenzoic acid in a suitable solvent, e.g. dichloromethane.

7) The compounds of the formula (I) where $R^2$ is a group of the formula:

and X, $X^1$, R, $R^1$ and m are as previously defined for a compound of the formula (I), can be prepared by deprotection of a compound of the formula:

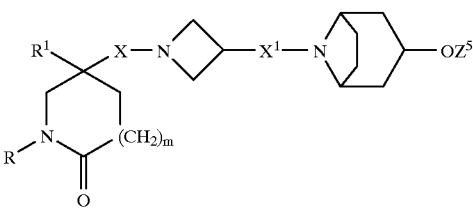

(XV)

where $Z^5$ is a suitable protecting group, e.g. acetyl (i.e. a compound of the formula (I) where $R^8$ is acetyloxy) or tetrahydropyran-2-yl, and X, $X^1$, R, $R^1$ and m are as previously defined for a compound of the formula (I).

Suitable protecting groups that may be used for this Method, together with methods for deprotection, are well known to the skilled person, e.g. see Greene et al, "Protective Groups in Organic Synthesis", Second Edition, 1991, Wiley-Interscience.

In a typical procedure where $Z^5$ is acetyl the deprotection can be carried out using an aqueous alcoholic solution of a suitable strong base, e.g. sodium hydroxide. The reaction is typically carried out in aqueous methanol at about room temperature.

The starting materials of the formula (XV) can be prepared by conventional methods such as by adaptation of the Methods described herein for preparing the compounds of the formula (I).

8) The compounds of the formula (I) where X, $X^1$, R, $R^1$, $R^2$ and m are as previously defined for a compound of the formula (I) except those where $R^2$ is —$CO_2H$, R is $C_1$–$C_6$ alkyl substituted by —COOH, W is $CHCO_2H$ or $W^1$ is $CHCO_2H$, can be prepared by intramolecular dehydration of a compound of the formula:

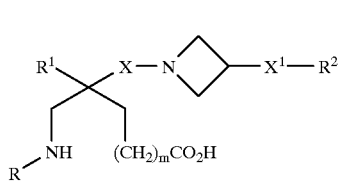

(XVI)

where X, $X^1$, R, $R^1$, $R^2$ and m are as previously defined for this Method.

In a typical procedure, the dehydration is carried out under Dean-Stark conditions in a suitable solvent, e.g. toluene, and in the presence of a suitable acid, e.g. p-toluenesulphonic acid. Alternatively, the dehydration can be carried out by stirring a solution of a compound of the formula (XVI) in a suitable solvent, e.g. dichloromethane, in the presence of silica gel.

The starting materials of the formula (XVI) can be prepared by conventional methods.

9) The compounds of the formula (I) where X, $X^1$, R, $R^1$, $R^2$ and m are as previously defined for a compound of the formula (I) except those where $R^2$ is —$CO_2H$, R is $C_1$–$C_6$ alkyl substituted by —COOH, W is $CHCO_2H$ or $W^1$ is $CHCO_2H$, can be prepared by cyclisation of a compound of the formula:

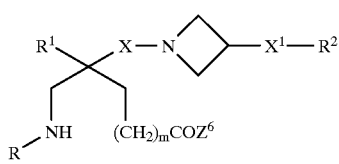

(XVII)

where X, X$^1$, R, R$^1$, R$^2$ and m are as previously defined for this Method and Z$^6$ is a suitable leaving group, e.g. C$_1$–C$_4$ alkoxy, benzyloxy, imidazol-1-yl or benzotriazol-1-yloxy.

In typical procedures:

(i) where Z$^6$ is C$_1$–C$_4$ alkoxy or benzyloxy, a solution of a compound of the formula (XVII) in a suitable solvent, e.g. methanol or ethanol, is heated at about the reflux temperature of the solvent;

(ii) where Z$^6$ is imidazol-1-yl, a compound of the formula (XVII) is derived by reacting a compound of the formula (XVI) with 1,1'-carbonyl-diimidazole in a suitable solvent, e.g. dichloromethane, and in situ cyclisation of the intermediate imidazolide provides the required product; and (iii) where Z$^6$ is benzotriazol-1-yloxy, a compound of the formula (XVII) is derived in situ by reacting a compound of the formula (XVI) with 1-hydroxybenzotriazole in the presence of a suitable dehydrating agent, e.g. 1,3-dicyclohexylcarbodiimide, and in a suitable solvent, e.g. dichloromethane, and in situ cyclisation provides the required product.

The starting materials of the formula (XVII) can be prepared by conventional methods such as from a compound of the formula (XVI), examples of which are described above.

10) The compounds of the formula (I) where X$^1$ is a direct link and R$^2$ is —NR$^3$R$^4$, (C$_3$–C$_7$ cycloalkyl-C$_1$–C$_4$ alkyl)R$^5$N—, (C$_3$–C$_7$ cycloalkyl-C$_1$–C$_4$ alkyl)$_2$N—, or is a group of the formula:

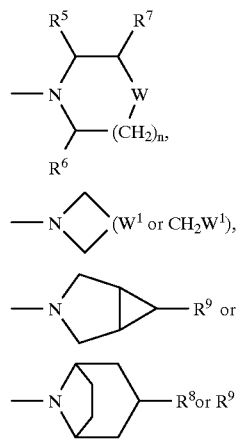

and X, W, W$^1$, R, R$^1$, R$^3$, R$^4$, R$^5$, R$^6$, R$^7$, R$^8$, R$^9$, m and n are as previously defined for a compound of the formula (I), can be prepared by reaction of a compound of the formula:

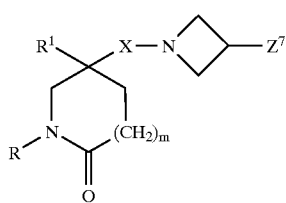

(XVIII)

where X, R, R$^1$ and m are as previously defined for a compound of the formula (I) and Z$^7$ is a suitable leaving group, e.g. methanesulphonyloxy or p-toluene sulphonyloxy, with a compound of the formula:

HNR$^3$R$^4$, (C$_3$–C$_7$ cycloalkyl-C$_1$–C$_4$ alkyl)R$^5$NH, (C$_3$–C$_7$ cycloalkyl-C$_1$–C$_4$ alkyl)$_2$NH,

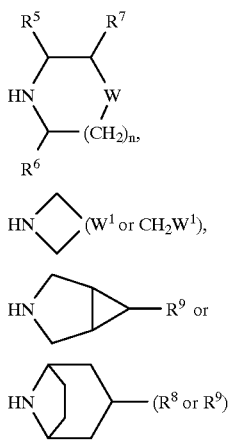

,respectively, where W, W$^1$, R$^3$, R$^4$, R$^5$, R$^6$, R$^7$, R$^8$, R$^9$ and n are as previously defined for a compound of the formula (I).

In a typical procedure, the reaction is carried out using an excess of the amine and in a suitable solvent, e.g. acetonitrile or dichloromethane, and at the reflux temperature of the solvent. Alternatively, a further suitable acid acceptor, e.g. potassium carbonate, can be added to the reaction mixture.

The starting amines can be prepared by conventional methods.

The starting materials of the formula (XVIII) can also be prepared by conventional methods such as by reductive amination using as starting materials a compound of the formula (II) and ammonia to prepare the corresponding primary amine, reaction of the amine with epichlorohydrin or 1,3-dichloropropan-2-ol to prepare the corresponding azetidin-3-ol derivative, followed by hydroxy functional group interconversion to provide a compound of the formula (XVIII).

11) The compounds of the formula (I) where X, X$^1$, R, R$^1$, R$^2$ and m are as previously defined for Method (10) can be prepared by reductive amination using as starting materials a compound of the formula:

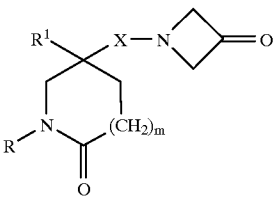
(XIX)

where X, R, $R^1$ and m are as previously defined for a compound of the formula (I), and a compound of the formula:

$HNR^3R^4$, $(C_3-C_7 \text{ cycloalkyl-}C_1-C_4 \text{ alkyl})R^5NH$, $(C_3-C_7 \text{ cycloalkyl-}C_1-C_4 \text{ alkyl})_2NH$,

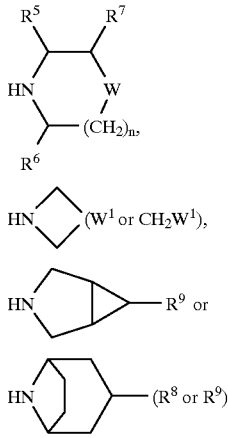

, as appropriate, or an acid addition salt thereof, where W, $W^1$, $R^3$, $R^4$, $R^5$, $R^6$, $R^7$, $R^8$, $R^9$ and n are as previously defined for a compound of the formula (I). The reaction is preferably carried out in the presence of a suitable acid, e.g. acetic acid.

A typical procedure that can be followed is described in Method (1).

If a primary amine is used, the reaction proceeds via an imine intermediate. If a secondary amine is used, the reaction proceeds via an intermediate iminium salt (cf. a compound of the formula (IIIA)). Both the imine and iminium salts may be stable and isolatable. The reaction is preferably carried out without isolation of the imine or iminium salt intermediate in which case it is reduced in situ to provide a compound of the formula (I).

The starting materials of the formula (XIX) can be prepared by oxidation of the corresponding azetidin-3-ol derivatives (preparation described in the preparation of the starting materials for Method (10)) under conventional conditions, e.g. using pyridinium chlorochromate or tetrapropylammonium perruthenate as the oxidising agent.

12) The compounds of the formula (I) where $R^2$ is morpholino and X, $X^1$, R, $R^1$ and m are as previously defined for a compound of the formula (I), can be prepared by reaction of a compound of the formula (I) where $R^2$ is $-NH_2$ and X, $X^1$, R, $R^1$ and m are as previously defined for a compound of the formula (I), with bis(2-chloroethyl) ether.

In a typical procedure, a compound of the formula (I) where $R^2$ is $-NH_2$ is reacted with bis(2-chloroethyl) ether in the presence of a suitable acid acceptor, e.g. triethylamine, and in a suitable solvent, e.g. dichloromethane.

Certain of the starting amine derivatives, i.e. 3-aminoazetidine derivatives, can be prepared by reacting a compound of the formula (XVIII) where $Z^7$ is a suitable leaving group, e.g., methanesulphonyloxy, with a suitable azide, e.g. sodium azide or trimethylsilyl azide, to provide the corresponding 3-azidoazetidine derivative, followed by reduction thereof, e.g. using sodium borohydride, to provide the required 3-aminoazetidine derivative (see also Method (10)).

13) The compounds of the formula (I) where X, $X^1$, R, $R^1$, $R^2$ and m are as previously defined for a compound of the formula (I) except those where $R^2$ is $-CO_2H$, R is $C_1-C_6$ alkyl substituted by $-COOH$, W is $CHCO_2H$ or $W^1$ is $CHCO_2H$, can be prepared by reductive cyclisation of a compound of the formula:

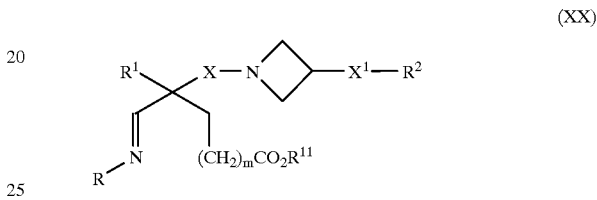
(XX)

where X, $X^1$, R, $R^1$, $R^2$ and m are as previously defined for this Method and $R^{11}$ is a suitable ester-forming group, e.g. $C_1-C_4$ alkyl, preferably methyl or ethyl, or benzyl.

In a typical procedure, a compound of the formula (XX) is first generated in situ by reacting a compound of the formula:

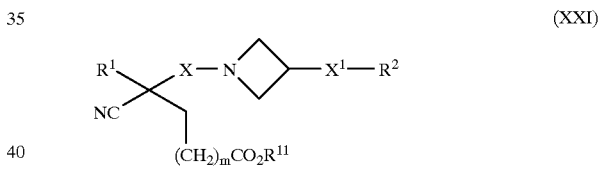
(XXI)

where X, $X^1$, $R^1$, $R^2$, $R^{11}$ and m are as previously defined for a compound of the formula (XX), with a compound of the formula $RNH_2$ where R is as previously defined for this Method and then the reductive cyclisation is facilitated by the presence of a suitable reducing agent, e.g. Raney nickel. The reaction is carried out in a suitable solvent, e.g. methanol or ethanol, and under an atmosphere of hydrogen.

The starting materials of the formula (XXI) can be prepared by conventional methods.

14) Certain compounds of the formula (I) can be prepared by derivatisation of certain amines of the formula (I). For example, a compound of the formula (I) wherein $R^2$ is

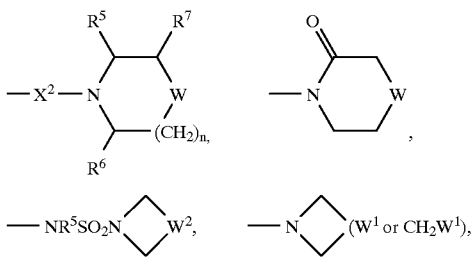

-continued

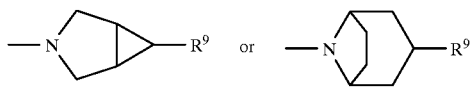

wherein W is NH or CHNHR$^5$, W$^1$ is CHNHR$^5$, W$^2$ is W$^1$, —CH$_2$W$^1$—, —CH$_2$WCH$_2$— or —CH$_2$CH$_2$WCH$_2$—, or R$^9$ is —NHR$^5$ and X, X$^1$, X$^2$, R, R$^1$, R$^5$, R$^6$, R$^7$, m and n are as previously defined for a compound of the formula (I), may be converted to (a) a compound of the formula (I) wherein W is NR$^5$ or CHNR$^5$R$^6$, W$^1$ is CHNR$^5$R$^6$ or R$^9$ is —NHR$^5$, or an acid addition salt thereof, as appropriate, wherein R$^5$ and R$^6$ are as previously defined for a compound of the formula (I) with the provisos that R$^5$ is not H and it has a methylene group bonded to the nitrogen atom, by reductive amination with an aldehyde of the formula (C$_1$–C$_3$ alkyl)CHO or (C$_3$–C$_7$ cycloalkyl-C$_1$–C$_3$ alkyl)CHO, said C$_1$–C$_3$ alkyl and C$_3$–C$_7$ cycloalkyl-C$_1$–C$_3$ alkyl being optionally substituted by fluoro.

Suitable conditions for this conversion are described in Method (1);

(b) a compound of the formula (I) wherein W is NCONHR$^6$ or CHNR$^5$CONHR$^6$, W$^1$ is CHNR$^5$CONHR$^6$ or R$^9$ is —NR$^5$CONHR$^6$, as appropriate, wherein R$^5$ and R$^6$ are as previously defined for a compound of the formula (I) with the proviso that R$^6$ is not H, by reaction with an isocyanate of the formula:

R$^6$NCO wherein R$^6$ is as previously defined for this Method.
The reaction is typically carried out using a suitable solvent, e.g. dichloromethane or tetrahydrofuran;

(c) a compound of the formula (I) wherein W is NSO$_2$CF$_3$ or CHNR$^5$SO$_2$CF$_3$, W$^1$ is CHNR$^5$SO$_2$CF$_3$ or R$^9$ is —NR$^5$SO$_2$CF$_3$, as appropriate, wherein R$^5$ is as previously defined for a compound of the formula (I), by reaction with trifluoromethanesulphonyl chloride or trifluoromethanesulphonic anhydride, optionally in the presence of a suitable acid acceptor, e.g. triethylamine, pyridine or potassium carbonate. The reaction is typically carried out in a suitable organic solvent, e.g. dichloromethane or acetonitrile;

(d) a compound of the formula (I) wherein W is NSO$_2$ (C$_1$–C$_4$ alkyl),NSO$_2$NR$^5$R$^6$, NSO$_2$ (morpholino), NSO$_2$ (aryl),CHNR$^5$(SO$_2$ C$_1$–C$_4$ alkyl) or CHNR$^5$SO$_2$NR$^5$R$^6$, W$^1$ is CHNR$^5$(SO$_2$ C$_1$–C$_4$ alkyl) or CHNR$^5$SO$_2$NR$^5$R$^6$, or R$^9$ is —NR$^5$(SO$_2$ C$_1$–C$_4$ alkyl) or —NR$^5$SO$_2$NR$^5$R$^6$, as appropriate, wherein R$^5$ and R$^6$ are as previously defined for a compound of the formula (I), by reaction with a C$_1$–C$_4$ alkanesulphonyl chloride or bromide, a C$_1$–C$_4$ alkanesulphonic anhydride or a compound of the formula:

R$^5$R$^6$NSO$_2$(Cl or Br), (morpholino)SO$_2$(Cl or Br) or (aryl)SO$_2$(Cl or Br)

, as appropriate, optionally in the presence of a suitable acid acceptor, e.g. triethylamine.

The reaction is typically carried out in a suitable organic solvent, e.g. dichloromethane, at from 0° C. to room temperature;

(e) a compound of the formula (I) wherein W is NCOR$^6$ or CHNR$^5$COR$^6$, W$^1$ is CHNR$^5$COR$^6$ or R$^9$ is —NR$^5$COR$^6$, as appropriate, wherein R$^5$ and R$^6$ are as previously defined for a compound of the formula (I) with the proviso that R$^6$ is not H, by reaction with a compound of the formula:

R$^6$CO(Cl or Br) or (R$^6$CO)$_2$O wherein R$^6$ is as previously defined for this Method, optionally in the presence of a suitable acid acceptor, e.g. triethylamine.

The reaction is typically carried out in a suitable organic solvent, e.g. dichloromethane, at from 0° C. to room temperature;

(f) a compound of the formula (I) wherein W, W$^1$ or R$^9$ is as previously defined for Method 14(e), as appropriate, by condensation with a compound of the formula:

R$^6$CO$_2$H wherein R$^6$ is as previously defined for this Method. The reaction can be performed under conventional conditions, e.g. using 1,1'-carbonyl-diimidazole or 1-hydroxybenzotriazole/1,3-dicyclohexylcarbodiimide (e.g. see Method (9)) to generate activated intermediates;

or (g) a compound of the formula (I) where W is NSO$_2$NR$^5$R$^6$ or CHNR$^5$SO$_2$NR$^5$R$^6$, W$^1$ is CHNR$^5$SO$_2$NR$^5$R$^6$ or R$^9$ is —NR$^5$SO$_2$NR$^5$R$^6$, as appropriate, wherein R$^5$ and R$^6$ are as previously defined for a compound of the formula (I), by reaction with a compound of the formula:

R$^5$R$^6$NSO$_2$NH$_2$.

The reaction is typically carried out at an elevated temperature in a suitable solvent, e.g. 1,4-dioxane.

15) The compounds of the formula (I) wherein R$^2$ is:

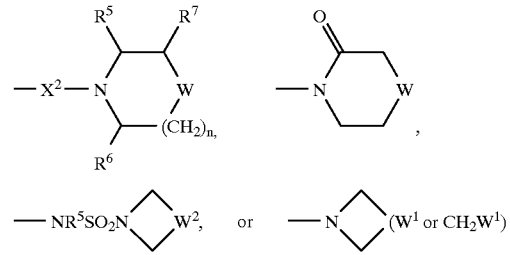

wherein W and W$^1$ are CHCO$_2$H and W$^2$ is W$^1$, —CH$_2$W$^1$—, —CH$_2$WCH$_2$— or —CH$_2$CH$_2$WCH$_2$— and X, X$^1$, X$^2$, R, R$^1$, R$^2$, R$^5$, R$^6$, R$^7$, m and n are as previously defined for a compound of the formula (I), may be prepared by hydrolysis of a compound of the formula (I) wherein W and W$^1$ are CHCO$_2$(C$_1$–C$_4$ alkyl), W$^2$ is W$^1$, —CH$_2$W$^1$—, —CH$_2$WCH$_2$— or —CH$_2$CH$_2$WCH$_2$— and X, X$^1$, X$^2$, R, R$^1$, R$^2$, R$^5$, R$^6$ R$^7$, m and n are as previously defined for a compound of the formula (I). Preferably, W and W are CHCO$_2$CH$_3$ or CH$_2$CO$_2$CH$_2$CH$_3$.

The hydrolysis is typically carried out using an aqueous solution of a suitable acid or base, e.g. a mineral acid such as hydrochloric or sulphuric acid or a base such as sodium or potassium hydroxide, optionally in the presence of a suitable organic co-solvent, e.g. methanol or ethanol.

16) The compounds of the formula (I) wherein $R^2$ is

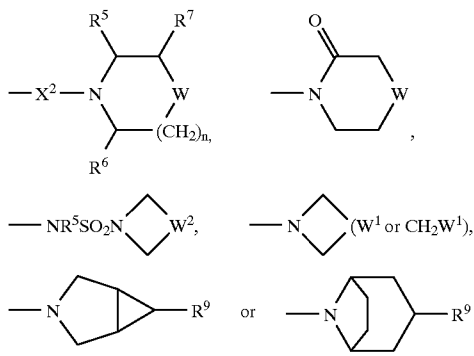

wherein W and $W^1$ are $CHNR^5R^6$, $W^2$ is $W^1$, —$CH_2W^1$—, —$CH_2WCH_2$— or —$CH_2CH_2WCH_2$—, $R^9$ is —$NR^5R^6$ and X, $X^1$, $X^2$, R, $R^1$, $R^2$, $R^5$, $R^6$, $R^7$, m and n are as previously defined for a compound of the formula (I) may be prepared by reaction of a compound of the formula:

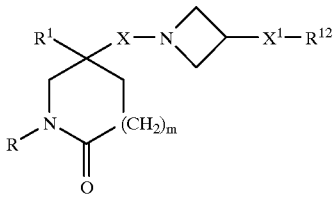

wherein $R^{12}$ is

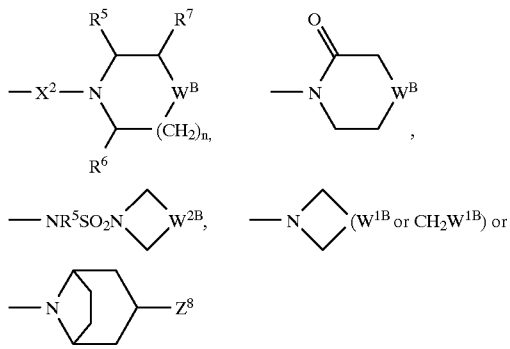

wherein $W^B$ and $W^{1B}$ are $CHZ^8$, $W^{2B}$ is $W^{1B}$, —$CH_2W^{1B}$—, —$CH_2W^BCH_2$— or —$CH_2CH_2W^BCH_2$—, $Z^8$ is a suitable leaving group, e.g. halo, (preferably chloro or bromo), methanesulphonyloxy, trifluoromethanesulphonyloxy or p-toluenesulphonyloxy, and X, $X^1$, $X^2$, R, $R^1$, $R^5$, $R^6$, $R^7$, m and n are as previously defined for a compound of the formula (I), with a compound of the formula:

$HNR^5R^6$ 

wherein $R^5$ and $R^6$ are as previously defined for a compound of the formula (I), optionally in the presence of a suitable additional acid acceptor, e.g. triethylamine or potassium carbonate.

The reaction is typically carried out in a suitable solvent such as acetonitrile.

17) The compounds of the formula (I) wherein $R^2$ is

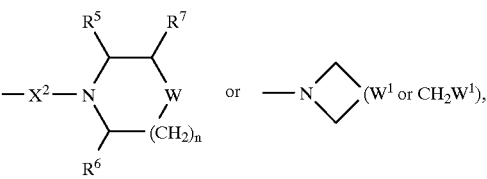

W and $W^1$ are $CHNR^5R^6$ and X, $X^1$, $X^2$, R, $R^1$, $R^5$, $R^6$, $R^7$, m and n are previously defined for a compound of the formula (I), may be prepared by reductive amination using as the starting materials a compound of the formula (I): wherein $R^2$ is

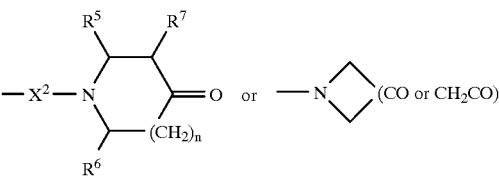

and X, $X^1$, $X^2$, R, $R^1$, $R^5$, R $R^7$, m and n are as previously defined for a compound of the formula (I), and a compound of the formula:

$HNR^5R^6$ 

wherein $R^5$ and $R^6$ are as previously defined for a compound of the formula (I).

Conventional conditions are used such as those described for Method (1). Again, the intermediate imine or iminium salt formed may be stable or isolatable. The reaction is preferably carried out without isolation of this intermediate in which case it is reduced in situ to provide a compound of the formula (I).

18) All the compounds of the formula (I) may be prepared by intramolecular cyclisation of a compound of the formula:

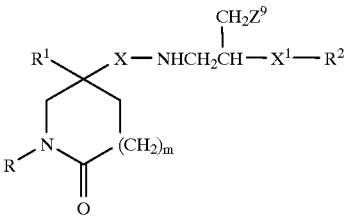

wherein X, $X^1$, R, $R^1$, $R^2$ and m are as previously defined for a compound of the formula (I) and $Z^9$ is a suitable leaving group, e.g. halo (preferably chloro or bromo), methanesulphonyloxy or p-toluenesulphonyloxy, optionally in the presence of a suitable acid acceptor, e.g. triethylamine.

The reaction is typically carried out in a suitable solvent, e.g. dichloromethane.

19) All the compounds of the formula (I) except those where m is 0 may be prepared by catalysed carbonyl addition-cyclisation of a compound of the formula:

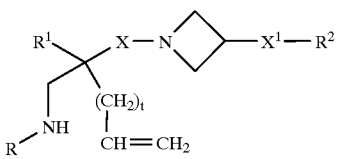

(XXIV)

wherein t is 0 or 1 and X, X$^1$, R, R$^1$ and R$^2$ are as previously defined for a compound of the formula (I).

The reaction is typically carried out under an atmosphere of carbon monoxide using a suitable catalyst, e.g. tetrakistriphenylphosphinepalladium(0), a suitable base, e.g. triethylamine, and in a suitable organic solvent, e.g. tetrahydrofuran, at about room temperature.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

A pharmaceutically acceptable acid addition or base salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of formula (I) and their salts for the human NK$_1$ receptor can be tested in vitro by testing their ability to inhibit [$^3$H]-Substance P binding to membranes prepared from the human IM9 cell line expressing the human NK$_1$ receptor using a modification of the method described in McLean, S. et al, J. Pharm. Exp. Ther., 267, 472–9 (1993) in which whole cells were used.

The affinity of the compounds of formula (I) and their salts for the human NK$_2$ receptor can be tested in vitro by testing their ability to compete with [$^3$H] or [$^{125}$I]NKA (neurokinin A) for binding to membranes prepared from Chinese hamster ovary cells expressing the cloned human NK$_2$ receptor. In this method, washed Chinese hamster ovary cell membranes are prepared as described for the previous method where IM9 cells are used instead. The membranes are incubated (90 min, 25° C.) with [$^3$H] NKA and with a range of concentrations of the test compound. Non-specific binding was determined in the presence of 10 $\mu$M NKA.

The NK$_2$ receptor antagonist activity of the compounds of the formula (I) can be tested, in vitro, by testing their ability to antagonise the contractile effects of the selective NK$_2$ receptor agonist [βAla$^8$]NKA$_{(4-10)}$ in the rabbit pulmonary artery, using the method of Patacchini and Maggi, Eur. J. Pharmacol., 236, 31–37 (1993).

The compounds of the formula (I) and their salts can be tested for Nk$_2$ receptor antagonist activity, in vivo, by testing their ability to inhibit bronchoconstriction induced by [βAla$^8$]NKA$_{(4-10)}$ in the anaesthetised guinea pig, using the method described by Murai et al, J. Pharm. Exp. Ther., 262, 403–408 (1992) or Metcalfe et al, Br. J. Pharmacol., 112, 563P (1994).

The compounds of the formula (I) and their salts can be tested for NK$_3$ receptor antagonist activity, in vitro, by testing their ability to antagonise the contractile effects of the selective NK$_3$ receptor agonist senktide in the guinea-pig ileum using the method of Maggi et al, Br. J. Pharmacol., 101, 996–1000 (1990).

For human use, the compounds of the formula (I) and their salts can be administered alone, but will generally be administered in admixture with a pharmaceutically acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) and their salts will be from 0.001 to 20, preferably from 0.01 to 20, more preferably from 0.5 to 5, and most preferably from 1 to 2, mg/kg (in single or divided doses). Thus tablets or capsules of the compounds will contain from 0.1 to 500, preferably from 50 to 200, mg of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

It is to be appreciated that reference to treatment includes prophylaxis as well as the alleviation of established symptoms of the disease.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the treatment of a disease by producing an antagonist effect on a tachykinin acting at the human NK$_1$, NK$_2$ or NK$_3$ receptor, or a combination thereof;

iv) use as in (iii) where the disease is an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a burn, herpetic neuralgia or post-herpetic neuralgia, cough or acute or chronic pain;

v) a method of treatment of a human to treat a disease by producing an antagonist effect on a tachykinin acting at the human $NK_1$, $NK_2$ or $NK_3$ receptor, or a combination thereof, which comprises treating said human with an effective amount of a compound of the formula (I) or with a pharmaceutically acceptable salt or composition thereof;

vi) a method as in (v) where the disease is an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, an urogenital tract disorder such as incontinence, hyperreflexia or cystitis, a pulmonary disorder such as chronic obstructive airways disease, an allergy such as eczema, contact dermatitis or rhinitis, a hypersensitivity disorder such as poison ivy, a peripheral neuropathy such as diabetic neuropathy, neuralgia, causalgia, painful neuropathy, a bum, herpetic neuralgia or post-herpetic neuralgia, cough or acute or chronic pain; vii) a compound of the formula (II), (IIIA), (XII), (XIV), (XV), (XVI), (XVII), (XVIII), (XIX), (XX), (XXI), (XXII), (XXIII) or (XXIV).

The following Examples illustrate the preparation of the compounds of the formula (I):

(REFERENCE) EXAMPLE 1

5-(3,4-Dichlorophenyl)-5-(2-[3-morpholinoazetidin-1-y]ethyl)-2(1H)-piperidone

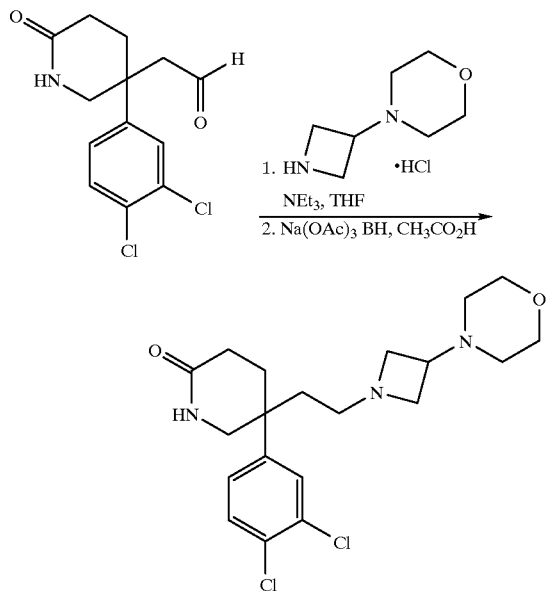

To a solution of the aldehyde (see Preparation 6) (150 mg, 0.52 mmol) and 3-morpholinoazetidine hydrochloride (see Preparation 56) (103 mg, 1.1 mol. equiv.) in tetrahydrofuran (7.5 ml) under nitrogen was added triethylamine (0.08 ml, 1.1 mol. equiv.). After one hour, sodium triacetoxyborohydride (171 mg 1.5 mol. equiv.) was added followed immediately by glacial acetic acid (0.03 ml) and the mixture was stirred for 2 hours. Water (1 ml) was then added followed by saturated aqueous sodium bicarbonate solution (10 ml), the mixture was extracted with dichloromethane (30×20 ml) and the combined organic layers dried over magnesium sulphate. The solution was filtered, the solvent removed from the filtrate under reduced pressure and the residue initially chromatographed on silica gel eluting with a solvent gradient of methanol:ethyl acetate (1:9 to 1:4, by volume) to remove major impurities and then rechromatographed using silica gel eluting with methanol:dichloromethane (1:9, by volume) to give the title compound (78 mg). TLC $R_f$=0.27 (silica, methanol:dichloromethane, 1:9, by volume). LRMS m/z=411 (m+1)$^+$. Found: C, 57.57; H, 6.76; N, 9.78. $C_{20}H_{27}Cl_2N_3O_2$.0.05 $CH_2Cl_2$ requires C, 57.81; H, 6.56: N, 10.09%.

$^1$H-NMR (CDCl$_3$)δ=1.60–1.70 (m,1H), 1.80–1.85 (m,1H), 2.00–2.40 (m, 10H), 2.65–2.75 (m,2H), 2.85–2.90 (m, 1H), 3.35–3.40 (m,3H), 3.65–3.75 (m,5H), 6.20 (s, br., 1H), 7.15–7.50 (m,3H) ppm.

EXAMPLES 2 to 59

The compounds of the following tabulated Examples of the general formula:

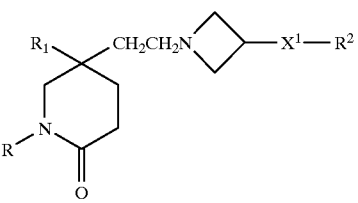

were prepared by a similar method to that of Example 1 using the appropriate aldehyde (see Preparations 39 to 43, 137 to 140 and 187 to 191) and azetidine (see Preparations 56, 61, 65, 66, 67, 70, 77 to 80, 82, 84, 85, 87, 89, 107 to 118, 121, 134, 154, 180 and 181) starting materials.

| Ex. No. | R | R¹ | -X¹-R² | m.p. | LRMS m/z | Analysis/¹H-NMR |
|---|---|---|---|---|---|---|
| 2[1] | 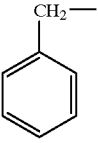 | 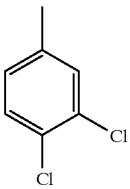 | 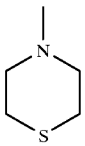 | — | 518/520 (m + 1)⁺ | Found: C, 60.88; H, 6.29; N, 7.69. $C_{27}H_{33}N_3Cl_2OS \cdot 0.25 CH_2Cl_2$ requires C, 60.63; H, 6.26, N, 7.78%. ¹H-NMR(CDCl₃): δ = 1.4–1.6(m,1H), 1.6–1.8(m,1H), 2.0–2.2(m,5H), 2.3–2.5 (m,5H), 2.5–2.7(m,6H), 2.8–3.0(m,1H), 3.1–3.3(m,1H), 3.25–3.5(m,3H), 4.4 (d,1H), 4.8(d,1H), 6.7–6.9(m,1H), 7.05 (s, 1H), 7.4–7.2(m,6H) ppm. |
| 3[1,2] | 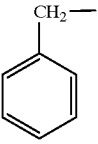 | 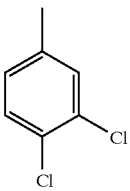 | 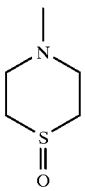 | — | 534 (m + 1)⁺ | Found: C, 57.91; H, 5.77; N, 7.58. $C_{27}H_{33}N_3Cl_2O_2S \cdot 0.37CH_2Cl_2$ requires C, 58.05; H, 6.01, N, 7.42%. ¹H-NMR(CDCl₃): δ = 1.1–1.3(m,1H), 1.4–1.8(m,1H), 1.9–2.3(m,5H), 2.4–2.6 (m,5H), 2.6–2.7(m,6H), 2.7–2.9(m,1H), 2.9–3.1 (m,1H), 3.2–3.4(m,2H), 3.4–3.6(m,1H), 4.4 (d,1H), 4.8(d,1H), 6.8 (d,1H), 7.1(s, 1H), 7.3–7.4(m,6H) ppm. |
| 4 | 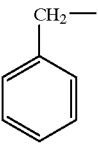 | 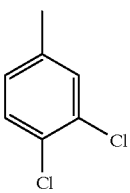 | 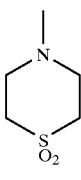 | — | 551 (m + 1)⁺ | Found: C, 54.96; H, 5.72; N, 6.96. $C_{27}H_{33}N_3Cl_2O_2S \cdot 0.63CH_2Cl_2$ requires C, 54.96; H, 5.72, N, 6.96%. ¹H-NMR(CDCl₃): δ = 1.4–1.8(m,3H), 1.9–2.2(m,5H),2.4–2.55 (m,1H), 2.6(q, 2H), 2.7–2.8 (m,4H), 3.0–3.1 (m,5H), 3.2–3.4(m,2H), 3.5–3.6(m,1H), 4.4(d,1H), 4.8(d,1H), 6.7(d,1H), 7.1 (s, 1H), 7.3–7.5(m,6H) ppm. |
| 5 | 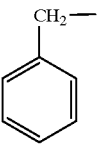 | 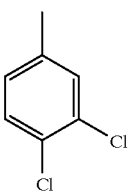 | 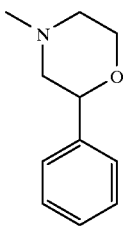 | — | 579 (m + 1)⁺ | Found: C, 67.36; H, 6.33; N, 6.81. $C_{33}H_{37}N_3Cl_2O_2 \cdot 0.125CH_2Cl_2$ requires C, 67.52; H, 6.37; N, 7.13%. ¹H-NMR(CDCl₃): δ = 1.4–1.6(m,2H), 1.6–1.8 (m,1H), 2.0–2.2(m,6H), 2.3–2.45(m,1H), 2.5–2.7 (m,1H), 3.2–3.4(m,3H), 2.8–3.0(m,1H), 3.2–3.4 (m,3H), 3.4–3.6(m,1H), 3.8(t, 1H), 3.9–4.05 (m,1H), 4.4(d,1H), 4.5 (d,1H), 4.8(d,1H), 6.8(d,1H), 7.05(s, 1H), 7.25–7.5 (m,11H) ppm. |
| 6[1] | 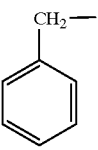 | 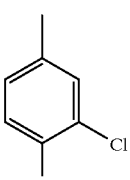 | 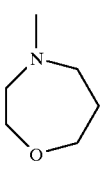 | — | 517 (m + 1)⁺ | ¹H-NMR(CDCl₃): δ = 1.4–1.8(m,4H), 1.7–1.9 (m,2H), 2.0–2.2(m,6H), 2.3–2.5(m,2H), 2.5–2.7 (m,2H), 3.1(t, 1H), 3.2 (d,1H), 3.3–3.45(m,2H), 3.5(t, 1H), 3.7(d,2H), 3.8(m,2H), 4.4(d,1H), 4.8(d,1H), 6.8(d,1H), 7.1(s, 1H), 7.3(m,6H) ppm. |

-continued

| Ex. No. | R | R[1] | -x[1]-R[2] | m.p. | LRMS m/z | Analysis/$^1$H-NMR |
|---|---|---|---|---|---|---|
| 7 | 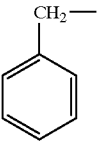 | 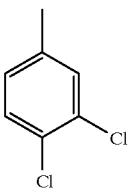 | 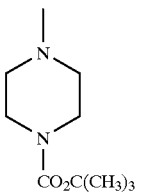 | — | 602 (m + 1)[+] | Found: C, 62.28; H, 7.10; N, 8.84. $C_{32}H_{42}N_4Cl_2O_3 \cdot 0.25CH_2Cl_2$ requires C, 62.18; H, 6.88; N, 9.00%. $^1$H-NMR (CDCl$_3$): δ = 1.3–1.5 (m,9H), 1.5–1.7(m,4H), 1.9–2.1(m,4H), 2.1–2.3 (m,6H), 2.4–2.6(m,1H), 2.6–2.8(m,2H), 2.7–2.9(m,1H), 3.3–3.5(m,4H), 3.5(d,1H), 4.4(d,1H), 4.8(d,1H), 6.8(d,1H), 7.1(s, 1H), 7.2–7.4(m,6H) ppm. |
| 8[1] | 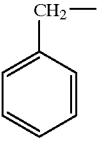 | 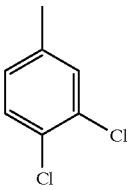 | 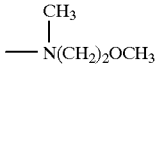 | — | 505 (m + 1)[+] | $^1$H-NMR(CDCl$_3$): δ = 2.1–2.3(m,8H), 2.3–2.5 (m,3H), 2.9–3.1(m,2H), 3.3(s, 3H), 3.3–3.5 (m,6H), 3.4–3.6(m,1H), 3.7–3.9(m,2H), 4.3 (d,1H), 4.9(d,1H), 6.8(d,1H), 7.1(s, 1H), 7.2–7.4 (m,6H) ppm. |
| 9[1] | 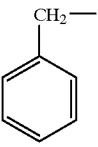 | 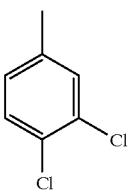 | 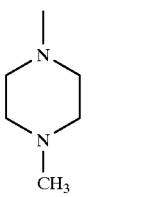 | — | 516 (m + 1)[+] | Found: C, 63.46; H, 7.04; N, 10.87. $C_{28}H_{36}N_4Cl_2O \cdot 0.25CH_2Cl_2$ requires C, 63.21; H, 6.85; N, 10.44%. $^1$H-NMR (CDCl$_3$): δ = 1.4–1.6(m,1H), 1.8–2.5(m,21H), 2.8–2.9 (m,1H), 3.3(d,1H), 3.5 (s, 1H), 3.55–3.6(m,1H), 4.4(d,1H), 4.9(d,1H), 6.8(d,1H), 7.1(s, 1H), 7.2–7.4(m,6H) ppm. |
| 10 | 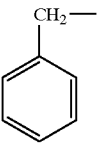 | 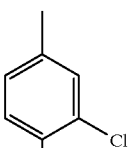 | 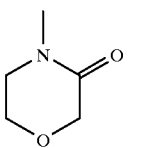 | — | 517 (m + 1)[+] | Found: C, 60.87; H, 5.91; N, 7.82. $C_{27}H_{31}N_3Cl_2O_3 \cdot 0.25CH_2Cl_2$ requires C, 60.47; H, 5.92; N, 7.70%. $^1$H-NMR(CDCl$_3$): δ =1.5–1.7(m,1H), 2.0–2.2 (m,2H), 2.3–2.6(m,5H), 2.8–3.0(m,2H), 3.3(d,1H), 3.3–3.5(m,4H), 3.5–3.6 (m,1H), 3.8–4.0(m,2H), 4.2(s, 2H), 4.4(d,1H), 4.8–4.9(m,2H), 6.75–6.85 (m,1H), 7.1(s, 1H), 7.2–7.5 (m,6H) ppm. |
| 11[1] | 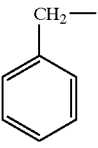 | 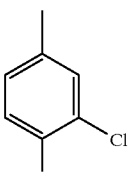 | 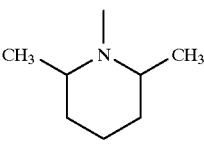 | — | 529 (m + 1)[+] | Found: C, 66.10; H, 7.10; N, 7.44. $C_{30}H_{39}N_3Cl_2O \cdot 0.25CH_2Cl_2$ requires C, 66.08; H, 7.24; N, 7.64%. $^1$H-NMR(CDCl$_3$): δ =0.8–1.0(m,6H), 1.2–1.8(m,10H), 1.95–2.2(m,4H), 2.4–2.9(m,2H), 3.2–3.3 (m,1H), 3.3–3.7(m,6H), 4.4(d,1H), 4.85(d,1H), 6.8(d,1H), 7.1(s, 1H), 7.2–7.4(m,6H) ppm. |

-continued

| Ex. No. | R | $R^1$ | -$X^1$-$R^2$ | m.p. | LRMS m/z | Analysis/$^1$H-NMR |
|---|---|---|---|---|---|---|
| 12[1,4] | benzyl (Ph-CH$_2$–) | 3,4-dichlorophenyl | 1-imidazolyl | — | 529 (m + 1)$^+$ | $^1$H-NMR(CDCl$_3$): δ = 1.6–1.7(m,1H), 1.7–2.0 (m,2H), 2.05–2.4(m,4H), 2.45–2.65(m,1H), 3.1–3.2(m,2H), 3.25–3.35(m,1H), 3.6–3.8(m,3H), 4.45(d,1H), 4.6–4.7(m,1H), 4.85 (d,1H), 6.8(d,1H), 7.05–7.2 (m,2H), 7.25–7.5(m ,7H), 7.6(s, 1H) ppm. |
| 13 | benzyl (Ph-CH$_2$–) | 3,4-dichlorophenyl | 4-morpholinyl | — | 502 (m + 1)$^+$ | Found: C, 64.31; H, 6.86; N, 8.15. C$_{27}$H$_{33}$N$_3$Cl$_2$O$_2$ requires C, 64.52; H, 6.62; N, 8.36%. $^1$H-NMR(CDCl$_3$): δ = 1.5–1.7(m,1H), 1.7–1.9(m,1H), 1.9–2.35 (m,9H), 2.35–2.5(m,1H), 2.6–2.7(m,2H), 2.9(t, 1H), 3.2(d,1H), 3.3–3.45 (m,2H), 3.5(d,1H), 3.6–3.7(m,4H), 4.4(d,1H), 4.9(d,1H), 6.7(d,1H), 7.1(s, 1H), 7.3–7.5 (m,6H) ppm. |
| 14 | benzyl (Ph-CH$_2$–) | 3,4-difluorophenyl | 4-(1-oxo-thiomorpholinyl) | — | 502 (m + 1)$^+$ | $^1$H-NMR(CDCl$_3$): δ = 1.4–1.8(m,3H), 1.9–2.2(m,5H), 2.4–2.6(m,5H), 2.6–2.9(m,6H), 3.2–3.4(m,4H), 4.4 (d,1H), 4.8(d,1H), 6.6–6.8(m,2H), 7.0 (q, 1H), 7.2–7.4(m,5H), ppm. |
| 15[1] | cyclohexylmethyl | 3,4-difluorophenyl | 4-morpholinyl | — | 435 (m)$^+$ | $^1$H-NMR(CDCl$_3$): δ = 0.9–1.1(m,3H), 1.2–1.4 (m,4H), 1.7–1.9(m,8H), 2.1–2.35(m,9H), 2.6–2.8(m,2H), 2.8–3.0(m,1H), 3.1–3.2 (m,1H), 3.3–3.45(m,4H), 3.7–3.9(m,4H), 6.9–7.1(m,3H) ppm. |
| 16[1] | benzyl (Ph-CH$_2$–) | 3,4-difluorophenyl | 1-piperidinyl | — | 468 (m + 1)$^+$ | $^1$H-NMR(CDCl$_3$): δ = 1.2–1.6(m,8H), 1.9–2.2(m,9H), 2.3–2.5(m,1H), 2.5–2.7(m,2H), 2.7–2.9 (m,1H), 3.2(d,1H), 3.3–3.5(m,2H), 3.5(d,1H), 4.4(d,1H), 4.8 (d,1H), 6.6(s, 1H), 6.6–6.8(m,1H), 7.0 (m,1H), 7.2–7.3(m,5H) ppm. |

-continued

| Ex. No. | R | R¹ | -x¹-R² | m.p. | LRMS m/z | Analysis/¹H-NMR |
|---|---|---|---|---|---|---|
| 17[1] | CH₂-phenyl | 3,4-dichlorophenyl | -NCH₂C(CH₃)₂ with CH₃, OH | — | 518/520 (m + 1)⁺ | Found: C, 62.20; H, 6.67; N, 7.44. $C_{28}H_{37}N_3Cl_2O \cdot 0.31 CH_2Cl_2$ requires C, 62.39; H, 6.96; N, 7.71%. ¹H-NMR(CDCl₃): δ = 1.1 (s, 6H), 1.5–1.6(m,1H), 1.6–1.8(m,1H), 1.9–2.3(m,11H), 2.4–2.5(m,1H), 2.6–2.7(m,2H), 3.1–3.2(m,1H), 3.2–3.4(m,3H), 3.6(d,1H), 4.4 (d,1H), 4.85(d,1H), 6.8(d,1H), 7.1(s, 1H), 7.2–7.4(m,6H) ppm. |
| 18[1] | CH₂-phenyl | 3-chlorophenyl | N-morpholinyl | — | 468 (m + 1)⁺ | Found: C, 66.66; H, 7.30; N, 8.61. $C_{27}H_{34}N_3ClO_2 \cdot H_2O$ requires C, 66.70; H, 7.50; N, 8.60%. ¹H-NMR(CDCl₃): δ = 1.45–1.9 (m,4H), 2.0–2.6(m,8H), 2.6–2.8 (m,3H), 2.8–3.0(m,1H), 3.5–3.8 (m,5H), 4.5(d,1H), 4.8(d, 1H), 6.9 (d,1H), 7.0(s, 1H), 7.1–7.5 (m,7H) ppm. |
| 19[1] | CH₂-phenyl | 4-chlorophenyl | N-morpholinyl | — | 468 (m + 1)⁺ | Found: C, 67.46; H, 7.47; N, 8.77. $C_{27}H_{34}N_3ClO_2 \cdot 0.66 H_2O$ requires C, 67.60; H, 7.40; N, 8.80%. ¹H-NMR (CDCl₃): δ = 1.5–1.6 (m,1H), 1.7–1.8(m,1H), 1.9–2.2(m,9H), 2.2–2.3(m,1H), 2.6–2.7(m,2H), 2.8–3.0(m,1H), 3.2–3.4(m,3H), 3.5–3.6(m,1H), 3.7–3.8(m,4H), 4.4 (d,1H), 4.8(d,1H), 6.9(d,2H), 7.2(d,2H), 7.2–7.4(m,5H) ppm. |
| 20[1] | CH₂-phenyl | 3,4-dichlorophenyl | N-piperazinyl-COCH₃ | — | 543 (m + 1)⁺ | Found: C, 62.48; H, 6.32; N, 9.70. $C_{29}H_{36}N_4Cl_2O_2 \cdot 0.25 CH_2Cl_2$ requires C, 62.20; H, 6.51; N, 9.92%. ¹H-NMR (CDCl₃): δ = 1.45–1.8 (m,2H), 1.9–2.3(m,12H), 2.4–2.5(m,1H), 2.6–2.7(m,2H), 2.8–2.9(m,1H), 3.1–3.4(m,3H), 3.4–3.6(m,5H), 4.4 (d,1H), 4.8(d,1H), 6.8–7.4(m,8H) ppm. |
| 21[1] | CH₂-phenyl | 3,4-dichlorophenyl | N-piperazinyl-SO₂CH₃ | — | 578 (m + 1)⁺ | ¹H-NMR(CDCl₃): δ = 1.45–1.8(m,2H), 1.9–2.15(m,5H), 2.3–2.5(m,5H), 2.6–2.95(m,16H), 3.2–3.35(m,7H), 3.5–3.6(m,1H), 4.4(d,1H), 4.8(d,1H), 6.8–7.4(m,8H) ppm. |

-continued

| Ex. No. | R | R$^1$ | -x$^1$-R$^2$ | m.p. | LRMS m/z | Analysis/$^1$H-NMR |
|---|---|---|---|---|---|---|
| 22 | benzyl-CH$_2$— | 3,4-difluorophenyl | N-morpholinyl | — | 470 (m + 1)$^+$ | Found: C, 65.52; H, 6.89; N, 8.34. C$_{27}$H$_{33}$N$_3$F$_2$O$_2$. 0.38CH$_2$Cl$_2$ requires C, 65.57; H, 6.78; N, 8.38%. $^1$H-NMR (CDCl$_3$): δ = 1.45–1.8 (m,2H), 1.95–2.3(m,9H), 2.4–2.5(m,1H), 2.6–2.7(m,2H), 2.8–2.95(m,1H), 3.2–3.4(m,3H), 3.5–3.6(m,1H), 3.65–3.75(m,4H), 4.4 (d,1H), 4.8(d,1H), 6.6–6.8(m,2H), 6.95–7.05(m,1H), 7.25–7.4(m,5H) ppm. |
| 23 | benzyl-CH$_2$— | 3,4-dichlorophenyl | —CON(CH$_3$)(CH$_2$)$_2$OCH$_3$ | — | 532/534 (m + 1)$^+$ | Found: C, 60.49; H, 6.50; N, 6.57. C$_{28}$H$_{35}$N$_3$Cl$_2$O$_3$·0.38CH$_2$Cl$_2$ requires C, 60.39; H, 6.39; N, 7.45%. $^1$H-NMR(CDCl$_3$): δ = 1.45–1.8 (m,3H), 1.9–2.2(m,4H), 2.2–2.5 (m,1H), 2.9(s, 3H), 2.95–3.1 (m,2H), 3.2–3.6(m,12H), 4.4 (d,1H), 4.85(d,1H), 6.75–6.8 (m,1H), 7.05–7.1(m,1H), 7.2–7.4 (m,6H) ppm. |
| 24$^3$ | benzyl-CH$_2$— | 3,4-dichlorophenyl | N-methyl-tropanyl-OCOCH$_3$ | — | — | Found: C, 63.29; H, 6.19; N, 7.20. C$^{32}$H$_{39}$Cl$_2$N$_3$O$_3$. 0.31CH$_2$Cl$_2$ requires C, 63.72; H, 6.88; N, 6.91%. $^1$H-NMR (CDCl$_3$): δ = 1.55–2.2 (m,18H), 2.4–2.5(m,1H), 2.55–2.7(m,2H), 2.95–3.05(m,2H), 3.1–3.2(m,1H), 3.2–3.35(m,3H), 3.55–3.6(m,1H), 4.35(d,1H), 4.85–4.95 (m,2H), 6.75–6.8(m,1H), 7.05(d,1H), 7.2–7.35(m,6H) ppm. |
| 25 | benzyl-CH$_2$— | 3,4-dichlorophenyl | —N(CH$_3$)CH$_2$CH$_2$OH | — | 491 (m + 1)$^+$ | Found: C, 61.03; H, 6.20; N, 7.62. C$_{26}$H$_{33}$Cl$_2$N$_3$O$_2$ .0.38CH$_2$Cl$_2$ requires C, 60.65; H, 6.51; N, 8.05%. $^1$H-NMR(CDCl$_3$): δ = 1.51–1.8 (m,2H), 1.9–2.25(m,9H), 2.35–2.5(m,3H), 2.6–2.7(m,2H), 3.05–3.1(m,1H), 3.25–3.3(m,1H), 3.4–3.45(m,2H), 3.55–3.6(m,3H), 4.35(d,1H), 4.85(d,1H), 6.75–6.8(m,1H), 7.05(d,1H), 7.25–7.4 (m,6H), ppm. |

-continued

| Ex. No. | R | R[1] | -x[1]-R[2] | m.p. | LRMS m/z | Analysis/$^1$H-NMR |
|---|---|---|---|---|---|---|
| 26[1] | benzyl (PhCH₂-) | 3,4-dichlorophenyl | 1-methylpiperidin-3-ol (N-linked) | — | 516 (m + 1)⁺ | Found: C, 60.00; H, 6.06; N, 6.70.$C_{28}H_{35}Cl_2N_3O_2$·0.69$CH_2Cl_2$ requires C, 59.93; H, 6.38; N, 7.31%. $^1$H-NMR(CDCl₃): δ = 1.45–2.35(m,16H), 2.4–2.5(m,1H), 2.6–2.7(m,2H), 2.85–2.95(m,1H), 3.2–3.3(m,1H), 3.35–3.45(m,2H), 3.5–3.6(m,1H), 3.75–3.8(m,1H), 4.4(d,1H), 4.85(d,1H), 6.75–6.8(m,1H), 7.05(d,1H), 7.25–7.45 (m,6H) ppm. |
| 27[1] | benzyl (PhCH₂-) | 3,4-dichlorophenyl | 1-methylpyrrolidin-3-ol (N-linked) | — | 501 (m)⁺ | Found: C, 62.42, H, 6.49; N, 7.52.$C_{27}H_{33}Cl_2N_3O_2$·0.25$CH_2Cl_2$ requires C, 62.49; H,1 6.45; N, 8.02%. $^1$H-NMR(CDCl₃): δ = 1.5–1.8(m,3H), 1.95–2.3(m,8H), 2.4–2.6(m,3H), 2.7–2.85(m,3H), 3.05–3.1(m,1H), 3.2–3.4(m,3H), 3.5–3.6(m,1H), 4.35(d,2H), 4.85(d,1H), 6.75–6.8(m,1H), 7.1(d,1H), 7.3–7.4(m,6H), ppm. |
| 28[1] | benzyl (PhCH₂-) | 3,4-dichlorophenyl | 1-methylpiperidin-4-ol (N-linked) | — | 517 (m + 1)⁺ | Found: C, 60.64; H, 6.75; N, 7.39.$C_{28}H_{35}Cl_2N_3O_2$·0.56$CH_2Cl_2$ requires C, 60.79; H, 6.45; N, 7.47%. $^1$H-NMR(CDCl₃): δ = 1.3–2.7(m,20H), 2.95(br.s, 1H), 3.2–3.43 (m,2H), 3.5–3.75(m,2H), 4.4(d,1H), 4.8(d,1H), 6.75–6.8(m,1H), 7.1(d,1H), 7.25–7.4 (m,6H) ppm. |
| 29[1] | benzyl (PhCH₂-) | 3,4-dichlorophenyl | pyrrolidin-1-ylcarbonyl | — | 514 (m + 1)⁺ | $^1$H-NMR(CDCl₃): δ = 1.4–1.8(m,4H), 1.8–2.2(m,6H), 2.4–2.5(m,1H), 3.0–3.1 (m,2H), 3.2–3.6(m,10H), 4.35(d,1H), 4.85(d,1H), 6.7–6.8(m,1H), 7.05(m,1H), 7.2–7.4 (m,6H) ppm. |
| 30[1] | benzyl (PhCH₂-) | 3,4-dichlorophenyl | cyclohexyl-NHCO- | — | 542 (m + 1)⁺ | $^1$H-NMR(CDCl₃): δ = 1.05–1.45(m,4H), 1.5–1.8(m,6H), 1.85–2.2(m,6H), 2.4–2.5(m,1H), 2.95–3.4(m,6H), 3.5–3.75(m,3H), 4.35(d,1H), 4.85(d,1H), 5.7(br.d,1H), 6.8(m,1H), 7.05(d,1H), 7.25–7.4 (m,6H) ppm. |

-continued

| Ex. No. | R | R¹ | -x¹-R² | m.p. | LRMS m/z | Analysis/¹H-NMR |
|---|---|---|---|---|---|---|
| 31[1] | benzyl (CH₂–Ph) | 3,4-dichlorophenyl | piperidin-1-yl-carbonyl | — | 528 (m + 1)⁺ | ¹H-NMR(CDCl₃): δ = 1.45–1.8(m,8H), 1.9–2.2(m,5H), 2.4–2.5(m,1H), 3.0–3.6(m,11H), 4.35(d,1H), 4.9(d,1H), 6.75(m,1H), 7.05(d,1H), 7.2–7.4(m,6H) ppm. |
| 32[1,5,9,10,17] | cyclopropylmethyl | 3,4-dichlorophenyl | 4-(aminosulfonyl)piperazin-1-yl | — | 544 (m)⁺ | ¹H-NMR(CDCl₃): δ = 0.25–0.4(m,2H), 0.5–0.7(m,2H), 1.0–1.1(m,1H), 1.6–1.9(m,2H), 1.95–2.2(m,5H), 2.3–2.4(m,5H), 2.7–2.8(m,2H), 2.9–3.0(m,1H), 3.15–3.2(m,5H), 3.3–3.5(m,4H), 3.8(d,1H), 4.3(s, 2H), 7.1–7.15(m,1H), 7.4–7.45(m,2H) ppm. Found: C, 49.17; H, 6.04; N, 11.17. $C_{24}H_{35}N_5O_3SCl_2 \cdot 0.75CH_2Cl_2$ requires: C, 48.87; H, 6.05; N, 11.52% |
| 33[1,5,6] | cyclopropylmethyl | 3,4-dichlorophenyl | morpholin-4-yl | — | 466 (m)⁺ | Found: C, 57.84; H, 6.47; N, 7.99. $C_{24}H_{33}N_3Cl_2O_2 \cdot 0.5CH_2Cl_2$ requires C, 57.82; H, 6.73; N, 8.25%. ¹H-NMR(CDCl₃): δ = 0.2–0.4(m,2H), 0.5–0.7(m,2H), 1.0–1.15(m,1H), 1.6–1.8(m,1H), 1.8–1.95(m,1H), 1.95–2.4(m,10H), 2.75–2.9(m,2H), 2.9–3.1(m,1H), 3.2–3.25(m,1H), 3.4–3.55(m,4H), 3.6–3.8(m,5H), 7.15(d,1H), 7.4(m,2H) ppm. |
| 34[1,5,7] | cyclohexylmethyl | 3,4-dichlorophenyl | morpholin-4-yl | — | 508 (m)⁺ | Found: C, 62.57; H, 7.55; N, 8.53. $C_{27}H_{39}Cl_2N_3O_2 \cdot CH_2Cl_2$ requires C, 62.96; H, 7.64; N, 8.13%. ¹H-NMR (CDCl₃): δ = 0.9–1.1 (m,2H), 1.1–1.3(m,3H), 1.5–2.9(m,9H), 1.9–2.4(m,10H), 2.6–2.8(m,2H), 2.85–3.0(m,1H), 3.1–3.2(m,1H), 3.3–3.6(m,4H), 3.6–3.8(m,4H), 7.1(d,1H), 7.3(d,1H), 7.4(d,1H) ppm. |

-continued

| Ex. No. | R | R¹ | -x¹-R² | m.p. | LRMS m/z | Analysis/¹H-NMR |
|---|---|---|---|---|---|---|
| 35[1,5,8] | CH₂—phenyl | 3,4-dichlorophenyl | N-methylmorpholine | — | — | Found: C, 63.67; H, 6.90; N, 8.35. C₂₇H₃₃Cl₂N₃O₂·0.5H₂O requires C, 63.38; H, 6.70; N, 8.21%. ¹H-NMR(CDCl₃): δ = 1.6–1.8 (m,1H), 1.95–2.3(m,10H), 2.35–2.5 (m,1H), 2.6–2.7(m,2H), 2.8–2.95 (m,1H), 3.2–3.35(m,3H), 3.45–3.6 (m,1H), 3.6–3.7(m,4H), 4.4 (d,1H), 4.8(d,1H), 6.8(d,1H), 7.2–7.4 (m,7H) ppm. |
| 36[1,5,7] | CH₂—4,4-difluorocyclohexyl | 3,4-dichlorophenyl | N-methylmorpholine | — | 544 (m + 1)⁺ | Found: C, 57.30; H, 6.66; N, 7.09. C₂₇H₃₇Cl₂F₂N₃O₂·0.33CH₂Cl₂ requires: C, 57.33; H, 6.65; N, 7.37%. ¹H-NMR (CDCl₃): δ = 1.2–1.9 (m,9H), 1.9–2.35(m,11H), 2.35–2.5(m,1H), 2.7–2.8(m,2H), 2.85–3.0(m,1H), 3.2–3.3(m,1H), 3.3–3.45(m,4H), 3.5–3.6(m,1H), 3.6–3.7 (m,4H), 7.0–7.05(m,1H), 7.3–7.35(m,1H), 7.4(d,1H) ppm. |
| 37[1,5,7,13] | CH₂—cyclopropyl | 3,4-dichlorophenyl | N-methyl-4-ethoxypiperidine | — | — | Found: C, 60.74; H, 7.29; N, 7.58. C₂₇H₃₉N₃Cl₂O₂·0.375CH₂Cl₂ requires: C, 60.84; H, 7.42; N, 7.78%. ¹H-NMR (CDCl₃): δ = 0.2–0.4 (m,2H), 0.5–0.7(m,2H), 0.95–1.1(m,1H), 1.1(t, 3H), 1.45–1.7 (m,4H), 1.7–2.3(m,12H), 2.3–2.4(m,1H), 2.45–2.6(m,2H), 2.6–2.8(m,2H), 2.8–2.95(m,1H), 3.1–3.5(m,5H), 3.7–3.8(m,1H), 7.1(d,1H), 7.4(m,2H) ppm. |
| 38[1,5,11,13,14] | H | 3,4-dichlorophenyl | N-methyl-N'-sulfamoylpiperazine | — | 490 (m)⁺ | ¹H-NMR(d₆-DMSO/CDCl₃): δ =1.5–1.7(m,1H), 1.75–1.8(m,1H), 1.9–2.2(m,5H), 2.2–2.35(m,5H), 2.6–2.65(m,2H), 2.8–2.95(m,1H), 3.0–3.2(m,4H), 3.25–3.4(m,3H), 3.65(d,1H), 5.25(s, 2H), 6.2(s, 1H), 7.05–7.1 (m,1H), 7.3–7.4(m,2H) ppm. |

-continued
| Ex. No. | R | R[1] | -x[1]-R[2] | m.p. | LRMS m/z | Analysis/$^1$H-NMR |
|---|---|---|---|---|---|---|
| 39[1,5,13] |  | 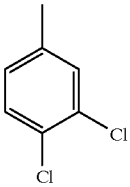 | 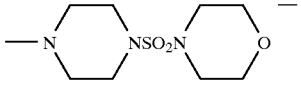 | — | 614 (m + 1)[+] | Found: C, 54.35; H, 6.20; N, 10.87. $C_{28}H_{41}Cl_2N_5O_4S \cdot 0.25H_2O$ requires: C, 54.31; H, 6.77; N, 11.31%. $^1$H-NMR $(CDCl_3)$: δ = 0.2–0.35 (m,2H), 0.5–0.7(m,2H), 1.0–1.15(m,1H), 1.7–1.9(m,1H), 1.95–2.25(m,5H), 2.3–2.45(m,5H), 2.65–2.8(m,2H), 2.95(t, 1H), 3.1–3.35 (m,9H), 3.35–3.55(m,5H), 3.65–3.8(m,5H), 7.15–7.2(m,1H), 7.4–7.45(m,2H) ppm. |
| 40[1,5,13] |  | 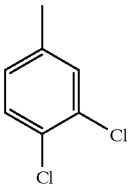 | 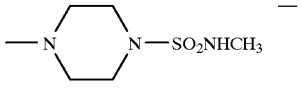 | — | 558 (m + 1)[+] | Found: C, 53.59; H, 6.86; N, 12.11. $C_{25}H_{37}Cl_2N_5O_3S$ requires: C, 53.75; H, 6.69; N, 12.54%. $^1$H-NMR $(CDCl_3)$: δ = 0.25–0.4(m,2H), 0.5–0.7(m,2H), 1.0–1.1(m,1H), 1.75–1.9(m,1H), 1.9–2.3(m,4H), 2.3–2.4(m,5H), 2.6–2.7(d,6H), 2.9–3.0(m,1H), 3.1–3.3(m,6H), 3.3–3.5(m,5H), 3.8(d,1H), 7.15–7.2 (m,1H), 7.4–7.45 (m,2H) ppm. |
| 41[1,5,7,13] |  | 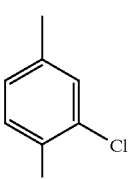 | 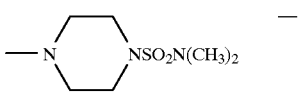 | — | 572 (m + 1)[+] | Found: C, 53.36; H, 7.05; N, 11.63. $C_{26}H_{39}Cl_2N_5O_3S \cdot 0.5H_2O$ requires: C, 53.69; H, 6.94; N, 12.04%. $^1$H-NMR $(CDCl_3)$: δ = 0.2–0.4(m,2H), 0.5–0.7(m,2H), 0.95–1.1(m,1H), 1.7–1.9(m,1H), 1.9–2.2(m,6H), 2.2–2.45(m,5H), 2.6–3.0(m,8H), 3.1–3.55(m,10H), 3.75(d,1H), 7.1(d,1H), 7.35–7.4(m,2H) ppm. |

| Ex. No. | R | R¹ | -x¹-R² | m.p. | LRMS m/z | Analysis/¹H-NMR |
|---|---|---|---|---|---|---|
| 42[1,5,7,13] | cyclopropyl-CH₂— | 3,4-dichlorophenyl | —N(piperidinyl)-OH | — | 481 (m + 1)⁺ | Found: C, 59.39; H, 6.91; N, 8.16. C₂₅H₃₅N₃O₂Cl₂·0.4CH₂Cl₂ requires: C, 59.30; H, 7.01; N, 8.17%. ¹H-NMR (CDCl₃): δ = 0.2–0.4 (m,2H), 0.5–0.7(m,2H), 0.95–1.1(m,1H), 1.4–1.7(m,4H), 1.7–2.2(m,10H), 2.2–2.4(m,1H), 2.45–2.6(m,2H), 2.6–2.7(m,2H), 2.8–2.95(m,1H), 3.1–3.2(m,1H), 3.35–3.5(m,4H), 3.6–3.8(m,2H), 7.1(d,1H), 7.35–7.4 (m,2H) ppm. |
| 43[1,5,7,13] | cyclopropyl-CH₂— | 3,4-dichlorophenyl | —N(piperazinyl)-NSO₂CH₃ | — | 543 (m)⁺ | ¹H-NMR(CDCl₃): δ = 0.2–0.4(m,2H), 0.5–0.65(m,2H), 0.95–1.1(m,1H), 1.65–1.9(m,3H), 1.95–2.25(m,4H), 2.3–2.45(m,5H), 2.6–2.8(m,5H), 2.9–3.0(m,1H), 3.05–3.3(m,5H), 3.3–3.5(m,4H), 3.75(d,1H), 7.1(d,1H), 7.35–7.4(m,2H) ppm. |
| 44[1,5,7,15] | cyclopropyl-CH₂CH₂— | 3,4-dichlorophenyl | —N(morpholinyl) | — | 480 (m)⁺ | ¹H-NMR(CDCl₃): δ = 0.0–0.2(m,2H), 0.4–0.5(m,2H), 0.6–0.75(m,1H), 1.45(q, 2H), 1.55–1.7 (m,1H), 1.75–1.9(m,1H), 1.9–2.4(m,10H), 2.65–2.8(m,2H), 2.85–3.0(m,1H), 3.2–3.45(m,4H), 3.45–3.8(m,6H), 7.05(d,1H), 7.2(d,1H), 7.4(d,1H) ppm. |
| 45[1,5,7,13] | cyclopropyl-CH₂CH₂— | 3,4-dichlorophenyl | —N(piperazinyl)-NSO₂CH₃ | — | 560 (m + 1)⁺ | Found: C, 54.63; H, 6.83; N, 9.99. C₂₈H₃₈N₄O₃Cl₂S·0.25CH₂Cl₂ requires: C, 54.57; H, 6.72; N, 9.70%. ¹H-NMR (CDCl₃): δ = 0.0–0.15 (m,2H), 0.4–0.5(m,2H), 0.6–0.75(m,1H), 1.45(q, 2H), 1.5–1.65 (m,1H), 1.7–1.9(m,1H), 1.9–2.2(m,5H), 2.3–2.45(m,5H), 2.6–2.8(m,5H), 2.95(t, 1H), 3.15–3.4 (m,8H), 3.5–3.7(m,2H), 7.05 (d,1H), 7.15(d,1H), 7.4(d,1H) ppm. |

-continued

| Ex. No. | R | R¹ | -x¹-R² | m.p. | LRMS m/z | Analysis/¹H-NMR |
|---|---|---|---|---|---|---|
| 46[1,5,7,13] | CH₂CH₂—cyclopropyl | 3,4-dichlorophenyl | 4-(NHCO₂C(CH₃)₃)-1-methylpiperidinyl | — | 593 (m+1)⁺ | ¹H-NMR(CDCl₃): δ = 0.0–0.15(m,2H), 0.4–0.5(m,2H), 0.6–0.75(m,1H), 1.3–1.5(m,9H), 1.5–2.2(m,12H), 2.25–2.4(m,1H), 2.5–2.7(m,3H), 2.8–2.9(m,1H), 3.2–3.5(m,9H), 3.5–3.7(m,2H), 4.4(br.s, 1H), 7.05(d,1H), 7.2(d,1H), 7.4(d,1H) ppm. |
| 47[1,5,7,13] | CH₂CH₂—cyclopropyl | 3,4-dichlorophenyl | 1-methyl-4-hydroxypiperidinyl | — | 494 (m)⁺ | Found: C, 61.02; H, 7.45; N, 8.47. C₂₆H₃₇N₃O₂Cl₂.0.25CH₂Cl₂ requires: C, 61.12; H, 7.34; N, 8.15%. ¹H-NMR (CDCl₃): δ = 0.0–0.15 (m,2H), 0.4–0.55 (m,2H), 0.6–0.75 (m,1H), 1.4–1.7 (m,5H), 1.7–2.2 (m,11H), 2.2–2.4 (m,1H), 2.5–2.6 (m,2H), 2.6–2.8 (m,2H), 2.95(t, 1H), 3.2–3.5(m,4H), 3.5–3.8(m,3H), 7.05(d,1H), 7.25(d,1H), 7.4(d,1H) ppm. |
| 48[1,5,7,13] | CH₂—cyclopropyl | 3,4-dichlorophenyl | 4-(NHCO₂C(CH₃)₃)-1-methylpiperidinyl | — | 579 (m)⁺ | ¹H-NMR(CDCl₃): δ = 0.2–0.4(m,2H), 0.5–0.7(m,2H), 0.95–1.1(m,1H), 1.3–1.4(m,10H), 1.55–1.65(m,1H), 1.7–1.9(m,5H), 1.9–2.4(m,6H), 2.5–2.7(m,6H), 2.95(t, 1H), 3.1–3.2(m,1H), 3.35–3.5 (m,4H), 3.75(d,1H), 4.4(br.s,1H), 7.1(d,1H), 7.4(m,2H) ppm. |
| 49[1,5,7,13] | CH₂—CH(cyclopropyl)₂ | 3,4-dichlorophenyl | 1-methyl-4-(NSO₂CH₃)piperazinyl | — | 597 (m)⁺ | Found: C, 56.98; H, 6.99; N, 9.25. C₂₉H₄₂N₄Cl₂O₃S.0.25CH₂Cl₂ requires: C, 56.76; H, 6.92; N, 9.05%. ¹H-NMR (CDCl₃): δ = 0.05–0.25 (m,4H), 0.4–0.55 (m,4H), 0.56–0.7 (m,3H), 1.5–1.7 (m,1H), 1.75–1.9 (m,1H), 1.9–2.25 (m,5H), 2.3–2.45 (m,5H), 2.6–2.8 (m,5H), 2.95(t, 1H), 3.1–3.3(m,5H), 3.3–3.4(m,2H), 3.5(q, 2H), 3.8–3.9 (m,1H), 7.05(d,1H), 7.3(d,1H), 7.4(d,1H) ppm. |

-continued

| Ex. No. | R | R[1] | -x[1]-R[2] | m.p. | LRMS m/z | Analysis/$^1$H-NMR |
|---|---|---|---|---|---|---|
| 50[1,5,7,15] | 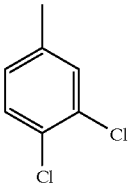 |  | 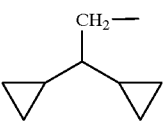 | — | 520 (m)+ | Found: C, 62.67; H, 6.88; N, 7.10. $C_{28}H_{39}N_3Cl_2O_2$. $0.25CH_2Cl_2$ requires: C, 62.63; H, 7.35; N, 7.76%. $^1$H-NMR (CDCl$_3$): δ = 0.5–2.05 (m,4H), 0.3–0.55 (m,4H), 0.55–0.7 (m,3H), 1.5–1.7 (m,1H), 1.8–1.95(m,1H), 1.95–2.4 (m,10H), 2.6–2.8 (m,2H), 2.8–2.9 (m,1H), 3.1–3.2 (m,1H), 3.3–3.45 (m,2H), 3.5(q, 2H), 3.6–3.7(m,4H), 3.85–4.0(m,1H), 7.05(m,1H), 7.3(m,1H), 7.4(m,1H) ppm. |
| 51[1,5,13,16] | 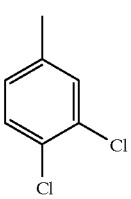 | 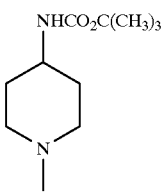 | 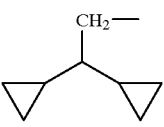 NHCO$_2$C(CH$_3$)$_3$ | — | 633 (m)+ | Found: C, 63.44; H, 7.69; N, 8.34. $C_{34}H_{50}N_4Cl_2O_3$. $0.125CH_2Cl_2$ requires: C, 63.61; H, 7.86; N, 8.70%. $^1$H-NMR (CDCl$_3$): δ = 0.0–2.1 (m,4H), 0.3–0.7 (m,7H), 1.2–2.2 (m,23H), 2.3–2.45 (m,1H), 2.5–2.7 (m,4H), 2.8–2.9 (m,1H), 3.1–3.2 (m,1H), 3.3–3.6 (m,4H), 3.8–3.95 (m,1H), 4.4(br.s,1H), 7.05(d,1H), 7.3(d,1H), 7.4(d,1H) ppm. |
| 52[1,5,13,16] | 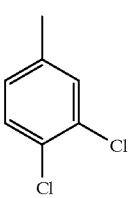 | 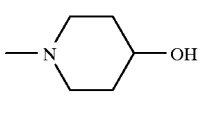 | —N⟨⟩—OH | — | 534 (m)+ | Found: C, 63.34; H, 7.86; N, 7.36. $C_{29}H_{41}N_3Cl_2O_2.0.25$ $CH_2Cl_2$ requires: C, 63.21; N, 7.53; N, 7.56%. $^1$H-NMR (CDCl$_3$): δ = 0.25–0.50(m,4H), 0.35–0.55(m,4H), 0.55–0.75(m,3H), 1.2–1.75(m,3H), 1.8–2.2(m,11H), 2.3–2.4(m,1H), 2.4–2.8(m,4H), 2.8–2.9(m,1H), 3.1–3.2(m,1H), 3.4–3.6(m,4H), 3.6–3.8(m,1H), 3.8–4.0(m,1H), 7.05(d,1H), 7.25(d,1H), 7.4(d,1H) ppm. |

| Ex. No. | R | R[1] | -x[1]-R[2] | m.p. | LRMS m/z | Analysis/$^1$H-NMR |
|---|---|---|---|---|---|---|
| 53[1,5,13,16] | CH₂—CH(cyclopropyl)(cyclopropyl) | 3,4-dichlorophenyl | piperazinyl-NSO₂NH₂ | — | 598 (m)⁺ | Found: C, 52.55; H, 7.00; N, 9.39. $C_{28}H_{41}N_5Cl_2O_3S \cdot 0.75 CH_2Cl_2$ requires: C, 52.13; H, 6.47; N, 10.50%. $^1$H-NMR(CDCl₃): δ = 0.0–0.3 (m,4H), 0.3–0.5(m,4H), 0.5–0.7 (m,3H), 1.5–1.6(m,1H), 1.7–1.8 (m,1H), 1.9–2.2(m,5H), 2.3–2.4 (m,5H), 2.6–2.8(m,2H), 2.9 (t, 1H), 3.1–3.2(m,4H), 3.3–3.4(m,2H), 3.5(q, 2H), 3.85–3.95(m,2H), 4.25(s, 2H), 7.05(d,1H), 7.25 (d,1H), 7.4(d,1H) ppm. |
| 54[1,5,13] | CH₂—(4,4-difluorocyclohexyl) | 3,4-dichlorophenyl | 1-methyl-4-(NHCO₂C(CH₃)₃)piperidinyl | — | 657 (m)⁺ | Found: C, 53.85; H, 6.78; N, 7.42. $C_{33}H_{46}N_4Cl_2O_3F_2 \cdot 0.2 CH_2Cl_2$ requires: C, 54.08; H, 6.69; N, 7.38%. $^1$H-NMR (CDCl₃): δ = 1.25–1.5(m,13H), 1.5–1.95(m,11H), 1.9–2.2(m,7H), 2.3–2.4(m,1H), 2.5–2.7(m,4H), 2.85(t, 1H), 3.1–3.3 (m,1H), 3.3–3.6(m,6H), 4.4(br.s,1H), 7.05(d,1H), 7.2(d,1H), 7.4(d,1H) ppm. |
| 55[1,5,7,13] | CH₂—(4,4-difluorocyclohexyl) | 3,4-dichlorophenyl | 1-methyl-4-hydroxypiperidinyl | — | 558 (m)⁺ | Found: C, 57.74; H, 6.73; N, 7.01. $C_{28}H_{39}N_3Cl_2O_2F_2 \cdot 0.4 CH_2Cl_2$ requires: C, 57.57; H, 6.77; N, 7.09%. $^1$H-NMR (CDCl₃): δ = 1.2–1.4 (m,2H), 1.4–2.3 (m,20H), 2.3–2.45 (m,2H), 2.5–2.6 (m,2H), 2.6–2.75 (m,2H), 2.9(t, 1H), 3.15–3.2(m,1H), 3.3–3.5(m,4H), 3.6–3.8(m,2H), 7.05(d,1H), 7.3(d,1H), 7.4(d,1H) ppm. |
| 56[1,5,7,13] | CH₂—(4,4-difluorocyclohexyl) | 3,4-dichlorophenyl | piperazinyl-NSO₂CH₃ | — | — | $^1$H-NMR(CDCl₃): δ = 1.25–1.5(m,2H), 1.5–1.9(m,8H), 1.9–2.3(m,7H), 2.3–2.4(m,4H), 2.6–2.8(m,5H), 2.95(t, 1H), 3.15–3.2 (m,5H), 3.3–3.4 (m,4H), 3.4(d,1H), 7.05 (d,1H), 7.25(d,1H), 7.4 (d,1H) ppm. |

-continued

| Ex. No. | R | R¹ | -x¹-R² | m.p. | LRMS m/z | Analysis/¹H-NMR |
|---|---|---|---|---|---|---|
| 57[1,5,7,13] | (CH₂)₅–CO₂C(CH₃)₃ | 3,4-dichlorophenyl | –N(piperazine)NSO₂NH₂ | — | 660 (m)⁺ | Found: C, 53.58; H, 7.11; N, 10.43. $C_{30}H_{47}Cl_2SN_5O_5 \cdot 0.5H_2O$ requires: C, 53.76; H, 7.24; N, 10.45%. ¹H-NMR(CDCl₃): δ =1.2–1.4(m,2H), 1.4(s, 9H), 1.4–1.7 (m,6H), 1.7–1.9 (m,1H), 1.9–2.25 (m,8H), 2.3–2.45 (m,4H), 2.7(q, 2H), 2.9–3.0(m,1H), 3.1–3.3(m,4H), 3.3–3.4(m,3H), 3.4–3.6(m,2H), 4.3(s, 2H), 7.05(d,1H), 7.2(d,1H), 7.4(d,1H) ppm. |
| 58[1,7,12,13] | cyclopropyl-CH₂– | 3,4-dichlorophenyl | –N(piperazine)NSO₂NH₂ | — | — | ¹H-NMR(CDCl₃): δ = 0.25–0.4(m,2H), 0.5–0.7(m,2H), 1.0–1.1(m,1H), 1.6–1.9(m,2H), 1.95–2.2(m,5H), 2.3–2.4(m,5H), 2.7–2.8(m,2H), 2.9–3.0(m,1H), 3.15–3.2(m,5H), 3.3–3.5(m,4H), 3.8(d,1H), 4.3(s, 2H), 7.1–7.15(m,1H), 7.4–7.45(m,2H) ppm. |
| 59[1,5,7] | cyclopropyl-CH₂– | 3,4-dichlorophenyl | –N(piperidine)CO₂CH₃ | — | 522 (m)⁺ | Found: C, 59.47; H, 7.33; N, 7.66. $C_{27}H_{37}Cl_2N_3O_3 \cdot 0.35CH_2Cl_2$ requires: C, 59.49; H, 6.88; N, 7.61%. ¹H-NMR(CDCl₃): δ = 0.2–0.4(m,2H), 0.5–0.77(m,2H), 0.9–1.1(m,1H), 1.6–2.4(m,15H), 2.5–2.7(m,2H), 2.7–2.8(m,2H), 2.85–3.0(m,1H), 3.1–3.2(m,1H), 3.3–3.6(m,4H), 3.65(s, 3H), 3.8(d,1H), 7.05(d,1H), 7.3–7.5 (m,2H) ppm. |

Footnotes

[1.] At least 2 mol. equiv. of triethylamine used.
[2.] See Example 103 for an alternative preparation.
[3.] Dichloromethane additionally used as a co-solvent for the reaction.
[4.] 3-(1H-Imidazol-1-yl)azetidine dihydrochloride used as the starting material was prepared by treatment of 1-(t-butoxycarbonyl)-3-(1H-imidazol-1-yl) azetidine with hydrogen chloride in dichloromethane by the method described in International Patent Publication No. WO93/19059.
[5.] (S)-enantiomer prepared.
[6.] Additional quantities of the azetidine starting material(ca. 1 mol. equiv.) triethylamine(ca. 2 mol. equiv.) and tetrahydrofuran, followed by sodium triacetoxyborohydride(ca. 1.5 mol. equiv.) and glacial acetic acid, were added later to drive the reaction towards completion. Methanol/dichloromethane was used as the column eluant.
[7.] A gradient elution was performed using dichloromethane followed by dichloromethane/methanol as the column eluant.
[8.] A gradient elution was initially performed using ethyl acetate followed by ethyl acetate/methanol as the column eluant and this was then changed to dichloromethane/methanol in the later stages.
[9.] 3-(4-Aminosulphonylpiperazin-1-yl)azetidine bistrifluoroacetate(see Preparation 154) was used as the starting material.
[10.] The crude reaction product was purified as the trifluoroacetate salt by chromatography on silica gel eluting with dichloromethane: methanol: 0.880 aqueous ammonia solution(89:10:1, by volume). The purified salt was treated with 10% aqueous potassium carbonate solution and the aqueous layer extracted several times with ethyl acetate. The combined organic extracts were dried(Na₂SO₄) and concentrated under reduced pressure to give the required product.
[11.] Purified by reverse phase chromatography using MCI gel(trade mark)(a high porous polystyrene polymer CHP 20P [75-150 μ] using methanol followed by methanol:water as the eluant.
[12.] (R)-enantiomer prepared.
[13.] The ditrifluoroacetate salt of the azetidine starting material was used.
[14.] Reference Example only.
[15.] The dihydrochloride salt of the azetidine starting material was used.

-continued

| Ex. No. | R | R¹ | -x¹-R² | m.p. | LRMS m/z | Analysis/¹H-NMR |
|---|---|---|---|---|---|---|

[16.] A gradient elution was performed using dichloromethane:methanol followed by dichloromethane:methanol:concentrated aqueous ammonia solution as the eluant.
[17.] $[\alpha]_D^{25}$ + 48.9° (c = 0.0009 in methanol)

EXAMPLE 60

5-(3,4-Dichlorophenyl)-1-(3-methoxybenzyl)-5-(2-[3-morpholinoazetidin-1-yl]ethyl)-2-piperidone

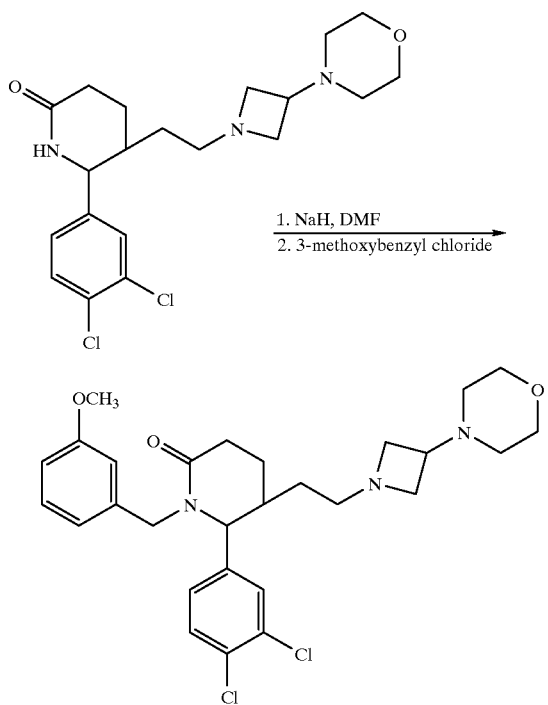

1. NaH, DMF
2. 3-methoxybenzyl chloride

To a solution of the piperidone (see Example 1) (350 mg, 0.85 mmol) in dry N,N-dimethylformamide (5 ml) under nitrogen was added 60% w/w sodium hydride dispersion in oil (37 mg, 1.05 mol. equiv.) and the mixture was stirred at room temperature for thirty minutes. After this time, 3-methoxybenzyl chloride (0.13 ml, 1.05 mol. equiv.) was added and the mixture was stirred for five minutes. Water (1 ml) was then added followed by saturated aqueous sodium bicarbonate solution (20 ml) and saturated aqueous ammonium chloride solution (20 ml). The mixture was extracted with ethyl acetate (2×20 ml) and the combined organic layers washed with saturated aqueous ammonium chloride solution (2×20 ml) and then dried over magnesium sulphate. Filtration and removal of the solvent from the filtrate under reduced pressure gave a gum which was chromatographed on silica gel eluting with a solvent gradient of methanol:dichloromethane (1:19 to 1:9, by volume) to give the title compound (140 mg). TLC $R_f$=0.45 (silica, methanol:dichloromethane, 1:9, by volume). LRMS m/z= 532(m)⁺. Found: C, 62.07; H, 6.74; N, 7.19. $C_{28}H_{35}Cl_2N_3O_3$. 0.1 $CH_2Cl_2$ requires C, 62.39; H, 6.56; N, 7.77%.

¹H-NMR (CDCl₃):δ=1.50–2.90 (m,16H), 3.25–3.80 (m,7H), 3.80 (s,3H), 4.30 (d,1H), 4.80 (d,1H), 6.80–6.90 (m,4H), 7.05 (d,1H), 7.25–7.30 (m,2H) ppm.

EXAMPLES 61 to 75

The compounds of the following tabulated Examples of the general formula:

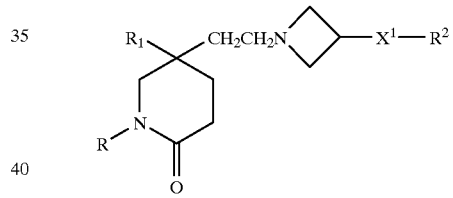

were prepared by a similar method to that of Example 60 (with heating of the reaction mixture, H necessary) using the appropriate piperidone (see Example 1) and chloro, bromo or methanesulphonyloxyalkane derivatives as the starting materials.

| Ex No. | R | R¹ | -x¹-R² | m.p. | LRMS m/z | Analysis/¹H-NMR |
|---|---|---|---|---|---|---|
| 61[3] | SO₂N(CH₃)₂ | (4-methyl-3-chlorophenyl)CH₂— (as drawn: benzyl with Cl, Cl substituents) | morpholinyl (as drawn) | — | 609 (m + 1)⁺ | Found: C, 56.15; H, 6.17; N, 8.45. $C_{29}H_{38}Cl_2N_4O_4S.0.15CH_2Cl_2$ requires C, 56.26; H, 6.20; N, 9.00%. ¹H-NMR(CDCl₃): δ = 1.4–1.8 (m, 3H), 1.95–2.4(m, 9H), 2.4–2.6 (m, 1H), 2.6–3.0(m, 8H), 3.25 – 3.4(m, 3H), 3.6–3.80(m, 5H), 4.55(d, 1H), 4.8(d, 1H), 6.9–6.95(m, 1H), 7.1(d, 1H), 7.25–7.4(m, 1H), 7.5–7.55(m, 2H), 7–7.8(m, 2H) ppm. |

-continued

| Ex No. | R | R¹ | -x¹-R² | m.p. | LRMS m/z | Analysis/¹H-NMR |
|---|---|---|---|---|---|---|
| 62[3] | 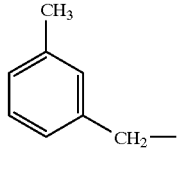 | 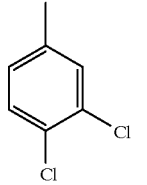 | 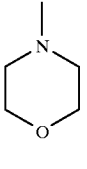 | — | 516 (m)⁺ | ¹H-NMR(CDCl₃): δ = 1.5–1.8 (m, 3H), 1.95–2.55(m, 12H), 2.6–2.75(m, 2H), 2.8–2.95(m, 1H), 3.2–3.35(m, 3H), 3.55–3.75(m, 5H), 4.35(d, 1H), 4.8(d, 1H), 6.8–6.85 (m, 1H), 7.05–7.3(m, 6H) ppm. |
| 63[3] | 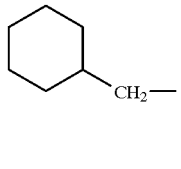 | 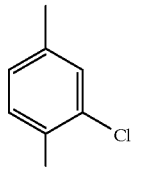 | 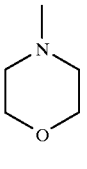 | 56–62° C. | 508 (m + 1)⁺ | Found: C, 62.87; H, 7.59; N, 7.95. $C_{27}H_{39}Cl_2N_3O_2 \cdot 0.1CH_2Cl_2$ requires C, 62.96; H, 7.64; N, 8.13%. ¹H-NMR(CDCl₃): δ = 0.9–1.1 (m, 2H), 1.15–1.35(m, 3H), 1.45–1.85(m, 8H), 1.95–2.4(m, 10H), 2.7–2.8(m, 2H), 2.85–2.95(m, 1H), 3.10–3.2(m, 1H), 3.3–3.4(m, 4H), 3.55(d, 1H), 3.65–3.75(m, 4H), 7.05–7.1(m, 1H), 7.25–7.35(m, 1H), 7.35–7.4(m, 1H) ppm. |
| 64[3] | 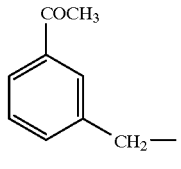 | 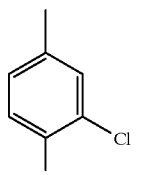 | 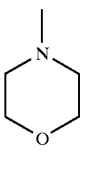 | — | 544 (m + 1)⁺ | ¹H-NMR(CDCl₃): δ =1.5–1.85 (m, 3H), 1.95–2.3(m, 8H), 2.4–2.55 (m, 1H), 2.6–2.7(m, 5H), 2.7–2.95 (m, 1H), 3.25–3.4(m, 3H), 3.5–3.7 (m, 5H), 4.4(d, 1H), 4.9(d, 1H), 6.8–6.9(m, 1H), 7.0–7.05(m, 1H), 7.3 (s, 1H), 7.5–7.55(m, 2H), 7.9–7.95 (m, 2H) ppm. |
| 65[3] | 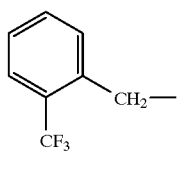 | 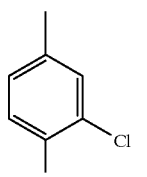 | 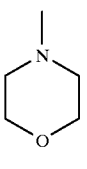 | — | 570 (m + 1)⁺ | Found: C, 58.09; H, 5.54; N, 8.57. $C_{28}H_{32}Cl_2N_3O_2F_3 \cdot 0.06CH_2Cl_2$ requires C, 58.54; H, 5.62; N, 7.30%. ¹H-NMR(CDCl₃): δ = 1.5–1.8 (m, 3H), 1.95–2.15(m, 3H), 2.2–2.4 (m, 5H), 2.5–2.75(m, 3H), 2.85–2.9 (m, 1H), 3.3–3.35(m, 3H), 3.5–3.6 (m, 1H), 3.65–3.7(m, 4H), 4.65 (d, 1H), 5.0(d, 1H), 6.9–7.75(m, 7H) ppm. |
| 66[2] | 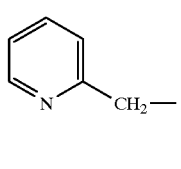 | 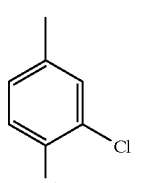 | 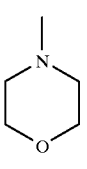 | — | 503 (m + 1)⁺ | ¹H-NMR(CDCl₃): δ = 1.55–2.5 (m, 12H), 2.65–2.8(m, 2H), 2.8–3.0 (m, 1H), 3.3–3.5(m, 3H), 3.65–3.9 (m, 5H), 4.5(d, 1H), 4.9(d, 1H), 6.9–7.0(m, 1H), 7.15–7.4(m, 4H), 7.6–7.7(m, 1H), 8.6–8.8(m, 1H) ppm. |
| 67[2] | 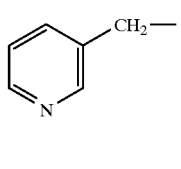 | 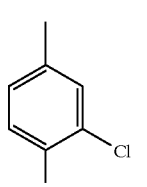 | 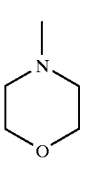 | — | 503 (m + 1)⁺ | Found: C, 60.96; H, 6.25; N, 10.88. $C_{26}H_{32}Cl_2N_4O_2 \cdot 0.15CH_2Cl_2$ requires C, 60.84; H, 6.31; N, 10.85%. ¹H-NMR(CDCl₃): δ = 1.45–1.6 (m, 1H), 1.6–1.8(m, 2H), 1.95–2.1 (m, 3H), 2.1–2.3(m, 5H), 2.4–2.5 (m, 1H), 2.65–2.7(m, 2H), 2.8–2.9 (m, 1H), 3.25–3.4(m, 3H), 3.5–3.6 (m, 1H), 3.6–3.75(m, 4H), 4.4 (d, 1H), 4.8(d, 1H), 6.8–6.9(d, 1H), 7.05(s, 1H), 7.25–7.35(m, 2H), 7.6–7.7(d, 1H), 8.5–8.6(m, 2H) ppm. |

-continued

| Ex No. | R | R¹ | -x¹-R² | m.p. | LRMS m/z | Analysis/¹H-NMR |
|---|---|---|---|---|---|---|
| 68[2] | 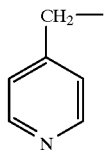 | 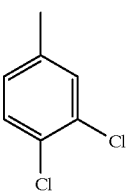 | 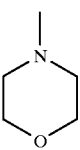 | 52–58° C. | 503 (m + 1)⁺ | Found: C, 60.11; H, 6.49; N, 10.72. $C_{26}H_{32}Cl_2N_4O_2 \cdot 0.15$ $CH_2Cl_2$ requires C, 60.84; H, 6.31; N, 10.85%. ¹H-NMR(CDCl₃): δ = 1.5–1.8 (m, 3H), 1.95–2.4(m, 8H), 2.4–2.55 (m, 1H), 2.65–2.75(m, 2H), 2.8–2.9 (m, 1H), 3.25–3.4(m, 3H), 3.5–3.7 (m, 5H), 4.45(d, 1H), 4.7(m, 1H), 6.9–6.95(m, 1H), 7.1–7.35(m, 4H), 8.6–8.65(m, 2H) ppm. |
| 69[3] | 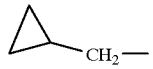 | 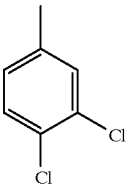 | 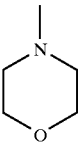 | — | 468 (m + 1)⁺ | Found: C, 60.94; H, 7.15; N, 9.99. $C_{24}H_{33}Cl_2N_3O_2 \cdot 0.08CH_2Cl_2$ requires C, 61.11; H, 7.06; N, 8,88%. ¹H-NMR(CDCl₃): δ = 0.25–0.4 (m, 2H), 0.55–0.7(m, 2H), 1.0–1.15 (m, 1H), 1.6–1.7(m, 1H), 1.8–1.9 (m, 1H), 1.95–2.4 (m, 10H), 2.7–2.8 (m, 2H), 2.85–3.0(m, 1H), 3.15–3.2 (m, 1H), 3.3–3.5(m, 4H), 3.75–3.8 (m, 5H), 7.15–7.45(m, 3H) ppm. |
| 70[4] | 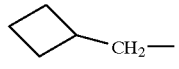 | 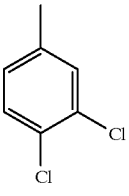 | 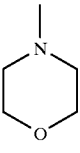 | — | 480 (m + 1)⁺ | Found: C, 61.75; H, 7.63; N, 8.77. $C_{25}H_{35}Cl_2N_3O_2 \cdot 0.05CH_2Cl_2$ requires C, 62.07; H, 7.30; N, 8.67%. ¹H-NMR(CDCl₃): δ = 1.55–2.4 (m, 18H), 2.6–2.8(m, 3H), 2.85–2.95 (m, 1H), 3.3–3.75(m, 10H), 7.05–7.45(m, 3H) ppm. |
| 71[4] | 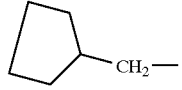 | 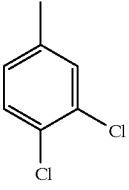 | 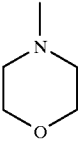 | — | 494 (m + 1)⁺ | Found: C, 61.89; H, 7.45; N, 8.11. $C_{26}H_{37}Cl_2N_3O_2 \cdot 0.05CH_2Cl_2$ requires C, 62.73; H, 7.50; N, 8.43%. ¹H-NMR(CDCl₃): δ = 1.15–1.3 (m, 2H), 1.45–2.4(m, 19H), 2.7–2.75 (m, 2H), 2.85–2.95(m, 1H), 3.2–3.7 (m, 10H), 7.1–7.4(m, 3H) ppm. |
| 72[4] | 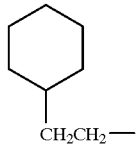 | 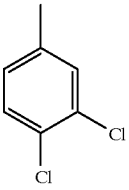 | 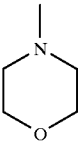 | 52–60° C. | 522 (m + 1)⁺ | Found: C, 63.50; H, 8.18; N, 7.89. $C_{28}H_{41}Cl_2N_3O_2 \cdot 0.1CH_2Cl_2$ requires C, 63.55; H, 7.82; N, 7.91%. ¹H-NMR(CDCl₃): δ = 0.85–1.0 (m, 2H), 1.1–1.3(m, 4H), 1.4–1.5 (m, 2H), 1.55–1.85(m, 8H), 1.95–2.4 (m, 9H), 2.65–2.75(m, 2H), 2.85–2.95(m, 1H), 3.3–3.7(m, 10H), 7.05–7.45(m, 3H) ppm. |
| 73[4] | 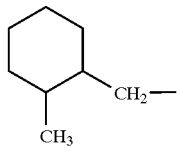 | 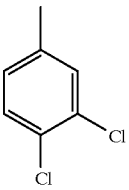 | 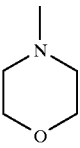 | 50–61° C. | 522 (m + 1)⁺ | Found: C, 64.71; H, 7.94; N, 7.98. $C_{28}H_{41}Cl_2N_3O_2 \cdot 0.08CH_2Cl_2$ requires C, 63.71; H, 7.84; N, 7.94%. ¹H-NMR(CDCl₃): δ = 0.9–1.15 (m, 4H), 1.15–1.4(m, 4H), 1.4–1.55 (m, 2H), 1.55–1.95(m, 6H), 1.95–2.3 (m, 9H), 2.3–2.5(m, 1H), 2.7–2.8 (m, 2H), 2.85–3.0(m, 1H), 3.2–3.5 (m, 4H), 3.5–3.6(m, 1H), 3.65–3.75 (m, 4H), 7.05–7.1(m, 1H), 7.3–7.35 (s, 1H), 7.4–7.45(d, 1H) ppm. |

-continued

| Ex No. | R | R¹ | -x¹-R² | m.p. | LRMS m/z | Analysis/¹H-NMR |
|---|---|---|---|---|---|---|
| 74[4] | cyclohexyl-CH(CH₃)- | 3,4-dichlorophenyl | morpholinomethyl | — | 522 (m + 1)⁺ | Found: C, 62.37; H, 7.89; N, 7.70. $C_{28}H_{41}Cl_2N_3O_2.0.2\ CH_2Cl_2$ requires C, 62.77; H, 7.73; N, 7.79%. ¹H-NMR (CDCl₃): δ = 0.8–1.5 (m, 10H), 1.5–2.05(m, 7H), 2.05–2.2 (m, 9H), 2.4–2.5(m, 1H), 2.65–2.8 (m, 2H), 2.85–3.1(m, 2H), 3.15–3.25 (s, 1H), 3.3–3.5(m, 2H), 3.8–3.95 (m, 4H), 7.1–7.2(m, 1H), 7.3–7.45 (m, 2H) ppm. |
| 75[1,3] | phenyl-CH(CH₃)- | 3,4-dichlorophenyl | morpholinomethyl | — | 516 (m + 1)⁺ | Enantiomeric pair A ¹H-NMR(CDCl₃): δ = 1.2–1.4 (m, 1H), 1.5–1.65(m, 3H), 1.75–2.15 (m, 4H), 2.15–2.35(m, 4H), 2.35–2.4 (m, 1H), 2.4–2.5(m, 1H), 2.5–2.6 (m, 2H), 2.75–2.9(m, 2H), 3.2–3.3 (m, 2H), 3.3–3.4(d, 1H), 3.6–3.8 (m, 4H), 6.15–6.25(m, 1H), 6.95–7.05(d, 1H), 7.25–7.5(m, 8H), ppm. |
| | | | | | 516 (m + 1)⁺ | Enantiomeric pair B Found: C, 61.84; H, 6.81; N, 7.02. $C_{28}H_{35}Cl_2N_3O_2.0.3CH_2Cl_2$ requires C, 62.71; H, 6.62; N, 7.75%. ¹H-NMR (CDCl₃): δ = 1.2–1.4 (m, 1H), 1.5–1.75(m, 4H), 1.75–2.1 (m, 4H), 2.1–2.35(m, 6H), 2.35–2.5 (m, 1H), 2.6–2.75(m, 2H), 2.8–2.95 (m, 1H), 3.1–3.2(d, 1H), 3.3–3.4 (m, 2H), 3.6–3.75(m, 4H), 6.15–6.25 (m, 1H), 6.35–6.4(d, 1H), 7.05–7.1 (d, 1H), 7.25–7.4(m, 6H) ppm. |

Footnotes
[1]·The two pairs of enantiomers in the product obtained after the work-up were separated by chromatography on silica gel eluting with a solvent gradient of methanol:dichloromethane (1:19 to 1:9). Enantiomeric pair A eluted first followed by the more polar enantiomeric pair B.
[2]·Chloroalkane derivative used as the starting material.
[3]·Bromoalkane derivative used as the starting material.
[4]·Methanesulphonyloxyalkane derivative used as the starting material.

EXAMPLE 76

1-Cycloheptylmethyl-5-(3,4-dichlorophenyl)-5-(2-[3-morpholinoazetidin-1-yl]ethyl)-2-piperidone

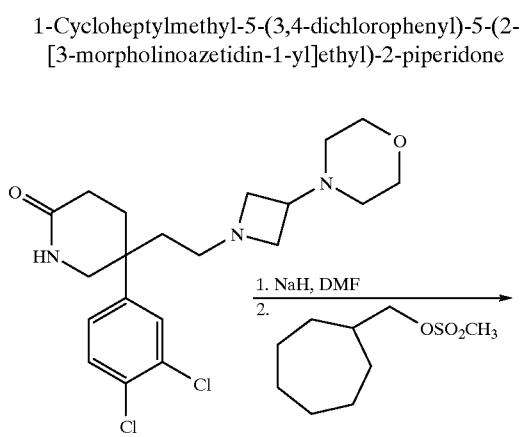

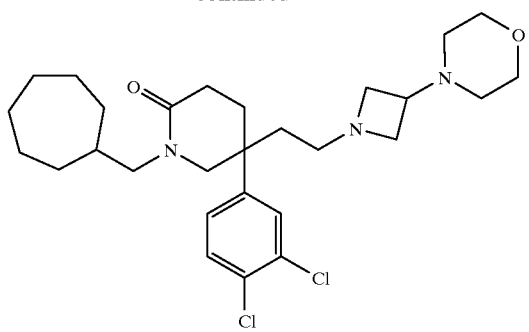

To a solution of the piperidone (see Example 1) (200 mg, 0.49 mmol) in dry N,N-dimethylformamide (3.5 ml) at 0° C. under nitrogen was added 60% w/w sodium hydride dispersion in oil (21 mg, 1.1 mol. equiv.) and the mixture was allowed to warm to room temperature over one hour. After this time, a solution of methanesulphonyloxymethylcycloheptane (see Preparation 13) (120 mg, 1.2 mol. equiv.) in dry N,N-dimethylformamide (0.5 ml) was added and the mixture was heated to 50° C. To effect complete reaction of the starting piperidone the mixture was cooled, further portions of sodium hydride (0.5 mol. equiv.) and the starting mesylate (0.5 mol. equiv.) were then added and the reaction was heated to 50° C. for two hours. The reaction was cooled to 0° C., water (1 ml) added and the dimethylformamide removed under reduced pressure. The residue was extracted with ethyl acetate (3×20 ml), and the combined extracts were dried over magnesium sulphate. Filtration and removal of the solvent from the filtrate under reduced pressure gave a foam which was chromatographed using silica gel eluting with a solvent gradient of dichloromethane:methanol (100:0 to 85:15, by volume) to give the title compound (120 mg). TLC $R_f$=0.45 (silica, methanol:dichloromethane, 1:9 by volume). LRMS m/z 522 (m+1)$^+$. Found: C, 62.11; H, 7.63; N, 7.55. $C_{28}H_{41}Cl_2N_3O_2.0.2\ CH_2Cl_2$ requires C, 62.78; H, 7.73; N, 7.79%.

$^1$H-NMR (CDCl$_3$):δ=1.1–1.3 (m,2H), 1.35–1.8 (m,11H), 1.8–1.95 (m,2H), 1.95–2.1 (m,1H), 2.1–2.35 (m,7H), 2.35–2.5 (m,1H), 2.75–2.95 (m,2H), 2.95–3.0 (m,2H), 3.05–3.2 (m,2H), 3.25–3.45 (m,2H), 3.45–3.6 (m,2H), 3.6–3.75 (m,4H), 7.05–7.1 (m,1H), 7.3–7.35 (m,1H), 7.4–7.45 (m,1H) ppm.

EXAMPLE 77

5-(3,4-Dichlorophenyl)-5-(2-[3-morpholinoazetidin-1-yl]ethyl)-1-(4-phenylbenzyl)-2-piperidone

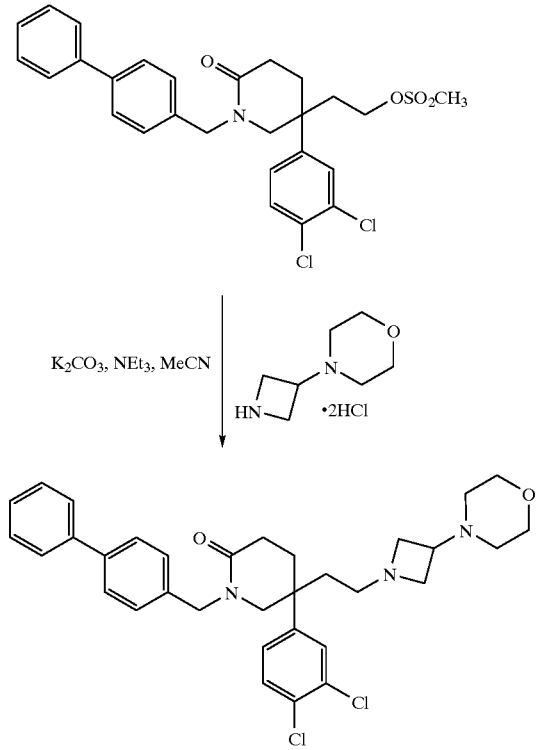

To a solution of the mesylate (see Preparation 35) (290 mg, 0.55 mmol) in dry acetonitrile (10 ml) was added 3-morpholinoazetidine dihydrochloride (see Preparation 56) (200 mg, 2.0 mol. equiv.) followed by triethylamine (0.15 ml, 2 mol. equiv.) and potassium carbonate (150 mg, 2 mol. equiv.). The mixture was heated under reflux for four hours. After this time, the reaction was cooled, water (1 ml) was added, the mixture was evaporated to dryness under reduced pressure and the residue taken up in a mixture of dichloromethane (10 ml) and water (10 ml). The organic phase was separated, washed with brine (10 ml), dried over magnesium sulphate, filtered, and the solvent removed from the filtrate under reduced pressure to give a gum which was chromatographed on silica gel eluting with a solvent gradient of methanol:dichloromethane (1:19 to 1:9, by volume) to give the title compound (85 mg). TLC $R_f$=0.47 (silica, methanol:dichloromethane, 1:9, by volume). m.p. 72–82° C. LRMS m/z=578 (m+1)$^+$. Found: C, 67.56; H, 6.27; N, 7.24. $C_{33}H_{37}Cl_2N_3O_2.0.13\ CH_2Cl_2$ requires C, 67.53; H, 6.37; N, 7.13%.

$^1$H-NMR (CDCl$_3$):δ=1.5–1.8 (m,3H), 1.95–2.3 (m,8H), 2.4–2.55 (m,1H), 2.6–2.75 (m,2H), 2.8–2.9 (m,1H), 3.3–3.35 (m,3H), 3.55–3.7 (m,5H), 4.4 (d,1H), 4.9 (d,1H), 6.85–6.9 (m,1H), 7.1 (s,1H), 7.25–7.7 (m,10H) ppm.

EXAMPLES 78 to 96

The compounds of the following tabulated Examples of the general formula:

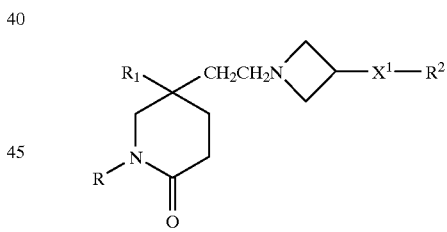

were prepared by a similar method to that of Example 77 using the appropriate mesylate (see Preparations 33, 34, 36, 37 and 38) and the appropriate azetidine (see Preparations 56, 68, 77, 81, 82, 83, 86, 87, 88, 119, 134, 154, 179 and 181) starting materials.

| Ex. No. | R | R¹ | —X¹—R² | m.p. | LRMS m/z | Analysis/¹H-NMR |
|---|---|---|---|---|---|---|
| 78 | 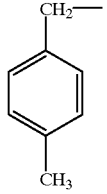 | 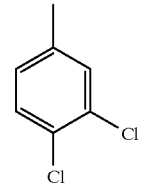 | 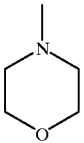 | — | 515 (m)⁺ | Found: C, 64.60; H, 6.68; N, 10.19. $C_{28}H_{35}Cl_2N_3O_2$ requires C, 65.11; H, 6.83; N, 8.14%. ¹H-NMR(CDCl₃): δ = 1.5–1.75 (m,3H), 1.95–2.3(m,8H), 2.35–2.5 (m,4H), 2.6–2.7(m,2H), 2.8–2.9 (m,1H), 3.2–3.35(m,3H), 3.45–3.5 (m,1H), 3.65–3.7(m,4H), 4.3 (d,1H), 4.8(d,1H), 6.8–6.85 (m,1H), 7.0–7.3(m,6H) ppm. |
| 79 | 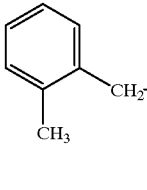 | 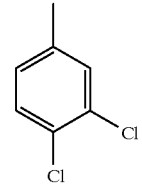 | 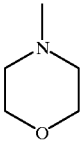 | — | 515 (m)⁺ | Found: C, 64.74; H, 6.78; N, 8.32. $C_{28}H_{35}Cl_2N_3O_2$ requires C, 65.11; H, 6.83; N, 8.14%. ¹H-NMR(CDCl₃): δ = 1.45–1.6 (m,1H), 1.6–1.8(m,2H), 1.95–2.1 (m,4H), 2.1–2.5(m,8H), 2.6–2.7 (m,2H), 2.8–2.9(m,1H), 3.1–3.2 (m,1H), 3.25–3.35(m,2H), 3.5–3.55 (m,1H), 3.7–3.75(m,4H), 4.35 (d,1H), 5.0(d,1H), 6.75–6.8 (m,1H), 7.0–7.05(m,1H), 7.15–7.3 (m,5H) ppm. |
| 80[1] | 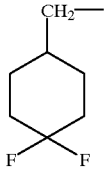 | 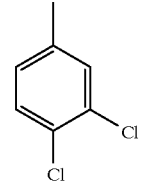 | 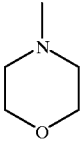 | — | 545 (m + 1)⁺ | ¹H-NMR(CDCl₃): δ = 1.2–1.45 (m,2H), 1.6–1.9(m,6H), 1.95–2.35 (m,13H), 2.7–2.8(m,2H), 2.85–3.0 (m,1H), 3.15–3.25(m,1H), 3.3–3.45 (m,4H), 3.5–3.6(d,1H), 3.65–3.7 (m,4H), 7.05–7.1(d,1H), 7.3–7.35 (s,1H), 7.4–7.45(d,1H) ppm. |
| 81[1] | 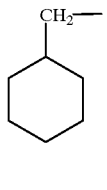 | 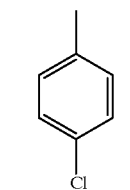 | 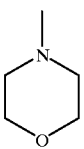 | — | 474 (m + 1)⁺ | ¹H-NMR(CDCl₃): δ = 0.95–1.1 (m,2H), 1.15–1.3(m,4H), 1.5–1.85 (m,10H), 1.95–2.4(m,6H), 2.7–2.8 (m,2H), 2.9–2.95(m,1H), 3.05–3.15 (m,1H), 3.3–3.7(m,10H), 7.15–7.35 (m,4H) ppm. |
| 82[2,3] | 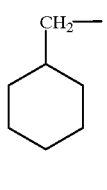 | 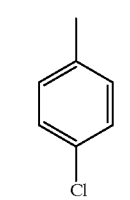 | 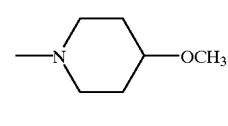 | — | 502.8 (m + 1)⁺ | Found: C, 64.27; H, 8.59; N, 7.78. $C_{29}H_{44}ClN_3O_2 \cdot 0.6\ CH_2Cl_2$ requires: C, 64.27; H, 8.25; N, 7.60%. ¹H-NMR(CDCl₃): δ = 0.9–1.1 (m,2H), 1.1–1.3(m,2H), 1.5–2.2 (m,19H), 2.3–2.6(m,3H), 2.6–2.8 (m,2H), 2.8–2.85(m,1H), 3.0–3.1 (m,1H), 3.15–3.3(m,1H), 3.3–3.6 (m,9H), 7.1–7.2(m,2H), 7.2–7.4 (m,2H) ppm. |
| 83[2,3] | 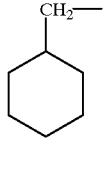 | 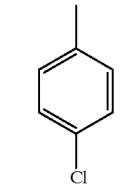 | 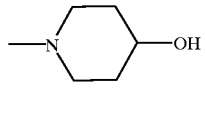 | — | 488.9 (m + 1)⁺ | ¹H-NMR(CDCl₃): δ = 0.9–1.05 (m,2H), 1.1–1.3(m,4H), 1.5–2.2 (m,20H), 2.3–2.4(m,1H), 2.45–2.6 (m,2H), 2.6–2.8(m,2H), 2.8–2.9 (m,1H), 2.0–3.1(m,1H), 3.3–3.6 (m,4H), 3.6–3.8(m,1H), 7.15 (d,2H), 7.3(d,2H) ppm. |

-continued

| Ex. No. | R | R¹ | —X¹—R² | m.p. | LRMS m/z | Analysis/¹H-NMR |
|---|---|---|---|---|---|---|
| 84[2,4] | 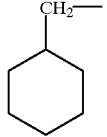 | 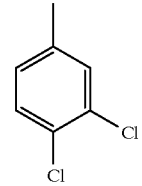 | 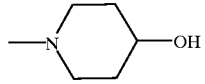 | — | 522 (m + 1)⁺ | Found: C, 61.71; H, 8.00; N, 7.63. $C_{28}H_{41}Cl_2N_3O_2 \cdot 0.31\, CH_2Cl_2$ requires: C, 61.93; H, 7.64; N, 7.65%. ¹H-NMR(CDCl₃): δ = 0.9–1.1 (m,2H), 1.1–1.5(m,4H), 1.5–2.3 (m,19H), 2.35–2.45(m,1H),2.5–2.6 (m,2H), 2.65–2.75(m,2H), 2.8–2.9 (m,1H), 3.1–3.3(m,1H), 3.3–3.4 (m,4H), 3.5–3.6(m,1H), 3.65–3.75 (m,1H), 7.05(d,1H), 7.2–7.25 (m,1H), 7.3(d,1H) ppm. |
| 85[2,4] | 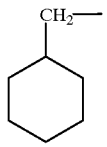 | 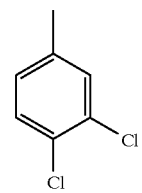 | 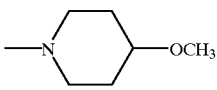 | — | 536 (m)⁺ | Found: C, 64.06; H, 7.81; N, 7.58. $C_{29}H_{43}N_3Cl_2O_2 \cdot 0.125\, CH_2Cl_2$ requires; C, 63.93; H, 7.97; N, 7.68%. ¹H-NMR(CDCl₃): δ = 0.9–1.1 (m,2H), 1.1–1.3(m,3H), 1.5–2.2 (m,19H), 2.3–2.6(m,3H), 2.6–2.75 (m,2H), 2.8–2.9(m,1H), 3.1–3.25 (m,2H), 3.25–3.45(m,7H), 3.5–3.6 (m,1H), 7.05(d,1H), 7.2–7.3 (m,1H), 7.35–7.4(m,1H) ppm. |
| 86[2,4] | 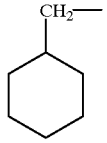 | 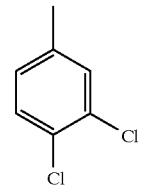 | 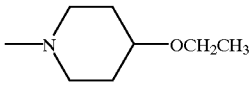 | — | 550 (m)⁺ | Found: C, 64.21; H, 8.03; N, 7.37. $C_{30}H_{45}N_3Cl_2O_2 \cdot 0.125\, CH_2Cl_2$ requires: C, 64.47; H, 8.03; N, 7.49%. ¹H-NMR(CDCl₃): 0.9–1.1(m,2H), 1.1–1.35(m,6H), 1.5–2.2(m,19H), 2.3–2.5(m,1H), 2.5–2.6(m,2H), 2.6–2.75(m,2H), 2.8–2.95(m,1H), 3.1–3.2(m,1H), 3.2–3.6(m,8H), 7.05 (d,1H), 7.2–7.25(m,1H), 7.4(d,1H) ppm. |
| 87[2,4] | 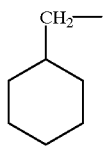 | 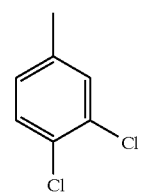 | 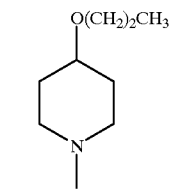 | — | 565 (m + 1)⁺ | ¹H-NMR(CDCl₃): δ = 0.9–1.1 (m,4H), 1.1–1.25(m,3H), 1.5–2.2(m,23H), 2.3–2.5(m,1H), 2.5–2.6(m,2H), 2.6–2.8(m,2H), 2.8–2.95(m,1H), 3.1–3.2(m,1H), 3.25–3.5(m,6H), 3.5–3.6(m,1H), 7.05 (d,1H), 7.3–7.35(m,1H), 7.4–7.45 (m,1H) ppm. |
| 88[4,5] | 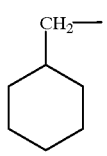 | 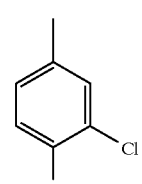 | 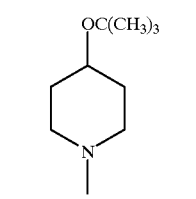 | — | 578 (m)⁺ | ¹H-NMR(CDCl₃): δ = 0.9–1.0 (m,1H), 1.15(s,9H), 1.4–1.8 (m,17H), 1.8–2.2(m,6H), 2.3–2.45 (m,1H), 2.5–2.6(m,2H), 2.65–2.8 (m,2H), 2.8–3.0(m,1H), 3.2–3.4 (m,1H), 3.3–3.45(m,5H), 3.5–3.6(m,1H), 7.05(d,1H), 7.3–7.35 (m,1H), 7.4–7.45(m,1H) ppm. |
| 89[2,3] | 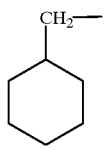 | 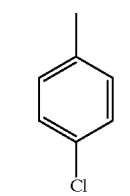 | 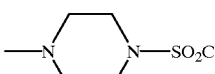 | — | 551 (m)⁺ | ¹H-NMR(CDCl₃): δ = 0.9–1.0 (m,4H), 1.1–1.3(m,5H), 1.5–1.9 (m,7H), 1.9–2.25(m,5H), 2.3–2.4 (m,4H), 2.75(s,3H), 2.95–3.1 (m,2H), 3.1–3.3(m,4H), 3.3–3.6 (m,5H), 7.15(d,2H), 7.35(d,2H) ppm. |

-continued

| Ex. No. | R | R¹ | —X¹—R² | m.p. | LRMS m/z | Analysis/¹H-NMR |
|---|---|---|---|---|---|---|
| 90[2,4] | cyclohexyl-CH₂— | 3,4-dichlorophenyl | N-methylpiperazinyl-SO₂CH₃ | — | 586 (m + 1)⁺ | Found: C, 56.54; H, 7.42; N, 8.78. C₂₈H₄₂N₄O₃SCl₂.0.188 CH₂Cl₂ requires: C, 56.28; H, 7.10; N, 9.31%. ¹H-NMR(CDCl₃): δ = 0.9–1.1 (m,2H), 1.1–1.35(m,3H), 1.5–1.9 (m,8H), 1.9–2.3(m,5H), 2.3–2.5 (m,5H), 2.7–2.8(m,5H), 2.9–3.05 (m,1H), 3.1–3.3(m,5H), 3.3–3.5 (m,4H), 3.5–3.6(m,1H), 7.05 (d,1H), 7.3–7.35(m,1H), 7.4(d,1H) ppm. |
| 91[2,4] | cyclohexyl-CH₂— | 3,4-dichlorophenyl | N-methylpiperazinyl-CO-phenyl | — | 611 (m + 1)⁺ | ¹H-NMR(CDCl₃): δ = 0.9–1.05 (m,2H), 1.1–1.25(m,3H), 1.5–1.85 (m,8H), 1.95–2.45(m,10H), 2.65–2.75(m,2H), 1.85–1.95(m,1H), 3.1–3.2(m,1H), 3.3–3.4(m,5H), 3.5–3.55 (m,2H), 3.6–3.85(m,2H), 7.05–7.1 (m,1H), 7.3–7.4(m,7H) ppm. |
| 92[2,4] | cyclohexyl-CH₂— | 3,4-dichlorophenyl | N-methylpiperazinyl-NSO₂NH₂ | — | 586 (m + 1)⁺ | Found: C, 51.52; H, 6.60; N, 11.09. C₂₇H₄₁Cl₂N₅O₃S.0.63 CH₂Cl₂ requires: C, 51.86; H, 6.70; N, 10.95%. ¹H-NMR(CDCl₃): δ = 0.95–1.05 (m,2H), 1.1–1.3(m,3H), 1.55–1.85 (m,8H), 1.95–2.25(m,5H), 2.35–2.45(m,5H), 2.7–2.75(m,2H), 2.9–2.95(m,1H), 3.1–3.25(m,5H), 3.3–3.4(m,4H), 3.5–3.55(m,1H), 4.35 (br.s,2H), 7.05–7.10(m,1H), 7.25–7.45(m,2H) ppm. |
| 93[2,4] | cyclohexyl-CH₂— | 3,4-dichlorophenyl | N-methylpiperazinyl-CONHCH₃ | — | 564 (m + 1)⁺ | Found: C, 58.33; H, 7.37; N, 11.67. C₂₉H₄₃Cl₂N₅O₂.0.5 CH₂Cl₂ requires: C, 58.30; H, 7.31; N, 11.54%. ¹H-NMR(CDCl₃): δ = 0.95–1.05 (m,2H), 1.15–1.30(m,3H), 1.5–1.8(m,8H), 1.95–2.30(m,9H), 2.3–2.4(m,1H), 2.65–2.75(m,2H), 2.8–2.85(m,3H), 2.9–2.95(m,1H), 3.1–3.2(m,1H), 3.3–3.4(m,8H), 3.5–3.55(m,1H), 4.35–4.4(m,1H), 7.05–7.1(m,1H), 7.25–7.4(m,2H) ppm. |
| 94[2,4] | cyclohexyl-CH₂— | 3,4-dichlorophenyl | N-methylpiperidinyl-benzoxazol-2-yl | — | 624 (m + 1)⁺ | ¹H-NMR(CDCl₃): δ = 0.95–1.1 (m,2H), 1.15–1.3(m,3H), 1.5–1.8 (m,10H), 1.95–2.25(m,11H), 2.35–2.45(m,1H), 2.7–2.8(m,3H), 2.9–3.0(m,1H), 3.1–3.2(m,1H), 3.3–3.55(m,5H), 7.1–7.7(m,7H) ppm. |

-continued

| Ex. No. | R | R¹ | —X¹—R² | m.p. | LRMS m/z | Analysis/¹H-NMR |
|---|---|---|---|---|---|---|
| 95[4,5] | 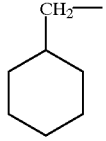 | 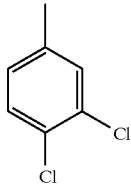 | 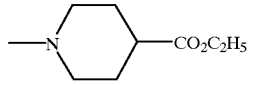 | — | — | ¹H-NMR(CDCl₃): δ = 0.95–1.1 (m,2H), 1.15–1.3(m,6H), 1.55–2.3(m,20H), 2.35–2.45(m,1H), 2.6–2.75(m,4H), 2.8–2.9(m,1H), 3.1–3.2(m,1H), 3.3–3.5(m,4H), 3.55–3.6(m,1H), 4.05–4.15(m,2H), 7.05–7.1(m,1H), 7.25–7.45(m,2H) ppm. |
| 96[2,4] | 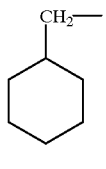 | 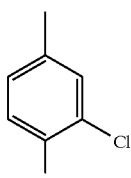 | 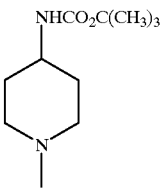 | — | 621 (m + 1)⁺ | Found: C, 61.30; H, 7.91; N, 8.44. $C_{33}H_{50}Cl_2N_4O_3 \cdot 0.38\ CH_2Cl_2$ requires: C, 61.33; H, 7.83; N, 8.57%. ¹H-NMR(CDCl₃): δ = 0.9–2.2 (m,35H), 2.3–2.45(m,1H), 2.55–2.7(m,2H), 2.8–2.9(m,1H), 3.1–3.15(m,1H), 3.3–3.55(m,6H), 4.35(br. s, 1H), 7.05–7.1(m,1H), 7.25–7.4(m,2H) ppm. |

Footnotes
[1] 3 mol. equiv. of the azetidine derivative starting material and 3 mol. equiv. of triethylamine were used in the reaction.
[2] The ditrifluoroacetate salt of the azetidine starting material was used.
[3] 10 mole equivalents of potassium carbonate were used instead of triethylamine as the acid acceptor.
[4] About 2.5 mole equivalents of potassium carbonate were used instead of triethylamine as the acid acceptor.
[5] The dihydrochloride salt of the azetidine starting material was used.

EXAMPLE 97

1-Benzyl-5-(2-[3-morpholinoazetidin-1-yl]ethyl)-5-phenyl-2-piperidone

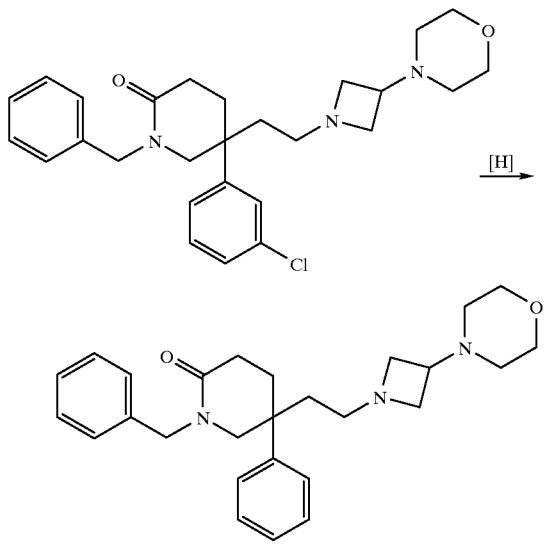

The piperidone (see Example 18) (95 mg, 0.2 mmol) was dissolved in ethanol which had been saturated with ammonia (20 ml) and Raney nickel (10 mg) was added. The mixture was then stirred at 50° C. under an atmosphere of hydrogen at 345 kPa (50 psi) for 10 hours. The catalyst was then removed by filtration and 5% palladium on carbon (10 mg) added. The mixture was then stirred for a further sixteen hours at 50° C. and 345 kPa under an atmosphere of hydrogen. The catalyst was then removed by filtration, the filtrate concentrated under reduced pressure and the residue chromatographed using silica gel eluting with a solvent gradient of methanol:dichloromethane (0:100 to 9:91, by volume) to give the title compound (19 mg). TLC $R_f$=0.3 (silica, methanol:dichloromethane, 1:9 by volume). LRMS m/z=434(m)⁺. Found: C, 66.22; H, 8.26; N, 8.60. $C_{27}H_{35}N_3O_2 \cdot 3H_2O$ requires C, 66.50; H, 8.47; N, 8.62%.

¹H-NMR (CDCl₃):δ=0.8–1.0 (d,2H), 1.1–1.4 (m,1H), 1.9–2.6 (m,12H), 2.6–2.8 (m,1H), 3.2–3.4 (m,2H), 3.5–3.8 (m,5H), 4.5 (d,1H), 4.8 (d,1H), 6.95–7.1 (m,2H), 7.2–7.4 (m,8H) ppm.

EXAMPLE 98

1-Benzyl-5-(3,4-dichlorophenyl)-5-(2-[3-piperazinoazetidin-1-yl]ethyl)-2 piperidone

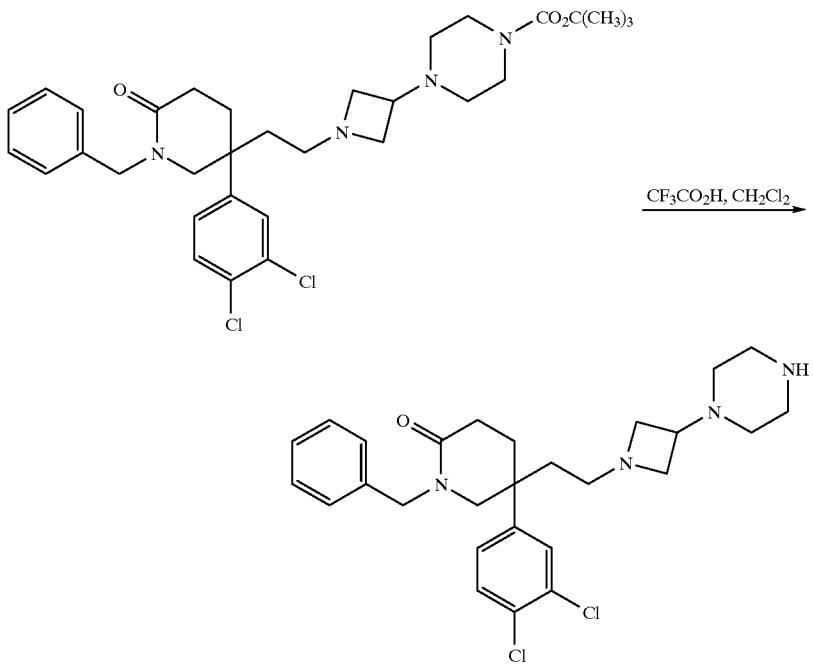

To a solution of the piperazine (see Example 7) (101 mg, 0.16 mmol) in dry dichloromethane (3.5 ml) under an atmosphere of nitrogen at room temperature was rapidly added trifluoroacetic acid (3.5 ml, 45 mmol). The reaction mixture was stirred for a further twenty minutes and then the solvent evaporated under reduced pressure. The reaction was azeotroped twice using dichloromethane (50 ml) to remove the excess trifluoroacetic acid. The reaction mixture was basified (pH 9) using saturated aqueous sodium carbonate solution (30 ml) and the aqueous phase extracted with ethyl acetate (4×50 ml). The organic extracts were combined, dried over anhydrous magnesium sulphate and evaporated to dryness under reduced pressure. The resulting foam was dissolved in dichloromethane (0.25 ml), filtered and the solvent removed from the filtrate under reduced pressure to give the title compound (88 mg). TLC $R_f$=0.16 (silica, methanol:dichloromethane:conc. aqueous ammonia solution, 9:90:1, by volume). LRMS m/z=467(m)$^+$. Found: C, 55.15; H, 5.74; N, 6.84. $C_{27}H_{34}N_4Cl_2O.0.125\ CH_2Cl_2$ requires C, 54.42; H, 5.93; N, 8.90%.

$^1$H-NMR (CDCl$_3$):δ=1.2–1.3 (m,1H), 1.4–1.6 (m,2H), 1.9–2.3 (m,6H), 2.3–2.5 30 (m,4H), 2.7–2.8 (m,2H), 2.9–3.25 (m,5H), 3.25 (d,1H), 3.3–3.5 (m,2H), 3.55 (d,1H), 4.4 (d,1H), 4.8 (d,1H), 6.8 (d,1H), 7.05 (s,1H), 7.2–7.4 (m,6H) ppm.

EXAMPLE 99

1-(2,4-Dichlorobenzyl)-5-(3,4-dichlorophenyl)-5-(2-[3-morpholinoazetidin-1-yl]ethyl)-2-piperidone

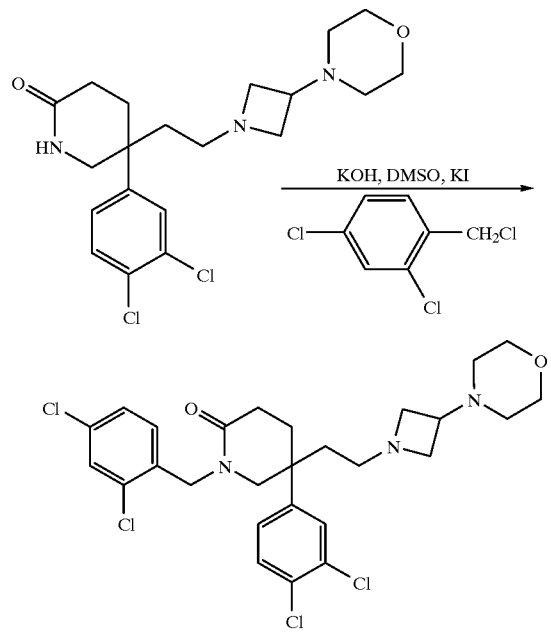

To a stirred solution of powdered potassium hydroxide (110 mg, 4 mol. equiv.) in dry dimethylsulphoxide (4 ml) was added a solution of the piperidone (see Example 1) (200 mg, 0.49 mmol) in dry dimethylsulphoxide (4 ml) followed by 2,4-dichlorobenzyl chloride (0.068 ml, 1 mol. equiv.) and potassium iodide (8 mg, 0.1 mol. equiv.). The mixture was then allowed to stir at room temperature for sixteen hours. Ethyl acetate (50 ml) was then added, the mixture washed with water (3×50 ml) and the organic phase dried over anhydrous magnesium sulphate. The solution was then filtered, the solvent removed from the filtrate under reduced pressure and the residue chromatographed using silica gel eluting with a solvent gradient of ethyl acetate:methanol:diethylamine (100:0:0 to 100:5:1, by volume) to give the title compound (49 mg). LRMS m/z=572(m+1)$^+$.

$^1$H-NMR (CDC$_3$):δ=1.55–1.8 (m,2H), 1.95–2.3 (m,10H), 2.4–2.5 (m,1H), 2.65–2.7 (m,1H), 2.85–2.9 (m,1H), 3.3–3.4 (m,3H), 3.6–3.7 (m,5H), 4.6 (d,1H), 4.85 (d,1H), 6.9–6.95 (m,1H), 7.05 (m,1H), 7.2–7.4 (m,4H) ppm.

EXAMPLE 100

5-(3,4-Dichlorophenyl)-1-(4-fluorobenzyl)-5-(2-[3-morpholinoazetidin-1 yl]ethyl)-2-piperidone

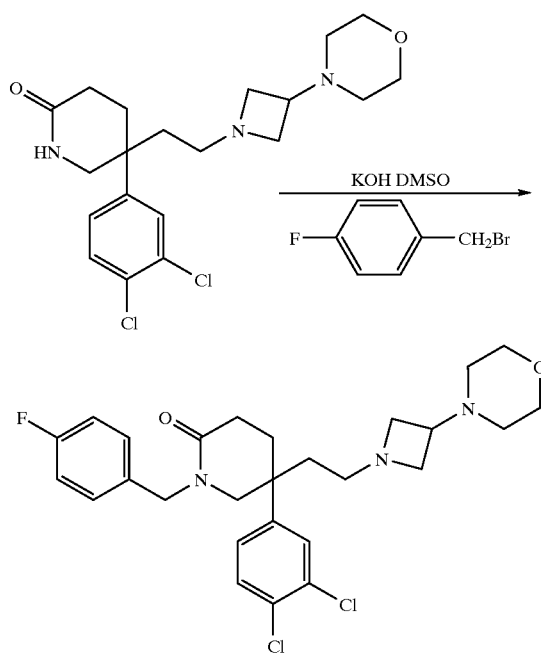

To dry dimethylsulphoxide (3 ml) at room temperature was added powdered potassium hydroxide (104 mg, 4 mol. equiv.) and the mixture was allowed to stir at room temperature for five minutes. A solution of the piperidone (see Example 1) (240 mg, 0.46 mmol) in dimethylsulphoxide (5 ml) was then added followed by 4-fluorobenzyl bromide (0.058 ml, 1 mol. equiv.) and the mixture allowed to stir at room temperature for fifty minutes. The reaction was poured into ethyl acetate (40 ml), washed with water (3×40 ml) and the organic phase dried over anhydrous magnesium sulphate. The solution was then filtered, the solvent removed from the filtrate under reduced pressure and the residue chromatographed on silica gel eluting with a solvent gradient of ethyl acetate:methanol:diethylamine (100:0:0 to 10:1:2 to 20:3:1, by volume) to give the title compound (lOOmg). LRMS m/z=521(m+1)$^+$. TLC Rf=0.4 (silica, ethyl acetate:methanol:diethylamine, 20:3:1, by volume). Found: C, 61.46; H, 6.27; N, 7.55. C$_{27}$H$_{32}$Cl$_2$N$_3$O$_2$F requires C, 62.31; H, 6.20; N, 8.07%.

$^1$H-NMR (CDCl$_3$):δ=1.5–1.85 (m,4H), 1.95–2.2 (m,8H), 2.6–2.75 (m,2H), 2.8–2.9 (m,1H), 3.15–3.35 (m,4H), 3.65–3.75 (m,4H), 4.3 (d,1H), 4.8 (d,1H), 6.8–7.3 (m,7H) ppm.

EXAMPLES 101 and 102

The compounds of the following tabulated Examples of the general formula:

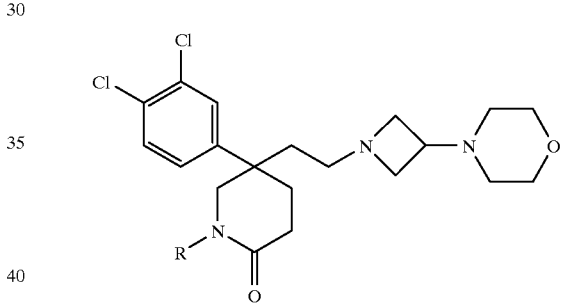

were prepared by a similar method to that of Example 100 using the same piperidone starting material and 3,5-di(trifluoromethyl)benzyl bromide or 2-methanesulphonyloxyethylcyclopropane (see Preparation 157), as appropriate.

| Ex. No. | R | LRMS m/z | Analysis/$^1$H-NMR |
|---|---|---|---|
| 101 | ![3,5-bis(trifluoromethyl)benzyl] CH$_2$— group with CF$_3$ at 3 and 5 positions | 638 (m + 1)$^+$ | $^1$H-NMR(CDCl$_3$): δ = 1.5–1.8(m, 5H), 2.0–2.15(m, 3H), 2.15–2.3(m, 5H), 2.65–2.75(m, 2H), 2.85–2.9(m, 1H), 3.3–3.35 (m, 3H), 3.6–3.7(m, 4H), 4.6–4.8(m, 2H), 6.85–6.9(m, 1H), 7.1–7.15(m, 1H), 7.3–7.35(m, 1H), 7.75(s, 2H), 7.85(s, 1H) ppm. |
| 102 | CH$_2$CH$_2$—cyclopropyl | 480 (m + 1)$^+$ | $^1$H-NMR(CDCl$_3$): δ = 0.1–0.15(m, 2H), 0.45–0.5(m, 2H), 0.6–0.7(m, 1H), 0.85–0.95(m, 1H), 1.45–1.55(m, 2H), 1.6–1.7 (m, 2H), 1.85–1.9(m, 1H), 1.95–2.4(m, 10H), 2.75–2.8(m, 2H), 2.9–2.95(m, 1H), 3.3–3.4(m, 3H), 3.55–3.7(m, 5H), 7.1–7.15 (m, 1H), 7.3–7.4(m, 2H) ppm. |

EXAMPLE 103

1-Benzyl-5-(3,4-dichlorophenyl)-5-(2-[3-(1-oxothiomorpholino)azetidin-1-yl]ethyl)-2-piperidone

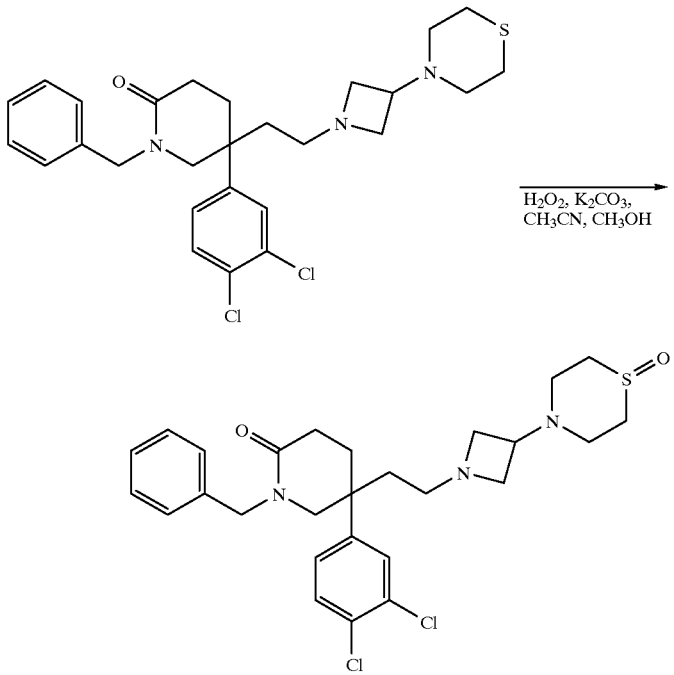

To an ice cooled solution of methanol (7 ml), the thiomorpholine (see Example 2) (0.76 ml, 1.0 mol. equiv.), acetonitrile (0.09 g, 1.5 mol. equiv.) and potassium carbonate (0.147 g, 0.72 mol. equiv.) was added, over thirty minutes, a solution of 30% w/v hydrogen peroxide in water (0.175 g, 1.05 mol. equiv.) in methanol (5 ml). The reaction was stirred at 0° C. for two hours and then allowed to warm to room temperature and stirred for a further sixteen hours. The majority of the solvent was then removed under reduced pressure at room temperature. Saturated aqueous sodium bicarbonate solution (20 ml) was added and the mixture extracted with ethyl acetate (3×50 ml). The combined organic layers were dried over magnesium sulphate and evaporated under reduced pressure. The oil obtained was purified by flash column chromatography on silica gel eluting with methanol:dichloromethane (1:9, by volume) to give the title compound (121 mg). TLC $R_f$ 0.10 (silica, methanol:dichloromethane, 1:9, by volume). LRMS m/z= 534(m+1)$^+$. Found: C, 57.91; H, 5.77; N, 7.58. $C_{27}H_{33}N_3C_{12}O_2S$. 0.37 $CH_2Cl_2$ requires C, 58.05; H, 6.01, N, 7.42%.

$^1$H-NMR (CDCl$_3$):δ=1.1–1.3 (m,1H), 1.4–1.8 (m,1H), 1.9–2.3 (m,5H), 2.4–2.6 (m,5H), 2.6–2.7 (m,6H), 2.7–2.9 (m,1H), 2.9–3.1 (m,1H), 3.2–3.4 (m,2H), 3.4–3.6 (m,1H), 4.4 (d,1H), 4.8 (d,1H), 6.8 (d,1H), 7.1 (s,1H), 7.3–7.4 (m,6H) ppm.

EXAMPLE 104

1-Benzyl-5-(3,4-dichlorophenyl)-5-(2-[3-(endo-3-hydroxy-8-azabicyolo[3,2,1]oct-8-yl)azetidin-1-yl]ethyl)-2-piperidone

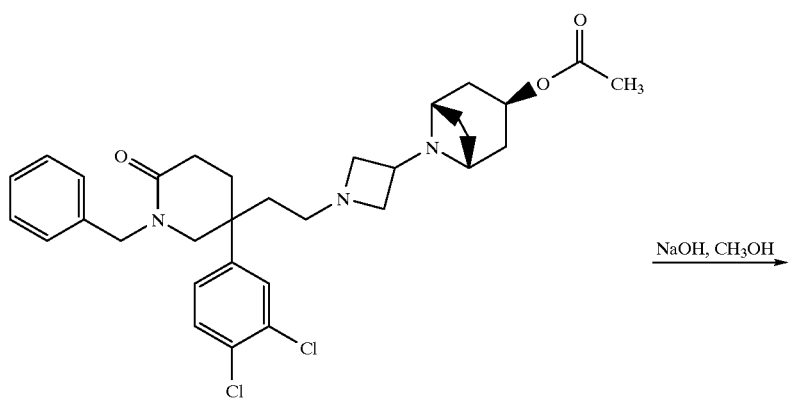

-continued

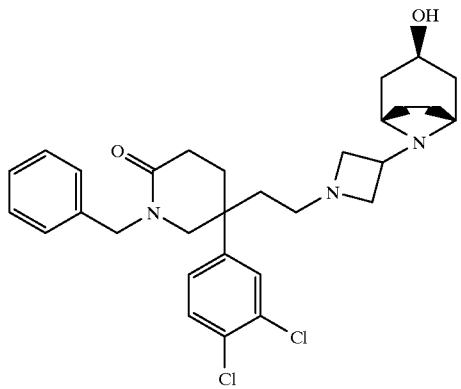

A mixture of the piperidone (see Example 24) (78 mg), 6N aqueous sodium hydroxide solution (0.5 ml) and methanol (1.5 ml) was stirred at room temperature for sixteen hours. The solution was concentrated under reduced pressure and water (5 ml) and dichloromethane (10 ml) were then added. The layers were separated and the aqueous phase was further extracted with dichloromethane (2×10 ml). The combined organic layers were dried over anhydrous sodium sulphate and then filtered. The solvent was removed from the filtrate under reduced pressure to give the title compound as a white foam (67 mg). LRMS m/z=543 (m+1)$^+$. Found: C, 62.15; H, 6.11; N, 7.43. $C_{30}H_{39}Cl_2N_3O$. 0.56 $CH_2Cl_2$ requires C, 62.40; H, 6.87; N, 7.16%.

$^1$H-NMR (CDCl$_3$):δ=1.5–2.2 (m,18H), 2.4–2.5 (m,1H), 2.6–2.7 (m,2H), 2.95 (br.s,2H), 3.1–3.2 (m,1H), 3.25–3.35 (m,3H), 3.5–3.6 (m,1H), 3.95–4.05 (m,1H), 4.2(d,1H), 4.8 (d,1H), 6.75–6.8 (m,1H), 7.1 (d,1H), 7.2–7.4 (m,6H) ppm.

EXAMPLE 105

5(S)-1-Cyclopropylmethyl-5-(3,4-dichlorophenyl)-5-(2-[3-(piperazin-1-yl)azetidin-1-yl]ethyl)-2-piperidone

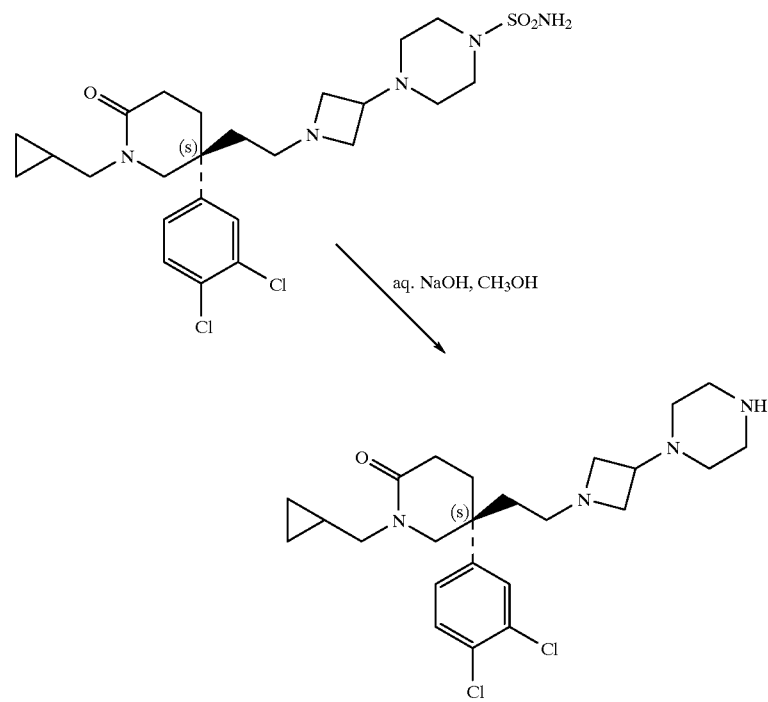

To a solution of the compound of Example 32 (1.36 g, 2.5 mmol) in methanol (15 ml) was added 10% w/w aqueous sodium hydroxide solution (5.44 ml). The mixture was heated under reflux for 48 hours. The methanol was then removed by evaporation under reduced pressure and the residue acidified to pH7 using 2N aqueous hydrochloric acid solution. The mixture was extracted with dichloromethane (2×40 ml). The combined organic extracts were evaporated to dryness under reduced pressure to give the title compound as a white foam (0.5 g).

TLC Rf=0.1 (silica, concentrated aqueous ammonia:methanol: dichloromethane, 20:80:320, by volume). LRMS m/z=465 (m)$^+$.

$^1$H-NMR (CDCl$_3$):δ=0.2–0.4 (m,2H), 0.5–0.7 (m,2H), 1.0–1.1 (m,1H), 1.6–2.6 (m,17H), 2.7–2.8 (m,2H), 2.9–3.05 (m,2H), 3.1–3.2 (m,1H), 3.4–3.6 (m,3H), 3.7–3.85 (m,1H), 7.1–7.2 (m,1H), 7.3–7.5 (m,2H) ppm.

EXAMPLE 106

5(S)-1-(2-Cyclopropylethyl)-5-(2-[3-(4-cyclopropylmethylaminopiperidin-1-yl)azetidin-1-yl]ethyl)-5-(3,4-dichlorophenyl)-2-piperidone

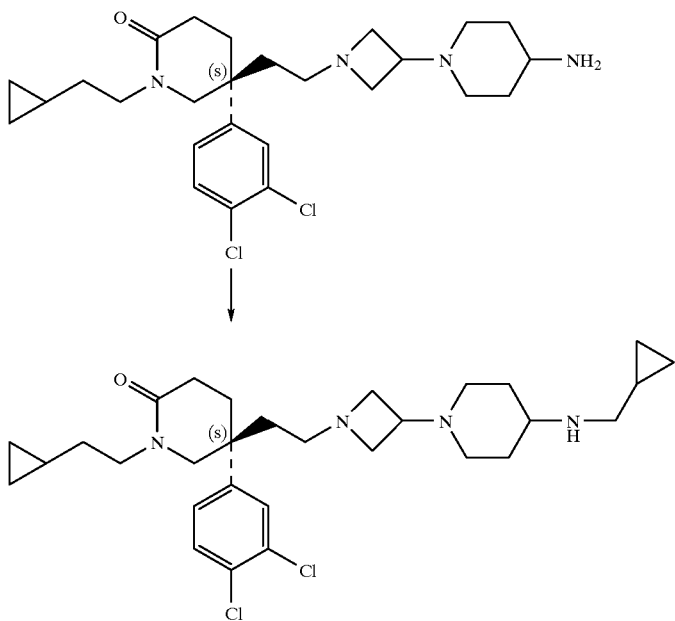

To a solution of the compound of Example 115 (0.1 g, 0.11 mmol) in tetrahydrofuran (3 ml) under nitrogen were added cyclopropylcarboxaldehyde (8 mg) and triethylamine (0.017 ml). After stirring for five minutes, sodium triacetoxyborohydride (32 mg) and glacial acetic acid (0.007 ml) were added and the reaction stirred at room temperature for sixteen hours. The reaction mixture was concentrated under reduced pressure and the residue partitioned between dichloromethane (12 ml) and 10% w/w aqueous sodium carbonate solution (4 ml). The layers were separated and the aqueous phase was extracted with dichloromethane (2×10 ml). The combined organic extracts were dried over anhydrous magnesium sulphate, filtered and the solvent removed from the filtrate by evaporation under reduced pressure. The residue was chromatographed on silica gel eluting with dichloromethane:methanol: concentrated ammonia solution, 89:10:1, by volume) to give the title compound (37 mg).

TLC Rf=0.18 (silica, dichloromethane:methanol:concentrated ammonia solution, 89:10:1, by volume). LRMS m/z=547 (m+1)$^+$.

$^1$H-NMR (CDCl$_3$):δ=0.1–0.15(m,4H), 0.4–0.5(m,4H), 0.6–0.7(m,1H), 0.9–1.0 (m, 1H), 1.25–1.4(m,2H), 1.45–1.7 (m,4H), 1.75–1.9(m,5H), 1.95–2.2(m,5H), 2.3–2.45(m,4H), 2.6–2.7(m,4H), 2.8–2.9(m,1H), 3.3–3.4(m,4H), 3.5–3.7(m, 2H), 7.0–7.4(m,3H) ppm.

EXAMPLES 107 and 108

The compounds of the following tabulated Examples of the general formula:

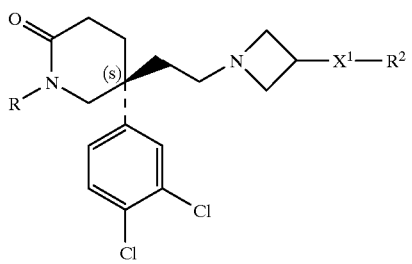

were prepared by a similar method to that of Example 106 using the appropriate amine starting materials (see Examples 105 and 113) and cyclopropylcarboxaldehyde.

| Ex. No. | R | —X¹—R² | m.p. | LRMS m/z | Analysis/¹H-NMR |
|---|---|---|---|---|---|
| 107 | (difluorocyclohexyl-CH₂—) | (piperidinyl-NH-CH₂-cyclopropyl) | — | 611 (m + 1)⁺ | ¹H-NMR(CDCl₃): δ = 0.1–0.15(m,2H), 0.45–0.5(m,2H), 0.85–1.0(m,1H), 1.25–2.55 (m,27H), 2.6–2.7(m,4H), 2.8–2.9(m,1H), 3.2–3.25(m,1H), 3.3–3.35(m,4H), 3.55–3.6 (m,1H), 7.1–7.4(m,3H) ppm. |
| 108 | (cyclopropyl-CH₂—) | (piperazinyl-CH₂-cyclopropyl) | — | 519 (m + 1)⁺ | ¹H-NMR(CDCl₃): δ = 0.15–0.4(m,3H), 0.55–0.7(m,3H), 0.85–1.1(m,2H), 1.6–1.9(m,2H), 2.0–2.2(m,4H), 2.5–2.6(m,10H), 2.7–3.0 (m,6H), 3.05–3.2(m,2H), 3.4–3.5(m,4H), 3.7–3.8(m,1H), 7.15–7.4(m,3H) ppm. |

EXAMPLE 109

5(S)-5-(2-[3-(4-Aminosulphonylpiperazin-1-yl)azetidin-1-yl]ethyl)-1-(5-carboxypentyl)-5-(3,4-dichlorophenyl)-2-piperidone ditrifluoroacetate

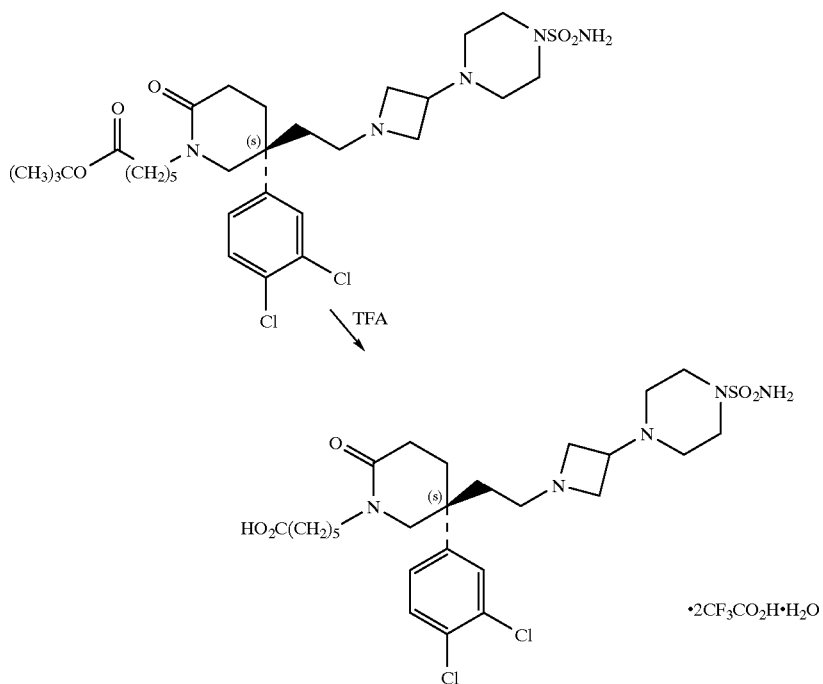

To a solution of the compound of Example 57 (30 mg, 0.045 mmol) in dichloromethane (1 ml) at 0° C. under nitrogen was added trifluoroacetic acid (0.05 ml). The mixture was stirred for 2 hours at room temperature. The dichloromethane solvent was removed under reduced pressure to give a gum which crystallised following trituration with diethyl ether to provide the title compound as a white solid (20 mg). TLC Rf=0.48 (silica, methanol: dichloromethane, 1:9, by volume). LRMS m/z=604 (m+1)⁺. Found: C,42.47; H,4.73; N,7.90. $C_{26}H_{39}Cl_2N_5O_5S$. 2 $CF_3CO_2H \cdot H_2O$ requires: C,42.46; H,4.88; N,8.25%.

EXAMPLE 110

5-(2-[3-(4-Carboxypiperidin-1-yl)azetidin-1-yl]
ethyl)-1-cyclohexylmethyl-5-(3,4-dichlorophenyl)-2-
piperidone

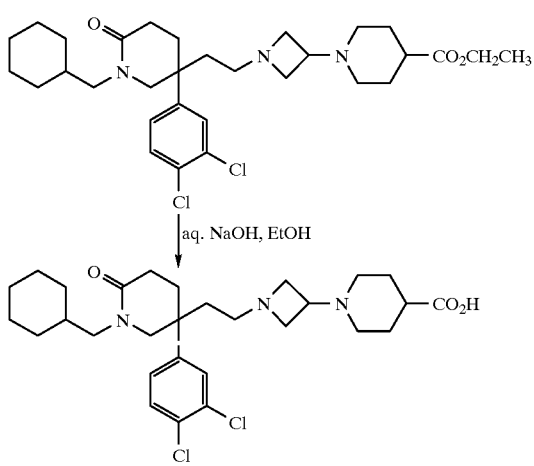

To a solution of the compound of Example 95 in ethanol (1 ml) was added 1 N aqueous sodium hydroxide solution (0.24 ml) and the mixture stirred at room temperature for sixteen hours. The ethanol was removed under reduced pressure and water (1 ml) was added to the residue. The solution was adjusted to pH5 using 2N aqueous hydrochloric acid solution to give an oil which crystallised when scratched. The resulting solid was filtered off, triturated with water (2×3 ml) followed by diethyl ether (3×3 ml), then dried under reduced pressure at 70° C. to give the title compound (40 mg). LRMS m/z=550 (m+1)$^+$. Found: C,55.80; H,7.14; N,6.44. $C_{29}H_{41}N_3Cl_2O_3 \cdot 0.75\ H_2O$. NaCl requires: C,55.95; H,6.88; N,6.75%.

EXAMPLE 111

5(S)-(2-[3-(4-Carboxypiperidin-1-yl)azetidin-1-yl]
ethyl)-1-cyclopropylmethyl-5-(3,4-dichlorophenyl)-
2-piperidone This compound was prepared by a similar method to that of Example 110 using the appropriate methyl ester starting material (see Example 59) and 3.8 mole equivalents of the aqueous sodium hydroxide solution. LRMS m/z=508(m)$^+$.

EXAMPLE 112

5 (S)-5-(2-[3-(4-Aminopiperidin-1-yl)azetidin-1-yl]
ethyl)-1-cyclopropylmethyl-5-(3,4-dichlorophenyl)-
2-piperidone tristrifluoroacetate

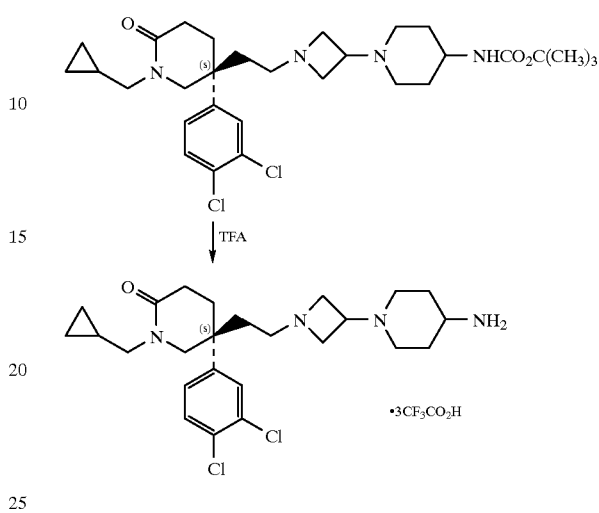

To a solution of the compound of Example 48 (1.4 g, 24.1 mmol) in dichloromethane (20 ml) at +40° C. under nitrogen was added trifluoroacetic acid (6.6 ml) and the reaction stirred at room temperature for one hour. The solvent and excess trifluoroacetic acid were removed under reduced pressure to give the title compound (907 mg). LRMS m/z=479 (m+1)$^+$.

EXAMPLES 113 to 115

The compounds of the following tabulated examples of the general formula:

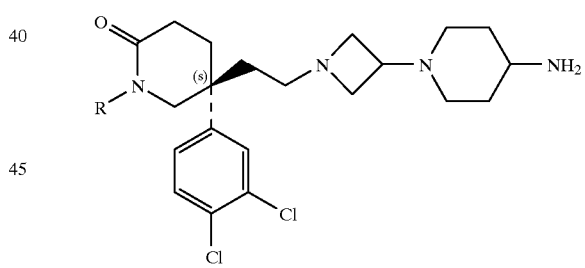

were prepared by a similar method to that of Example 112 using the appropriate t-butoxycarbonyl-protected amine (see Examples 46, 51 and 54) and trifluoroacetic acid.

| Ex. No. | R | m.p. | LRMS m/z | Analysis/$^1$H-NMR |
|---|---|---|---|---|
| 113 | ![F,F-cyclohexyl-CH2-] | — | 557 (m + 1)$^+$ | Found: C, 44.81; H, 4.77; N, 6.11. $C_{28}H_{40}Cl_2F_2N_4O \cdot 3CF_3CO_2H \cdot 0.25CH_2Cl_2$ requires: C, 45.39; H, 4.82; N, 6.23%. |

-continued

| Ex. No. | R | m.p. | LRMS m/z | Analysis/$^1$H-NMR |
|---|---|---|---|---|
| 114 | ![cyclopropyl-CH(cyclopropyl)-CH2-] | — | 535 (m + 1)$^+$ | Found: C, 46.11; H, 5.27; N, 6.01. $C_{29}H_{42}Cl_2N_4O$. $3CF_3CO_2H$. $2H_2O$ requires: C, 46.11; H, 5.42; N, 6.15%. |
| 115 | ![cyclopropyl-CH2CH2-] | — | 493 (m + 1)$^+$ | — |

EXAMPLE 116

5-(2-[3-(4-Aminopiperidin-1-yl)azetidin-1-yl]ethyl)-1-cyclohexylmethyl-5-(3,4-dichlorophenyl)-2-piperidone tristrifluoroacetate

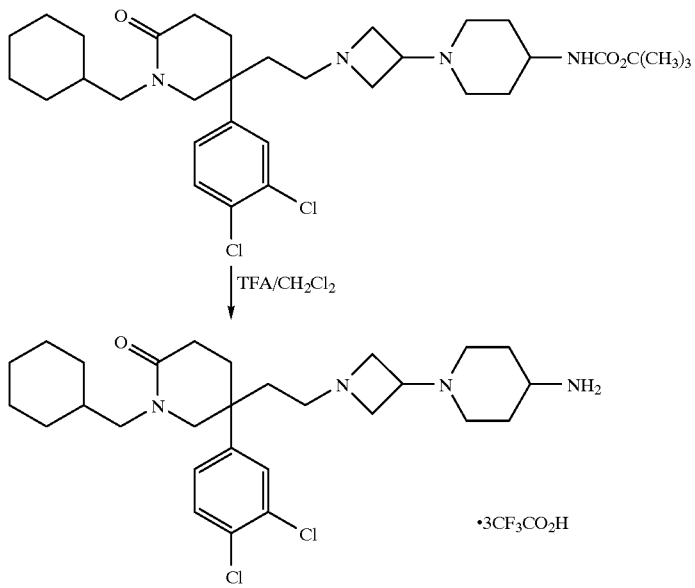

To a solution of the compound of Example 96 (0.53 g, 0.85 mmol) in dichloromethane (5 ml) at 0° C. under nitrogen was slowly added trifluoroacetic acid and the solution allowed to stir at room temperature for 1 hour. The excess trifluoroacetic acid and dichloromethane were removed under reduced pressure, the residue treated with dichloromethane (5 ml) and the solvent removed under reduced pressure. The residue was triturated with diethyl ether, filtered and the solid obtained rapidly washed with diethyl ether, then dried under reduced pressure at 70° C. to give the title compound (580 mg). LRMS m/z=522 (m+1 )$^+$.

$^1$H-NMR (CDCl$_3$)/d$_6$-DMSO):δ=0.75–0.9(m,2H), 0.95–1.1(m,3H), 1.35–4.0 (m,32H), 6.95–7.0(m, 1H), 7.15–7.20(m, 1H), 7.30–7.35(m,1H), 8.35(br.s,2H) ppm.

EXAMPLE 117

1-Cyclohexylmethyl-5-(3,4-dichlorophenyl)-5-(2-[3-(4-methanesulphonamidopiperidin-1-yl)azetidin-1-yl]ethyl)-2-piperidone

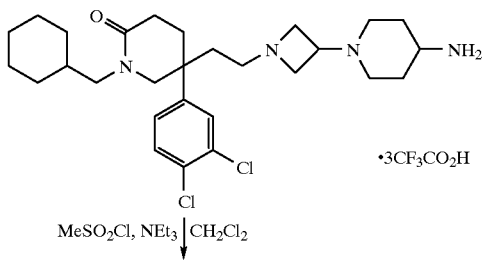

-continued

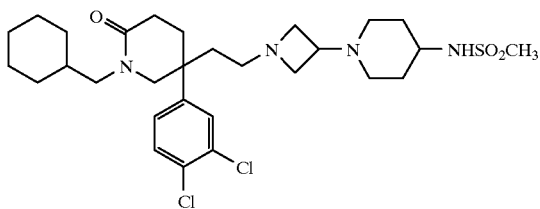

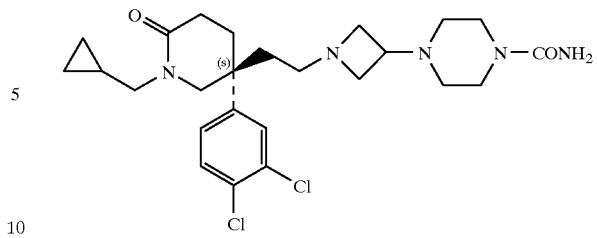

To a solution of the compound of Example 116 (0.29 g, 0.34 mmol) and triethylamine (0.23 ml) in dichloromethane (6 ml) at 0° C. under nitrogen was added methanesulphonyl chloride (0.035 ml). The mixture was allowed to stir at room temperature for sixteen hours. The dichloromethane was removed under reduced pressure, the residue taken up in ethyl acetate (30 ml) and washed with 1% w/w aqueous sodium bicarbonate solution (5 ml). The organic phase was dried using anhydrous magnesium sulphate, filtered and the solvent removed from the filtrate under reduced pressure to give an oil. This oil was chromatographed on silica gel eluting with methanol:dichloromethane (1:9, by volume) to give the title compound (85 mg). TLC Rf 0.25 (silica, methanol: dichloromethane, 1:9, by volume).

$^1$H-NMR (CDCl$_3$):δ=0.9–1.1 (m,2H), 1.15–1.30(m,3H), 1.45–2.25(m, 19H), 2.30–2.40(m, 1H), 2.55–2.7(m,4H), 3.8–3.9(m, 1H), 2.95(s,3H), 3.1–3.2(m, 1H), 3.3–3.4 (m,5H), 3.5–3.6(m,1H), 4.1–4.15(m,1H), 7.1–7.15(m,1H), 7.3–7.45(m,2H) ppm.

EXAMPLE 118

5(S)-1-Cyclopropylmethyl-5-(3,4-dichlorophenyl)-5-(2-[3-(4-methanesulphonamidopiperidin-1-yl)azetidin-1-yl]ethyl)-2-piperidone The title compound was prepared by a similar method to that used in Example 117 using the appropriate aminopiperidine starting material (see Example 112). LRMS m/z= 557(m+1)$^+$.

$^1$H-NMR (CDC$_{13}$):δ=0.25–0.35(m,2H), 0.5–0.65(m,2H), 0.8–1.1 (m,3H), 1.2–1.35 (m,3H), 1.5–1.7(m,3H), 1.8–2.4 (m,9H), 2.6–2.8(m,3H), 2.85–3.0(m,3H), 3.1–3.2 (m, 1H), 3.25–3.5(m,4H), 3.7–3.8(m,1H), 4.15–4.2(m, 1H), 7.1–7.4 (m,3H) ppm.

EXAMPLE 119

5(S)-5-(2-[3-(4-Carbamoylpiperazin-1-yl)azetidin-1-yl]ethyl)-1-(cyclopropylmethyl)-5-(3,4-dichlorophenyl)-2-piperidone

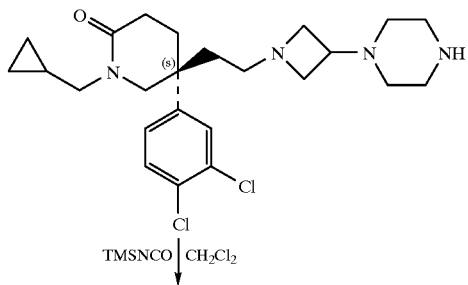

TMSNCO | CH$_2$Cl$_2$

To a solution of the compound of Example 105 (10 mg, 0.2 mmol) in dichloromethane (3 ml) at room temperature under nitrogen was added trimethylsilylisocyanate (0.032 ml) and the mixture was stirred at room temperature for sixteen hours. The solvent was removed under reduced pressure and the product was purified by column chromatography using silica gel eluting with dichloromethane:methanol:concentrated ammonia solution (89:10:1, by volume) to give the title compound (69 mg). TLC Rf=0.25 (silica, dichloromethane:methanol:concentrated ammonia solution, 89:10:1, by volume). LRMS m/z=508 (m+1)$^+$.

$^1$H-NMR (CDCl$_3$):δ=0.25–0.4(m,2H), 0.55–0.7(m,2H), 0.95–1.1(m,1H), 1.6–1.9 (m,2H), 1.95–2.4(m, 10H), 2.7–2.75(m,2H), 2.9–2.95(m, 1H), 3.1–3.2(m, 1H), 3.35–3.5 (m,8H), 3.7–3.8(m,$_{11}$H), 4.4(br.s,2H), 7.1–7.4(m,3H) ppm.

EXAMPLE 120

5(S)-5-(2-[3-(4-Acetamidopiperidin-1-yl)azetidin-1-yl]ethyl)-1-cyclopropylmethyl-5-(3,4-dichlorophenyl)-2-piperidone

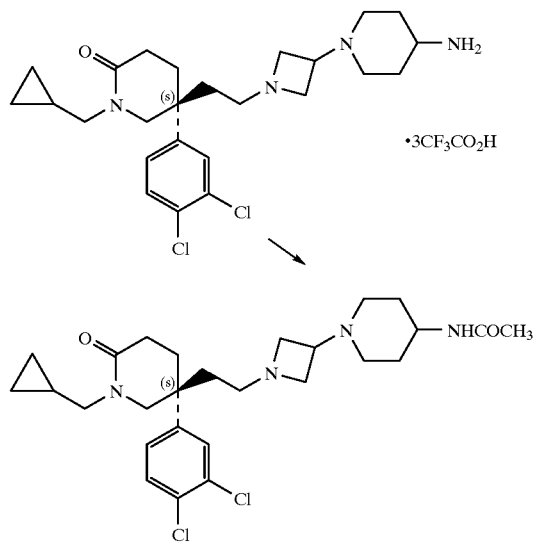

To a solution of the compound of Example 112 (300 mg, 3.65 mmol) and triethylamine (255 µl) in dichloromethane (40 ml) under nitrogen at room temperature was added acetic anhydride (4 µl) and the reaction was stirred for eighteen hours. A further portion of acetic anhydride (80 µl) was then added and stirring continued for 1 hour. The reaction was washed with water (2× 30 ml) followed by brine (30 ml). The combined organic layers were dried using anhydrous magnesium sulphate and then evaporated under reduced pressure to give a yellow oil. This was dissolved in ethyl acetate (40 ml) and extracted with 2N aqueous hydrochloric acid solution (2×100 ml). The combined acidic aqueous extracts were basified using saturated aqueous sodium bicarbonate solution and the aqueous layer extracted using ethyl acetate (2×100 ml). The combined organic layers were dried using anhydrous sodium sulphate. The solvent was removed under reduced pressure to provide the title compound (53 mg). TLC Rf=0.1 (silica, methanol:dichloromethane; 1:9, by volume). LRMS m/z=629 (m)+.

$^1$H-NMR (CDC$_{l3}$):δ=0.2–0.4(m,2H), 0.5–0.7(m,2H), 0.95–1.05(m,1H), 1.3–1.4(m,2H), 1.5–1.7(m,1H), 1.75–2.2 (m,$_{1}$ 3H), 2.3–2.4(m, 1H), 2.5–2.7(m,4H), 2.95(t, 1H), 3.05–3.1 (m, 1H), 3.4–3.6(m,4H), 3.8(d,2H), 5.2(s, 1H), 7.1 (d, 1H), 7.35–7.4(m,2H) ppm.

EXAMPLES 121 and 122

The compounds of the following tabulated Examples of the general formula:

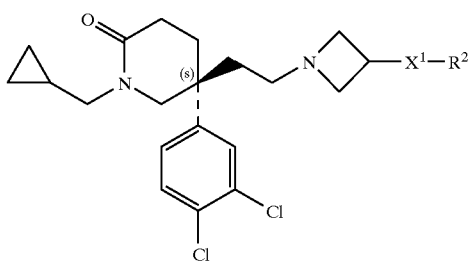

were prepared by a similar method to that of Example 120 using the appropriate piperazine starting material (see Example 105) and the appropriate acylating agent.

| Ex. No. | —X$^1$—R$^2$ | m.p. | LRMS m/z | Analysis/$^1$H-NMR |
|---|---|---|---|---|
| 121[1,2] | —N⟨⟩NCOCH$_3$ | — | — | $^1$H-NMR(CDCl$_3$): δ = 0.25–0.4(m,2H), 0.5–0.7 (m,2H), 1.0–1.1(m,1H), 1.5–1.7(m,2H), 1.7–1.9 (m,1H), 1.95–2.4(m,12H), 2.6–2.8(m,2H), 2.8–2.95(m,1H), 3.1–3.2(m,1H), 3.3–3.5(m,6H), 3.5–3.65(m,2H), 3.7–3.8(m,1H), 7.1(d,1H), 7.35–7.45(m,2H) ppm. |
| 122[1,3] | —N⟨⟩N—COCF$_3$ | — | — | $^1$H-NMR(CDCl$_3$): δ = 0.2–0.4(m,2H), 0.5–0.7 (m,2H), 1.0–1.1(m,1H), 1.5–1.7(m,2H), 1.7–1.9 (m,1H), 1.95–2.4(m,9H), 2.65(q,2H), 2.85–3.0 (m,1H), 3.1–3.2(m,1H), 3.25–3.5(m,4H), 3.5–3.8 (m,5H), 7.1(d,1H), 7.35–7.4(m,2H) ppm. |

Footnotes:
[1]Purified by column chromatography using silica gel eluting with dichloromethane:methanol (90:10, by volume).
[2]Acetyl chloride was used as the acylating agent.
[3]Trifluoroacetic anhydride was used as the acylating agent.

EXAMPLE 123

5(S)-5-(2-[3-(4-Aminosulphonylpiperazin-1-yl) azetidin-1-yl]ethyl)-1-cyclopropylmethyl-5-(3,4-dichlorophenyl)-2-piperidone

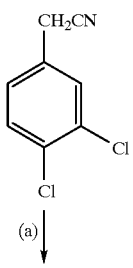

(a) ↓

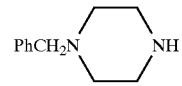

(e) ↓

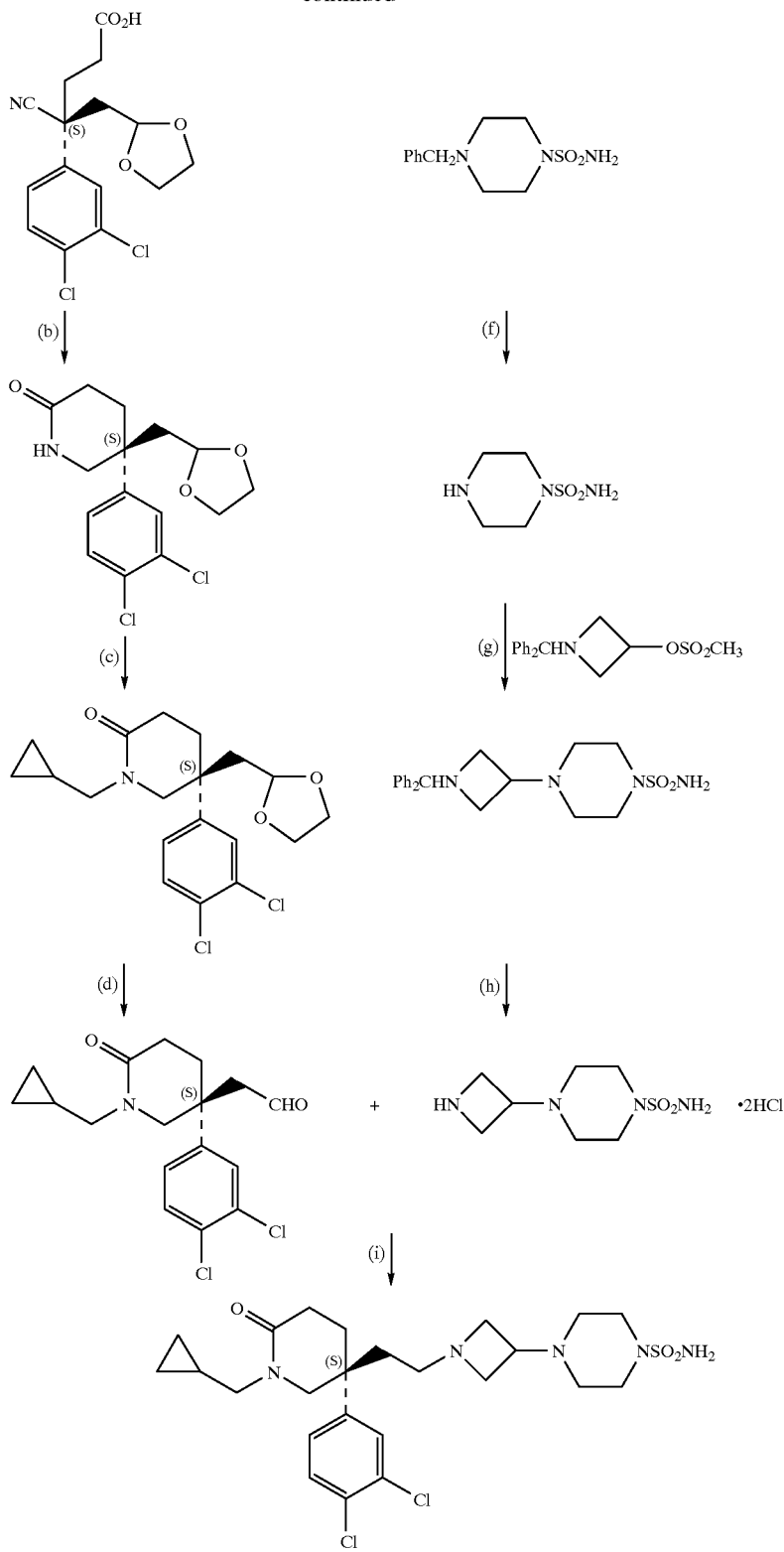

(a) 4(S)-4-Cyano-4-(3,4-dichlorophenyl)-5-(1,3-dioxolan-2-yl)pentan-1-oic acid

To a 1.0M solution of lithium hexamethyldisilylazide in tetrahydrofuran (4.691) at 5° C. under nitrogen was added a solution of 3,4-dichlorophenylacetonitrile (750 g, 4.28 moles) in tetrahydrofuran (750 ml), dropwise, over 45 minutes. The reaction was allowed to stir for 2 hours. The reaction was cooled again to 5° C. and a solution of 2-bromomethyl-1,3-dioxolane (782 g) in tetrahydrofuran (780 ml) added, dropwise, over fifty minutes. Tetra-n- butylammonium iodide (75 g) was added, portionwise, and the mixture allowed to warm to room temperature and stirred for 14 hours. The reaction was then cooled to 5° C. and a 1.0M solution of lithium hexamethyidisilylazide in tetrahydrofuran (4.69 l) was added, dropwise. The mixture was stirred for 5 hours at room temperature. The solution was cooled to 5° C. and a solution of ethyl 3-bromopropanoate (840.5 g) in tetrahydrofuran (840 ml) was added, dropwise, over 50 minutes. The reaction was allowed to stir for 14 hours. The reaction mixture was cooled to 5° C. and 1.5M aqueous sodium hydroxide solution (containing 255 g of sodium hydroxide) was added and the mixture stirred for 14 hours. Water (5l) was added and the mixture was extracted with ethyl acetate (2×3 l). The combined organic extracts were washed with water (2×5 l). The aqueous phases were combined and acidified to pH1 using 5N aqueous hydrochloric acid solution and then extracted with ethyl acetate (2×3 l). The combined organic extracts were concentrated under reduced pressure to a concentration of approximately 3 ml/g based on the theoretical yield of the product.

The above experimental procedure was then repeated on an identical scale. To the combined organic solutions from both reactions was added (S)-(-)-alpha-methylbenzylamine (1.13 kg) and the mixture stirred for 14 hours. The thick slurry was then stirred with cooling in an ice-bath for 2 hours, filtered, the solid washed with ethyl acetate (2×1 l) and then dried under reduced pressure at 35° C. to give 1.85 kg of material. A portion of this material (1.34 kg) was dissolved in a mixture of butanone (2 l) and water (503 ml) that was heated under reflux. A further portion of butanone (4.7 l) was added and the solution was allowed to cool slowly to room temperature overnight. The resulting solid was filtered off (the filtrate was used in Preparation 192), washed with butanone (2×1 l) and ried under reduced pressure at 35° C. for 10 hours to give 563 g of material (93.8% e.e.). A further recrystallisation from butanone/water gave the title compound as a (S)-(-)-alpha-methylbenzylamine salt in 99.8% e.e. To a stirred solution of this salt in ethyl acetate and water was added 5N aqueous hydrochloric acid solution until pH1 was achieved. The mixture was stirred for a further 30 minutes, the layers separated and the aqueous phase extracted with ethyl acetate. The combined organic layers were washed with water and the solvent removed by evaporation under reduced pressure to give the title compound.

$^1$H-NMR (CDCl$_3$):δ=2.05–2.35(m,4H), 2.4–2.65(m,2H), 3.7–4.0(m,4H), 4.75–4.85(m, 1H), 7.25–7.55(m,3H), 9.9(s, br., 1H,acid) ppm.

(b) 5(S)-5-(3,4-Dichlorophenyl)-5-(1,3-dioxolan-2-ylmethyl)-2(1H)-piperidone

To a solution of the compound of Example 123(a) (13.5 g, 39.22 mmol) in glacial acetic acid (130 ml) was added platinum oxide (1.21 g) and the mixture stirred under an atmosphere of hydrogen at 414 kPa (60 psi) and at room temperature for 17 hours. The catalyst was removed by filtration and a further portion of platinum oxide (1.21 g) added. The reaction mixture was then stirred under an atmosphere of hydrogen 414 kPa (60 psi) and at room temperature for 48 hours. The catalyst was removed by filtration and the solution concentrated under reduced pressure. The residue was dissolved in ethyl acetate (80 ml) and washed with saturated aqueous sodium bicarbonate solution (2×75 ml). The organic phase was then separated and the solvent removed under reduced pressure. The resulting solid was stirred in a solution of hexane (20 ml) and ethyl acetate (20 ml) for 2 hours at 0° C. and then filtered off to give the title compound (8.15 g).

$^1$H-NMR (CDCl$_3$):δ=1.85–1.95(m,1H), 2.0–2.25(m,4H), 2.35–2.4(m,1H), 3.45–3.55(m, 1H), 3.65–3.75(m,2H), 3.8–3.9(m,3H), 4.35–4.4(m, 1H), 6.15(s,br., 1H), 7.2–7.45 (m,3H) ppm.

(c) 5(S)-1-Cyclopropylmethyl-5-(3,4-dichlorophenyl)-5-(1,3-dioxolan-2-ylmethyl)-2-piperidone To a solution of the compound of Example 123(b) (38.6 g, 117 mmol) in dimethyl sulphoxide (190 ml) was added potassium hydroxide (19.7 g) and the mixture stirred at room temperature for 20 minutes. Bromomethylcyclopropane (17.37 g) was then added over 20 minutes and the reaction stirred for a further 140 minutes. The reaction was poured into a mixture of ice (10 g) and water (900 ml) and the mixture extracted with dichloromethane (2×400 ml). The combined organic layers were washed with water (400 ml) and the solvent removed under reduced pressure to give the title compound (45.4 g).

$^1$H-NMR (CDCl$_3$):δ=0.3–0.4(m,2H), 0.55–0.65(m,2H), 1.05–1.15(m,1H), 1.9–1.95(m, 1H), 2.0–2.25(m,4H), 2.35–2.45(m, 1H), 3.15–3.2(m, 1H), 3.5–3.55(m,2H), 3.65–3.75(m,2H), 3.9–4.0(m,3H), 4.35–4.4(m, 1H), 7.2–7.5 (m,3H) ppm.

(d) 5(S)-1-Cyclopropylmethyl-5-(3,4-dichlorophenyl)-5-formylmethyl-2-piperidone

To a solution of the compound of Example 123(c) (73.16 g, 190 mmol) in tetrahydrofuran (730 ml) at 5° C. was added 5N aqueous hydrochloric acid solution (730 ml) over 20 minutes. The reaction mixture was stirred at room temperature for 17 hours. The tetrahydrofuran was removed under reduced pressure, the residue diluted with water (200 ml) and extracted with ethyl acetate (2×500 ml). The combined organic layers were then washed with water (500 ml) and the solvent removed under reduced pressure to give the title compound (62.1 g).

$^1$H-NMR (CDC$_{13}$):δ=0.25–0.35(m,2H), 0.55–0.65(m, 2H), 1.05–1.1(m,1H), 2.15–2.25(m,3H), 2.35–2.5(m,1H), 2.65–2.75(m,1H), 2.95–3.05(m,1H), 3.15–3.2(m,1H), 3.45–3.6(m,2H), 3.95–4.0(m, 1H), 7.2–7.45(m,3H), 9.5(s, 1H) ppm.

(e) 1-Aminosulphonyl-4-benzylpiperazine

A solution of 1-benzylpiperazine (5 g, 28.4 mmol) and sulphamide (2.77 g) in 1,4-dioxane (25 ml) was heated under reflux for 24 hours. The solution was cooled and poured into water (100 ml). The solid was filtered off, washed with toluene (100 ml) and dried under reduced pressure to give the title compound (4.75 g).

$^1$H-NMR (d$_6$-DMSO):δ=2.41–2.5(m,4H), 2.95–3.0(m, 4H), 3.5(s,2H), 6.75(s,2H), 7.25–7.35(m,5H) ppm.

(f) 1-Aminosulphonylpiperazine

A mixture of the compound of Example 123(e) (20 g, 78.3 mmol) and 10% w/w palladium-on-carbon (4 g) in ethanol (140 ml) was stirred under an atmosphere of hydrogen at 345 kPa (50 psi) and at 50° C. for 23 hours. The catalyst was removed by filtration and washed with ethanol (100 ml). The filtrate was concentrated under reduced pressure to approximately 40 ml in volume and the slurry kept at 0–5° C. for 12 hours. The solid was filtered off to give a first crop of the title compound (2 g). The catalyst separated earlier was heated under reflux in ethanol (150 ml). The mixture was filtered whilst hot and the pad washed with ethanol (50 ml). The solvent was removed under reduced pressure. The solid was slurried with acetone (100 ml) and filtered off to give a second crop of the title compound (8 g).

$^1$H-NMR (d$_6$-DMSO):δ=2.3–2.9(m,9H), 6.65(s,br.,1H) ppm.

(g) 1-Aminosulphonyl-4-(1-diphenylmethylazetidin-3-yl) piperazine

A solution of 1-diphenylmethyl-3-methanesulphonyloxyazetidine (see Preparation 54) (4.8 g, 15.1 mmol) and 1-aminosulphonylpiperazine (see Example 123(f)) (5 g) in acetonitrile (50 ml) was heated under reflux for 4 hours. The reaction was cooled and the solid filtered off and washed with acetonitrile (50 ml). The filtrate was concentrated under reduced pressure and the residue slurried in hot toluene (50 ml), cooled, the solid filtered off and washed with toluene (50 ml). The product was then further purified by slurrying in hot ethyl acetate (3 ml), cooling and filtering to give the title compound (0.47 g).

$^1$H-NMR (d$_6$-DMSO):δ=2.25–2.3(m,4H), 2.7–2.75(m, 2H), 2.85–2.95(m,3H), 3.05–3.1 (m,2H), 3.2–3.25(m,2H), 4.4(m, 1H), 6.7(m,2H), 7.15–7.4(m, 10H) ppm.

(h) 1-Aminosulphonyl-4-(azetidin-3-yl)piperazine dihydrochloride

To a solution of the compound of Example 123(g) (5 g) in methanol (50 ml) was added 10% aqueous hydrochloric acid solution (9.4 ml) and Pearlman's catalyst (20% w/w Pd(OH)-on-carbon) (0.6 g). The mixture was shaken under an atmosphere of hydrogen using a Parr shaker for 14 hours.

After this time the catalyst was removed by filtration, the filtrate returned to the Parr shaker and a further 0.6 g of Pearlman's catalyst added. The reaction was shaken under an atmosphere of hydrogen for 14 hours. The catalyst was removed by filtration and washed with water (100 ml). The filtrate was concentrated under reduced pressure. The residue was stirred in acetonitrile (50 ml) for 1 hour and the mixture left to stand for 14 hours. The solid was filtered off and dried under reduced pressure to give the title compound (3.28 g).

$^1$H-NMR (d$_6$-DMSO):δ=2.35–2.45(m,5H), 2.9–3.0(m, 4H), 3.25–3.35(m,1H), 3.75–3.9(m,4H), 6.8(s,br.,2H) ppm.

(i) 5(S)-5-(2-[3-(4-Aminosuphonylpiperazin-1-yl)azetidin-1-yl]ethyl)-1-cyclopropylmethyl-5-(3,4-dichlorophenyl)-2-piperidone To a solution of the compound of Example 123(h) (18.97 g) in tetrahydrofuran (140 ml) at room temperature was added triethylamine (18 ml) and the mixture stirred for 30 minutes. A solution of the compound of Example 123(d) (20 g) in tetrahydrofuran (60 ml) was then added. After 2 hours, the solution was cooled to 2° C. and sodium triacetoxyborohydride (17.44 g) was added, portionwise, followed by acetic acid (3.37 ml) and the reaction was allowed to warm to room temperature and stirred for 2 hours. The reaction was poured into water (50 ml) and a 10% w/w aqueous sodium bicarbonate solution was added until pH9 was achieved. Ethyl acetate (200 ml) was added and the layers separated. The aqueous phase was extracted with ethyl acetate (50 ml), the combined organic extracts were washed with a 10% w/w aqueous sodium bicarbonate solution (100 ml) and the solvent was removed under reduced pressure to give the title compound (28.27 g).

$^1$H-NMR—as for the compound of Example 32.

Pharmacological Data

A representative selection of the compounds of the Examples were tested in vitro for their affinity to the human NK$_2$ receptor by testing their ability to compete with [$^{125}$I] NKA for binding to membranes prepared from Chinese hamster ovary cells expressing the cloned human NK$_2$ receptor (Method A) and for their ability to antagonise the contractile effects of [βAla$^8$] NKA$_{(4-10)}$ in the rabbit pulmonary artery (Method B) by the methods described on pages 40 and 41 of the specification.

The results are tabulated below:

| EXAMPLE NO. | METHOD A (pIC$_{50}$) | METHOD B (pA$_2$) |
| --- | --- | --- |
| 14 | 7.2 | 7.9 |
| 31 | 9.0 | 8.3 |
| 73 | 9.5 | 8.9 |
| 75 (enantiomeric pair A) | 8.3 | 9.1 |
| 89 | 8.2 | 8.6 |
| 104 | 8.8 | 9.2 |

The following Preparations illustrate the preparation of certain starting materials used in the syntheses of the compounds of the preceding Examples.

Preparation 1

2-(3,4-Dichlorophenyl)-4-(tetrahydropyran-2-yloxy) butanenitrile

To a mixture of 60% w/w sodium hydride dispersion in oil (19.24 g, 1.05 mol. equiv.) in dry tetrahydrofuran (450 ml) at 0° C. under nitrogen was added a solution of 3,4-dichlorophenylacetonitrile (89.5 g, 1 mol. equiv.) in dry tetrahydrofuran (450 ml), dropwise over forty minutes. After a further thirty minutes, a solution of 2-bromoethoxytetrahydropyran (100 g , 1 mol. equiv.) in tetrahydrofuran (100 ml) was added and the mixture allowed to warm to room temperature and stirred for fourteen hours. 30% Aqueous ammonium chloride solution (500 ml) was added and the mixture extracted with diethyl ether (2×400 ml). The organic layers were combined and washed with water (2×400 ml), dried over magnesium sulphate, and the solvent removed under reduced pressure. The residue was then chromatographed using silica gel eluting with a solvent gradient of diethyl ether:hexane (1:9 to 1:1, by volume) to give the title compound (51 g). TLC R$_f$=0.55 (silica, methyl tert-butyl ether:hexane, 1:1, by volume). LRMS m/z=333 (m+NH$_4$)$^+$.

$^1$H-NMR (CDCl$_3$):δ=1.5–1.9 (m,6H), 2.05–2.3 (m,2H), 2.4–2.65 (m,2H), 2.8–2.95 (m,2H), 4.0–4.1 (m,1H), 4.5–4.6 (m,1H), 7.2–7.25 (m,1H), 7.25–7.5 (m,2H), ppm.

Preparation 2

Ethyl 4-cyano-4-(3,4-dichlorophenyl)-6-(tetrahydropyran-2-yloxy)hexanoate

To a solution of diisopropylamine (15 ml, 0.77 mol. equiv.) in tetrahydrofuran (80 ml) at −78° C. under nitrogen was added n-butyllithium (77.3 ml of a 2.5 M solution in hexane, 1.4 mol. equiv.) and the solution was then allowed to warm to room temperature over two hours. The solution was cooled to −78° C. and a solution of the compound of Preparation 1 (43.9 g, 138 mmol) in tetrahydrofuran (180 ml) was added slowly. The resulting solution was allowed to warm to room temperature slowly over two hours. The solution was then cooled to −78° C. and a solution of ethyl 3-bromopropanoate (22.36 ml, 1.3 mol. equiv.) in tetrahydrofuran (70 ml) added dropwise. Tetra-n-butylammonium iodide (50 g, 1 mol. equiv.) was then added, the reaction allowed to warm to room temperature and stirred for fourteen hours. Water (10 ml) was then added and the solution concentrated under reduced pressure. Water (400 ml) and brine (400 ml) were added and the mixture extracted with ethyl acetate (2×500 ml). The combined organic layers were washed with water (2×300 ml), dried over magnesium sulphate, and the solvent removed under reduced pressure. Chromatography using silica gel eluting with diethyl ether:hexane (1:1, by volume) gave the title compound (35 g). TLC R$_f$=0.30 (silica, diethyl ether:hexane, 1:1, by volume).

$^1$H-NMR (CDCl$_3$):67 =1.25 (t,3H), 1.35–1.8 (m,6H), 2.0–2.55 (m,6H), 3.3–3.45 (m,2H), 3.65–3.8 (m,2H), 4.0–4.1 (m,2H), 4.4–4.5 (m,1H), 7.2–7.55 (m,3H) ppm.

Preparation 3

5-(3,4-Dichlorophenyl)-5-(2-[tetrahydropyran-2-yloxy]ethyl)-2(1H)-piperidone

The compound of Preparation 2 (18.7 g, 45.2 mmol) was dissolved in saturated ammoniacal ethanol solution (500 ml) which contained Raney nickel (3.5 g). The mixture was stirred under hydrogen at atmospheric pressure for seven hours. The catalyst was then removed by filtration, the ethanol removed under reduced pressure and the residue chromatographed using silica gel eluting initially with diethyl ether and then with methanol:dichloromethane (1:9, by volume) to give the title compound (10.4 g). TLC R$_f$=0.45 (silica, methanol:dichloromethane, 1:9, by volume). LRMS m/z=372(m+1)$^+$.

$^1$H-NMR (CDCl$_3$):δ=1.4–1.8 (m,6H), 1.9–2.1 (m,5H), 2.3–2.45 (m,1H), 3.0–3.2 (m,1H), 3.0–3.2 (m,1H), 3.35–3.85 (m,4H), 4.35–4.4 (m,1H), 6.05 (s,br.,1H), 7.15–7.45 (m,3H) ppm.

Preparation 4

5-(3,4-Dichlorophenyl)-5-(2-hydroxyethyl)-2(1H)-piperidone

To a saturated solution of hydrogen chloride in methanol (350 ml) at room temperature was added the compound of Preparation 3 (10.4 g, 28 mmol). Hydrogen chloride gas was then bubbled through the solution with stirring for forty minutes and the reaction then left to stir at room temperature for fourteen hours. The solvent was removed under reduced pressure. Saturated aqueous sodium bicarbonate solution (300 ml) was added and the aqueous phase extracted with ethyl acetate (4×300 ml). The combined organic layers were dried over magnesium sulphate, filtered, and the solvent removed under reduced pressure to give a white solid. This was crystallised from ethyl acetate to give the title compound (5.5 g). TLC R$_f$=0.23 (silica, methanol:dichloromethane, 1:9, by volume). m.p. 167–168° C. LRMS m/z=288(m+1)$^+$. Found: C, 54.02; H, 5.03; N, 4.52. C$_{13}$H$_{15}$Cl$_2$NO$_2$ requires C, 54.18; H, 5.25; N, 4.84%.

$^1$H-NMR (d$_6$-DMSO):δ=1.7–2.2 (m,6H), 3.1–3.15 (m,2H), 3.25–3.3 (m,1H), 3.6–3.7 (m,1H), 4.3–4.35 (m,1H), 7.35–7.65 (m,4H) ppm.

Preparation 5

5-(3,4-Dichlorophenyl)-5-(2-methanesulphonyloxyethyl)-2(1H)-piperidone

To a solution of the compound of Preparation 4 (5.44 g, 18.9 mmol) in dry dichloromethane (100 ml) was added triethylamine (3.95 ml, 1.5 mol. equiv.) and the solution cooled to 0° C. Methanesulphonyl chloride (1.9 ml, 1.3 mol. equiv.) was then added and the reaction allowed to warm to room temperature and stirred for 2.5 hours. The reaction was washed with water (3×200 ml), dried over magnesium sulphate, filtered and the solvent removed under reduced pressure to give the title compound (7.1 g). TLC R$_f$=0.24 (silica, methanol:dichloromethane, 1:19, by volume).

$^1$H-NMR (CDCl$_3$):δ=2.0–2.5 (m,6H), 2.9 (s,3H), 3.45–4.1 (m,4H), 6.7 (s,br.,1H), 7.2–7.5 (m,3H) ppm.

Preparation 6

5-(3,4-Dichlorophenyl)-5-formylmethyl-2(1H)-piperidone

To a solution of oxalyl chloride (1.6 ml, 1.1 mol.equiv.) in dry dichloromethane (200 ml) at −78° C. was added dry dimethylsulphoxide (3.0 ml, 2.4 mol. equiv.), dropwise, and the solution allowed to stir for one hour. A solution of the compound of Preparation 4 (5 g) in a mixture of dichloromethane (100 ml) and dry dimethylsulphoxide (10 ml) was then added, dropwise over fifteen minutes, and the mixture allowed to stir at −78° C. for one hour. Triethylamine (12 ml, 5 mol. equiv.) was then added and the mixture allowed to warm to room temperature over four hours. Water (25 ml) was added and the mixture extracted with dichloromethane (3×100 ml). The combined organic layers were dried over magnesium sulphate, filtered and the solvent removed under reduced pressure to give a gum which was chromatographed using silica gel eluting with a solvent gradient of methanol:dichloromethane (1:49 to 1:5, by volume) to give the title compound (1.09 g).

$^1$H-NMR (CDCl$_3$):δ=2.05–2.2 (m,2H), 2.35–2.5 (m,1H), 2.7–2.75 (m,1H), 2.95–3.0 (m,1H), 3.45–3.6 (m,2H), 3.85–3.9 (m,1H), 6.0 (s,br.,1H), 7.2–7.45 (m,3H), 9.5 (m,1H) ppm.

Preparation 7

5-(3,4-Dichlorophenyl)-1-(4-phenylbenzyl)-5-(2-[tetrahydropyran-2-oxy]ethyl)-2-piperidone To a solution of the compound of Preparation 3 (500 mg, 1.34 mmol) in dry dimethylformamide (10 ml) at room temperature under nitrogen was added 60% w/w sodium hydride dispersion in oil (54 mg, 1.05 mol. equiv.) and the mixture allowed to stir at room temperature for one hour. A solution of 4-phenylbenzyl bromide (365 mg, 1.1 mol. equiv.) in dimethylformamide (1 ml) was then added dropwise and the mixture allowed to stir at room temperature for two hours. Water (2 ml) was then added followed by saturated aqueous sodium bicarbonate solution (10 ml) and saturated ammonium chloride solution (10 ml). The mixture was then extracted with ethyl acetate (3×50 ml) and the combined organic layers were washed with saturated aqueous ammonium chloride solution (2×50 ml). The organic phase was dried over magnesium sulphate, filtered, and the solvent removed under reduced pressure to give a white foam. This crude product was then chromatographed using silica gel eluting with ethyl acetate to give the title compound (456 mg). TLC Rf=0.47 (silica, ethyl acetate).

$^1$H-NMR (CDCl$_3$):δ=1.5–1.8 (m,6H), 1.8–2.05 (m,2H), 2.05–2.2 (m,3H), 2.4–2.55 (m,1H), 2.85–3.1 (m,1H), 3.3–3.75 (m,4H), 3.75–3.85 (m,1H), 4.2–4.4 (m,2H), 5.0–5.1 (d,1H), 6.8–6.9 (t,1H), 7.05–7.1 (d,1H), 7.2–7.3 (m,1H), 7.3–7.5 (m,5H), 7.55–7.65 (m,4H) ppm.

Preparation 8

5-(4-Chlorophenyl)-1-(cyclohexyimethyl)-5-(2-hydroxyethyl)-2-piperidone

To a methanolic solution (20 ml) of the compound of Preparation 51 (1 g, 1 mol. equiv.) was added Amberlyst H-15 (trade mark) ion exchange resin (0.33 g, 0.33 w/w equiv.) and the reaction stirred for twenty hours at room temperature. The resin was removed by filtration and the methanol removed from the filtrate under reduced pressure. The residue was dissolved in ethyl acetate (20 ml) and the mixture washed with water (5 ml) and brine (5 ml). The organic layer was dried using anhydrous magnesium sulphate, filtered and the filtrate evaporated to dryness under reduced pressure to give the title compound as a white solid (0.81 g) which was used without further purification. TLC $R_f$=0.7 (silica, methanol: dichloromethane, 1:9 by volume). LRMS m/z=350(m+1)$^+$.

Preparation 9

Ethyl 4,4-difluorocyclohexanecarboxylate

To a solution of diethylaminosulphur trifluoride (7.76 ml, 2 mol. equiv.) in carbon tetrachloride (75 ml) at 0° C. was added ethyl 4-oxocyclohexanecarboxylate (5 g, 29.4 mmol), dropwise, and the mixture was allowed to stir at room temperature for fourteen hours.

Water (50 ml) was then added carefully. The organic phase was washed with water (3×50 ml), dried over anhydrous magnesium sulphate, filtered and the solvent removed under reduced pressure to give the title compound as a yellow oil (1.96 g) which was purified by distillation.

$^1$H-NMR (CDCl$_3$):δ=1.2–1.3 (t,3H), 1.65–1.9 (m,4H), 1.95–2.2 (m,3H), 2.2–2.45 (m,2H), 4.05–4.2 (q,2H) ppm.

Preparation 10

4,4-Difluorocyclohexylmethanol

To a stirred suspension of lithium aluminium hydride (350 mg) in dry diethyl ether (30 ml) at 0° C. under nitrogen was added a solution of the compound of Preparation 9 (1.96 g) in dry diethyl ether (15 ml), dropwise. The mixture was then allowed to stir for one hour. Water (0.5 ml) was then added followed by 2N aqueous sodium hydroxide solution (0.5 ml) and then water (0.5 ml). The inorganic solids were removed by filtration and the filtrate concentrated under reduced pressure to give the title compound as a colourless oil (1.59 g).

$^1$H-NMR (CDCl$_3$):δ=1.15–1.4 (m,2H), 1.4–1.5 (m,2H), 1.5–1.7 (m,1H), 1.7–2.0 (m,3H), 2.0–2.3 (m,2H), 3.45–3.6 (m,2H) ppm.

Preparation 11

4,4-Difluoro-1-(4-methylphenylsulphonyloxymethyl) cyclohexane

To a solution of the compound of Preparation 10 (500 mg, 3.33 mmol) in dichloromethane (10 ml) at room temperature was added triethylamine (0.62 ml, 1.5 mol. equiv.) followed by p-toluenesulphonyl chloride (570 mg, 1 mol. equiv.) and the reaction mixture allowed to stir for fourteen hours. Water (25 ml) was then added, the layers separated, the organic phase further washed with water (2×25 ml) and the organic layer dried over anhydrous magnesium sulphate. The solution was filtered and the solvent removed under reduced pressure. The crude product was then passed through a short pad of silica eluting with diethyl ether:hexane (1:4, by volume). The solvent was removed from the eluted fraction under reduced pressure and the product crystallised by trituration using hexane to give the title compound as a white solid (100 mg).

$^1$H-NMR (CDCl$_3$):δ=1.2–1.35 (m,2H), 1.55–1.7 (m,1H), 1.7–1.85 (m,4H), 2.0–2.15 (m,2H), 2.45–2.5 (s,3H), 3.85–3.9 (d,2H), 7.3–7.4 (d,2H), 7.75–8.0 (d,2H) ppm.

Preparation 12

5-(3,4-Dichlorophenyl)-1-(4,4-difluorocyclohexylmethyl)-5-(2-[tetrahydropyran-2-oxy]ethyl)-2-piperidone To a solution of the compound of Preparation 3 (121 mg, 0.33 mmol) in dry dimethylformamide (3 ml) under nitrogen was added 60% w/w sodium hydride dispersion in oil (14 mg) and the mixture was allowed to stir at room temperature for forty-five minutes. To this mixture was added the compound of Preparation 10 (99 mg, 1 mol. equiv.) and the mixture heated at 50° C. for five hours. To effect a more complete reaction a further portion of 60% w/w sodium hydride dispersion in oil (7 mg, 0.5 mol. equiv.) was added and the reaction heated at 50° C. for a further three hours. Water (1 ml) was then added and the mixture evaporated to dryness under reduced pressure. The residue was then dissolved in ethyl acetate (20 ml) and the organic phase washed with water (2× 20 ml). The organic phase was then dried over anhydrous magnesium sulphate, filtered and the solvent removed under reduced pressure to give a gum. This was purified by column chromatography using silica gel eluting with a solvent gradient of dichloromethane:methanol (100:0 to 9:1, by volume) to give the title compound (80 mg). LRMS m/z=506(m+1)$^+$.

$^1$H-NMR (CDCl$_3$):δ=1.15–1.6 (m,8H), 1.6–1.9 (m,5H), 1.9–2.3 (m,7H), 2.4–2.5 (m,1H), 3.0–3.3 (m,2H), 3.3–3.6 (m,4H), 3.6–3.8 (m,2H), 4.3–4.4 (m,1H), 7.05–7.15 (d,1H), 7.3–7.4 (s,1H), 7.4–7.45 (d,1H) ppm.

Preparation 13

Methanesulphonyloxymethylcycloheptane

To a solution of cycloheptylmethanol (1.0 g, 7.81 mmol) in dichloromethane (20 ml) at 0° C. under nitrogen was added triethylamine (1.63 ml, 1.5 mol. equiv.) Methanesulphonyl chloride (0.73 ml, 1.2 mol. equiv.) was added, dropwise, and the reaction allowed to stir for two hours at room temperature. Water (50 ml) and dichloromethane (50 ml) were added. The organic phase was separated, washed with water (2×50 ml) and then dried over anhydrous magnesium sulphate. The solution was then filtered and the solvent removed under reduced pressure to give the title compound as an oil (1.66 g).

$^1$H-NMR (CDCl$_3$):δ=1.15–1.3 (m,2H), 1.4–1.6 (m,6H), 1.6–1.8 (m,4H), 1.85–2.0 (m,1H), 2.95–3.0 (s,3H), 3.95–4.05 (d,2H) ppm.

Preparations 14 to 16

The compounds of the following tabulated Preparations of the general formula:

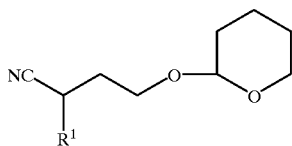

were prepared by a similar method to that used in Preparation 1 using the appropriate acetonitrile derivative starting materials.

| Prep. No. | R¹ | LRMS m/z | Analysis/¹H-NMR |
|---|---|---|---|
| 14 | 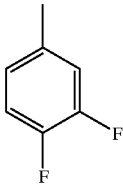 | — | ¹H-NMR(CDCl₃): δ = 1.5–1.9(m,6H), 2.05–2.3(m,2H), 3.4–4.1(m,5H), 4.55–4.65(m,1H), 7.05–7.3(m,3H) ppm. |
| 15 | 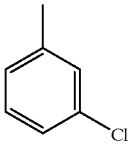 | 297 (m + NH₄)⁺ | ¹H-NMR(CDCl₃): δ = 1.5–1.7(m,4H), 1.7–1.9(m,2H), 2.05–2.3(m,2H), 3.45–3.6(m,2H), 3.8–4.1(m,3H), 4.6–4.65(m,1H), 7.25–7.4(m,4H) ppm. |
| 16 | 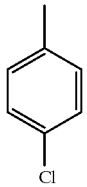 | 297 (m + NH₄)⁺ | ¹H-NMR(CDCl₃): δ = 1.5–1.85(m,6H), 2.05–2.2(m,2H), 3.45–3.6(m,2H), 3.8–3.95(m,2H), 4.05–4.1(m,1H), 4.55–4.65(m,1H), 7.3–7.4(m,4H) ppm. |

Preparations 17 to 19

The compounds of the following tabulated Preparations of the general formula:

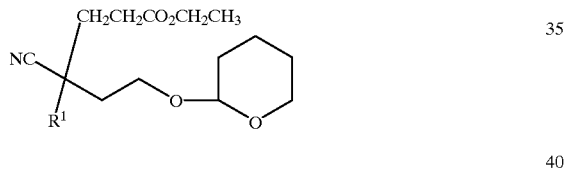

were prepared by a similar method so that used in Preparation 2 using the appropriate butanenitrile derivative starting materials (see Preparations 14 to 16).

| Prep. No. | R¹ | LRMS m/z | Analysis/¹H-NMR |
|---|---|---|---|
| 17 | 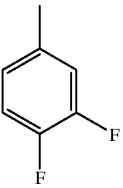 | — | Found: C, 62.80; H, 6.42; N, 3.85. C₂₀H₂₅NO₄F₂ requires C, 62.98; H, 6.61; N, 3.67%.<br>¹H-NMR(CDCl₃): δ = 1.2–1.3(m,3H), 1.4–1.8(m,6H), 2.05–2.55(m,6H), 3.3–3.5(m,2H), 3.65–3.85(m,2H), 4.05–4.15(m,2H), 4.4–4.5(m,1H), 7.15–7.3(m,3H) ppm. |
| 18 | 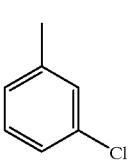 | 397 (m + NH₄)⁺ | ¹H-NMR(CDCl₃): δ = 1.2–1.3(m,5H), 1.4–1.8(m,6H), 2.05–2.55(m,6H), 3.35–3.5(m,1H), 3.65–3.8(m,1H), 4.0–4.1(m,2H), 7.3–7.45(m,4H) ppm. |

-continued

| Prep. No. | R¹ | LRMS m/z | Analysis/¹H-NMR |
|---|---|---|---|
| 19 | 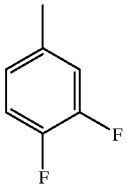 | 397 (m + NH₄)⁺ | ¹H-NMR(CDCl₃): δ = 1.2–1.75(m,10H), 2.05–2.55(m,5H), 3.25–3.45(m,2H), 3.6–3.85(m,2H), 3.95–4.1(m,2H), 4.45–4.5(m,1H), 7.4(s,4H) ppm. |

Preparations 20 to 22

The compounds of the following tabulated Preparations of the general formula:

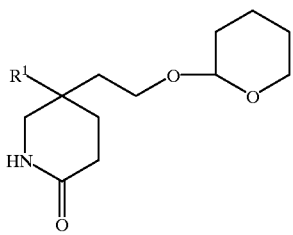

were prepared by a similar procedure to that used in Preparation 3 using the appropriate butanoate derivative starting materials (see Preparations 17 to 19).

Preparations 23 to 32

The compounds of the following tabulated Preparations of the general formula:

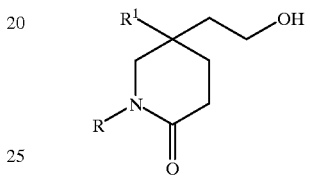

were prepared by a similar method to that of Preparation 4 using the appropriate tetrahydropyran derivative starting materials (see Preparations 7, 12, 44 to 50 and 52).

| Prep. No. | R¹ | LRMS m/z | Analysis/¹H-NMR |
|---|---|---|---|
| 20[1] | 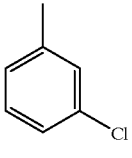 | 340 (m + 1)⁺ | ¹H-NMR(CDCl₃): δ = 1.45–1.75(m,5H), 1.85–2.15(m,5H), 2.35–2.45(m,1H), 3.0–3.15(m,1H), 3.35–3.55(m,4H), 3.65–3.8(m,2H), 4.35–4.4(m,1H), 5.95(br.s,1H), 7.05–7.2 (m,3H) ppm. |
| 21[2] | 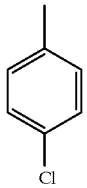 | 338 (m + 1)⁺ | ¹H-NMR(CDCl₃): δ = 1.4–1.8(m,6H), 1.9–2.0(m,1H), 2.05–2.25(m,4H), 2.3–2.4(m,1H), 3.0–3.2(m,1H), 3.4–3.6 (m,3H), 3.65–3.85(m,2H), 4.3–4.4(m,1H), 6.2(br.s,1H), 7.15–7.3(m,4H) ppm. |
| 22[1] | 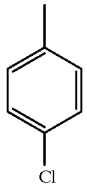 | 338 (m + 1)⁺ | ¹H-NMR(CDCl₃): δ = 1.4–1.8(m,6H), 1.9–2.45(m,6H), 3.0–3.1(m,1H), 3.35–3.85(m,5H), 4.35–4.4(m,1H), 6.05 (br.s,1H), 7.25–7.35(m,4H) ppm. |

Footnotes
1. Reaction carried out at about 414 kPa (60 psi) and 50° C.
2. Reaction carried out at 50° C.

| Prep. No. | R | R¹ | LRMS m/z | Analysis/¹H-NMR |
|---|---|---|---|---|
| 23 | 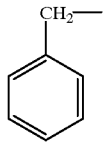 | 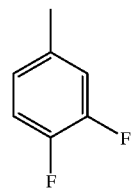 | 352 (m + 1)⁺ | Found: C, 69.16; H, 6.14; N, 3.92. $C_{20}H_{21}NF_2O_2$ requires C, 69.55; H, 6.13; N, 4.06%. ¹H-NMR(CDCl₃): δ = 1.75–1.95(m,2H), 2.0–2.25(m,4H), 2.45–2.5(m,1H), 3.2–3.4 (m,3H), 3.65–3.7(m,1H), 4.4(d,1H), 4.85 (d,1H), 6.7–6.85(m,2H), 6.9–7.05(m,1H), 7.3–7.4(m,5H) ppm. |
| 24 | 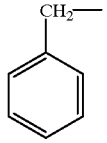 | 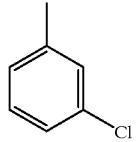 | 344 (m + 1)⁺ | ¹H-NMR(CDCl₃): δ = 1.75–2.25(m,6H), 2.45–2.5(m,1H), 3.2–3.4(m,3H), 3.65–3.7 (m,1H), 4.45(d,1H), 4.75(d,1H), 6.9–7.4 (m,9H) ppm. |
| 25 | 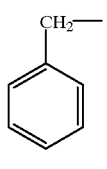 | 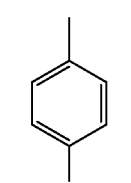 | 344 (m + 1)⁺ | ¹H-NMR(CDCl₃): δ = 1.75–1.85(m,1H), 1.9–2.25(m,5H), 2.4–2.5(m,1H), 3.2–3.4 (m,3H), 3.65–3.7(m,1H), 4.45(d,1H), 4.8 (d,1H),, 6.9–7.4(m,9H) ppm. |
| 26 | 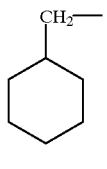 | 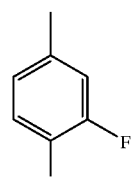 | 352 (m + 1)⁺ | ¹H-NMR(d₆-DMSO): δ = 0.8–0.9(m,2H), 1.0–1.25(m,2H), 1.4–1.8(m,6H), 1.85–2.05(m,3H), 2.1–2.3(m,2H), 3.0–3.3 (m,6H), 3.35–3.45(m,1H), 3.6–3.7 (m,1H), 4.3–4.4(m,1H), 7.1(m,1H), 7.3–7.5(m,2H) ppm. |
| 27 | 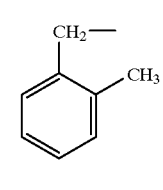 | 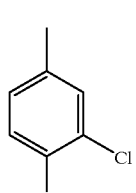 | 391 (m)⁺ | ¹H-NMR(CDCl₃): δ = 1.75–1.95(m,2H), 2.05–2.35(m,7H), 2.45–2.55(m,1H), 3.2–3.4(m,3H), 3.65(d,1H), 4.45(d,1H), 5.05 (d,1H), 6.8–7.3(m,7H) ppm. |
| 28 | 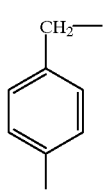 | 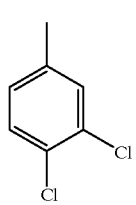 | 391 (m)⁺ | ¹H-NMR(CDCl₃): δ = 1.75–2.2(m,6H), 2.35–2.5(m,4H), 3.2–3.35(m,3H), 3.65 (d,1H), 4.3(d,1H), 4.7(d,1H), 6.8–6.9 (m,1H), 7.05–7.1(m,1H), 7.15–7.3(m,5H) ppm. |
| 29 | 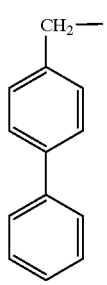 | 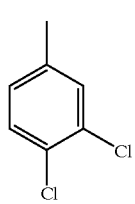 | 454 (m + 1)⁺ | ¹H-NMR(CDCl₃): δ = 1.8–2.25(m,5H), 2.4–2.55(m,1H), 3.2–3.4(m,4H), 3.7–3.8 (m,1H), 4.35(d,1H), 4.95(d,1H), 6.85–7.65(m,12H) ppm. |

| Prep. No. | R | R¹ | LRMS m/z | Analysis/¹H-NMR |
|---|---|---|---|---|
| 30 | 4,4-difluorocyclohexyl-CH₂— | 3,4-dichlorophenyl | 420 (m + 1)⁺ | ¹H-NMR(d₆-DMSO): δ = 1.05–1.25(m,2H), 1.6–2.05(m,9H), 2.15–2.3(m,2H), 3.0–3.2 (m,3H), 3.2–3.3(m,3H), 3.4–3.5(m,1H), 3.65–3.75(m,1H), 4.35–4.45(m,1H), 7.3– 7.4(d,1H), 7.55–7.65(m,2H) ppm. |
| 31 | phenyl-CH₂— | 3,4-dichlorophenyl | — | ¹H-NMR(CDCl₃): δ = 1.1–1.15(m,1H), 1.8– 2.0(m,2H), 2.0–2.3(m,3H), 2.4–2.5 (m,1H), 3.2–3.5(m,3H), 3.6–3.8(m,1H), 4.4(d,1H), 4.85(d,1H), 6.75–6.85 (m,1H), 7.1–7.5(m,7H) ppm. |
| 32 | cyclohexyl-CH₂— | 3,4-dichlorophenyl | — | Found: C, 62.49; H, 7.22; N, 3.51. C₂₀H₂₇NCl₂O₂ requires: C, 62.50; H, 7.08; N, 3.64%. ¹H-NMR(CDCl₃): δ = 0.95–1.1(m,2H), 1.15–1.30(m,4H), 1.55–1.75(m,6H), 1.85– 2.2(m,5H), 2.35–2.45(m,1H), 3.1–3.2 (m,1H), 3.35–3.50(m,4H), 3.65–3.75(m,1H), 7.1–7.15(m,1H), 7.3–7.4(m,2H) ppm. |

Preparations 33 to 38

The compounds of the following tabulated Preparations of the general formula:

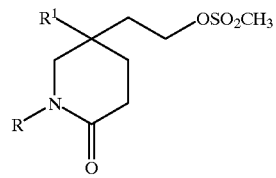

were prepared by a similar method to that used in Preparation 5 using the appropriate ethanol derivative starting materials (see Preparations 8, 27 to 30 and 32).

| Prep. No. | R | R¹ | LRMS m/z | Analysis/¹H-NMR |
|---|---|---|---|---|
| 33 | 2-methylphenyl-CH₂— | 3,4-dichlorophenyl | 470 (m + 1)⁺ | ¹H-NMR(CDCl₃): δ = 1.95–2.35(m,8H), 2.45–2.6(m,1H), 2.8(s,3H), 3.25(d,1H), 3.6–3.75(m,2H), 3.9–4.0(m,1H), 4.25 (d,1H), 5.1(d,1H), 6.75–7.3(m,7H) ppm. |
| 34 | 4-methylphenyl-CH₂— | 3,4-dichlorophenyl | 470 (m + 1)⁺ | ¹H-NMR(CDCl₃): δ = 1.95–2.25(m,6H), 2.4 (s,3H), 2.45–2.55(m,1H), 2.85(s,3H), 3.6–3.95(m,3H), 4.2(d,1H), 4.9(d,1H), 6.8–6.85(m,1H), 7.15–7.3(m,6H) ppm. |

-continued

| Prep. No. | R | R¹ | LRMS m/z | Analysis/¹H-NMR |
|---|---|---|---|---|
| 35 | 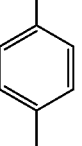 | 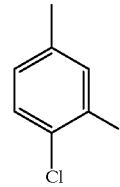 | — | ¹H-NMR(CDCl₃): δ = 2.05–2.25(m,5H), 2.45–2.55(m,1H), 2.85(s,1H), 3.4(d,1H), 3.7–3.95(m,3H), 4.3(d,1H), 5.0(d,1H), 6.85–7.65(m,12H) ppm. |
| 36 | 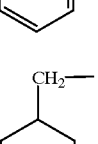 | 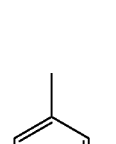 | — | ¹H-NMR(CDCl₃): δ = 1.15–1.5(m,2H), 1.6–1.9(m,5H), 2.0–2.35(m,7H), 2.4–2.53 (m,1H), 2.85–3.1(m,3H), 3.2–3.5(m,1H), 3.4–3.55(m,2H), 3.65–3.75(m,1H), 3.9–4.05(m,2H), 7.1–7.15(d,1H), 7.3–7.36 (s,1H), 7.4–7.5(d,1H) ppm. |
| 37 | 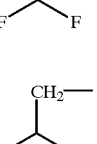 | 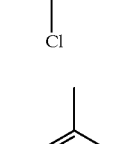 | 428 (m)⁺ | — |
| 38 | 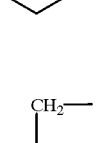 | 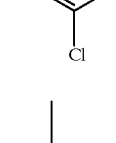 | — | ¹H-NMR(CDCl₃): δ = 0.9–1.05(m,2H), 1.1–1.3(m,3H), 1.55–1.75(m,6H), 2.05–2.30 (m,5H), 2.35–2.50(m,1H), 2.90(s,3H), 3.1–3.2(m,1H), 3.35–3.45(m,2H), 3.60–3.65 (m,1H), 3.9–4.0(m,2H), 7.1–7.15(m,1H), 7.35–7.50(m,2H) ppm. |

Preparations 39 to 43

The compounds of the following tabulated Preparations of the general formula:

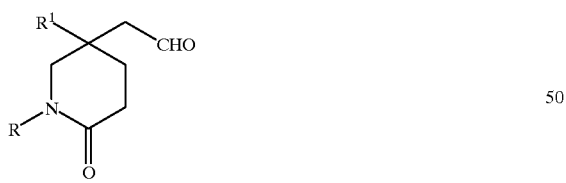

were prepared by a similar method to that used in Preparation 6 using the appropriate ethanol derivative starting materials (see Preparations 23 to 26 and 31).

| Prep. No. | R | R¹ | LRMS m/z | Analysis/¹H-NMR |
|---|---|---|---|---|
| 39 | CH₂-phenyl | 3,4-difluorophenyl | — | ¹H-NMR(CDCl₃): δ = 2.1–2.3(m,3H), 2.4–2.6(m,2H), 2.85(d,1H), 3.4(d,1H), 3.7(d,1H), 4.4(d,1H), 4.8(d,1H), 6.7–7.3(m,8H), 9.35(s,1H) ppm. |
| 40 | CH₂-cyclohexyl | 3,4-difluorophenyl | 350 (m + 1)⁺ | ¹H-NMR(CDCl₃): δ = 0.95–1.05(m,2H), 1.15–1.3(m,4H), 1.6–2.5(m,9H), 2.65–2.75(m,1H), 2.95–3.05(m,1H), 3.1–3.2(m,1H), 3.4–3.5(m,2H), 3.7–3.8(m,1H), 7.05–7.3(m,3H), 9.45(s,1H) ppm. |
| 41 | CH₂-phenyl | 3-chlorophenyl | 342 (m + 1)⁺ | ¹H-NMR(CDCl₃): δ = 2.1–2.3(m,2H), 2.4–2.55(m,2H), 2.8–2.9(m,1H), 3.3–3.4(m,2H), 3.7–3.8(m,1H), 4.45–4.6(m,1H), 4.7–4.8(m,1H), 6.9–7.4(m,9H), 9.4(s,1H) ppm. |
| 42 | CH₂-phenyl | 4-chlorophenyl | 342 (m + 1)⁺ | ¹H-NMR(CDCl₃): δ = 2.15–2.3(m,2H), 2.45–2.6(m,2H), 2.8–2.9(m,1H), 3.4–3.5(m,2H), 3.75–3.85(m,1H), 4.45(d,1H), 4.8(d,1H), 6.95–7.35(m,9H), 9.35(m,1H) ppm. |
| 43 | CH₂-phenyl | 3,4-dichlorophenyl | 376 (m + 1)⁺ | ¹H-NMR(CDCl₃): δ = 2.1–2.3(m,2H), 2.4–2.7(m,3H), 2.8–2.9(m,1H), 3.4(d,1H), 3.75(d,1H), 4.4(d,1H), 4.8(d,1H), 6.8–6.85(m,1H), 7.2–7.4(m,7H), 9.4(s,1H) ppm. |

Preparations 44 to 52

The compounds of the following tabulated Preparations of the general formula:

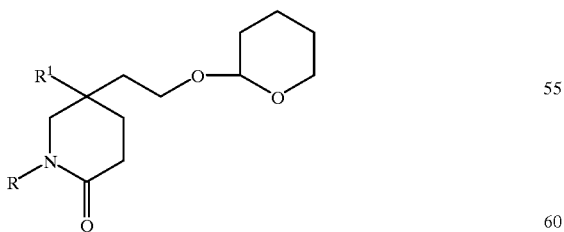

were prepared by a similar method to that used in Preparation 7 using the appropriate 2(1H)-piperidone derivatives (see Preparations 3, 20, 21 and 22) and alkyl bromides as the starting materials.

| Prep. No. | R | R¹ | LRMS m/z | Analysis/¹H-NMR |
|---|---|---|---|---|
| 44 | benzyl (PhCH₂–) | 3,4-difluorophenyl | — | Found: C, 69.55; H, 6.81; N, 2.71. C₂₅H₂₉NF₂O₃ requires C, 69.91; H, 6.81; N, 3.26%. ¹H-NMR(CDCl₃): δ = 1.4–1.75(m,8H), 1.85–1.95(m,2H), 2.05–2.2(m,2H), 2.4–2.5(m,1H), 2.8–3.05(m,1H), 3.3–3.5 (m,3H), 3.6–3.75(m,1H), 4.25–4.4 (m,2H), 4.9–5.0(m,1H), 6.6–6.8(m,2H), 6.95–7.05(m,1H), 7.25–7.4(m,5H) ppm. |
| 45 | cyclohexylmethyl | 3,4-difluorophenyl | 436 (m + 1)⁺ | — |
| 46 | benzyl | 3-chlorophenyl | 428 (m + 1)⁺ | ¹H-NMR(CDCl₃): δ = 1.4–1.75(m,7H), 1.85–2.25(m,4H), 2.4–2.55(m,1H), 2.85–3.05(m,1H), 3.3–3.8(m,5H), 4.25–4.45 (m,2H), 4.85–4.95(m,1H), 6.85–7.4 (m,9H) ppm. |
| 47 | benzyl | 4-chlorophenyl | 428 (m + 1)⁺ | ¹H-NMR(CDCl₃): δ = 1.35–1.6(m,6H), 1.8–2.2(m,6H), 2.4–2.5(m,1H), 2.85–3.05 (m,1H), 3.3–3.85(m,4H), 4.2–4.35 (m,2H), 4.9–4.95(m,1H), 6.9–7.35(m,9H) ppm. |
| 48 | 2-methylbenzyl | 3,4-dichlorophenyl | 476 (m + 1)⁺ | ¹H-NMR(CDCl₃): δ = 1.35–2.5(m,15H), 2.8–3.1(m,1H), 3.2–3.4(m,3H), 3.45–3.6 (m,1H), 3.65–3.7(m,2H), 4.2–4.35 (m,2H), 5.0–5.15(m,1H), 6.75–6.85 (m,1H), 7.0–7.1(m,5H) ppm. |
| 49 | 4-methylbenzyl | 3,4-dichlorophenyl | 476 (m + 1)⁺ | ¹H-NMR(CDCl₃): δ = 1.4–1.75(m,6H), 1.8–1.9(m,2H), 2.05–2.2(m,3H), 2.4(s,3H), 2.4–2.5(m,1H), 2.85–3.1(m,1H), 3.3–3.75 (m,5H), 4.2–4.35(m,2H), 4.9–4.95 (m,1H), 6.8–6.85(m,1H), 7.0–7.1(m,1H), 7.15–7.3(m,5H) ppm. |
| 50 | benzyl (cyclohexadienyl?) | 3,4-dichlorophenyl | 462 (m + 1)⁺ | ¹H-NMR(CDCl₃): δ = 1.35–1.7(m,6H), 1.8–2.05(m,2H), 2.05–2.2(m,2H), 2.35–2.5 (m,1H), 2.8–3.1(m,1H), 3.3–3.8(m,6H), 4.25–4.4(m,2H), 4.9–5.05(m,1H), 6.7–6.8 (m,1H), 7.1–7.15(m,1H), 7.2–7.5(m,6H) ppm. |

-continued

| Prep. No. | R | R¹ | LRMS m/z | Analysis/¹H-NMR |
|---|---|---|---|---|
| 51 | CH₂—cyclohexyl | 4-chlorophenyl methyl | 434 (m)⁺ | ¹H-NMR(CDCl₃): δ = 0.9–1.1(m,2H), 1.1–1.3(m,4H), 1.4–1.8(m,11H), 1.85–2.2 (m,5H), 2.3–2.5(m,1H), 3.0–3.2(m,2H), 3.4–3.6(m,4H), 3.6–3.8(m,2H), 4.3–4.4 (m,1H), 7.1–7.4(m,4H) ppm. |
| 52 | CH₂—cyclohexyl | 3,4-dichlorophenyl methyl | 468 (m + 1)⁺ | ¹H-NMR(CDCl₃): δ = 0.95–2.2(m,22H), 2.35–2.5(m,1H), 3.05–3.25(m,2H), 3.35–3.85(m,6H), 4.35–4.45(m,1H), 7.1–7.15 (m,1H), 7.35–7.45(m,2H) ppm. |

¹Potassium iodide was added to the reaction mixture and then the mixture heated at 50° C. for four hours.

Preparation 53

1-Diphenylmethylazetidin-3-ol

A solution of benzhydrylamine (200 ml, 1.16 mol) and epichlorohydrin (186 ml, 1 mol. equiv.) in methanol (600 ml) was stirred at room temperature for five days and then heated at 40° C. for two days. The solvent was then removed under reduced pressure, the residue dissolved in isopropyl alcohol (500 ml) and the solution heated under reflux for six hours. The solution was cooled to room temperature and the precipitate filtered off. This solid was partitioned between dichloromethane (400 ml) and saturated aqueous sodium bicarbonate solution (500 ml). The aqueous phase was extracted with dichloromethane (2×400 ml) and the combined organic phases dried over magnesium sulphate. The solution was then filtered and the solvent removed from the filtrate under reduced pressure to give the title compound (86 g) as a crystalline solid.

¹H-NMR (CDCl₃):δ=1.8–2.3 (s,br,1H), 2.85–2.9 (m,2H), 3.5–3.55 (m,2H), 4.35 (s,1H), 4.4–4.5 (m,1H), 7.15–7.4 (m,10H) ppm.

Preparation 54

1-Diphenylmethyl-3-methanesulphonyloxyazetidine

To a solution of 1-diphenylmethylazetidin-3-ol (see Preparation 53 (65.9 g, 275.7 mmol) in dry dichloromethane (700 ml) at 0° C. under nitrogen was added triethylamine (57 ml, 1.5 mol. equiv.). After five minutes, methanesulphonyl chloride (25.6 ml, 1.2 mol. equiv.) was added and the mixture stirred for one hour. Water (300 ml) was then added and the mixture extracted with dichloromethane (3×300 ml). The combined organic layers were dried over magnesium sulphate. The solution was then filtered and the solvent removed from the filtrate under reduced pressure. The residue was chromatographed using silica gel eluting with methanol:dichloromethane (1.49, by volume) to give the title compound (73.4 g) as a solid.

¹H-NMR (CDCl₃):δ=2.95 (s,3H), 3.15–3.25 (m,2H), 3.6–3.65 (m,2H), 4.4 (s,1H), 5.05–5.15 (m,1H), 7.15–7.4 (m,10H) ppm.

Preparation 55

1-Diphenylmethyl-3-morpholinoazetidine

A solution of 1-diphenylmethyl-3-methanesulphonyloxyazetidine (see Preparation 54) (24.46 g, 7.72 mmol), potassium carbonate (32 g, 3 mol. equiv.) and morpholine (7.34 ml, 1.09 mol. equiv.) in acetonitrile (200 ml) was heated under reflux for four hours. The solution was then cooled to room temperature, water (50 ml) added and the mixture concentrated under reduced pressure. The residue was partitioned between ethyl acetate (400 ml) and water (400 ml) and the organic phase separated and washed with water (2×400 ml). The organic phase was dried over magnesium sulphate, filtered and the solvent removed from the filtrate under reduced pressure. The residue was then chromatographed using silica gel eluting with hexane:diethyl ether (1:1, by volume) to give the title compound (16.5 g).

¹H-NMR (CDCl₃):δ=2.25–2.3 (m,4H), 2.85–3.05 (m,3H), 3.35–3.4 (m,2H), 3.7–3.75 (m,4H), 4.45 (s,1H), 7.15–7.45 (m,10H) ppm.

Preparation 56

3-Morpholinoazetidine dihydrochloride

A mixture of 1-diphenylmethyl-3-morpholinoazetidine (see Preparation 55) (18.6 g, 60.4 mmol), palladium hydroxide (2 g), ethanol (200 ml) and 1 N aqueous hydrochloric acid solution (52 ml) was stirred under an atmosphere of hydrogen at 345 kPa (50 p.s.i.) for three days. The catalyst was then removed by filtration and the filtrate evaporated to dryness. Addition of dichloromethane (100 ml) to the residue and trituration yielded a solid which was recrystallised from methanol to give the title compound (10.2 g) as a crystalline solid. LRMS m/z=179(m+1)⁺. (N.B. The monohydrochloride, used instead of the dihydrochloride in some reactions, can be similarly prepared using one molar equivalent of hydrogen chloride.

Preparation 57

3-Cyano-1-(diphenylmethyl)azetidine

To a solution of the compound of Preparation 54 (10 g, 31.5 mmol) in dimethylformamide (100 ml) was added a solution of sodium cyanide (4.63 g, 3 mol. equiv.) in water (50 ml) in five portions over two minutes. The mixture was then heated at 70° C. for sixteen hours. The reaction was cooled to room temperature and then poured into an ice-water mixture (300 ml). The brown solid that formed was removed by filtration, dissolved in dichloromethane and the solution dried over anhydrous magnesium sulphate. The solution was filtered and the solvent removed from the filtrate under reduced pressure. The residue was then chromatographed using silica gel eluting with ethyl acetate:hexane (1:3, by volume) to give the title compound (5.9 g).

$^1$H-NMR (CDCl$_3$): δ=3.2–3.35 (m,3H), 3.45–3.5 (m,2H), 4.4 (s,1H), 7.15–7.45 (m,10H) ppm.

Preparation 58

1-(Diphenylmethyl)azetidine-3-carboxyl ic acid

To a suspension of the compound of Preparation 57 (5.9 g, 23.8 mmol) in n-butanol (60 ml) was added a solution of potassium hydroxide (4.8 g) in water (9 ml), dropwise over three minutes. The mixture was then heated at 90–100° C. for twenty hours. The reaction was cooled to room temperature and the solvent removed under reduced pressure. The residue was poured into ethyl acetate (100 ml) and water (100 ml). The aqueous layer was separated and filtered, then acidified to pH4 using 2N aqueous hydrochloric acid solution. The precipitated white solid was filtered off, washed with ethyl acetate (15 ml) and dried under reduced pressure to give the title compound (3.5 g). LRMS m/z=268(m+1)$^+$.

$^1$H-NMR (d$_6$DMSO): δ=3.1–3.3 (m,5H), 4.4 (br.s,1H), 7.15–7.4 (m,10H), 12.3 (br.s,1H) ppm.

Preparation 59

1-Diphenylmethyl-3-(N-[2-hydroxyethyl]-N-methylcarbamoyl)azetidine

A mixture of 1-diphenylmethylazetidine-3-carboxylic acid (see Preparation 58) (1.8 g, 6.73 mmol), 2-methylaminoethanol (0.76 g, 1.5 mol. equiv.), 1-[3-dimethylaminopropyl]-3-ethylcarbodiimide hydrochloride (1.27 g, 1.1 mol. equiv.), 1-hydroxybenzotriazole hydrate (1.08 g, 1.05 mol. equiv.) and N-methylmorpholine (1.5 g, 2.2 mol. equiv.) in dry dichloromethane (50 ml) was stirred at room temperature for sixteen hours. The solvent was removed under reduced pressure and the residue partitioned between ethyl acetate (50 ml) and saturated aqueous sodium bicarbonate solution (50 ml). The layers were separated and the aqueous layer further extracted with ethyl acetate (30 ml). The combined organic layers were dried over anhydrous sodium sulphate. The solution was filtered, the solvent removed from the filtrate under reduced pressure and the residue chromatographed using silica gel eluting with methanol:dichloromethane (7:93, by volume) to give the title compound (1.76 g). TLC Rf 0.3 (silica, methanol:dichloromethane, 7:93, by volume). LRMS m/z= 325(m+1)$^+$. Found C, 71.99; H, 7.60; N, 8.47. C$_{20}$H$_{24}$N$_2$O$_2$.0.13 CH$_2$Cl$_2$ requires C, 72.14; H, 7.30; N, 8.36%.

$^1$H-NMR (CDCl$_3$): δ=2.85–2.95 (m,5H), 3.2–3.35 (m,2H), 3.45–3.55 (m,4H), 3.65–3.8 (m,2H), 4.4 (s,1H), 7.15–7.45 (m,10H) ppm.

Preparation 60

1-Diphenylmethyl-3-(N-[2-methoxyethyl)-N-methylcarbamoyl)azetidine

To a solution of the compound of Preparation 59 (0.93 g, 2.87 mmol) in tetrahydrofuran (12 ml) at 0° C. under nitrogen was added, in two portions, 60% w/w sodium hydride dispersion in oil (0.126 g, 1.1 mol. equiv.). After thirty minutes stirring, methyl iodide (0.197 ml, 1.1 mol. equiv.) was added and the mixture stirred for sixteen hours. The solvent was removed under reduced pressure and the residue partitioned between ethyl acetate (50 ml) and saturated aqueous sodium bicarbonate solution (50 ml). The organic layer was dried over anhydrous sodium sulphate, filtered and the solvent removed under reduced pressure to give an oil. This crude product was purified by column chromatography using silica gel eluting with methanol:dichloromethane (1:19, by volume) to give the title compound (0.95 g). TLC Rf=0.45 (silica, methanol: dichloromethane, 1:19, by volume). LRMS m/z=339 (m+1)$^+$. Found: C, 72.42; H, 7.60; N, 7.89. C$_{21}$H$_{26}$N$_2$O$_2$.0.13 CH$_2$Cl$_2$ requires C, 72.69; H, 7.58; N, 8.03%.

$^1$H-NMR (CDCl$_3$): δ=2.9–2.95 (m,3H), 3.2–3.35 (m,6H), 3.4–3.55 (m,6H), 4.4 (m,1H), 7.1–7.45 (m,10H) ppm.

Preparation 61

N-(2-Methoxyethyl)-N-methylcarbamoylazetidine dihydrochloride

To a solution of the compound of Preparation 60 (473 mg, 1.4 mmol) in dichloromethane (5 ml) at 0° C. under nitrogen was added alpha-chloroethyl chloroformate (0.22 ml, 1.1 mol. equiv.), dropwise. After twenty minutes, a further portion of alpha-chloroethyl chloroformate (0.1 ml, 0.5 mol. equiv.) was added and the reaction allowed to warm to room temperature over twenty minutes. After this time, the solvent was removed under reduced pressure, the residue dissolved in methanol (7.5 ml) and potassium carbonate (620 mg, 3 mol. equiv.) was added. The mixture was then heated under reflux for one hour. The reaction mixture was cooled to room temperature, filtered and the filtrate acidified to pH 3 using ethereal HCl. The solid was removed by filtration. The solvent was removed from the filtrate under reduced pressure to give a gum which was washed several times with diethyl ether and dried under reduced pressure to give the title compound as a crude product (0.35 g) that was used directly.

Preparations 62 to 64

The compounds of the following tabulated Preparations of the general formula:

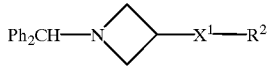

were prepared by a similar procedure to that of Preparation 59 using 1-diphenylmethylazetidine-3-carboxylic acid and the appropriate amine as starting materials.

| Prep. No. | —X¹—R² | LRMS m/z | Analysis/¹H-NMR |
|---|---|---|---|
| 62 | —CONH—⬡ | 349 (m + 1)⁺ | Found: C, 78.75; H, 8.49; N, 8.1. $C_{23}H_{28}N_2O$ requires C, 79.26; H, 8.10; N, 8.04%. ¹H-NMR($CDCl_3$): δ = 1.1–1.3(m,3H), 1.35–1.45(m,2H), 1.55–1.75(m,3H), 1.85–1.95(m,2H), 2.95–3.05(m,1H), 3.25–3.4(m,4H), 3.75–3.85(m,1H), 4.45(s,1H), 5.95–6.05 (m,1H), 7.15–7.4(m,10H) ppm. |
| 63 | —CON⬠ | 321 (m + 1)⁺ | Found: C, 76.67; H, 6.98; N, 8.02. $C_{21}H_{24}N_2O \cdot 0.33\ CH_2Cl_2$ requires C, 76.64; H, 7.38; N, 8.46%. ¹H-NMR($CDCl_3$): δ = 1.75–1.95(m,4H), 3.2–3.35(m,4H), 3.4–3.5(m,5H), 4.4(s,1H), 7.15–7.45(m,10H) ppm. |
| 64 | —CON⬡ | 335 (m + 1)⁺ | Found: C, 78.43; H, 7.93; N, 8.42. $C_{22}H_{26}N_2O$ requires C, 79.00; H, 7.84; N, 8.38%. ¹H-NMR($CDCl_3$): δ = 1.4–1.7(m,6H), 3.15–3.35(m,4H), 3.4–3.55(m,5H), 4.4(s,1H), 7.15–7.45(m,10H) ppm. |

Preparations 65 to 68

The hydrochloride salts of the compounds of the following tabulated Preparations of the general formula:

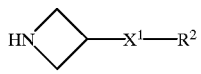

were prepared using a similar method to that of Preparation 61 using the appropriate azetidine starting materials (see Preparations 62 to 64 and 105).

| Prep. No. | —X¹—R² | LRMS m/z | Analysis/¹H-NMR |
|---|---|---|---|
| 65¹ | —CONH—⬡ | — | — |
| 66¹ | —CON⬠ | — | — |
| 67¹ | —CON⬡ | — | — |
| 68¹,² | —N⬡—$CO_2C_2H_5$ | — | — |

Footnotes:
¹Crude product used directly in next step.
²Only 1.05 mole equivalents of alpha-chloroethyl chloroformate were used and potassium carbonate was not added in the work-up procedure.

Preparation 69

1-(t-Butoxycarbonyl)-3-(3-hydroxypiperidyl) azetidine

A mixture of 1-(t-butoxycarbonyl)-3-methanesulphonyloxyazetidine (see International Patent Application Publication no. WO93/19059) (1.5 g, 4.78 mmol) and 3-hydroxypiperidine (1.9 g, 4 mol. equiv.) was heated at 110° C. for sixteen hours. The mixture was cooled to room temperature and partitioned between ethyl acetate (100 ml) and 5% aqueous sodium bicarbonate solution (100 ml). The layers were separated and the aqueous phase was extracted with a further portion of ethyl acetate (100 ml). The combined organic layers were dried over anhydrous magnesium sulphate. The solution was filtered, the solvent removed from the filtrate under reduced pressure and the crude product purified by column chromatography using silica gel eluting with methanol:dichloromethane (1:9, by volume) to give the title compound (1.4 g). TLC Rf=0.3 (silica, methanol:dichloromethane, 1:9, by volume).

¹H-NMR ($CDCl_3$):δ=1.45 (s,9H), 1.5–1.85 (m,6H), 2.15–2.45 (m,4H), 3.05–3.15 (m,1H), 3.25–3.95 (m,4H) ppm.

Preparation 70

3-(3-Hydroxypiperidyl)azetidine bistrifluoroacetate

To a solution of the compound of Preparation 69 (1.4 g, 5.8 mmol) in dichloromethane (10 ml) at 0° C. under nitrogen was added trifluoroacetic acid (5 ml), dropwise. The mixture was then allowed to warm to room temperature and stirred for one hour. The mixture was concentrated under reduced pressure, the resulting gum washed with diethyl ether, then triturated with diethyl ether and filtered to give the title compound as a white solid (1.2 g). Found: C, 37.32; H, 4.73; N, 7.03. $C_8H_{16}N_2O \cdot 2\ CF_3CO_2H$ requires C, 37.51; H, 4.72; N, 7.29%.

Preparations 71 to 76

The compounds of the following tabulated Preparations of the general formula:

were prepared using a similar method to that of Preparation 69 using 1-(t-butoxycarbonyl)-3-methanesulphonyloxyazetidine and the appropriate amines as the starting materials.

| Prep. No. | —X¹—R² | LRMS m/z | Analysis/¹H-NMR |
|---|---|---|---|
| 71 | 4-hydroxy-1-methylpiperidine | — | ¹H-NMR(CDCl₃): δ = 1.35–1.5(m,10H), 1.55–1.65(m,2H), 1.9–2.1(m,4H), 2.6–2.7(m,2H), 3.0–3.1(m,1H), 3.7–3.95 (m,5H) ppm. |
| 72 | 3-hydroxy-1-methylpyrrolidine | — | ¹H-NMR(CDCl₃): δ = 1.4–1.45(m,9H), 1.75–1.85(m,2H), 2.15–2.35(m,2H), 2.5–2.7(m,2H), 2.8–2.9(m,1H), 3.2–3.3 (m,1H), 3.8–3.95(m,4H), 4.4(br.s,1H) ppm. |
| 73[1] | 1-methylpiperazine | — | — |
| 74 | —NCH₂CH₂OH with CH₃ | — | ¹H-NMR(CDCl₃): δ = 1.4(s,9H), 2.1(s,3H), 2.5(m,3H), 3.25(m,1H), 3.6(t,2H), 3.7–3.8(m,2H), 3.95(t,2H), ppm. |
| 75 | —NHCH₂CH₂OH | — | ¹H-NMR(CDCl₃): δ = 1.4(s,9H), 1.8(m,1H), 2.75(t,2H), 3.45(s,1H), 3.6–3.8(m,5H), 4.0–4.2(m,2H) ppm. |
| 76 | 1-methyl-4-(benzoxazol-2-yl)piperidine | — | ¹H-NMR(CDCl₃): δ = 1.45(s,9H), 2.0–2.25 (m,6H), 2.8–3.15(m,4H), 3.8–3.95(m,4H), 7.3–7.35(m,2H), 7.45–7.5(m,1H), 7.65–7.7(m,1H) ppm. |

Footnote:
[1] In the work-up, the reaction mixture was cooled and excess piperazine removed under reduced pressure. The crude product was used directly.

Preparations 77 to 89

The compounds of the following tabulated Preparations of the general formula:

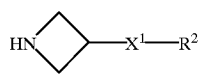

were prepared using a similar method to that used in Preparation 70 using the appropriate azetidine derivative starting materials (see Preparations 71,72,74,76, 90, 170 and 172 to 178).

| Prep. No. | —X¹—R² | LRMS m/z | Analysis/¹H-NMR |
|---|---|---|---|
| 77[2] | 4-hydroxypiperidine | — | Found: C, 36.88; H, 4.67; N, 6.93. C⁸H₁₆N₂O. 2 CF₃CO₂H requires C, 37.51; H, 4.72; N, 7.29%. |

| Prep. No. | —X¹—R² | LRMS m/z | Analysis/¹H-NMR |
|---|---|---|---|
| 78[2] | pyrrolidine with OH at 3-position, N-methyl | — | Found: C, 35.13; H, 4.14; N, 7.25. $C_7H_{14}N_2O \cdot 2\,CF_3CO_2H$ requires C, 35.68; H, 4.36; N, 7.57%. |
| 79[2] | —N(CH₃)CH₂CH₂OH | 157 (m + 1)⁺ | ¹H-NMR(d₆-DMSO): δ = 2.5–2.7(s,3H), 2.8–3.05(m,2H), 3.5–3.6(m,3H), 4.0–4.3(m,6H), 8.6–9.0(s,br,2H) ppm. |
| 80[1] | 4-methyl-3-oxomorpholine | 157 (m + 1)⁺ | ¹H-NMR(CDCl₃): δ = 3.3–3.6(m,2H), 3.8–4.0(m,2H), 4.0–4.2(m,4H), 4.2–4.4(m,2H), 4.8–5.0(m,1H), 8.6–9.0 (s,br,2H) ppm. |
| 81[2] | N-methylpiperidine with 4-OCH₃ | — | Found: C, 39.08; H, 5.17; N, 6.78, $C_9H_{18}N_2O \cdot 2\,CF_3CO_2H$ requires: C, 39.20; H, 5.06; N, 7.03%. |
| 82[2] | N-methylpiperidine with 4-OCH₂CH₃ | — | Found: C, 40.48; H, 5.37; N, 6.50. $C^{10}H_{20}N_2O \cdot 2CF_3CO_2H$ requires: C, 40.78; H, 5.38; N, 6.80%. |
| 83[2] | N-methylpiperidine with 4-OCH₂CH₂CH₃ | 199 (m + 1)⁺ | — |
| 84[2,3] | piperazine with —SO₂N(CH₃)₂ | 249 (m + 1)⁺ | ¹H-NMR(d₆-DMSO): δ = 2.4–2.5(m,10H), 3.15–3.2(m,4H), 3.35–3.45(m,1H), 3.8–4.05(m,4H), 8.75(s,br.,1H) ppm. |
| 85[2,3] | piperazine with —SO₂-morpholine | 291 (m + 1)⁺ | ¹H-NMR(d₆-DMSO): δ = 2.4–2.5(m,4H), 3.1–3.25(m,7H), 3.35–3.4(m,1H), 3.6–3.65(m,3H), 3.8–4.05(m,4H), 8.7(s,br.,1H) ppm. |
| 86[2] | N-methylpiperidine-4-yl benzoxazole | — | Found: C, 47.04; H, 4.31; N, 8.24. $C^{15}H_{19}N_3O \cdot 2CF_3CO_2H$ requires: C, 47.01; H, 4.36; N, 8.66%. |
| 87[2] | piperazine with —SO₂CH₃ | 220 (m + 1)⁺ | ¹H-NMR(d₆-DMSO): δ = 2.4–2.5(m,2H), 2.9 (s,3H), 3.1–3.2(m,4H), 3.3–3.5(m,1H), 3.8–4.0 (m,4H), 8.7–8.9(m,3H) ppm. |
| 88[2] | piperazine with —CONHCH₃ | 199 (m + 1)⁺ | — |

| Prep. No. | —X¹—R² | LRMS m/z | Analysis/¹H-NMR |
|---|---|---|---|
| 89[2,3] | —N⟨⟩NSO₂NHCH₃ | 235 (m + 1)⁺ | ¹H-NMR(d₄-CH₃OH): δ = 1.05–1.1(m,4H), 1.15(s,3H), 1.75–1.8(m,5H), 1.95–2.1(m,1H), 2.55–2.7(m,4H), ppm. |

Footnotes:-
[1]Prepared as the trifluoroacetate salt.
[2]Prepared as the bistrifluoroacetate salt.
[3]A final ethyl acetate trituration was used in the work-up.

Preparation 90

1-(t-Butoxycarbonyl)-3-(2-oxomorpholino)azetidine

To a stirred suspension of sodium hydride (60% w/w dispersion in mineral oil, 0.29 g, 1 mol. equiv.) in toluene (20 ml) at room temperature under nitrogen was added the compound of Preparation 75 (1.57 g, 1 mol. equiv.), portionwise. The reaction was stirred for thirty minutes and then cooled to 0° C. Ethyl chloroacetate (0.78 ml, 1 mol. equiv.) was then added over fifteen minutes, the reaction stirred for a further 1 hour at room temperature and then heated under reflux for ninety minutes. The solution was cooled, diluted with diethyl ether (20 ml) and washed with saturated aqueous sodium bicarbonate solution (30 ml). The organic layer was dried over anhydrous sodium sulphate. The organic solvent was removed under reduced pressure and the residue purified by flash column chromatography on silica gel eluting with methanol:dichloromethane (4:96, by volume) to give the title compound (0.8 g). TLC Rf=0.23 (silica, methanol:dichloromethane, 4:96, by volume).

¹H-NMR (CDCl₃):δ=1.4 (s,9H), 3.5–3.6 (m,2H), 3.9–4.0 (m,4H), 4.1–4.2 (m,4H), 5.2–5.4 (m,1H) ppm.

g). TLC Rf=0.39 (silica, methanol:dichloromethane, 1:9, by volume). LRMS m/z=335 (m+1)⁺. Found: C, 80.29; H, 9.00; N, 8.14. C₂₃H₃₀N₂ 0.125 CH₂Cl₂ requires C, 80.48; H, 8.84; N, 8.12%.

¹H-NMR (CDCl₃):δ=1.0 (s,6H), 1.4–1.8 (m,6H), 2.7–2.9 (m,4H), 3.35–3.4 (m,2H), 3.7 (s,1H), 4.4 (s,1H), 7.1–7.4 (m,10H) ppm.

Preparations 92 and 93

The compounds of the following tabulated Preparations of the general formula:

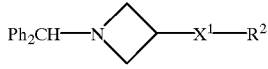

(where Ph=phenyl) were prepared by a similar method to that used in Preparation 91 using 1-diphenylmethyl-3-methanesulphonyloxyazetidine and the appropriate amines as the starting materials.

| Prep. No. | —X¹—R² | LRMS m/z | Analysis/¹H-NMR |
|---|---|---|---|
| 92 | —N(CH₃)CH₂C(CH₃)₂OH | — | ¹H-NMR(CDCl₃): δ = 1.1(s,6H), 2.2(s,2H), 2.25(s,3H), 2.8 (t,2H), 3.0(s,1H), 3.15–3.25(m,1H), 3.35–3.4(m,2H), 4.35 (s,1H), 7.1–7.3(m,6H), 7.35–7.4(m,4H) ppm. |
| 93 | —N(CH₃)CH₂CH₂OH | — | ¹H-NMR(CDCl₃): δ = 2.1(s,3H), 2.3–2.5(m,2H), 2.55–2.65 (m,1H), 2.8–2.9(m,2H), 3.1–3.2(m,1H), 3.4–3.45(m,2H), 3.5–3.65(m,2H), 4.4(s,1H), 7.2–7.4(m,6H), 7.4–7.55 (m,4H) ppm. |

Preparation 91

1-Diphenylmethyl-3-(2,6-dimethylpiperidinyl)azetidine

1-Diphenylmethyl-3-methanesulphonyloxyazetidine (see Preparation 54) (2 g, 1 mol. equiv.) and 2,6-dimethylpiperidine (6.79 ml, 3 mol. equiv.) were heated together at 110° C. under nitrogen for six hours. Saturated aqueous sodium bicarbonate solution (60 ml) was added and the mixture extracted with ethyl acetate (3×40 ml). The combined organic extracts were dried using magnesium sulphate. The organic solvent was removed under reduced pressure and the residue purified by flash column chromatography on silica gel eluting with methanol:dichloromethane (1:9, by volume) to give the title compound (0.48

Preparation 94

1-Diphenylmethyl-3-(piperidin-1-yl)azetidine

A mixture of 1-diphenylmethyl-3-methanesulphonyloxyazetidine (see Preparation 54) (1.5 g, 1 mol. equiv.), piperidine (0.6 g, 1.5 mol. equiv.) and potassium carbonate (1.31 g, 2 mol. equiv.) in acetonitrile (20 ml) was heated under reflux under nitrogen for four hours. Saturated aqueous sodium bicarbonate solution and brine were added and the mixture extracted with ethyl acetate (2×40 ml). The organic extracts were combined and dried using magnesium sulphate. The organic solvent was removed under reduced pressure and the residue purified by flash column chromatography on silica gel eluting with methanol:dichloromethane (1:9, by volume) to give the title compound (0.65 g). TLC Rf=0.5 (silica, methanol:dichloromethane, 1:9, by volume). LRMS m/z= 307(m+1)$^+$. Found: C, 81.50; H, 8.51; N, 9,02. $C_{21}H_{26}N_2.0.06\ CH_2Cl_2$ requires C, 81.14; H, 8.45; N, 8.99%.

$^1$H-NMR (CDCl$_3$):δ=1.4–1.5 (m,2H), 1.5–1.6 (m,5H), 2.1–2.3 (m,4H), 2.9–3.0 (m,2H), 3.4–3.5 (m,2H), 4.4 (s,1H), 7.1–7.3 (m,6H), 7.35–7.5 (m,4H) ppm.

Preparations 95 to 106

The compounds of the following tabulated Preparations of the general formula:

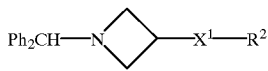

(where Ph=phenyl) were prepared by a similar method to that used in Preparation 94 using 1-diphenylmethyl-3-methanesulphonyloxyazetidine and the appropriate amines as the starting materials.

| Prep. No. | —X$^1$—R$^2$ | LRMS m/z | Analysis/$^1$H-NMR |
|---|---|---|---|
| 95 | (2-phenylmorpholine, N-methyl) | 385 (m + 1)$^+$ | Found: C, 80.24; H, 7.28; N, 7.12. $C_{26}H_{28}N_2O.0.06\ CH_2Cl_2$ requires C, 80.29; H, 7.27; N, 7.19%. $^1$H-NMR(CDCl$_3$): δ = 1.9(t,1H), 2.1–2.25(m,1H), 2.6(d,1H), 2.8(d,1H), 2.9–3.1(m,3H), 3.3–3.5(m,2H), 3.8–3.9(m,1H), 4.0–4.1(m,1H), 4.4(s,1H), 4.5–4.6(m,1H),7.1–7.5 (m,15H) ppm. |
| 96 | (1,4-dimethylpiperazine, CH$_3$) | 322 (m + 1)$^+$ | Found: C, 75.56; H, 8.48; N, 12.52. $C_{21}H_{27}N_3\ 0.188\ CH_2Cl_2$ requires C, 75.42; H, 8.18; N, 12.45%. $^1$H-NMR(CDCl$_3$): δ = 2.15(s,3H), 2.3–2.6(m,8H), 2.85–3.1 (m,3H), 3.35–3.45(m,2H), 4.4(s,1H), 7.1–7.3(m,6H), 7.35–7.55(m,4H) ppm. |
| 97 | (1-Boc-4-piperazine, CO$_2$C(CH$_3$)$_3$) | 408 (m + 1)$^+$ | $^1$H-NMR(CDCl$_3$): δ = 1.4–1.6(s,9H), 2.2–2.4(m,4H), 2.8–3.1 (m,3H), 3.3–3.5(m,6H), 4.4(m,1H), 7.1–7.5(m,10H) ppm. |
| 98 | (N-methyl-4-acetoxypiperidine, OCOCH$_3$) | 391 (m + 1)$^+$ | Found: C, 76.91; H, 7.72; N, 6.88. $C_{25}H_{30}N_2O_2$ requires C, 76.89; H, 7.74; N, 7.18%. $^1$H-NMR(CDCl$_3$): δ = 1.55(s,1H), 1.6–1.7(m,2H), 1.9–1.95 (m,4H), 2.0(s,3H), 2.05–2.1(m,1H), 2.8–2.9(m,2H), 3.0–3.05(m,2H), 3.2–3.25(m,1H), 3.35–3.45(m,2H), 4.45 (s,1H),4.95(t,1H), 7.15–7.3(m,6H), 7.45–7.55(m,4H) ppm. |
| 99 | (N-methylthiomorpholine S-oxide) | 357 (m + 1)$^+$ | Found: C, 66.05; H, 6.72; N, 7.25. $C_{20}H_{24}N2O_2S.\ 0.125\ CH_2Cl_2$ requires C, 65.84; H, 6.66; N, 7.63%. $^1$H-NMR(CDCl$_3$): δ = 2.75–3.0(m,6H), 3.0–3.15(m,4H), 3.15–3.4(m,1H), 3.4–3.5(m,2H), 4.4–4.5(m,1H), 7.2–7.5 (m,10H) ppm. |
| 100 | (N-methylhomomorpholine) | 323 (m + 1)$^+$ | $^1$H-NMR(CDCl$_3$): δ = 1.8–1.95(m,2H), 2.4–2.5(m,4H), 2.8–2.9(m,2H), 3.15–3.3(m,1H), 3.35–3.45(m,2H), 3.65–3.75 (m,2H), 3.8–3.9(m,2H), 4.4(s,1H), 7.1–7.3(m,6H), 7.3–7.5 (m,4H) ppm. |

| Prep. No. | —X¹—R² | LRMS m/z | Analysis/¹H-NMR |
|---|---|---|---|
| 101 | 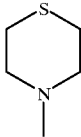 | — | ¹H-NMR(CDCl₃): δ = 2.45–2.6(m,4H), 2.6–2.7(m,4H), 2.85–2.95(m,2H), 3.0–3.1(m,1H), 3.4–3.5(m,2H), 4.45(s,1H), 7.2–7.5(m,10H) ppm. |
| 102² | 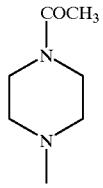 | 350 (m + 1)⁺ | Found: C, 72.81; H, 7.70; N, 11.31. $C_{22}H_{27}N_3O.0.05\ C_4H_8O_2$ requires C, 73.25; H, 7.94; N, 10.68%. ¹H-NMR(CDCl₃): δ = 2.1(s,3H), 2.2–2.4(m,4H), 2.85–3.0 (m,3H), 3.3–3.5(m,4H), 3.6–3.7(m,2H), 4.5(s,1H), 7.2–7.4 (m,6H), 7.4–7.5(m,4H) ppm. |
| 103 | 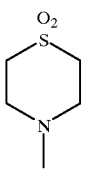 | 357 (m + 1)⁺ | Found: C, 66.05; H, 6.72; N, 7.25. $C_{20}H_{24}N_2O_2S.0.125$ $CH_2Cl_2$ requires C, 65.84; H, 6.66; N, 7.63%. ¹H-NMR(CDCl₃): δ = 2.7–2.9(m,6H), 3.0–3.1(m,4H), 3.15–3.25(m,1H), 3.35–3.5(m,2H), 4.4–4.5(m,1H), 7.1–7.4 (m,10H) ppm. |
| 104 | 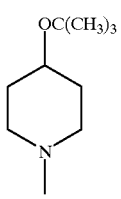 | 379 (m + 1)⁺ | ¹H-NMR(CDCl₃): δ = 1.2(s,9H), 1.4–1.6(m,2H), 1.6–1.7(m,2H), 1.9–2.0(m,2H), 2.55–2.65(m,2H), 2.8–3.0(m,3H), 3.3–3.45(m,3H), 4.2(s,1H), 7.1–7.3(m,6H), 7.35–7.45(m,4H) ppm. |
| 105 | 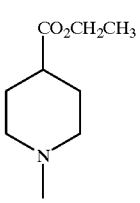 | 379 (m + 1)⁺ | ¹H-NMR(CDCl₃): δ = 1.2–1.25(m,3H), 1.65–1.9 (m,6H), 2.2–2.3(m,1H), 2.65–2.7(m,2H), 2.8–2.95 (m,3H), 3.35–3.4(m,2H), 4.1–4.15(m,2H), 4.4 (s,1H), 7.15–7.3(m,6H), 7.35–7.4(m,4H) ppm. |
| 106 | 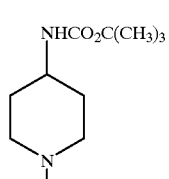 | — | ¹H-NMR(CDCl₃): δ = 1.35–1.45(m,11H), 1.85–1.95(m,4H), 2.6–2.7(m,2H), 2.85–2.95(m,3H), 3.35–3.45(m,3H), 4.35–4.4(m,2H), 7.15–7.3 (m,6H), 7.35–7.4(m,4H) ppm. |

Footnotes
¹Homomorpholine hydrochloride (see Preparation 127) was used as the amine starting material.
²The pH of the reaction mixture was adjusted to 9 using N-methylmorpholine prior to heating under reflux.

Preparation 107

3-(Piperidin-1-yl)azetidine dihydrochloride

To a solution of the compound of Preparation 94 (0.64 g) in dry dichloromethane (7 ml) at 0° C. under nitrogen was added α-chloroethyl chloroformate (0.3 ml, 1 mol. equiv.) and the reaction stirred for thirty minutes. The solvent was removed under reduced pressure and the residue redissolved in methanol (10 ml) and heated under reflux for forty five minutes. The solvent was then removed under reduced pressure and the resultant gum triturated with diethyl ether (5 ml) to give the title compound as a beige powder (0.14 g). LRMS m/z=141 (m+1)⁺.

¹H-NMR (d₆-DMSO):δ=1.3–1.4 (m,1H), 1.7–1.9 (m,5H), 2.7–2.9 (m,2H), 3.3–3.5 (m,2H), 4.1–4.2 (m,3H), 4.4–4.6 (m,2H), 9.15 (s,br,1H), 9.7 (s,br, 1H), 12.0 (s,br, 1H) ppm.

Preparations 108 to 119

The compounds of the following tabulated Preparations of the general formula:

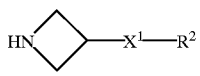

were prepared using a similar procedure to that of Preparation 107 using the appropriate azetidine derivative starting materials (see Preparations 91,92,95,96,98 to 103, 104 and 120).

| Prep. No. | —X¹—R² | LRMS m/z | Analysis/¹H-NMR |
|---|---|---|---|
| 108¹ | (2-phenylmorpholin-4-yl) | 219 (m + 1)⁺ | ¹H-NMR(d₆-DMSO): δ = 2.7–2.9(m,2H), 3.2–3.6(m,4H), 3.9–4.1(m,5H) 4.3–4.5(m,2H), 4.8(d,1H); 7.3–7.4(m,5H), 9.15(s,br,1H), 9.6(s,br,1H) ppm. |
| 109¹ | 4-methylpiperazin-1-yl (CH₃ on both N) | 156 (m + 1)⁺ | ¹H-NMR(d₆-DMSO): δ = 2.6–2.8(m,3H), 2.9–3.1(m,4H), 3.05–3.1(m,2H), 3.3–3.5(m,2H), 3.8–4.0(m,5H), 9.0–9.5 (m,2H), 11.0(m,1H) ppm. |
| 110¹ | 1,2,6-trimethylpiperidin-4-yl | 169 (m + 1)⁺ | ¹H-NMR(d₆-DMSO): δ = 1.2–1.3(m,4H), 1.4–2.0(m,8H), 3.3–3.4(m,1H), 3.5–4.2(m,3H), 4.6–4.8(m,3H), 9.2 (s,br,1H), 10.0(s,br,1H) ppm. |
| 111¹ | —NCH₂C(CH₃)₂ with CH₃, OH | 159 (m + 1)⁺ | ¹H-NMR(d₆-DMSO): δ = 1.1(s,3H), 2.8–2.9(m,2H), 2.9–3.1 (m,1H), 3.2–3.6(m,9H), 4.0–4.4(m,2H), 9.2(s,br,1H), 9.4 (s,br,1H) ppm. |
| 112¹ | —NCH₂CH₂OCH₃ with CH₃ | 145 (m + 1)⁺ | — |
| 113¹ | (8-methyl-8-azabicyclo[3.2.1]oct-3-yl) OCOCH₃ | — | — |
| 114² | 4-methylthiomorpholine-1-oxide | 191 (m + 1)⁺ | ¹H-NMR(d₆-DMSO): δ = 2.8–3.0(m,4H), 3.1–3.2(m,4H), 3.6–3.8(m,1H), 3.8–4.0(m,4H), 9.1(s,br,1H), 9.3(s,br,1H) ppm. |

| Prep. No. | —X$^1$—R$^2$ | LRMS m/z | Analysis/$^1$H-NMR |
|---|---|---|---|
| 115$^1$ | [1,4-oxazepane structure] | 157 (m + 1)$^+$ | $^1$H-NMR(d$_6$-DMSO): δ = 2.4–3.5(m,10H), 3.6–3.8(m,1H), 3.8–4.0(m,4H), 9.2(s,br,1H), 9.4–9.9(m,2H) ppm. |
| 116$^1$ | [thiomorpholine structure] | 159 (m + 1)$^+$ | $^1$H-NMR(d$_6$-DMSO): δ = 2.6–3.8(m,8H), 3.8–4.5(m,5H), 9.1 (s,br,1H), 9.7(s,br,1H), ppm. |
| 117$^1$ | [4-acetylpiperazine structure, COCH$_3$] | — | — |
| 118$^1$ | [thiomorpholine 1,1-dioxide structure, O$_2$] | 191 (m + 1)$^+$ | $^1$H-NMR(d$_6$DMSO): δ = 2.8–2.95(m,4H), 3.05–3.2(m,4H), 3.6–3.8(m,1H), 3.8–4.0(m,4H), 9.0–9.2(s,br,1H), 9.2–9.4 (s,br,1H) ppm. |
| 119$^1$ | [4-t-butoxypiperidine structure, OC(CH$_3$)$_3$] | 213 (m + 1)$^+$ | — |

Footnotes:
$^1$Obtained as the dihydrochloride salt.
$^2$Obtained as the hydrochloride salt.

Preparation 120

1-Diphenylmethyl-3-(N-f2-methoxyethyl]-N-methylam ino)azetidine

To a solution of the compound of Preparation 93 (0.85 g, 1 mol. equiv.) in tetrahydrofuran (12 ml) at 0° C. under nitrogen was added 60% w/w sodium hydride dispersion in oil (0.126 g, 1.1 mol. equiv.) and the reaction stirred at room temperature for one hour. Methyl iodide (0.448 g, 1.1 mol. equiv.) was then added to the mixture and the reaction stirred for a further two hours. A portion of the solvent (10 ml) was removed under reduced pressure saturated aqueous sodium bicarbonate solution (25 ml) was added and the mixture extracted with ethyl acetate (3×35 ml). The combined organic extracts were dried using magnesium sulphate. The organic solvent was removed under reduced pressure and the residue purified by flash column chromatography on silica gel eluting with methanol:dichloromethane (4:96, by volume) to give the title compound (0.64 g). TLC Rf=0.3 (silica, methanol:dichloromethane, 4:96, by volume). LRMS m/z=311 (m+1)$^+$.

$^1$H-NMR (CDCl$_3$):δ=2.1 (s,3H), 2.4 (t,2H), 2.85–2.95 (m,2H), 3.0–3.1 (m,1H), 3.3 (s,3H), 3.4–3.45 (m,4H), 4.4 (s,1H), 7.15–7.3 (m,6H), 7.4–7.45 (m,4H) ppm.

Preparation 121

3-(4-t-Butoxycarbonylpiperazinyl)azetidine hydrochloride

The compound of Preparation 97 (1.471 g, 1 mol. equiv.) was dissolved in a mixture of 1 M aqueous hydrochloric acid solution (4 ml) and ethanol (16.6 ml) and 10% palladium-on-carbon (14.7 mg) was added. The mixture was stirred under an atmosphere of hydrogen at 345 kPa (50 psi) for sixteen hours. The catalyst was then filtered off and the solvent removed under reduced pressure, removing final traces of water by azeotroping with ethanol, to give the title compound as a cream solid (0.83 g) which was used without further purification. TLC Rf=0.84 (silica, ethyl acetate:hexane, 1:2, by volume). LRMS m/z=242(m+1)⁺. Found: C, 50.30; H, 8.33; N, 14.39. $C_{12}H_{23}N_3O_2 \cdot HCl \cdot 0.5 H_2O$ requires C, 50.25; H, 8.79; N, 14.65%.

¹H-NMR ($d_6$-DMSO):δ=1.4 (s,9H), 2.3–2.5 (m,4H), 3.4–3.5 (m,6H), 3.9–4.2 (m,4H), 9.7 (s,br,1H) ppm.

Preparation 122

4-Acetyl-1-(t-butoxycarbonyl)piperazine

To a solution of N-t-butoxycarbonylpiperazine (7 g, 1 mol. equiv.) in dichloromethane (140 ml) at 0° C. under nitrogen was added triethylamine (6.29 ml, 1.2 mol. equiv.). The reaction mixture was vigorously stirred and acetyl chloride (3.21 ml, 1.2 mol. equiv.) was added, dropwise. The mixture was stirred for twenty four hours. The reaction mixture was washed with saturated aqueous sodium bicarbonate solution (30 ml), and the organic layer dried using magnesium sulphate. The organic solvent was removed under reduced pressure and the residue purified by flash column chromatography on silica gel eluting with methanol:ethyl acetate (1:19, by volume) to give the title compound (8.19 g). TLC Rf=0.33 (silica, methanol:ethyl acetate, 1:19, by volume). LRMS m/z=229(m+1)⁺. Found: C, 57.83; H, 8.83; N, 12.27. $C_{11}H_{20}N_2O_3$ requires C, 57.87; H, 8.92; N, 12.14%.

¹H-NMR (CDCl₃):δ=1.4 (s,9H), 2.1 (s,3H), 3.3–3.4 (m,6H), 3.5–3.6 (m,2H) ppm.

Preparation 123

N-Acetylpiperazine trifluoroacetate

To a solution of the compound of Preparation 122(8.2 g, 1 mol. equiv.) in dichloromethane (78 ml) at 0° C. under nitrogen was added trifluoroacetic acid (39 ml). The mixture was then warmed to room temperature and stirred for a further thirty minutes. The solvent was then evaporated under reduced pressure and the resulting oil azeotroped with dichloromethane (30 ml) to give the title compound as a gum (11.7 g). LRMS m/z=129(m+1)⁺.

¹H-NMR (CDCl₃):δ=2.0 (s,3H), 3.0–3.2 (m,4H), 3.5–3.7 (m,4H), 8.8–9.0 (s,br,2H) ppm.

Preparation 124

Pyran-4-one oxime

To a solution (240 ml) of hydroxylamine hydrochloride (60.53 g, 4 mol. equiv.) in water (240 ml) was carefully added 3.6M aqueous sodium hydroxide solution (240 ml). Pyran-4-one (20 g, 1 mol. equiv.) was added over a five minute period. The mixture was heated under reflux for one and a half hours, cooled and then stirred for a further eighteen hours at room temperature. The reaction mixture was extracted with dichloromethane (4×50 ml) and the combined extracts dried over magnesium sulphate. Removal of the solvent under reduced pressure gave the title compound as a white solid (18.86 g).

¹H-NMR (CDCl₃):δ=2.4 (t,2H), 2.7 (t,2H), 3.7–3.9 (m,4H), 7.35 (s,1H) ppm.

Preparation 125

Homomorpholin-5-one

To methanesulphonic acid (228.8 ml, 27 mol. equiv.) under nitrogen was added, portionwise, phosphorous pentoxide (37.72 g, 2 mol. equiv.) over five minutes. The solution was stirred at room temperature for two hours and then pyran-4-one oxime (see Preparation 124)(14.97 g, 1 mol. equiv.) was added, portionwise, over ten minutes. The mixture was heated slowly to 100° C. and stirred for one hour at this temperature. The reaction was then further stirred for eighteen hours at room temperature. The mixture was slowly added to water (500 ml) and sodium bicarbonate was added, portionwise, until the mixture was basic (pH 9). The mixture was filtered and the pad washed several times with dichloromethane (3×50 ml). The filtrate was extracted with dichloromethane (7×60 ml). The combined extracts were dried over magnesium sulphate, filtered and the filtrate evaporated under reduced pressure. The resulting solid was triturated with diethyl ether to give the title compound as a white foam (2.1 g). LRMS m/z=16(m+1)⁺.

¹H-NMR (CDCl₃):δ=2.6–2.8 (m,2H), 3.3–3.4 (m,2H), 3.7–3.9 (m,4H), 6.2 (s,br.,1H) ppm.

Preparation 126

4-(t-Butoxycarbonyl)homomorpholine

To a stirred suspension of lithium aluminium hydride (777 mg, 2 mol. equiv.) in tetrahydrofuran (87 ml) under nitrogen at the reflux temperature was slowly added a solution of homomorpholin-5-one (see Preparation 125) (1.1 g, 1 mol. equiv.) in tetrahydrofuran (37 ml) over thirty minutes. The mixture was heated under reflux for two hundred and ten minutes, cooled to room temperature and a 1:1 v/v tetrahydrofuran:water solution (25 ml) added slowly over ten minutes, followed by 1M aqueous sodium hydroxide solution (1.24 ml). The mixture was cooled to 0° C. and a solution of di-tert-butyl dicarbonate (2.46 g, 1.1 mol. equiv.) in dichloromethane (25 ml) was added over fifteen minutes. The reaction was then allowed to warm to room temperature and stirred for sixteen hours. Sodium sulphate (25 g) was added to the mixture with vigorous stirring. The resulting granular white solid was filtered off and washed several times with dry dichloromethane. The combined filtrates and washings were then evaporated under reduced pressure and the residue dissolved in dichloromethane (50 ml). The solution was dried over magnesium sulphate, filtered and the filtrate evaporated under reduced pressure to give an oil. This oil was purified using flash column chromatography on silica gel eluting with ethyl acetate:hexane (1:1, by volume) to give the title compound (1.7 g). TLC Rf=0.5 (silica, ethyl acetate:hexane, 1:1, by volume).

¹H-NMR (CDCl₃):δ=1.5 (s,9H), 1.8–2.0 (m,2H), 3.45–3.6 (m,4H), 3.7–3.8 (m,4H) ppm.

Preparation 127

Homomorpholine hydrochloride

The compound of Preparation 126 (1.7 g) was dissolved in ethyl acetate (51 ml) and the solution cooled to 0° C. Dry hydrogen chloride gas was then bubbled into the mixture for thirty minutes and the reaction stirred for a further thirty minutes. Nitrogen was then bubbled into the solution for sixteen hours. During this time a white solid precipitated which was filtered off and then washed with cold ethyl acetate (5 ml). The white solid was then dried under reduced pressure for four hours to give the title compound (0.92 g).

¹H-NMR (CDCl₃):δ=2.25–2.4 (m,2H), 3.25–3.45 (m,4H), 3.9 (t,2H), 3.95–4.0 (m,2H), 9.75 (s,br,2H) ppm.

Preparation 128

4-Benzyloxycarbonylthiomorpholine

To a solution of thiomorpholine (5 g, 1 mol. equiv.) and triethylamine (5.4 g, 1.1 mol. equiv.) in dichloromethane (200 ml) at 0° C. under nitrogen was slowly added benzyl chloroformate (8.68 g, 1.05 mol. equiv.) over fifteen minutes. The reaction was then allowed to warm to room temperature and stirred for a further sixteen hours. The reaction was washed with a saturated aqueous sodium bicarbonate solution. The organic layer was dried using magnesium sulphate, filtered and the solvent removed under reduced pressure. The residue was purified by flash column chromatography on silica gel eluting with dichloromethane to give the title compound (10 g). TLC=Rf 0.3 (silica, dichloromethane). Found: C, 59.24; H, 6.49; N, 5.78. $C_{12}H_{15}NO_2S$ requires C, 59.12; H, 6.23: N, 5.70%.

$^1$H-NMR (CDCl$_3$):δ=2.5–2.75 (m,4H), 3.7–3.9 (m,4H), 5.15 (s,2H), 7.2–7.4 (m,5H) ppm.

Preparation 129

4-Benzyloxycarbonylthiomorpholine-1,1-dioxide

To a solution of 4-benzyloxycarbonylthiomorpholine (see Preparation 128) (4.11 g, 1 mol. equiv.) in dichloromethane (240 ml) under nitrogen was added meta-chloroperbenzoic acid (11.96 g, 2.2 mol. equiv.) and the reaction stirred for sixteen hours at room temperature. The resultant solid that formed was filtered off and the filtrate washed with a saturated aqueous sodium carbonate solution. The organic layer was dried over magnesium sulphate, filtered, and evaporated to dryness under reduced pressure. The resultant solid was then purified by flash column chromatography on silica gel eluting with dichloromethane: methanol (95:5, by volume) to give the title compound (0.83 g). TLC Rf=0.75 (silica, methanol:dichloromethane, 1:19, by volume). Found:C, 53.21; H, 5.68; N, 5.14. $C_{12}H_{15}NO_4S$ requires C, 53.51; H, 5.61: N; 5.20%.

$^1$H-NMR (CDCl$_3$):δ=2.9–3.1 (m,4H), 3.9–4.05 (m,4H), 5.15 (s,2H), 7.35–7.5 (m,5H) ppm.

Preparation 130

Thiomorpholine-1,1-dioxide

The compound of Preparation 129 (3.5 g, 1 mol. equiv.) was dissolved in a methanol (120 ml) and 10% palladium on carbon (0.4 g) added. The mixture was then stirred under hydrogen at atmospheric pressure for four and a half hours. The catalyst was filtered off and the solvent removed under reduced pressure, final traces of methanol being removed by azeotroping with dichloromethane. This gave the title compound as an oil which was used without further purification (1.6 g). TLC=Rf 0.3 (silica, ammonium hydroxide:methanol:dichloromethane, 1:10:90, by volume). LRMS m/z=136(m+1)$^+$.

$^1$H-NMR (CDCl$_3$):δ=2.95–3.05 (m,4H), 3.35–3.45 (m,5H) ppm.

Preparation 131

1-(t-Butoxycarbonyl)-4-methanesulphonylpiperazine

To a solution of 1-(t-butoxycarbonyl)piperazine (7 g, 1 mol. equiv.) in dichloromethane (ml) at 0° C. under nitrogen was added triethylamine (6.29 ml, 1.2 mol. equiv.). The mixture was vigorously stirred whilst methanesulphonyl chloride (3.49 ml, 1.2 mol. equiv.) was added, dropwise. The mixture was then stirred for twenty four hours. The reaction mixture was washed with a saturated aqueous sodium bicarbonate solution (30 ml) and the organic layer dried using magnesium sulphate. The organic solvent was removed under reduced pressure and the residue purified by flash column chromatography on silica gel eluting with ethyl acetate:hexane (1:2, by volume) to give the title compound (6.93 g). TLC Rf=0.37 (silica, ethyl acetate:hexane, 1:2, by volume). LRMS m/z=282(m+NH$_4$)$^+$. Found: C, 45.25; H, 7.68; N, 10.49. $C_{10}H_{20}N_2SO_4$ requires C, 45.43; H, 7.63; N, 10.60%.

$^1$H-NMR (CDCl$_3$):δ=1.4 (s,9H), 2.8 (s,3H), 3.15–3.2 (m,4H), 3.5–3.6 (m,4H) ppm.

Preparation 132

1-Methanesulphonylpiperazine trifluoroacetate

To a solution of the compound of Preparation 131(6.9 g, 1 mol. equiv.) in dichloromethane (78 ml) at 0° C. under nitrogen was added trifluoroacetic acid (28 ml). The mixture was then warmed to room temperature and stirred for a further thirty minutes. The solvent was removed under reduced pressure and the resulting oil azeotroped with dichloromethane (30 ml). The resultant gum was triturated with diethyl ether (10 ml) giving the title compound as a white solid (7 g). LRMS m/z=164(m)$^+$. Found: C, 30.10; H, 4.80; N, 10.00. $C_5H_{12}N_2SO_2$ .$CF_3CO_2H$ requires C, 30.21; H, 4.71; N, 10.07%.

$^1$H-NMR (d$_6$-DMSO):δ=2.9 (s,3H), 3.1–3.2 (m,4H), 3.3–3.4 (m,4H), 9.0–9.2 (s,br,2H) ppm.

Preparation 133

1-Diphenylmethyl-3-(4-methanesulphonylpiperazin-1-yl)azetidine

A solution of the compound of Preparation 54 (1.5 g, 1 mol. equiv.), N,N-diisopropylethylamine (7.4 ml, 9 mol. equiv.) and 1-methanesulphonylpiperazine (see Preparation 113) (1.97 g, 1.5 mol. equiv.) in acetonitrile (20 ml) under nitrogen was stirred and heated under reflux for eighteen hours. Saturated aqueous sodium bicarbonate solution (45 ml) was added and the mixture extracted with ethyl acetate (3×60 ml). The organic extracts were combined and dried using magnesium sulphate. The organic solvent was removed under reduced pressure and the residue purified by flash column chromatography on silica gel eluting initially with diethyl ether and then with methanol:ethyl acetate (1:9, by volume) to give the title compound (0.38 g). TLC Rf=0.51 (silica, methanol:ethyl acetate, 1:9, by volume). LRMS m/z=350(m+1)$^+$.

$^1$H-NMR (CDCl$_3$):δ=2.3–2.4 (m,4H), 2.7 (s,3H), 2.9–3.0 (m,2H), 3.0–3.2 (m,1H), 3.2–3.3 (m,4H), 3.4–3.5 (m,2H), 4.4 (s,1H), 7.2–7.4 (m,6H), 7.4–7.5 (m,4H) ppm.

Preparation 134

3-(4-Methanesulphonylpiperazin-1-yl)azetidine dihydrochloride

To a solution of the compound of Preparation 133 (0.350 g, 1 mol. equiv.) in dichloromethane (5 ml) at 0° C. was added α-chloroethyl chloroformate (0.15 ml, 1.5 mol. equiv.) and the reaction stirred for twenty four hours. The solvent was removed under reduced pressure and the residue dissolved in methanol (10 ml) and heated under reflux for one hour. The mixture was then adjusted to pH 3 using a saturated solution of hydrogen chloride in diethyl ether and filtered. The filtrate was evaporated to dryness under reduced pressure and the resultant gum triturated with diethyl ether (5 ml) to give the title compound as a white solid (0.12 g). LRMS m/z=219 (m)$^+$.

Preparation 135

Endo-3-Acetoxy-8-methyl-8-azabicyclo[3,2,1]octane

A mixture of tropine (10 g), acetic anhydride (20 ml) and pyridine (1 ml) was stirred at room temperature for twenty hours under nitrogen. The mixture was then poured onto ice, four drops of concentrated hydrochloric acid were added and the solution was allowed to stand for thirty minutes. A portion of the solvent was removed under reduced pressure and the mixture was partitioned between saturated aqueous sodium bicarbonate solution (20 ml) and ethyl acetate (50 ml). The layers were separated and the aqueous layer further extracted with ethyl acetate (2×50 ml). The organic extracts were combined and dried (MgSO$_4$). The solvent was removed under reduced pressure to give the title compound (4 g). TLC Rf=0.2 (silica, ammonium hydroxide:methanol:dichloromethane, 1:9:90, by volume).

$^1$H-NMR (CDCl$_3$):δ=1.6–1.7 (m,2H), 1.9–2.2 (m,7H), 2.05–2.15 (m,2H), 2.25 (s,3H), 3.1–3.2 (m,2H), 5.1 (t,1H) ppm.

Preparation 136

Endo-3-Acetoxy-8-azabicyclo[3,2,1]octane hydrochloride

To a solution of the compound of Preparation 135 (3.8 g, 1 mol. equiv.) in dry 1,2-dichloroethane (40 ml) at 0° C. under nitrogen was added α-chloroethyl chloroformate (2.37 ml, 1 mol. equiv.) and the reaction stirred for thirty minutes. The solvent was then removed under reduced pressure and the residue dissolved in methanol (50 ml) and heated under reflux for one hour. The solvent was then removed under reduced pressure and the resultant gum triturated with diethyl ether (10 ml) and ethyl acetate (5 ml) to give the title compound as a yellow powder (3.7 g).

$^1$H-NMR (d$_6$-DMSO):δ=1.8–2.4 (m,11H), 3.8–4.0 (m,2H), 4.9–5.0 (m,1H), 8.9–9.4 (m,2H) ppm.

Preparation 137

5(S)-1-Cyclopropylmethyl-5-(3,4-dichlorophenyl)-5-formylmethyl-2-piperidone

Into a solution of the compound of Preparation 141 (0.763 g, 1 mol. equiv.) in methanol (24 ml) under nitrogen at –78° C. was bubbled ozone at a rate of 50 ml/min. (using a charge of 1.5A to generate the ozone from oxygen) for thirty minutes. After this time the amperage was reduced to zero and oxygen bubbled through the reaction at a rate of 5 ml/min. for two minutes. The oxygen supply was then removed and nitrogen bubbled through the reaction mixture for twenty minutes. After this time a solution of dimethyl sulphide (1.7 ml, 10 mol. equiv.) in methanol (3.5 ml) was cautiously added dropwise and the reaction left to warm to room temperature over eighteen hours. The solvent was removed under reduced pressure and the reaction mixture was partitioned between ethyl acetate (20 ml) and water (15 ml). The organic layer was separated and the aqueous portion further extracted with ethyl acetate (2×20 ml). The organic layers were then combined, dried using sodium sulphate, filtered and the filtrate evaporated to dryness under reduced pressure to give the title compound (0.69 g) which was used without further purification. TLC R$_f$=0.31 (silica, ethyl acetate). LRMS m/z=340(m)$^+$.

$^1$H-NMR (CDCl$_3$):δ=0.2–0.4 (m,2H), 0.5–0.7 (m,2H), 1.0–1.15 (m,1H), 2.0–2.25 (m,2H), 2.3–2.45 (m,1H), 2.6–2.8 (m,1H), 2.9–3.05 (m,1H), 3.1–3.2 (m,1H), 3.4–3.6 (m,2H), 3.9–4.0 (m,1H), 4.05–4.15 (m,1H), 7.15–7.2 (m,1H), 7.3–7.5 (m,2H), 9.5 (s,1H) ppm.

Preparations 138 to 140

The compounds of the following tabulated Preparations of the general formula:

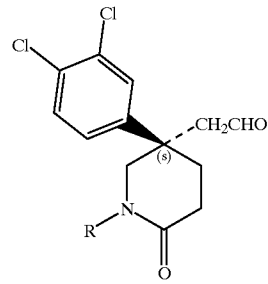

were prepared by a similar method to that used in Preparation 137 using the appropriate allylpiperidone starting materials (see Preparations 142 to 144).

| Prep. No. | R | LRMS m/z | Analysis/$^1$H-NMR |
|---|---|---|---|
| 138 | CH$_2$—⌬(phenyl) | — | $^1$H-NMR(CDCl$_3$): δ = 2.1–2.3(m,3H), 2.4–2.6(m,2H), 2.8–2.85(m,1H), 3.4(d,1H), 3.7(d,1H), 4.4(d,1H), 4.8(d,1H), 6.95(d,1H), 7.2–7.4(m,7H), 9.4(s,1H) ppm. |
| 139$^1$ | CH$_2$—⌬(cyclohexyl) | 384.5 (m + 1)$^+$ | $^1$H-NMR(CDCl$_3$): δ = 0.9–1.1(m,2H), 1.1–1.35(m,3H), 1.5–1.8(m,6H), 2.1–2.3(m,3H), 2.35–2.5(m,1H), 2.7(d,1H), 2.95(d,1H), 3.1–3.15(m,1H), 3.3–3.55(m,2H), 3.8(d,1H), 7.15(d,1H), 7.4–7.5(m,2H), 9.5(s,1H) ppm. |

-continued

| Prep. No. | R | LRMS m/z | Analysis/¹H-NMR |
|---|---|---|---|
| 140 | CH₂— (4,4-difluorocyclohexylmethyl) | — | ¹H-NMR(CDCl₃): δ = 1.3–1.6(m,4H), 1.6–1.9(m,4H), 2.0–2.3(m,4H), 2.3–2.5(m,1H), 2.7(d,1H), 2.95(d,1H), 3.2–3.3(m,1H), 3.4–3.6(m,2H), 3.8(d,1H), 7.2(d,1H), 7.4–7.5 (m,2H), 9.5(s,1H) ppm. |

Footnote:
¹Purified by flash column chromatography eluting with a solvent gradient of ethyl acetate:hexane (60:40 to 100:0, by volume).

Preparation 141

5(S)-5-Allyl-1-cyclopropylmethyl-5-(3,4-dichlorophenyl)-2-piperidone

Potassium hydroxide (0.78 g, 1 mol. equiv.) was added portionwise to dimethyl sulphoxide under nitrogen and the mixture stirred for fifteen minutes at room temperature. To this solution was added a solution of the compound of Preparation 145 (0.982 g, 1 mol. equiv.) and cyclopropylmethyl bromide (0.37 ml, 1.1 mol. equiv.) in dimethyl sulphoxide (20 ml). The reaction was stirred at room temperature for eighteen hours.

The reaction mixture was partitioned between ethyl acetate (50 ml) and water (20 ml) and the aqueous layer removed. The organic layer was then washed with water (3×20 ml), dried using sodium sulphate, filtered and evaporated to dryness under reduced pressure. The resulting gum was purified by flash column chromatography on silica gel eluting with methanol:dichloromethane (1:19, by volume) to give the title compound (0.763 g). TLC $R_f$=0.33 (silica, methanol:dichloromethane, 1:19, by volume). LRMS m/z= 338 (m)⁺.

¹H-NMR (CDCl₃):δ=0.2–0.4 (m,2H), 0.5–0.7 (m,2H), 1.0–1.15 (m,1H), 2.0–2.25 (m,3H), 2.3–2.6 (m,3H), 3.1–3.25 (m,1H), 3.4–3.6 (m,2H), 3.65–3.8 (m,1H), 5.0–5.05 (m,2H), 5.2–5.5 (m,1H), 7.15–7.2 (m,1H), 7.4–7.5 (m,2H) ppm.

Preparations 142 to 144

The compounds of the following tabulated Preparations of the general formula:

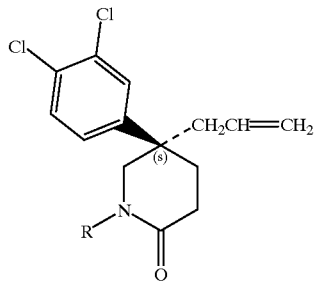

were prepared by a similar method to that used in Preparation 141 using the same piperidone and the appropriate bromo- or p-toluenesulphonyloxyalkane derivative starting materials.

| Prep. No. | R | LRMS m/z | Analysis/¹H-NMR |
|---|---|---|---|
| 142¹ | CH₂—phenyl | — | ¹H-NMR(CDCl₃): δ = 1.95–2.05(m,1H), 2.1–2.3(m,3H), 2.4–2.55(m,2H), 3.25(d,1H), 3.5(d,1H), 4.4(d,1H), 4.8–5.0(m,3H), 5.2–5.4(m,1H), 6.8(d,1H), 7.1–7.4(m,7H) ppm. |
| 143¹ | CH₂—cyclohexyl | 382 (m + 1)⁺ | ¹H-NMR(CDCl₃): δ = 0.9–1.4(m,5H), 1.6–1.8(m,6H), 2.0–2.3(m,3H), 2.3–2.6(m,3H), 3.1–3.2(m,1H), 3.3–3.4 (m,2H), 3.5–3.6(m,1H), 4.95–5.1(m,2H), 5.2–5.45(m,1H), 7.1(d,1H), 7.25–7.4(m,2H) ppm. |

-continued

| Prep. No. | R | LRMS m/z | Analysis/$^1$H-NMR |
|---|---|---|---|
| 144[2] | 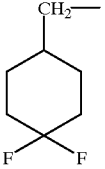 | 416 (m + 1)$^+$ | $^1$H-NMR(CDCl$_3$): δ = 1.25–1.6(m,2H), 1.6–1.9(m,5H), 1.95–2.3(m,5H), 2.3–2.6(m,3H), 3.2–3.3(m,1H), 3.3–3.4 (m,2H), 3.5–3.55(m,1H), 4.9–5.05(m,2H), 5.3–5.45 (m,1H), 7.05–7.2(m,1H), 7.3–7.45(m,2H) ppm. |

Footnotes:
[1]Bromoalkane derivative used as the starting material.
[2]p-Toluenesulphonyloxyalkane derivative used as the starting material.

Preparation 145

5(S)-5-Allyl-5-(3,4-dichlorophenyl)-2(1H)-piperidone

A solution of the compound of Preparation 146 (120 mg) in ethanol (5 ml) heated under reflux with concentrated sulphuric acid (0.4 ml) for twenty four hours. The reaction was diluted with water (5 ml) and basified using sodium carbonate. The solution was extracted with ethyl acetate (2×10 ml). The combined organic layers were dried using anhydrous magnesium sulphate, filtered and the filtrate evaporated to dryness under reduced pressure. The residue was chromatographed on silica gel eluting with a solvent gradient of dichloromethane:methanol (100:0 to 97:3 to 95:5, by volume) to give the title compound (10 mg). TLC R$_f$=0.4 (silica, dichloromethane: methanol, 95:5, by volume). LRMS m/z=284 (m+1)$^+$. $[α]_{589}^{25}$=31.2° (c=0.00125).

$^1$H-NMR (CDCl$_3$):δ=2.0–2.2 (m,3H), 2.3–2.5 (m,2H), 2.5–2.6 (m,1H), 3.4 (d,1H), 3.6 (d,1H), 4.9–5.05 (m,2H), 5.25–5.4 (m,1H), 6.0 (s,br,1H), 7.15–7.2 (m,1H), 7.4–7.5 (m,2H) ppm.

Preparation 146

2-(3(S)-3-Aminomethyl-3-(3,4-dichlorophenyl)hex-5-en-1-yl)-4(S)-4-isopropyloxazoline hydrochloride A solution of the compound of Preparation 147 (1 g, 1 mol. equiv.) in diethyl ether (200 ml) was added dropwise over one hour to a stirred suspension of lithium aluminium hydride (3.7 g, 1 mol. equiv.) in diethyl ether (200 ml) under nitrogen at 0° C. The reaction was stirred for one hour at 0° C. Water (3.7 ml) was added, followed by a 15% w/w aqueous sodium hydroxide solution (3.7 ml) and further water (11.1 ml). The mixture was stirred for fifteen minutes, filtered and the filtrate evaporated to dryness under reduced pressure to give an oil which gave a gelatinous gum on standing for eighteen hours. The gum was partitioned between ethyl acetate (200 ml) and 2N aqueous hydrochloric acid solution (100 ml). The organic portion was separated, dried using anhydrous magnesium sulphate, filtered and the solvent evaporated from the filtrate under reduced pressure. The resultant solid was chromatographed on silica gel eluting with a solvent gradient of dichloromethane:methanol (100:0 to 95:5 to 90:10, by volume) to give the title compound (21.4 g). LRMS m/z=369(m)$^+$.

$^1$H-NMR (CDCl$_3$):δ=0.7–0.8 (m,3H), 0.9–1.0 (m,3H), 1.6–1.8 (m,1H), 1.95–2.2 (m,3H), 2.2–2.4 (m,1H), 2.4–2.55 (m,1H), 2.8–3.0 (m,1H), 3.3–3.5 (m,2H), 3.6–4.0 (m,3H), 4.9–5.1 (m,2H), 5.3–5.45 (m,1H), 7.1 (d,1H), 7.3–7.7 (m,2H), 8.9 (d,br,1H), 9.4 (d,br,1H), 10.1 (s,br,1H) ppm.

Preparation 147

2-(3(S)-3-Cyano-3-(3,4-dichlorophenyl)hex-5-en-1-yl)-4(S)-4-isopropyloxazoline

A solution of the compound of Preparation 148 (3 g, 1 mol. equiv.) and S-valinol (1.04 g, 1 mol. equiv.) in toluene (30 ml) was heated under reflux under Dean-Stark conditions for eighteen hours. More toluene was then added and the reaction heated under reflux for a further forty eight hours. The toluene was then removed by evaporation under reduced pressure and the residue chromatographed on silica gel eluting with a solvent gradient of hexane:diethyl ether (100:0 to 80:20 to 60:40, by volume) to give the title compound (1 g). LRMS m/z=365(m)$^+$.

$^1$H-NMR (CDCl$_3$):δ=0.8 (d,3H), 0.95 (m,3H), 1.6–1.8 (m,1H), 2.05–2.3 (m,2H), 2.4–2.55 (m,2H), 2.6–2.8 (m,2H), 3.8–4.0 (m,2H), 4.15–4.2 (m,1H), 5.1–5.2 (m,2H), 5.5–5.7 (m,1H), 7.2–7.25 (m,1H), 7.5–7.55 (m,2H) ppm.

REPARATION 148

4(S)-4-Cyano-4-(3,4-dichlorophenyl)hept-6-enoic acid

To a stirred solution of the compound of Preparation 149 (5.5 g) in dichloromethane (100 ml) was added 1N aqueous hydrochloric acid solution (100 ml). The aqueous layer was then removed and the organic portion washed with 1 N aqueous hydrochloric acid solution (70 ml). The organic layer was dried using anhydrous magnesium sulphate, filtered, and the filtrate evaporated to dryness under reduced pressure to give the title compound (3.6 g). LRMS m/z=316(m+NH$_4$)$^+$.

$^1$H-NMR (CDCl$_3$):δ=2.15–2.8 (m,6H), 5.1–5.25 (m,2H), 5.55–5.7 (m,1H), 7.2–7.25 (m,1H), 7.5–7.55 (m,2H) ppm.

Preparation 149

4(S)-4-Cyano-4-(3,4-dichlorophenyl)hept-6-enoic acid (R)-(+)-1-(1-naphthyl)ethylamine salt To a solution of the compound of Preparation 150 (16 g) in ethyl acetate (50 ml) was added R-(+)-1-(1-naphthyl) ethylamine (4.8 g). The solution was stirred for thirty minutes at room temperature and then the solvent removed under reduced pressure to give a gum. This gum was partially dissolved in hexane:diethyl ether (4:1, by volume, 150 ml) and the sides of the flask scratched to induce

147 crystallisation. The white solid that formed was filtered off and cystallised three times from ethyl acetate to give the title compound (4.9 g). m.p. 153–154° C. $[\alpha]_{589}^{25}$ −7.1° (c=0.0012).

$^1$H-NMR (CDCl$_3$):δ=1.6 (d,3H), 2.0–2.2 (m,2H), 2.25–2.5 (m,2H), 2.5–2.7 (m,2H), 3.8–4.1 (s,br,3H), 5.0–5.2 (m,3H), 5.5–5.7 (m,1H), 7.15–7.25 (m,1H), 7.4–7.6 (m,6H), 7.75 (d,1H), 7.9 (d,1H), 8.1 (d,1H) ppm.

Preparation 150

4-Cyano-4-(3,4-dichlorophenyl)hept-6-enoic acid

To a stirred suspension of 60% w/w sodium hydride oil dispersion (231 g) in tetrahydrofuran (17L) under nitrogen at −10° C. was added a solution of 3-bromopropanoic acid (806.5 g) in tetrahydrofuran (6L) dropwise over three hours. The reaction was allowed to warm to room temperature over 22 hours. The reaction was then cooled to −10° C. Simultaneously, a solution of the compound of Preparation 151 (1633.5 g) in tetrahydrofuran (2.5L) was added dropwise over two hours to a stirred tetrahydrofuran suspension (2.5L) of 60% w/w sodium hydride oil dispersion (221 g) in tetrahydrofuran (2.5L) under nitrogen at −10° C. When the addition was complete, this second reaction was allowed to warm to room temperature over eighteen hours. This reaction was then cooled to −10° C. and cannulated into the above 3-bromopropanoic acid sodium salt mixture over 3 hours. The reaction mixture was heated at 50° C. for five hours. The reaction was then cooled, poured into water (8L) and basified to pH 9.3 using aqueous sodium bicarbonate solution. This mixture was washed with dichloromethane (5×2L) and the aqueous portion acidified to pH 1.0 using concentrated hydrochloric acid. The aqueous solution was extracted with dichloromethane (4×2.5L) and the organic layers were combined, dried using anhydrous magnesium sulphate, filtered and the filtrate concentrated under reduced pressure to give a yellow oil. This oil was then triturated with hexane (1.5L) to give the title compound as a cream solid (1155.3 g) which was used without any further purification. TLC R$_f$=0.42 (silica, methanol:dichloromethane, 1:9, by volume). LRMS m/z=316(m+NH$_4$)$^+$.

$^1$H-NMR (CDCl$_3$):δ=2.15–2.8 (m,6H), 5.1–5.25 (m,2H), 5.55–5.7 (m,1H), 7.2–7.25 (m,1H), 7.5–7.55 (m,2H) ppm.

Preparation 151

2-(3,4-Dichlorophenyl)pent-4-enenitrile

To a stirred solution of 3,4-dichlorophenylacetonitrile (800 g, 4.3 mol.) in cyclohexane (16L) at room temperature was carefully. added aqueous sodium hydroxide solution (1600 g of sodium hydroxide in 8L of water). This addition caused an elevation of the reaction temperature to 50° C. Allyl bromide (572 g, 1.1 mol. equiv.) and tetra-n-butylammonium chloride hydrate (40 g, 0.03 mol. equiv.) were then added and the reaction stirred for one hour at 50° C. The aqueous phase was removed and the organic layer washed with water (10L). The organic phase was filtered through silica gel (1 kg) under reduced pressure to give a yellow filtrate solution. The solvent was removed from the filtrate under reduced pressure to give the title compound as an oil (960 g) of 70% purity which was used without any further purification. TLC R$_f$=0.71 (silica, diethyl ether:hexane, 1:1, by volume). LRMS m/z=226(m)$^+$.

$^1$H-NMR (CDCl$_3$):δ=2.6–2.75 (m,2H), 3.85 (t,1H), 5.1–5.25 (m,2H), 5.7–5.9 (m,1H), 7.2–7.25 (m,1H), 7.5–7.55 (m,2H) ppm.

148

Preparation 152

1-(t-Butoxycarbonyl)-3-(piperazin-1-yl)azetidine methanesulphonate

Piperazine (149.2 g, 8 mol. equiv.) was heated to a melt and 1-(t-butoxycarbonyl)-3-methanesulphonyloxy-azetidine (see International Patent Application Publication no. WO93/19059) (54.5 g, 217 mmol) was then added. The mixture was heated at 115° C. for twenty four hours. The reaction was cooled and the excess piperazine removed under reduced pressure. The residue was purified by flash column chromatography on silica gel using methanol:dichloromethane (5:95, by volume) as the eluant to give the title compound (51 g). LRMS m/z=242 (m+1)$^+$.

$^1$H-NMR (CDCl$_3$):δ=1.4 (m,9H), 2.5–2.6 (m,4H), 3.1–3.25 (m,5H), 3.7–3.8 (m,2H), 3.9–3.95 (m,2H), 4.6 (br. s,1H) ppm.

Preparation 153

3-(4-Aminosulphonylpiperazin-1-yl)-1-(t-butoxycarbonyl azetidine

A solution of the compound of Preparation 152 (50 g, 132.6 mmol) and sulphamide (88 g, 6.9 mol. equiv.) in 1,4-dioxane (1300 ml) was heated under reflux for fifty five hours. The solution was cooled and the solvent removed under reduced pressure. The residue was purified by flash column chromatography on silica gel using methanol: dichloromethane (5:95, by volume) as the eluant to give the title compound (50 g).

$^1$H-NMR (CDCl$_3$):δ=1.45 (s,9H), 2.4–2.5 (m,4H), 3.1–3.2 (m,1H), 3.25–3.3 (m,4H), 3.75–3.8 (m,2H), 3.85–3.9 (m,2H), 4.3 (br. s,2H) ppm.

Preparation 154

3-(4-Aminosulphonylpiperazin-1-yl)azetidine bistrifluoroacetate

To a solution of the compound of Preparation 153 (364 mg, 1.14 mmol) in dichloromethane (6 ml) under an atmosphere of nitrogen at 0° C. was slowly added trifluoroacetic acid (3 ml, 35 mol. equiv.) and the reaction mixture was allowed to warm to room temperature over two hours. The solvent was then removed under reduced pressure and the residue azeotroped with dichloromethane (3×10 ml). The resulting oil was triturated with diethyl ether to give the title compound (379 mg) which was used without further purification.

$^1$H-NMR (CDCl$_3$):δ=2.4–2.6 (m,4H), 2.95–3.15 (m,4H), 3.35–3.5 (m,1H), 3.8–4.1 (m,4H), 6.6–6.8 (m,2H), 8.6–8.85 (m,3H) ppm.

Preparation 155

1,1-Dicyclopropylethene

To a stirred suspension of methyltriphenylphosphonium bromide (133.5 g, 3 mol. equiv.) in dimethylsulphoxide (200 ml) under nitrogen was added a solution of potassium tert-butoxide (42 g, 3 mol. equiv.) in dimethylsulphoxide (200 ml), dropwise, over 15 minutes. Dicyclopropyl ketone (13.8 g, 0.125 mol.) was added and the solution heated at 60° C. for 1 hour and then stirred at room temperature for 16 hours. The reaction was poured into 20% w/w aqueous sodium chloride solution (900 ml) and ice (200 g) added. The mixture was extracted with diethyl ether (2 l) and the organic extract washed with water (2×1.5 l), dried using anhydrous magnesium sulphate and filtered. The solvent was then removed from the filtrate under reduced pressure and the residue shaken with a mixture of diethyl ether (50 ml) and hexane (50 ml). The mixture was filtered, the solvent removed from the filtrate under reduced pressure and the residue shaken with a mixture of hexane:diethyl ether (50 ml, 9:1, by volume). The mixture was filtered and the solvent removed from the filtrate under reduced pressure to give the title compound (4.5 g).

$^1$H-NMR (CDCl$_3$):δ=0.55–0.7(m,8H), 1.3–1.45(m,2H), 4.6(s,2H) ppm.

Preparation 156

2,2-Dicyclopropylethanol

To a solution of the compound of Preparation 155 (1 g, 9.24 mmol) in tetrahydrofuran (15 ml) under nitrogen was added 9-borabicyclo[3.3.1]nonane (18.5 ml of a 0.5M solution in tetrahydrofuran, 1 mol. equiv.) and the solution stirred for 18 hours. Sodium hydroxide (3.08 ml of a 3M aqueous solution, 1 mol. equiv.) was added followed by ethanol (5 ml). The reaction was cooled to 5° C. and hydrogen peroxide (3.14 ml of a 30% w/w aqueous solution, 3 mol. equiv.) added. The reaction was stirred at room temperature for 1 hour.

The reaction was partitioned between ethyl acetate (50 ml) and water (50 ml), the organic phase separated and dried using anhydrous magnesium sulphate. The solution was filtered and the solvent removed from the filtrate under reduced pressure to give an oil which was chromatographed on silica gel, eluting with diethyl ether:hexane (2:1, by volume) to give the title compound (160 mg).

$^1$H-NMR (CDCl$_3$):δ=0.1–0.35(m,4H), 0.4–0.55(m,4H), 0.6–0.8 (m,2H), 1.65(t,1H), 3.7(t,2H) ppm.

Preparation 157

2-Methanesulphonyloxyethylcyclopropane

The title compound was prepared by a similar method to that used in Preparation 13 except using 1.2 mole equivalents of triethylamine and 1.3 mole equivalents of methanesulphonyl chloride. LRMS m/z=182 (m+NH$_4$)$^+$.

$^1$H-NMR (CDCl$_3$):δ=0.1–0.15(m,2H), 0.5–0.55(m,2H), 0.7–0.8(m,1H), 1.6–1.7(m,2H), 3.00(s,3H), 4.25–4.3(m,2H) ppm.

Preparation 158

2,2-Dicyproryl-1-methanesulphonyloxyethane

To a solution of the compound of Preparation 156 (1 g, 7.9 mmol) in dichloromethane (20 ml) at 5° C. under nitrogen was added triethylamine (1.32 ml, 1.2 mol. equiv.) followed by methanesulphonyl chloride (0.67 ml, 1.1 mol. equiv.) and the reaction stirred for 2 hours. The solution was concentrated under reduced pressure and the residue partitioned between ethyl acetate (100 ml) and water (100 ml). The organic layer was separated, dried using anhydrous magnesium sulphate, filtered and the solvent removed from the filtrate under reduced pressure. The residue was chromatographed on silica gel eluting with diethyl ether:hexane (2:1, by volume) to give the title compound (1.5 g).

$^1$H-NMR (CDCl$_3$):δ=0.1–0.15(m,4H), 0.2–0.3(m,5H), 0.35–0.4(m,2H), 3.0(s,3H), 4.15(d,2H) ppm.

Preparation 159

N-Methylsulphamoyl chloride

To a solution of sulphuryl chloride (35.7 ml, 3 mol. equiv.) in acetonitrile (30 ml) under nitrogen was added methylamine hydrochloride (10 g, 148 mmol) followed by acetonitrile (30 ml). The reaction was heated under reflux for 20 hours. The reaction was cooled to room temperature and the mixture concentrated under reduced pressure to give the title compound (20.51 g) which was used without further purification.

$^1$H-NMR (CDCl$_3$):δ=3.0(d,3H), 5.7(s,br.,1H) ppm.

Preparations 160 and 161

The compounds of the following tabulated preparations were prepared by a similar method to that of Preparation 159 using sulphuryl chloride and the appropriate amines.

| Prep. No. | Compound | LRMS m/z | Analysis/$^1$H-NMR |
|---|---|---|---|
| 160 | (CH$_3$)$_2$NSO$_2$Cl | — | $^1$H-NMR(CDCl$_3$): δ = 2.9(s,6H) ppm. |
| 161 | ⟨hexyl⟩NSO$_2$Cl | 211 (m + 1)$^+$ | $^1$H-NMR(CDCl$_3$): δ = 3.3–3.35(m,4H), 3.8–3.85 (m,4H) ppm. |

Preparation 162

Tert-butyl 6-bromohexanoate

To a solution of 6-bromohexanoic acid (9 g; 0.046 mol.) in dichloromethane (50 ml) at −78° C. was added fuming sulphuric acid (0.5 ml). To this solution was added liquid isobutylene (50 ml), dropwise. The reaction was allowed to warm to room temperature and stirred for 18 hours.

The mixture was poured into ice-cooled saturated aqueous sodium carbonate solution. The mixture was extracted with dichloromethane (2×40 ml), and the combined extracts washed with brine (40 ml). The organic layer was dried using magnesium sulphate. The mixture was filtered and the solvent removed from the filtrate under reduced pressure to provide the title compound as a yellow oil which was used with further purification. TLC Rf=0.25 (silica, methanol: dichloromethane, 1:9, by volume). LRMS m/z=267.8(m+ 18)$^+$.

$^1$H-NMR (CDCl$_3$):δ=1.3–1.45(m,11H), 1.45–1.6(m,2H), 1.7–1.85(m,2H), 2.15(t,2H), 3.35(t,2H) ppm.

Preparation 163

4-(2-Benzoxazolyl)piperidine

A mixture of 2-aminophenol (20 g, 183 mmol), isonipecotic acid (23.7 g, 1 mol. equiv.) and polyphosphoric acid (50 ml) was heated together for 2 hours with stirring. The reaction mixture was cooled, poured onto ice (400 g) and solid sodium hydroxide (85 g) added until the solution achieved pH8. The solid was filtered off, slurried in water (500 ml) and filtered to give the title compound (4.5 g).

A second crop of the title compound was obtained by extracting the above filtrate with dichloromethane (4×200 ml). The combined organic extracts were dried using anhydrous magnesium sulphate, filtered and the solvent removed from the filtrate under reduced pressure to give the title compound (9 g).

$^1$H-NMR (CDCl$_3$):δ=1.9–2.1 (m,3H), 2.15–2.3(m,2H), 2.8–2.9(m,2H), 3.1–3.3(m,3H), 7.3–7.35(m,2H), 7.5–7.55 (m, 1H), 7.7–7.75(m,1H) ppm.

Preparation 164

1-Benzyl-4-(tert-butoxycarbonylamino)piperidine

To a solution of 4-amino-1-benzylpiperidine (10 g, 53 mmol) in dichloromethane (200 ml) at 0° C. was added di-tert-butyl dicarbonate (12.6 g, 1.1 mol. equiv.) and the mixture stirred a t room temperature for 16 hours.

The crude reaction mixture was washed with 2% w/w aqueous sodium bicarbonate solution (300 ml), dried using anhydrous magnesium sulphate and the solution filtered. Removal of the solvent from the filtrate under reduced pressure gave a beige solid which was purified by column chromatography on silica gel eluting with dichloromethane:methanol (95:5, by volume) to give the title compound (13.1 g). TLC Rf=0.3 (dichloromethane:methanol, 95:5, by volume).

$^1$H-NMR (CDCl$_3$):δ=1.35–1.5(m,11H), 1.85–1.95(m, 2H), 2.05–2.15(m,2H ), 2.75–2.8(m,2H), 3.4–3.5(m,3H), 4.4(s,br., 1H), 7.2–7.3(m,5H) ppm.

Preparation 165

4-(Tert-butoxycarbonylamino)piperidine

To a solution of the compound of Preparation 164 (13.1 g, 45.1 mmol) in ethanol (135 ml) was added 10% w/w palladium-on-carbon (0.6 g) and the mixture stirred under an atmosphere of hydrogen at 414 kPa (60 p.s.i.) for 16 hours. After this time, a further 0.6 g of the catalyst was added and the mixture stirred under an atmosphere of hydrogen at 414 kPa (60 p.s.i.) for a further 72 hours. The reaction mixture was then filtered through a cellulose-based filter aid and the filtrate concentrated under reduced pressure to give a solid. This was triturated with diethyl ether (50 ml), filtered and the solid obtained dried under reduced pressure to give the title compound (8.1 g).

$^1$H-NMR (CDCl$_3$):δ=1.15–1.3(m,2H), 1.35–1.5(m,10H), 1.9–1.95(m,2H), 2.6–2.7(m,2H), 3.0–3.1 (m,2H), 3.5(s,br., 1H), 4.4(s,br., 1H) ppm.

Preparation 166

1-Benzyloxycarbonyl-4-hydroxypiperidine

To a solution of 4-hydroxypiperidine (4.2 g, 41 mmol) in dichloromethane (50 ml) at 0° C. under an atmosphere of nitrogen was slowly added benzyl chloroformate (7.7 ml, 1.3 mol. equiv.) followed by triethylamine (6.94 ml, 1.2 mol. equiv.). The reaction was stirred at room temperature for 15 hours.

The reaction was washed with saturated sodium bicarbonate solution (2×50 ml) and the organic layer dried using anhydrous magnesium sulphate, filtered and the filtrate evaporated under reduced pressure to dryness. The crude product was purified by flash chromatography on silica gel eluting with methanol:dichloromethane (1:20, by volume) to give the title compound (9.24 g). TLC Rf=0.68 (silica, methanol:dichloromethane, 1:10, by volume). LRMS m/z= 236 (m+1)$^+$.

$^1$H-NMR (CDCl$_3$):δ=1.35–1.55(m,2H), 1.75(m,1H), 1.8–2.0(m,2H), 3.1–3.2(m,2H), 3.8–4.0(m,3H), 5.15(s,2H), 7.35(s,5H) ppm.

Preparation 167

1-Benzyloxycarbonyl-(4-tert-butyloxy)piperidine

To a solution of the compound of Preparation 166 (9.24 g) in cyclohexane: dichloromethane (120 ml, 3:1, by volume) at 0° C. under a nitrogen atmosphere was added t-butyl trichloroacetimidate (14.1 ml, 2 mol. equiv.) and boron trifluoride etherate (0.8 ml, 0.16 mol. equiv.). The reaction was allowed to warm to room temperature and stirred for 48 hours.

The solvent was removed from the reaction by evaporation under reduced pressure. The reaction was taken up in ethyl acetate (50 ml) and washed with saturated sodium bicarbonate solution (30 ml). The aqueous layer was extracted with ethyl acetate (2×30 ml). The organic layers were combined, dried using anhydrous magnesium sulphate, filtered and the filtrate evaporated under reduced pressure to dryness. The residue was then purified by flash column chromatography on silica gel eluting with methanol:dichloromethane (3:97 by volume), followed by flash column chromatography for a second time on silica gel eluting with methanol:dichloromethane (1:5, by volume). This gave the title compound (9 g). TLC Rf=0.56 (silica, methanol:dichloromethane, 1:20, by volume). LRMS m/z= 292 (m+1)$^+$.

$^1$H-NMR (CDCl$_3$):δ=1.2(s,9H), 1.4–1.55(m,2H), 1.65–1.8(m,2H), 3.1–3.25(m,2H), 3.6–3.7(m,1H), 3.8–4.0 (m,2H), 5.15(s,2H), 7.4(s,5H) ppm.

Preparation 168

4-(Tert-butyloxy)piperidine

The compound of Preparation 167 (8.41 g, 28.8 mmol) was dissolved in ethanol (100 ml) and 10% w/w palladium-on-carbon (0.34 g) added. The mixture was stirred under hydrogen at 414 kPa (60 p.s.i.) for 24 hours. The catalyst was filtered off and the solvent removed from the filtrate under reduced pressure. The resulting oil has purified by column chromatography on silica gel eluting with concentrated aqueous ammonia solution:methanol:dichloromethane (1:10:89, by volume) to give the title compound (2.48 g). TLC Rf=0.23 (silica, concentrated aqueous ammonia solution:methanol:dichloromethane 1:10:89, by volume). LRMS m/z=158 (m+1)$^+$.

Preparation 169

1-(Tert-butoxycarbonyl)-3-(1-piperazinyl)azetidine

Piperazine (23.69 g, 8 mol. equiv.) was melted and 1-(t-butoxycarbonyl)-3-methanesulphonyloxyazetidine (see International Patent Application Publication no. WO93/ 19059) (8.64 g, 34.4 mmol) added. The mixture was heated at 120° C. for 15 hours under nitrogen. The reaction was cooled to room temperature and the excess piperazine removed under reduced pressure. The residue was then chromatographed on silica gel using gradient elution (methanol:dichloromethane 1:19 changing to 1:4, by volume) to give the title compound (6.32 g). LRMS m/z= 242 (m+1)$^+$.

$^1$H-NMR (d$_6$-DMSO):δ=1.35(s,9H), 2.4–2.5(m,4H), 3.0–3.1(m,5H), 3.2–4.2 (m,br.,5H) ppm.

Preparation 170

1-(Tert-butoxycarbonyl)-3-(4-methylsulphonylpiperazin-1-yl)azetidine

To a solution of the compound of Preparation 169 (8.06 g, 21.3 mmol) in dichloromethane (160 ml) was added triethylamine (13.4 ml). The solution was kept under a nitrogen atmosphere and cooled to 0° C. Methanesulphonyl chloride (5.25 ml, 7.77 g, 3 mol. equiv.) was added, dropwise, over 30 minutes. The reaction was allowed to warm to room temperature over 2.5 hours and then stirred for a further 18 hours. The reaction was washed with water (3×50 ml) and then brine (2×30 ml). The organic layer was dried using anhydrous magnesium sulphate. The mixture was then filtered and the solvent removed from the filtrate under reduced pressure. The residue was chromatographed on silica gel eluting with concentrated aqueous ammonia:methanol:dichloromethane (1:10:89, by volume). The product from this chromatography step was then column chromatographed again on silica gel eluting with methanol:ethyl acetate (1:10, by volume) to give the title compound (0.9 g). TLC Rf=0.6 (silica, concentrated aqueous ammonia solution:methanol:dichloromethane, 1:10:89 by volume). LRMS m/z=320 (m+1 )⁺.

$^1$H-NMR (CDCl$_3$):δ=1.4(s,9H), 2.45(t,4H), 3.8(s,3H), 3.1–3.2(m,1H), 3.2–3.3(m,4H), 3.75–3.8(m,2H), 3.9–4.0(m, 2H) ppm.

Preparation 171

3-(4-Benzoylpiperazin-1-yl)-1-(tert-butoxycarbonyl)azetidine

To a solution of the compound of Preparation 169 (3.3 g) in dichloromethane (70 ml) at room temperature under nitrogen was added triethylamine (4.06 ml) and benzoyl chloride (2.30 ml). The mixture was allowed to stir at room temperature for 16 hours. The reaction mixture was washed with water (3×100 ml) and brine (3×100 ml), dried using anhydrous magnesium sulphate, filtered and the solvent removed from the filtrate under reduced pressure. The residue was column chromatographed on silica gel eluting with ethyl acetate to yield the title compound (2.3 g).

Preparation 172

1-(Tert-butoxycarbonyl)-3-(4-methylcarbamoylpiperazin-1-yl)azetidine

To a solution of the compound of Preparation 169 (3.3 g) in dichloromethane (70 ml) was added methyl isocyanate and the mixture allowed to stir at room temperature for 72 hours. After this time, the dichloromethane was removed by bubbling nitrogen through the solution. The residue was taken up in dichloromethane (100 m) and washed with 10% w/w aqueous sodium bicarbonate solution (100 ml) followed by brine (100 ml). The organic layer was dried using anhydrous magnesium sulphate, filtered and the solvent removed from the filtrate under reduced pressure. The residue was chromatographed on silica gel eluting with dichloromethane:methanol (95:5, by volume) to give the title compound (1.8 g). LRMS m/z=299 (m+1)⁺.

$^1$H-NMR (CDCl$_3$):δ=1.40(s,9H), 2.25–2.35(m,4H), 2.8–2.85(m,3H), 3.0–3.1 (m, 1H), 3.35–3.4(m,4H), 3.75–3.85(m,2H), 3.9–3.95(m,2H), 4.4(s,br., 1H) ppm.

Preparation 173

1-(Tert-butoxycarbonyl)-3-(4-methylaminosulphonylpiperazin-1-yl)azetidine

To a solution of the compound of Preparation 169 (500 mg, 2.07 mmol) in acetonitrile (5 ml) under nitrogen was added triethylamine (0.43 ml, 1.5 mol. equiv.). A solution of the compound of Preparation 159 (295 mg, 1.1 mol. equiv.) in acetonitrile (2 ml) was added, dropwise, and the reaction heated at 90° C. for 3 hours. The reaction was cooled to room temperature and the solvent removed under reduced pressure. The residue was partitioned between ethyl acetate (50 ml) and water (50 ml). The organic layer was separated and washed with brine (50 ml), dried using anhydrous magnesium sulphate, filtered and the solvent removed from the filtrate under reduced pressure. The residue was chromatographed on silica gel eluting with methanol:dichloromethane (1:19, by volume) to give the title compound (374 mg). TLC Rf=0.73 (silica, methanol: dichloromethane, 1:9, by volume). LRMS m/z=335(m+1)⁺.

$^1$H-NMR (CDCl$_3$):δ=1.4(s,9H), 2.4–2.45(m,4H), 2.7–2.75(m,3H), 3.1–3.15(m,1H), 3.25–3.3(m,4H), 3.75–3.9(m,4H), 4.15–4.2(m,1H) ppm.

Preparations 174 and 175

The compounds of the following tabulated Preparations of the general formula:

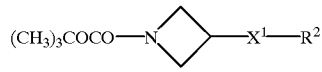

were prepared by a similar method to that of Preparation 173 using the same piperazine starting material together with the appropriate sulphamoyl chlorides (see Preparations 160 and 161).

| Prep. No. | —X$^1$—R$^2$ | LRMS m/z | Analysis/$^1$H-NMR |
|---|---|---|---|
| 174 | —N⟨⟩N—SO$_2$N(CH$_3$)$_2$ | 349 (m + 1)⁺ | $^1$H-NMR(CDCl$_3$): δ = 1.45(s,9H), 2.4(m,4H), 2.85(m,6H), 3.1–3.2(m,1H), 3.3–3.35(m,4H), 3.75–3.95(m,4H) ppm. |
| 175 | —N⟨⟩N—SO$_2$N⟨⟩O | 391 (m + 1)⁺ | $^1$H-NMR(CDCl$_3$): δ = 1.45(s,9H), 2.4–2.45 (m,4H), 3.1–3.15(m,1H), 3.2–3.35(m,8H), 3.7–3.95(m,8H) ppm. |

Preparation 176

1-(Tert-butoxycarbonyl)-3-(4-methoxypiperidin-1-yl)azetidine

To a solution of the compound of Preparation 71 (1 g, 4.12 mmol) in tetrahydrofuran (12 ml) at 0° C. under nitrogen, was added, in two portions, 60% w/w sodium hydride/dispersion in oil (0.198 mg, 1.2 mol. equiv.). After 30 minutes stirring, methyl iodide (0.282 ml, 1.1 mol. equiv.) was added and the mixture stirred for 16 hours.

155

The solvent was removed under reduced pressure and the residue partitioned between ethyl acetate (50 ml) and saturated aqueous sodium bicarbonate solution (50 ml). The organic layer was separated and dried using anhydrous sodium sulphate. The mixture was filtered and the solvent removed from the filtrate under reduced pressure to give an oil. This crude product was purified by column chromatography on silica gel eluting with methanol:dichloromethane (3:97, by volume) to give the title compound as a colourless oil (0.84 g). TLC Rf=0.2 (silica, methanol:dichloromethane, 3:97, by volume).

$^1$H-NMR (CDCl$_3$):δ=1.4(m,9H), 1.55–1.7(m,2H), 1.8–2.0(m,2H), 2.0–2.15(m,2H), 2.55–2.65(m,2H), 3.0–3.1 (m, 1H), 3.2–3.3(m, 1H), 3.35(s,3H), 3.75–3.8(m,2H), 3.9–4.0(m,2H) ppm.

Preparations 177 and 178

The compounds of the following tabulated Preparations of the general formula:

were prepared using a similar method to that of Preparation 176 using the same piperidinol starting material and ethyl iodide or n-propyl iodide, as appropriate, as the alkylating agent.

156

Preparation 180

3-(4-Methoxycarbonylpiperidin-1-yl)azetidine dihydrochloride

To a solution of the compound of Preparation 105 (7.5 g, 19.81 mmol) in dichloromethane (100 ml) at 0° C. under nitrogen was added α-chloroethyl chloroformate (2.6 ml, 1.2 mol. equiv.) and the reaction warmed to room temperature over 1 hour. Methanol (150 ml) and potassium carbonate (8.2 g, 3 mol. equiv.) were then added and the reaction heated under reflux for 3 hours.

The reaction was cooled to room temperature, filtered and the filtrate acidified to pH3 with methanolic hydrogen chloride. The mixture was filtered and the solvent removed by evaporation under reduced pressure. The residue was washed with diethyl ether (3×100 ml) and then triturated with diethyl ether to give a solid that was filtered off and dried to yield the title compound (5.1 g). LRMS m/z=199 (m+1)$^+$.

Preparation 181

3-(4-Tert-butoxycarbonylaminopiperidin-1-yl) azetidine bistrifluoroacetate

To a solution of the compound of Preparation 106 (6.8 g, 16.1 mmol) in dichloromethane (70 ml) at 0° C. under nitrogen was added alpha-chloroethyl chloroformate (1.91 ml, 1.1 mol. equiv.) and the mixture stirred at room temperature for 1 hour. After this time, the solvent was removed

| Prep. No. | —X$^1$—R$^2$ | LRMS m/z | Analysis/$^1$H-NMR |
|---|---|---|---|
| 177 | —N⟨piperidine⟩—OCH$_2$CH$_3$ | — | $^1$H-NMR(CDCl$_3$): δ = 1.2(t,3H), 1.4(s,9H), 1.55–1.7(m,2H), 1.8–1.95(m,2H), 1.95–2.1(m,2H), 2.5–2.7(m,2H), 3.0–3.1(m,1H), 3.3–3.4(m,1H), 3.5 (q,2H), 3.75–3.8(m,2H), 3.9–3.95(m,2H) ppm. |
| 178 | —N⟨piperidine⟩—OCH$_2$CH$_2$CH$_3$ | 299.2 (m + 1)$^+$ | — |

Preparation 179

3-(4-Benzoylpiperazin-1-yl)azetidine bistrifluoroacetate

To a solution of the compound of Preparation 171 (2.3 g) in dichloromethane (18 ml) at 0° C. under nitrogen was added trifluoroacetic acid (9 ml), dropwise, and the mixture allowed to stir at room temperature for 1 hour. The solvent was carefully removed by evaporation under reduced pressure and the residue azeotroped with dichloromethane (3×20 ml). The resulting oil was washed with diethyl ether (3×20 ml). Ethyl acetate (50 ml) was then added and the precipitate collected by filtration and dried to give the title compound (132 mg). A second crop of the title compound (186 mg) was obtained by concentration of the filtrate under reduced pressure to give an oil. This was triturated with diethyl ether and ethyl acetate and the solid obtained collected by filtration and dried to give the title compound (0.32 g).

$^1$H-NMR (d$_6$-DMSO):δ=2.3–2.45(m,4H), 3.3–3.7(m, 5H), 3.8–4.05(m,5H), 7.3–7.4(m,5H), 8.65(s,br.,1H) ppm.

by evaporation under reduced pressure, the residue dissolved in methanol (80 ml) and potassium carbonate (4.9 g, 2.2 mol. equiv.) added. The mixture was then heated under reflux for 1 hour. The reaction mixture was cooled to room temperature, filtered and the filtrate acidified to pH5 by the dropwise addition of trifluoroacetic acid. The solvent was removed under reduced pressure to give a gum which was triturated with diethyl ether to give a solid. This solid was collected by filtration and dried under reduced pressure to give the title compound as a crude product that was used directly.

Preparation 182

5(S)-5-(3,4-Dichlorophenyl)-1-(4,4-difluorocyclohexylmethyl)-5-(1,3-dioxolan-2-ylmethyl)-2-piperidone To a stirred mixture of dimethyl sulphoxide (50 ml) and potassium hydroxide (2.1 g) at room temperature under nitrogen was added a solution of the compound of Example 123(b) (3 g, 9.1 mmol) in dimethyl sulphoxide (50 ml) followed by the compound of Preparation 11 (3.1 g) and the mixture stirred at room temperature for 16 hours. Water (300 ml) and brine (300 ml) were added and the mixture extracted with ethyl acetate (3×300 ml). The combined organic extracts were washed with brine (300 ml), dried using anhydrous magnesium sulphate, filtered and the solvent removed from the filtrate by evaporation under reduced pressure. The residue was chromatographed on silica gel eluting with a solvent gradient of ethyl acetate:hexane (1:1 changing to 7:3 changing to 4:1 changing to neat ethyl acetate) to give the title compound (3.3 g). LRMS m/z=462 (m+1)+.

$^1$H-NMR (CDCl$_3$):δ=1.3–1.45(m,2H), 1.6–1.95(m,6H), 2.1–2.2(m,6H), 2.4–2.55 (m, 1H), 3.2–3.3(m, 1H), 3.4–3.5 (m,2H), 3.65–3.75(m,3H), 3.85–3.95(m,2H), 4.3–4.35(m, 1H), 7.1–7.4(m,3H) ppm.

Preparations 183 to 186

The compounds of the following tabulated Preparations of the general formula:

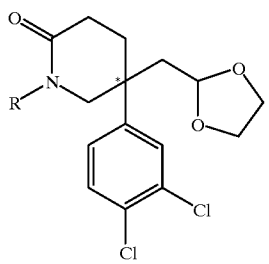

were prepared by a similar method to that of Preparation 182 using the appropriate piperidone (see Example 123(b) and Preparation 193) and the appropriate mesylate starting materials for Preparations 183 and 184 and the appropriate bromide starting materials for Preparations 185 and 186.

Preparation 187

5(S)-5-(3,4-Dichlorophenyl)-5-formylmethyl-2(1H)-piperidone

A solution of the compound of Example 123(b) (280 mg, 0.85 mmol) in tetrahydrofuran (3 ml) and 5N aqueous hydrochloric acid solution (3 ml) was stirred at room temperature under nitrogen for 4 hours. The reaction was poured into a mixture of ethyl acetate (20 ml) and saturated aqueous sodium bicarbonate solution (20 ml). The organic phase was separated, dried using anhydrous magnesium sulphate, filtered and the solvent removed by evaporation under reduced pressure to give the title compound (283 mg) which was used without further purification. TLC Rf=0.26 (silica, methanol:dichloromethane, 1:9, by volume).

Preparations 188 to 191

The compounds of the following tabulated Preparations of the general formula:

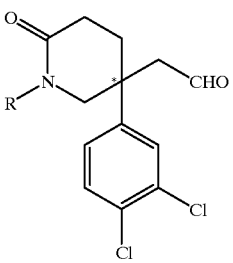

were prepared by a similar method to that of Preparation 187 using the appropriate dioxolane starting materials (see Preparations 183 to 186).

| Prep. No. | R | m.p. | LRMS m/z | Analysis/$^1$H-NMR |
|---|---|---|---|---|
| 183[1] | CH$_2$CH$_2$—cyclopropyl | — | 398 (m + 1)+ | $^1$H-NMR(CDCl$_3$): δ = 0.1–0.15(m,2H), 0.45–0.5(m,2H), 0.6–0.75(m,1H), 1.5–1.6(m,2H), 1.9–1.95(m,1H), 2.1–2.2(m,4H), 2.35–2.5(m,1H), 3.3–3.4(m,1H), 3.5–3.6(m,1H), 3.65–3.75(m,4H), 3.85–3.9(m,2H), 4.35–4.4(m,1H), 7.1–7.45(m,3H) ppm. |
| 184[1] | dicyclopropyl-CH$_2$— | — | 438 (m + 1)+ | $^1$H-NMR(CDCl$_3$): δ = 0.1–0.25(m,4H), 0.35–0.55(m,4H), 0.6–0.7(m,3H), 1.9–2.5(m,6H), 3.15–3.2(m,1H), 3.55–3.95(m,7H), 4.35–4.4(m,1H), 7.1–7.4(m,3H) ppm. |
| 185[1] | —CH$_2$(CH$_2$)$_4$CO$_2$C(CH$_3$)$_3$ | — | 500 (m)+ | $^1$H-NMR(CDCl$_3$): δ = 1.3–1.4(m,2H), 1.4(s,9H), 1.55–1.7(m,5H), 2.0–2.5(m,6H), 3.2–3.3(m,1H), 3.4–3.6(m,2H), 3.7–3.8(m,3H), 3.85–3.95(m,2H), 4.3–4.4(m,2H), 7.05(d,1H), 7.3(d,1H), 7.4(d,1H) ppm. |
| 186[2] | CH$_2$—cyclopropyl | — | — | $^1$H-NMR(CDCl$_3$): δ = 0.3–0.4(m,2H), 0.55–0.65(m,2H), 1.05–1.15(m,1H), 1.9–1.95(m,1H), 2.0–2.25(m,4H), 2.35–2.45(m,1H), 3.15–3.2(m,1H), 3.5–3.55(m,2H), 3.65–3.75(m,2H), 3.9–4.0 (m,3H), 4.35–4.4(m,1H), 7.2–7.5(m,3H), ppm. |

Footnotes:-
[1](S)-enantiomer prepared
[2](R)-enantiomer prepared.

| Prep. No. | R | m.p. | LRMS m/z | Analysis/¹H-NMR |
|---|---|---|---|---|
| 188[1,4] | 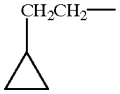 CH₂CH₂— cyclopropyl | — | 354 (m + 1)⁺ | — |
| 189[2,4] | 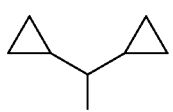 (dicyclopropylmethyl)CH₂— | — | — | ¹H-NMR(CDCl₃): δ = 0.1–0.25(m,4H), 0.35–0.5(m,4H), 0.55–0.7(m,3H), 2.1–2.3(m,3H), 2.35–2.5(m,1H), 2.7–2.75(m,1H), 2.9–2.95(m,1H), 3.15–3.25(m,1H), 3.6–3.9(m,3H), 7.1–7.45 (m,3H), 9.5(m,1H) ppm. |
| 190[4] | —CH₂(CH₂)₄CO₂C(CH₃)₃ | — | 456 (m)⁺ | ¹H-NMR(CDCl₃): δ = 1.3–1.4(m,2H), 1.4(s,9H), 1.55–1.7(m,5H), 2.1–2.25(m,5H), 2.3–2.45(m,1H), 2.7(d,1H), 2.95(d,1H), 3.2–3.35 (m,1H), 3.4–3.6(m,2H), 3.75(d,1H), 7.05(d,1H), 7.3(d,1H), 7.4(d,1H), 9.45(s,1H) ppm. |
| 191[3] |  CH₂— cyclopropyl | — | — | ¹H-NMR(CDCl₃): δ = 0.25–0.35(m,2H), 0.55–0.65(m,2H), 1.05–1.1(m,1H), 2.15–2.25(m,3H), 2.35–2.5(m,1H), 2.65–2.75(m,1H), 2.95–3.05 (m,1H), 3.15–3.2(m,1H), 3.45–3.6(m,2H), 3.95–4.0(m,1H), 7.2–7.45(m,3H), 9.5(s,1H) ppm. |

Footnotes:-
[1]Product contaminated with ca. 35% of the dioxolane starting material by ¹H-NMR spectroscopy.
[2]Product contaminated with ca. 6% of the dioxolane starting material by ¹H-NMR spectroscopy.
[3](R)-enantiomer prepared.
[4](S)-enantiomer prepared.

Preparation 192

4(R)-4-Cyano-4-(3,4-dichlorophenyl)-5-(1,3-dioxolan-2-yl)pentan-1-oic acid

The filtrate taken from the fractional crystallisation of the (S)-(−)-alpha-methylbenzylamine salts of 4(R)- and 4(S)-4-cyano-4-(3,4-dichlorophenyl)-5-(1,3-dioxolan-2-yl)pentan-1-oic acid (see Example 123(a)) was evaporated to dryness under reduced pressure to provide a solid (800 g). This solid was dissolved in methyl ethyl ketone (3 l) and water (300 ml) by heating under reflux. Further methyl ethyl ketone (1 l) was added and the mixture cooled. A pure seed crystal of the required compound was added. No crystallisation occurred. The solution was therefore reduced to half-volume by evaporation under reduced pressure. The mixture was left to stand for 72 hours to provide a solid which was filtered off and washed with methyl ethyl ketone (2×200 ml). This white solid was dried at 35° C. for 3 hours under reduced pressure and then dissolved in methyl ethyl ketone (1.5 l) and water (165 ml). The solution was heated under reflux for 1 hour. Methyl ethyl ketone (700 ml) was added and the mixture again seeded with the required compound and left to stand for 56 hours. The resulting solid was filtered off and washed with methyl ethyl ketone (2×100 ml), then dried under reduced pressure at 35° C. for 4 hours to give the (S)-(−)-alpha-methylbenzylamine salt of the title compound (133 g). HPLC (Ultron ES-OVM column, mobile phase=0.01M KH₂PO₄ buffer at pH 6.6: acetonitrile, 92:8, by volume, flow rate=1 ml/min.) showed this salt to be present in 98.4% e.e.

This salt was converted to the title compound by a similar method to that described in Example 123(a) for its enantiomer.

¹H-NMR (CDCl₃):δ=2.05–2.35(m,4H), 2.4–2.65(m,2H), 3.7–4.0(m,4H), 4.75–4.85(m, 1H), 7.25–7.55(m,3H), 9.9(s, br., 1H,acid) ppm.

Preparation 193

5(R)-5-(3,4-Dichlorophenyl)-5-(1,3-dioxolan-2-ylmethyl)-2(1H)-piperidone

The title compound was prepared by a similar method to that used in Example 123(b) except the compound of Preparation 192 was used as the starting material.

¹H-NMR (CDCl₃):δ=1.85–1.95(m,1H), 2.0–2.25(m,4H), 2.35–2.4(m,1H), 3.45–3.55(m, 1H), 3.65–3.75(m,2H), 3.8–3.9(m,3H), 4.35–4.4(m, 1H), 6.15(s,br., 1H), 7.2–7.45 (m,3H) ppm.

We claim:

1. A compound of the formula:

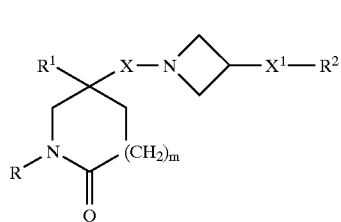

(I)

or a pharmaceutically acceptable salt thereof, wherein
R is $C_3$–$C_7$ cycloalkyl, aryl or $C_1$–$C_6$ alkyl, said $C_1$–$C_6$ alkyl being optionally substituted by fluoro, —COOH, —COO($C_1$–$C_4$ alkyl), $C_3$–$C_7$ cycloalkyl, adamantyl, aryl or het¹, and said $C_3$–$C_7$ cycloalkyl being optionally substituted by 1 or 2 substituents each independently selected from $C_1$–$C_4$ alkyl, $C_3$–$C_7$ cycloalkyl, $C_1$–$C_4$ alkoxy, hydroxy, fluoro, fluoro($C_1$–$C_4$)alkyl and fluoro ($C_1$–$C_4$)alkoxy;

$R^1$ is phenyl, naphthyl, thienyl, benzothienyl or indolyl, each optionally substituted by 1 or 2 substituents each independently selected from $C_1$–$C_4$ alkyl, $C_1$–$C_4$ alkoxy, halo and trifluoromethyl;

$R^2$ is —$CO_2H$, —$CONR^3R^4$, —$CONR^5(C_3$–$C_7$ cycloalkyl), —$NR^5(C_2$–$C_5$ alkanoyl), —$NR^3R^4$, —$NR^5CONR^5R^6$, ($C_3$–$C_7$ cycloalkyl-$C_1$–$C_4$ alkyl)$R^5N$—, ($C_3$–$C_7$ cycloalkyl-$C_1$–$C_4$ alkyl)$_2N$—, —$NR^5COCF_3$, —$NR^5SO_2CF_3$, —$NR^5(SO_2C_1$–$C_4$ alkyl), —$NR^5SO_2NR^5R^6$, —$NR^5(SO_2$ aryl), —N(aryl)($SO_2$ $C_1$–$C_4$ alkyl), —$OR^5$, —O($C_3$–$C_7$ cycloalkyl), —$SO_2NR^5R^6$, het$^3$ or a group of the formula:

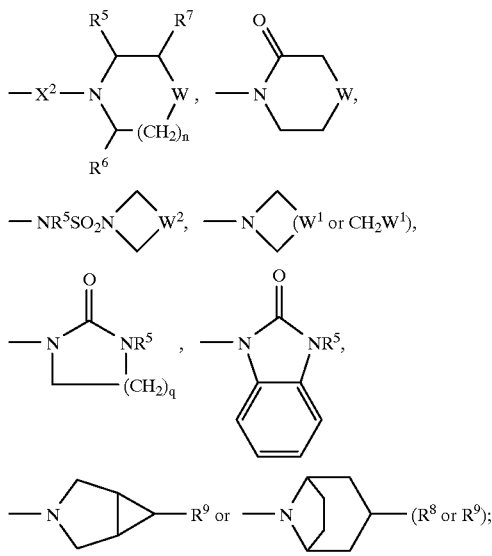

$R^3$ and $R^4$ are each independently selected from H and $C_1$–$C_4$ alkyl optionally substituted by hydroxy, $C_1$–$C_4$ alkoxy, —$S(O)_p(C_1$–$C_4$ alkyl), amino, —$NH(C_1$–$C_4$ alkyl), —$N(C_1$–$C_4$ alkyl)$_2$ or het$^2$;

$R^5$ and $R^6$ are each independently selected from H, $C_1$–$C_4$ alkyl and $C_3$–$C_7$ cycloalkyl-$C_1$–$C_4$ alkyl, said $C_1$–$C_4$ alkyl and $C_3$–$C_7$ cycloalkyl-$C_1$–$C_4$ alkyl being optionally substituted by fluoro;

$R^7$ is H, $C_1$–$C_4$ alkyl, hydroxy, fluoro($C_1$–$C_4$)alkyl or phenyl, said phenyl being optionally substituted by 1 or 2 substituents each independently selected from $C_1$–$C_4$ alkyl, fluoro($C_1$–$C_4$)alkyl, halo, $C_1$–$C_4$ alkoxy and fluoro($C_1$–$C_4$)alkoxy;

$R^8$ is H, fluoro, hydroxy, $C_1$–$C_4$ alkoxy, $C_2$–$C_5$ alkanoyl or $C_2$–$C_5$ alkanoyloxy;

$R^9$ is —$NR^5R^6$, —$NR^5COR^5$, —$NR^5SO_2CF_3$, —$NR^5(SO_2C_1$–$C_4$ alkyl), —$NR^5SO_2NR^5R^6$, —$NR^5COO(C_1$–$C_4$ alkyl), —$NR^5CONR^5R^6$, —$NR^5(SO_2$ morpholino), —$NR^5(SO_2$ aryl), —N(aryl)($SO_2C_1$–$C_4$ alkyl) or a group of the formula:

X is $C_1$–$C_4$ alkylene;

$X^1$ is a direct link or $C_1$–$C_6$ alkylene;

$X^2$ is a direct link, CO, $SO_2$ or $NR^5CO$;

W is methylene, CO, CH(OH), C(OH)$_2$, CH($C_1$–$C_4$ alkoxy), $CHCO_2H$, $CHCO_2(C_1$–$C_4$ alkyl), $CHCONR^5R^6$, CHF, $CF_2$, CH(azetidin-1-yl), CH(pyrrolidin-1-yl), CH(piperidin-1-yl), CH(morpholino), CH(benzoxazol-2-yl), $CHR^9$, O, $S(O)_p$, $NR^5$, N($C_3$–$C_7$ cycloalkyl), $NSO_2(C_1$–$C_4$ alkyl), $NSO_2NR^5R^6$, $NSO_2CF_3$, $NSO_2$(morpholino), $NSO_2$(aryl),

$NCONR^5R^6$, $NCOR^5$, NCO(aryl) or $NCO_2(C_1$–$C_4$ alkyl);

$W^1$ is methylene, CO, CH(OH), C(OH)$_2$, CH($C_1$–$C_4$ alkoxy), $CHCO_2H$, $CHCO_2(C_1$–$C_4$ alkyl), $CHCONR^5R^6$, CHF, $CF_2$, CH(azetidin-1-yl), CH(pyrrolidin-1-yl), CH(piperidin-1-yl), CH(morpholino) or $CHR^9$;

$W^2$ is $W^1$, —$CH_2W^1$—, —$CH_2WCH_2$— or —$CH_2CH_2WCH_2$—;

m is 0, 1 or 2;

n is 1 or 2 when W is other than methylene and is 0, 1 or 2 when W is methylene;

p is 0, 1 or 2;

q is 1 or 2;

r is 1, 2, 3 or 4;

"aryl", used in the definition of R, $R^2$, $R^9$ and W, means naphthyl or phenyl, each optionally substituted by $C_1$–$C_4$ alkyl, halo, —$OR^5$, fluoro($C_1$–$C_4$)alkyl, $C_2$–$C_5$ alkanoyl, —CON $R^5R^6$, —$SO_2NR$ $R^6$ or phenyl;

"het$^1$", used in the definition of R, means thienyl or a 5- or 6-membered ring heteroaryl group containing either 1 or 2 nitrogen heteroatoms, or one nitrogen heteroatom and one oxygen or sulphur heteroatom, each optionally substituted by 1 or 2 substituents each independently selected from $C_1$–$C_4$ alkyl, $C_1$–$C_4$ alkoxy, halo, fluoro($C_1$–$C_4$)alkyl and fluoro($C_1$–$C_4$)alkoxy;

"het$^2$", used in the definitions of $R^3$ and $R^4$, means a 4- to 7-membered ring, non-aromatic, heterocyclic group containing 1 or 2 heteroatoms each independently selected from nitrogen, oxygen and $S(O)_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —$CONR^5R^6$ or —$SO_2NR^5R^6$ substituent;

and "het$^3$", used in the definition of $R^2$, means an optionally benzo-fused, N-linked, 5-membered ring heteroaryl group containing from 1 to 4 nitrogen heteroatoms, optionally substituted, including in the benzo-fused portion, by 1 or 2 substituents each independently selected from $C_1$–$C_4$ alkyl, fluoro and fluoro($C_1$–$C_4$)alkyl.

2. A compound as claimed in claim 1 wherein

R is $C_1$–$C_6$ alkyl optionally substituted by —COOH, —COO($C_1$–$C_4$ alkyl), $C_3$–$C_7$ cycloalkyl, aryl or het$^1$, said cycloalkyl being optionally substituted by 1 or 2 substituents each independently selected from $C_1$–$C_4$ alkyl and fluoro;

$R^1$ is phenyl optionally substituted by 1 or 2 halo substituents;

$R^2$ is —$CONR^3R^4$, —$CONR^5(C_3$–$C_7$ cycloalkyl), —$NR^3R^4$, het$^3$ or a group of the formula:

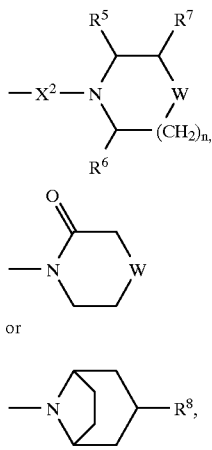

or

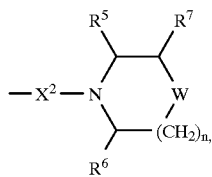

where $R^3$ and $R^4$ are each independently selected from $C_1$–$C_4$ alkyl and $C_1$–$C_4$ alkyl substituted by hydroxy or $C_1$–$C_4$ alkoxy, $R^5$ and $R^6$ are each independently selected from H, $C_1$–$C_4$ alkyl optionally substituted by fluoro and $C_3$–$C_7$ cycloalkyl-$C_1$–$C_4$ alkyl, $R^7$ is H, hydroxy or phenyl, $R^8$ is hydroxy or $C_2$–$C_5$ alkanoyloxy, W is methylene, CH(OH), CH($C_1$–$C_4$ alkoxy), CHCO$_2$H, CHCO$_2$($C_1$–$C_4$ alkyl), CH(benzoxazol-2-yl), CHNR$^5$R$^{6,}$ CHN R$^5$COR$^5$, CHNR$^5$(SO$_2$C$_1$–C$_4$ alkyl), CHNR$^5$COO(C$_1$–C$_4$ alkyl), O, S(O)$_p$, NR$^5$, NSO$_2$(C$_1$–C$_4$ alkyl), NSO$_2$NR$^5$R$^6$, NSO$_2$(morpholino), NCONR$^5$R$^6$, NCOR$^5$, NCO(aryl) or NCO$_2$(C$_1$–C$_4$ alkyl), n is 1 or 2 when W is other than methylene and is 0 or 1 when W is methylene, and p is 0,1 or 2;

and X, $X^1$, $X^2$, m, aryl and het$^3$ are as previously defined in claim 1.

3. A compound as claimed in claim 2 wherein

R is $C_1$–$C_6$ alkyl optionally substituted by —COOH, —COO($C_1$–$C_4$ alkyl), $C_3$–$C_7$ cycloalkyl optionally substituted by 1 or 2 substituents each independently selected from $C_1$–$C_4$ alkyl and fluoro, phenyl optionally substituted by 1 or 2 substituents each independently selected from $C_1$–$C_4$ alkyl, halo, $C_1$–$C_4$ alkoxy, fluoro($C_1$–$C_4$)alkyl, $C_2$–$C_5$ alkanoyl, —SO$_2$N($C_1$–$C_4$ alkyl)$_2$ and phenyl, or a 5- or 6-membered ring heteroaryl group containing 1 or 2 nitrogen heteroatoms;

$R^1$ is phenyl optionally substituted by 1 or 2 substituents each independently selected from fluoro and chloro;

$R^2$ is —CONR$^3$R$^4$, —CONR$^5$(C$_3$–C$_7$ cycloalkyl), —NR$^3$R$^4$, a N-linked, 5-membered ring heteroaryl group containing 1 or 2 nitrogen heteroatoms, or a group of the formula:

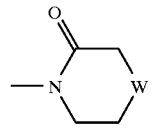

or where $R^3$ and $R^4$ are each independently selected from methyl and $C_1$–$C_4$ alkyl substituted by hydroxy or methoxy, $R^5$ and $R^6$ are each independently selected from H, methyl, trifluoromethyl and cyclopropylmethyl, $R^7$ is H, hydroxy or phenyl, $R^8$ is hydroxy or acetyloxy, W is methylene, CH(OH), CHOCH$_3$, CHOCH$_2$CH$_3$, CHO(CH$_2$)$_2$CH$_3$, CHOC(CH$_3$)$_3$, CHCO$_2$H, CHCO$_2$CH$_3$, CHCO$_2$CH$_2$CH$_3$, CH(benzoxazol-2-yl), CHNH$_2$, CHNHCH$_2$(cyclopropyl), CH NHCOCH$_3$, CHNHSO$_2$CH$_3$, CHNHCO$_2$C(CH$_3$)$_3$, O, S(O)$_p$, NH, NCH$_3$, NCH$_2$(cyclopropyl), NSO$_2$CH$_3$, NSO$_2$NH$_2$, NSO$_2$NHCH$_3$, NSO$_2$N(CH$_3$)$_2$, NSO$_2$(morpholino), NCONH$_2$, NCONHCH$_3$, NCOCH$_3$, NCOCF$_3$, NCO(phenyl) or NCO$_2$C(CH$_3$)$_3$, n is 1 or 2 when W is other than methylene and is 0 or 1 when W is methylene, and p is 0, 1 or 2;

and X, $X^1$, $X^2$ and m are as previously defined in claim 2.

4. A compound as claimed in claim 3 wherein

R is $C_1$–$C_6$ alkyl optionally substituted by —COOH, —COO($C_1$–$C_4$ alkyl), $C_3$–$C_7$ cycloalkyl optionally substituted by 1 or 2 substituents each independently selected from methyl and fluoro, phenyl optionally substituted by 1 or 2 substituents each independently selected from methyl, fluoro, chloro, methoxy, trifluoromethyl, acetyl, —SO$_2$N(CH$_3$)$_2$ and phenyl, or pyridinyl;

and $R^1$, $R^2$, X, $X^1$, $X^2$ and m are as previously defined in claim 3.

5. A compound as claimed in claim 4 wherein

R is 5-carboxypentyl, 5-tert-butyloxycarbonylpentyl, cyclopropylmethyl, dicyclopropylmethyl, cyclobutylmethyl, cyclopentylmethyl, cyclohexylmethyl, 2-methylcyclohexylmethyl, 4,4-difluorocyclohexylmethyl, 2-cyclopropylethyl, 2,2-dicyclopropylethyl, 1-cyclohexylethyl, 2-cyclohexylethyl, cycloheptyl-methyl, benzyl, 2-methylbenzyl, 3-methylbenzyl, 4-methylbenzyl, 4-fluorobenzyl, 2,4-dichlorobenzyl, 3-methoxybenzyl, 2-trifluoromethylbenzyl, 3,5-di(trifluoromethyl)benzyl, 3-acetylbenzyl, 3-(N,N-dimethylsulphamoyl)-benzyl, 4-phenylbenzyl, 1-phenylethyl, 2-pyridinylmethyl, 3-pyridinylmethyl or 4-pyridinylmethyl;

$R^1$ is phenyl, 3,4-difluorophenyl, 3-chlorophenyl, 4-chlorophenyl or 3,4-dichlorophenyl;

$R^2$ is N-(2-methoxyethyl)-N-methylcarbamoyl, N-cyclohexylcarbamoyl, N-(2-hydroxyethyl)-N-methylamino, N-(2-hydroxy-2-methylpropyl)-N-methylamino, N-(2-methoxyethyl)-N-methylamino, imidazol-1-yl, 3-hydroxypyrrolidin-1-yl, piperidin-1-yl, 2,6-dimethylpiperidin-1-yl, 3-hydroxypiperidin-1-yl, 4-hydroxypiperidin-1-yl, 4-methoxypiperidin-1-yl, 4-ethoxypiperidin-1-yl, 4-(n-propoxy)piperidin-1-yl, 4-(t-butoxy)piperidin-1-yl, 4-carboxypiperidin-1-yl, 4-methoxycarbonylpiperidin-1-yl, 4-ethoxycarbonylpiperidin-1-yl, 4-(benzoxazol-2-yl)piperidin-1-yl, 4-aminopiperidin-1-yl, 4-cyclopropylmethylaminopiperidin-1-yl, 4-acetamidopiperidin-1-yl, 4-methane-sulphonamidopiperidin-1-yl, 4-(t-butoxycarbonylamino)piperidin-1-yl, morpholino, 2-phenylmorpholino, homomorpholino, thiomorpholino, 1-oxothiomorpholino, 1,1-dioxothiomorpholino, piperazin-1-yl, 4-methylpiperazin-1-yl, 4-cyclopropylmethylpiperazin-1-yl, 4-methane-sulphonylpiperazin-1-yl, 4-aminosulphonylpiperazin-1-yl, 4-methylamino-sulphonylpiperazin-1-yl, 4-dimethylaminosulphonylpiperazin-1-yl, 4-morpholinosulphonylpiperazin-1-yl, 4-carbamoylpiperazin-1-yl, 4-N-methylcarbamoylpiperazin-1-yl, 4-acetylpiperazin-1-yl, 4-trifluoroacetyl-piperazin-1-yl, 4-benzoylpiperazin-1-yl, 4-(t-butoxycarbonyl)piperazin-1-yl, pyrrolidin-1-ylcarbonyl, piperidin-1-ylcarbonyl, 3-oxomorpholino, 3-hydroxy-8-azabicyclo[3,2,1]oct-8-yl or 3-acetyloxy-8-azabicyclo[3,2,1]oct-8-yl;

X is ethylene or propylene;

$X^1$ is a direct link;

$X^2$ is a direct link or CO;

and m is as previously defined in claim 4.

6. A compound as claimed in claim 5 wherein

R is cyclopropylmethyl, dicyclopropylmethyl, 2-cyclopropylethyl, 2,2-dicyclopropylethyl, cyclohexylmethyl, 4,4-difluorocyclohexylmethyl, cycloheptylmethyl or benzyl;

$R^1$ is 3,4-difluorophenyl, 4-chlorophenyl or 3,4-dichlorophenyl;

$R^2$ is 4-aminopiperidin-1-yl, 4-carboxypiperidin-1-yl, 4-hydroxypiperidin-1-yl, morpholino, 1-oxothiomorpholino, 4-aminosulphonylpiperazin-1-yl, 4-methanesulphonylpiperazin-1-yl, 4-methylaminosulphonylpiperazin-1-yl, 4-morpholinosulphonylpiperazin-1-yl, 4-fluoropiperidin-1-yl, 4,4-difluoropiperidin-1-yl, 4-oxopiperidin-1-yl, 4-(pentafluorophenylsulphonyl)-piperazin-1-yl and 4-(4-fluorophenylsulphonyl)piperazin-1-yl;

X is ethylene;

$X^2$ is a direct link;

m is 1;

and $X^1$ is as previously defined in claim 5.

7. A compound as claimed in claim 1 wherein X is —CH$_2$CH$_2$— and which has the (S)-stereochemistry at the position of attachment of the X and $R^1$ groups to the lactam ring.

8. A compound as claimed in claim 1 wherein (i) R is cyclopropylmethyl, $R^1$ is 3,4-dichlorophenyl, $R^2$ is morpholino, X is —CH$_2$CH$_2$—, $X^1$ is a direct link and m is 1;

(ii) R is 4,4-difluorocyclohexylmethyl, $R^1$ is 3,4-dichlorophenyl, $R^2$ is morpholino, X is —CH$_2$CH$_2$—, $X^1$ is a direct link and m is 1;

(iii) R is 4,4-difluorocyclohexylmethyl, $R^1$ is 3,4-dichlorophenyl, $R^2$ is 4-aminopiperidin-1-yl, X is —CH$_2$CH$_2$—, $X^1$ is a direct link and m is 1;

(iv) R is cyclopropylmethyl, $R^1$ is 3,4-dichlorophenyl, $R^2$ is 4-aminosulphonylpiperazin-1-yl, X is —CH$_2$CH$_2$—, $X^1$ is a direct link and m is 1;

(v) R is 4,4-difluorocyclohexylmethyl, $R^1$ is 3,4-dichlorophenyl, $R^2$ is 4-hydroxypiperidin-1-yl, X is —CH$_2$CH$_2$—, $X^1$ is a direct link and m is 1;

(vi) R is 2-cyclopropylethyl, $R^1$ is 3,4-dichlorophenyl, $R^2$ is morpholino, X is —CH$_2$CH$_2$—, $X^1$ is a direct link and m is 1;

(vii) R is 2-cyclopropylethyl, $R^1$ is 3,4-dichlorophenyl, $R^2$ is 4-methanesulphonylpiperazin-1-yl, X is —CH$_2$CH$_2$—, $X^1$ is a direct link and m is 1;

(viii) R is cyclopropylmethyl, $R^1$ is 3,4-dichlorophenyl, $R^2$ is 4-fluoropiperidin-1-yl, X is —CH$_2$CH$_2$—, $X^1$ is a direct link and m is 1;

(ix) R is 4,4-difluorocyclohexylmethyl, $R^1$ is 3,4-dichlorophenyl, $R^2$ is 4-oxopiperidin-1-yl, X is —CH$_2$CH$_2$—, $X^1$ is a direct link and m is 1;

(x) R is cyclopropylmethyl, $R^1$ is 3,4-dichlorophenyl, $R^2$ is 4-carboxypiperidin-1-yl, X is —CH$_2$CH$_2$—, $X^1$ is a direct link and m is 1; or (xi) R is cyclohexylmethyl, $R^1$ is 3,4-dichlorophenyl, $R^2$ is 4-carboxypiperidin-1-yl, X is —CH$_2$CH$_2$—, $X^1$ is a direct link and m is 1:

or any such compound with the (S)-stereochemistry at the position of attachment of the X and $R^1$ groups to the lactam ring, or a pharmaceutically acceptable salt of any thereof.

9. A pharmaceutical composition comprising a compound of the formula (I), or a pharmaceutically acceptable salt thereof, as claimed in claim 1, together with a pharmaceutically acceptable diluent or carrier.

10. A pharmaceutical composition for a disorder or condition that can be treated by producing an antagonist effect on a tachykinin acting at the human NK$_1$, NK$_2$, or Nk$_3$ receptor or a combination thereof, comprising an amount of a compound of claim 1, or a pharmaceutically acceptable salt thereof, that is effective in treating such disorder or condition.

11. A method of treating a disorder or condition that can be treated by producing an antagonist effect on a tachykinin acting at the human NK$_1$, NK$_2$, or Nk$_3$ receptor or a combination thereof, which comprises administering to said human an effective amount of a compound of claim 1, or a pharmaceutically acceptable salt thereof.

12. A compound as claimed in claim 1 of the formula:

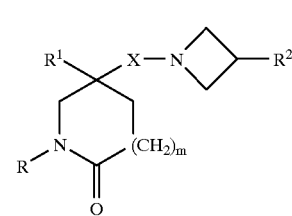

(I)

or a pharmaceutically acceptable salt thereof, wherein

R is $C_1$–$C_6$ alkyl optionally substituted by fluoro, $C_3$–$C_7$ cycloalkyl, adamantyl, aryl or het$^1$, said cycloalkyl being optionally substituted by 1 or 2 substituents each independently selected from $C_1$–$C_4$ alkyl, $C_1$–$C_4$ alkoxy, hydroxy, fluoro, fluoro($C_1$–$C_4$ alkyl) and fluoro ($C_1$–$C_4$)alkoxy;

$R_1$ is phenyl optionally substituted by 1 or 2 substituents each independently selected from $C_1$–$C_4$ alkyl, $C_1$–$C_4$ alkoxy, halo and trifluoromethyl, or is naphthyl or thienyl;

$R^2$ is —CO$_2$H, —CONR$^3$R$^4$, —CONH(C$_3$–C$_7$ cycloalkyl), —CON(C$_1$–C$_4$ alkyl)(C$_3$–C$_7$ cyclbalkyl), —NH($C_2$–$C_5$ alkanoyl), —N($C_1$–$C_4$ alkyl)($C_2$–$C_5$ alkanoyl), —NR$^3$R$^4$ het$^3$ or a group of the formula:

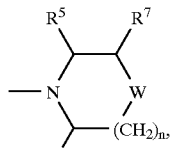

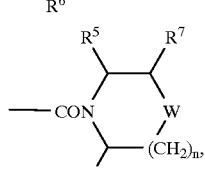

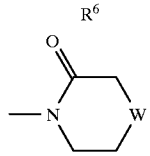

or

R$^3$ and R$^4$ are each independently selected from H and $C_1$–$C_4$ alkyl optionally substituted by hydroxy, $C_1$–$C_4$ alkoxy, —S(O)$_p$($C_1$–$C_4$ alkyl), amino, —NH($C_1$–$C_4$ alkyl), —N($C_1$–$C_4$ alkyl)$_2$ or het$^2$;

R$^5$ and R$^6$ are each independently selected from H and $C_1$–$C_4$ alkyl;

R$^7$ is H, $C_1$–$C_4$ alkyl, hydroxy, fluoro($C_1$–$C_4$)alkyl or phenyl optionally substituted by 1 or 2 substituents each independently selected from $C_1$–$C_4$ alkyl, halo, $C_1$–$C_4$ alkoxy and fluoro($C_1$–$C_4$)alkoxy;

R$^8$ is H, fluoro, hydroxy, $C_1$–$C_4$ alkoxy, $C_2$–$C_5$ alkanoyl or $C_2$–$C_5$ alkanoyloxy;

X is $C_1$–$C_4$ alkylene;

W is methylene, CH(OH), CH($C_1$–$C_4$ alkoxy), CHF, CF$_2$, CHNH($C_1$–$C_4$ alkyl), CHN($C_1$–$C_4$ alkyl)$_2$, CH (azetidin-1-yl), CH(pyrrolidin-1-yl), CH(piperidin-1-yl), CHNH($C_2$–$C_5$ alkanoyl), CHN($C_1$–$C_4$ alkyl)($C_2$–$C_5$ alkanoyl), CHNHSO$_2$($C_1$–$C_4$ alkyl), CHN($C_1$–$C_4$ alkyl)(SO$_2$($C_1$–$C_4$ alkyl)), O, S(O)$_p$, NH, N($C_1$–$C_4$ alkyl), NSO$_2$($C_1$–$C_4$ alkyl), NSO$_2$NH$_2$, NSO$_2$NH($C_1$–$C_4$ alkyl), NSO$_2$N($C_1$–$C_4$ alkyl)$_2$, NCONH$_2$, NCONH($C_1$–$C_4$ alkyl), NOON($C_1$–$C_4$ alkyl)$_2$, N($C_2$–$C_5$ alkanoyl) or NCO$_2$($C_1$–$C_4$ alkyl);

m is 0 or 1;

n is 1 or 2 when W is other than methylene and is 0, 1 or 2 when W is methylene;

p is 0, 1 or 2;

"aryl", used in the definition of R, means naphthyl or phenyl, both optionally substituted by 1 or 2 substituents each independently selected from $C_1$–$C_4$ alkyl, halo, $C_1$–$C_4$ alkoxy, fluoro($C_1$–$C_4$)alkyl, fluoro($C_1$–$C_4$)alkoxy, $C_2$–$C_5$ alkanoyl, —CONH$_2$, —CONH($C_1$–$C_4$ alkyl), —CON($C_1$–$C_4$ alkyl)$_2$, —SO$_2$NH$_2$, —SO$_2$NH ($C_1$–$C_4$ alkyl), —SO$_2$N($C_1$–$C_4$ alkyl)$_2$ and phenyl;

"het$^1$", used in the definition of R, means a 5- or 6-membered ring heteroaryl group containing either 1 or 2 nitrogen heteroatoms, or one nitrogen heteroatom and one oxygen or sulphur heteroatom;

"het$^2$", used in the definitions of R$^3$ and R$^4$, means a 4- to 7-membered ring, non-aromatic, heterocyclic group containing 1 or 2 heteroatoms each independently selected from nitrogen, oxygen and S(O)$_p$, said group being optionally C-substituted by 1 or 2 substituents each independently selected from $C_1$–$C_4$ alkyl, $C_1$–$C_4$ alkoxy and fluoro($C_1$–$C_4$)alkyl, and said ring nitrogen heteroatom optionally bearing a H, $C_1$–$C_4$ alkyl, $C_2$–$C_5$ alkanoyl, —CONH$_2$, —CONH($C_1$–$C_4$ alkyl), —CON ($C_1$–$C_4$ alkyl)$_2$, —SO$_2$NH$_2$, —SO$_2$NH($C_1$–$C_4$ alkyl) or —SO$_2$N($C_1$–$C_4$ alkyl)$_2$ substituent;

and "het$^3$", used in the definition of R$^2$, means a N-linked, 5-membered ring heteroaryl group containing from 1 to 4 nitrogen heteroatoms and optionally substituted by 1 or 2 substituents each independently selected from $C_1$–$C_4$ alkyl and fluoro($C_1$–$C_4$)alkyl.

* * * * *